United States Patent
Dunn et al.

(10) Patent No.: US 11,253,536 B2
(45) Date of Patent: Feb. 22, 2022

(54) METHODS FOR DIRECTED FOLDING ASSEMBLY OR DIMERIZATION OF PROTEINS BY TEMPLATED ASSEMBLY REACTIONS

(71) Applicant: TriBiotica LLC, Madison, WI (US)

(72) Inventors: Ian Dunn, Madison, WI (US); Matthew Lawler, Madison, WI (US)

(73) Assignee: TriBiotica LLC, Madison, WI (US)

( * ) Notice: Subject to any disclaimer, the term of this patent is extended or adjusted under 35 U.S.C. 154(b) by 0 days.

(21) Appl. No.: 16/462,332

(22) PCT Filed: Nov. 17, 2017

(86) PCT No.: PCT/US2017/062267
§ 371 (c)(1),
(2) Date: May 20, 2019

(87) PCT Pub. No.: WO2018/094195
PCT Pub. Date: May 24, 2018

(65) Prior Publication Data
US 2019/0314397 A1  Oct. 17, 2019

Related U.S. Application Data

(60) Provisional application No. 62/424,642, filed on Nov. 21, 2016.

(51) Int. Cl.
*A61K 31/713* (2006.01)
*C12N 15/11* (2006.01)
(Continued)

(52) U.S. Cl.
CPC ............ *A61K 31/713* (2013.01); *C12N 15/11* (2013.01); *C12P 19/34* (2013.01); *G01N 33/50* (2013.01); *C12N 2310/3513* (2013.01)

(58) Field of Classification Search
CPC .................. A61K 31/713; C12N 15/11; C12N 2310/3513; C12N 15/111; C12N 15/1068;
(Continued)

(56) References Cited

U.S. PATENT DOCUMENTS 5,514,546 A   5/1996  Kool
5,858,731 A   1/1999  Sorge
(Continued)

FOREIGN PATENT DOCUMENTS

CN   101538613   9/2009
EP   2796150    10/2014
(Continued)

OTHER PUBLICATIONS

Inobe et al, Rapamycin-induced oligomer formation system of FRB-FKBP fusion proteins, 2016, Journal of Bioscience and Bioengineering, 122,40-46 (Year: 2016).*
(Continued)

*Primary Examiner* — Narayan K Bhat
(74) *Attorney, Agent, or Firm* — Stradley Ronon Stevens & Young, LLP

(57) ABSTRACT

The present disclosure provides nucleic acid molecules, compositions, and kits comprising the same, and methods for producing templated assembly products.

3 Claims, 35 Drawing Sheets

Specification includes a Sequence Listing.

(51) Int. Cl.
  *C12P 19/34* (2006.01)
  *G01N 33/50* (2006.01)
(58) Field of Classification Search
  CPC . C12N 15/1048; C12N 15/1138; C12P 19/34; G01N 33/50; C07D 401/12; C07D 401/14; C40B 30/00; C40B 50/04; G16B 5/00; G16B 15/00
  See application file for complete search history.

(56) References Cited

U.S. PATENT DOCUMENTS

| | | | |
|---|---|---|---|
| 5,925,517 | A | 7/1999 | Tyagi et al. |
| 2002/0172965 | A1 | 11/2002 | Kamb et al. |
| 2005/0026178 | A1 | 2/2005 | Nilsen-Hamilton |
| 2005/0048192 | A1 | 3/2005 | Raines et al. |
| 2005/0287548 | A1 | 12/2005 | Bao |
| 2006/0099592 | A1 | 5/2006 | Freskgard |
| 2006/0147963 | A1 | 7/2006 | Barone et al. |
| 2006/0223777 | A1 | 10/2006 | Vermeulen et al. |
| 2006/0292438 | A1 | 12/2006 | Greenfield et al. |
| 2007/0099222 | A1 | 5/2007 | Gee et al. |
| 2007/0190597 | A1 | 8/2007 | Agnew et al. |
| 2008/0044834 | A1 | 2/2008 | Heyduk et al. |
| 2008/0050731 | A1 | 2/2008 | Agnew et al. |
| 2008/0071074 | A1 | 3/2008 | Skrzypczynski et al. |
| 2009/0124571 | A1 | 5/2009 | Morvan et al. |
| 2010/0048866 | A1 | 2/2010 | Raines et al. |
| 2010/0055728 | A1 | 3/2010 | Yang |
| 2012/0009566 | A1 | 1/2012 | Soukka |
| 2015/0203841 | A1 | 7/2015 | Rasmussen |
| 2016/0025726 | A1 | 1/2016 | Altin et al. |
| 2016/0106854 | A1 | 4/2016 | Dunn et al. |

FOREIGN PATENT DOCUMENTS

| | | | | |
|---|---|---|---|---|
| JP | H10512446 | | 12/1998 | |
| JP | 2009528988 | | 8/2009 | |
| JP | 2014055167 | | 3/2014 | |
| WO | 1997031899 | | 9/1997 | |
| WO | 0061775 | | 10/2000 | |
| WO | 2004011486 | | 2/2004 | |
| WO | 2006053571 | | 5/2006 | |
| WO | 2006058496 | | 6/2006 | |
| WO | 2009129281 | | 10/2009 | |
| WO | 2011089393 | | 7/2011 | |
| WO | 2012057689 | | 5/2012 | |
| WO | 2013012434 | | 1/2013 | |
| WO | 2014197547 | | 11/2014 | |
| WO | WO-2014197547 | A1 * | 12/2014 | ............ A61P 31/04 |
| WO | 2015122835 | | 8/2015 | |
| WO | 2015175747 | | 11/2015 | |
| WO | 2016089958 | | 6/2016 | |
| WO | 2016134232 | | 8/2016 | |
| WO | 2017049094 | | 3/2017 | |
| WO | 2017205277 | | 11/2017 | |
| WO | 2018093978 | | 5/2018 | |

OTHER PUBLICATIONS

Gajadhar et al, A proximity ligation assay using transiently transfected, epitope-tagged proteins: application for in situ detection of dimerized receptor tyrosine kinases, 2009, Biotechniques, 48, 145-152 (Year: 2009).*
Official Action dated Dec. 11, 2019 in related U.S. Appl. No. 15/601,449.
Official Action dated Dec. 6, 2019 in related U.S. Appl. No. 15/529,807.
Notice of Allowance dated Nov. 21, 2019 in related U.S. Appl. No. 14/895,398.
El-Sagheer et al., "Click chemistry with DNA", Chemical Society Reviews, 2010, 39(4), pp. 1388.
Gu et al., "Protein tag-mediated conjugation of oligonucleotides to recombinant affinity binders for proximity ligation", New Biotechnology, 2012, 30(2), pp. 144-152.
He et al., "Visual detection of single-base mismatches in DNA using hairpin oligonucleotide with double-target DNA binding sequences and gold nanoparticles", Biosensors and Bioelectronics, 2012, 34(1), pp. 37-43.
Hu et al., "Simple and fast electrochemical detection of sequence-specific DNA via click chemistry-mediated labeling of hairpin DNA probes with ethylnylferrocene", Analyst, 2015, 140(12), pp. 4154-4161.
Lloyd et al., "Modulation of oligonucleotide duplex and triplex stability via hydrophobic interactions", Nucleic Acids Research, 1993, 21(5), pp. 5909-5915.
Mao et al., "Molecular beacon-functionalized gold nanoparticles as probes in dry-reagent strip biosensor for DNA analysis", Chemical Communications, 2009, 21, pp. 3065.
Nakagawa et al., "Targeted Intracellular Delivery of Antisense Oligonucleotides via Conjugation with Small-Molecule Ligands", JACS, 2010, 132(26), pp. 8848-8849.
Pyati et al., "Optimising expression of the recombinant fusion protein biopesticide [omega]-hexatoxin-Hv1a/GNA in Pichia pastoris: sequence modifications and a simple method for the generation of multi-copy strains", Journal of Industrial Microbiology & Biotechnology, 2014, 41(8), pp. 1237-1247.
Qian et al., "A novel signal-on electrochemical DNA sensor based on target catalyzed hairpin assembly strategy", Biosensors and Bioelectronics, 2014, 64, pp. 177-181.
Sonntag et al., "An intein-cassette integration approach used for the generation of a split TEV protease activated by conditional protein splicing", Molecular Biosystems, 2011, 7(6), pp. 2031.
Sun et al., "Electrochemical Detection of Peanut Allergan Ara h 1 Using a Sensitive DNA Biosensor Based on Stem-Loop Probe", Journal of Agricultural and Food Chemistry, 2012, 60(44), pp. 10979-10984.
Xu et al., "Effect of location of the His-tag on the production of soluble and functional Buthus martensii Karsch insect toxin", Protein Expression and Purification, 2008, 59(1), pp. 103-109.
Yaqin et al., "Tenison promoted circular probe for highly selective microRNA detection and imaging", Biosensors and Bioelectronics, 2016, 85, pp. 151-156.
Zhou, "Synthesis of new tetrazines functionalized with photoactive and electroactive groups", 2012, PhD Thesis, Ecole normale superieure de Cachan-ENS Cachan.
Zimnik et al., "Mutually exclusive STAT1 modifications identified by Ubc9/substrate dimerization-dependent SUMOylation", Nucleic Acids Research, 2008, 37(4), pp. e30.
Final Official Action dated Jul. 28, 2020 in related U.S. Appl. No. 15/601,449.
Kaur et al., "Perspectives on Chemistry and Therapeutic Applications of Locked Nucleic Acid (LNA)", Chem Rev, 2007, 107, pp. 4672-4697.
Pinheiro et al., "The XNA world: progress towards replication and evolution of synthetic genetic polymers", Current Opinion in Chemical Biology, 2012, 16, pp. 245-252.
Non-Final Office Action dated Dec. 22, 2020 in related U.S. Appl. No. 16/462,324.
Niwayama et al., "A Pyrene Maleimide with a Flexible Linker for Sampling of Longer Inter-Thiol Distances by Excimer Formation", PLoS ONE, 2011, 6(10), e26691.
Notice of Allowance dated Mar. 2, 2020 in related U.S. Appl. No. 15/529,807.
Riemer et al., "Matching of trastuzumab (Herceptin/\(R)) epitope mimics onto the surface of Her-2/neu—a new method of epitope definition", Pergamon, 2005, 42(9), pp. 1121-1124.
Wu et al., "Aptmpers: Active Targeting Ligands for Cancer Diagnosis and Therapy", Theranostics, 2015, 5(4), pp. 322-344.
Bendifallah et al., "Evaluation of Cell-Penetrating Peptides (CPPs) as Vehicles for Intracellular Delivery of Antisense Peptide Nucleic Acid (PNA)", Bioconjugate Chem., 2006, 17:750-758.

(56) References Cited

OTHER PUBLICATIONS

Blanco-Canosa and Dawson, "An efficient Fmoc-SPPS approach for the generation of thioester peptide precursors for use in native chemical ligation", Angew Chem Int Ed Engl, 2008, 47(36):6851-6855.
Clackson et al., "Redesigning an FKBP-ligand interface to generate chemical dimerizers with novel specificity", PNAS USA, 1998, 95(18):10437-10442.
D.Y. Wu and B. Wallace "The Ligation Amplification Reaction (LAR)—Amplification of Specific DNA Sequences Using Sequential Rounds of Template-Dependent Ligation", Genomics, 1989, 4:560-569.
Imoto et al., "DNA-template click chemistry for creation of novel DNA binding molecules", Bioorganic & Medicinal Chem Lett, 2008, 18(20):5660-5663.
International Search Report and Written Opinion for PCT/US2015/063368.
Kalia et al., "Reactivity of Intein Thioesters: Appending a Functional Group to a Protein", ChemBioChem, 2006, 7:1375-1383.
Kazane et al., "Self-Assembled Antibody Multimers Through Peptide Nucleic Acid Conjugation", JACS, 2012, 135:340-346.
Knecht et al., "Oligohis-tags: mechanisms of binding to Ni2+ surfaces", J Mol Recognit, 2009, 22:270-279.
LeGall et al., "Protable flanking sequences modulate CTL epitope processing", J Clin Invest, 2007, 117(11):3563-3575.
Monroy-Contreras et al., "Molecular Beacons: Powerful Tools For Imaging RNA in Living Cells", J Nuc Acids, 2011, 5-6.
Official Action dated Aug. 6, 2018 in U.S. Appl. No. 14/895,398.
Official Action dated Jun. 11, 2019 in related U.S. Appl. No. 14/895,398.
Official Action dated Mar. 6, 2019 in related U.S. Appl. No. 15/529,807.
Official Action dated Nov. 15, 2017 in related U.S. Appl. No. 14/895,398.
Overkamp et al., "Benchmarking various green fluorescent protein variants in Bacillus subtilis, *Streptococcus pneumoniae*, and Lactococcus lactis for live cell imaging", Appl Environ Microbiol, 2013, 79(20):6481-6490.
Pai et al., "Using RNA aptamers and the proximity ligation assay for the detection of cell surface antigens", Methods Mol Biol, 2009, 504:385-398.
Paulmurugan et al., "Monitoring protein-protein interactions using split synthetic renilla luciferase protein-fragment-assisted complementation", Anal Chem, 2003, 75(7):1584-1589.
Ponomarenko et al., "Recent advances in self-assembled fluorescent DNA structures and probes", Curr Top Med Chem, 2015, 15(13):1162-1178.
Restriction Requirement dated Mar. 28, 2017, issued in related U.S. Appl. No. 14/895,398.
Roosild et al., "Structure of anti-FLAG M2 Fab domain and its use in the stabilization of engineered membrane proteins", Acta Crystallogr Sect F Struct Biol Cryst Commun, 2006, 62(9):835-839.
Sletten et al., "From mechanism to mouse: a tale of two bioorthogonal reactions", Acc Chem Res, 2011, 44(9):666-676.
Tam and Raines, "Coulombic effects on the traceless Staudinger ligation in water", Bioorg Med Chem, 2009, 17(3):1055-1063.
Tam et al., "Water-soluble phosphinothiols fortraceless Staudinger ligation and integration with expressed protein ligation", J Am Chem Soc, 2007, 129(37):11421-11430.
Walder et al., "Complementary carrier peptide synthesis: general strategy and implications for prebiotic origin of peptide synthesis", PNAS, 1979, 76(1):51-55.
Weisbrod et al., "Synthesis of Water-Soluble Phosphinophenol for Traceless Staudinger Ligation", Synlett, 2010, 6:787-789.
Zhao et al., "Solid-phase synthesis and evaluation of TAR RNA targeted beta-carboline-nucleoside conjugates", Organic and Biomolecular Chemistry, 2008, 6(20):3741-3750.
Notice of Allowance dated Jul. 27, 2021 in related U.S. Appl. No. 16/462,324.
Non-Final Office Action dated May 26, 2021 in related U.S. Appl. No. 16/637,858.
GenBank entry KQ142094, uploaded 2015.
Desai et al., "Geologists discover new extremophiles in anartic ice self", blog "the swaddle", http://theswaddle.com/geologists-discover-new-extremophiles-in-antarctic-ice-shelf/#:~:text=Geologists%20have%20discovered%20a%20new, The%20discover%20was%20accidental., posted Feb. 2021.
Mallikaratchy et al., "Evolution of complex target selex to identify aptamers against mammalian cell surface antigens", Molecules, 2017, 22(215), pp. 1-12.
Reynolds et al., "A functional proteomic method for biomarker discovery", PLoS ONE, 2011, 6(7), pp. e22471.
Park et al., "Hybridization based aptamer labeling using complementary oligonucleotide platform for PET and optical imaging", Biomaterials, 2016, 100, pp. 143-151.
Gilboa et al., "Use of oligonucleotide aptamer ligands to modulate the function of immune receptors", Clin Canc Res, 2013, 19(5), pp. 1054-1063.
Mammen et al., "Polyvalent interactions in biological systems: implications for design and use of multivalent ligands and inhibitors", Angew Chem Int Ed, 1998, 37, pp. 2754-2494.
Non-Final Office Action dated Aug. 17, 2021 in related U.S. Appl. No. 15/601,449.
Final Office Action dated Oct. 5, 2021 in related U.S. Appl. No. 16/637,858.
Ke et al., "The thermal stability of DNA fragments with tandem mismatches at a d(CXYG-d(CY'X'G) site", Nucleic Acids Research, 1996, 24(4), pp. 707-712.
Henke et al., "Peptide-conjugated antisense oligonucleotides for targeted inhibition of a transcriptional regular in vivo". Nature Biotechnology, 2008, 26(1), pp. 91-100.
Advisory Action dated Dec. 15, 2021 in related U.S. Appl. No. 16/637,858.

* cited by examiner

Natural Chemical Dimerizers

The immunosuppressive drug FK506 forms a ternary complex with calcineurin and the immunophilin FK-binding protein (FKBP). The FKBP-FK506 domain has been widely exploited for generating dimerization between fusion proteins.

Rapamycin also binds FKBP, but in addition forms a ternary complex with a segment of mTOR (FRB, aka FRAP)

FKM-NHS

FKM-sulfo-NHS

FKM-PEG3-NHS

Small-molecule LD-TAPER Protein Dimerization - Architecture 1

A. Promotion of dimerization of pre-folded monomers with template Architecture 1:

Small-molecule LD-TAPER Protein Dimerization - Architecture 2

A. Promotion of dimerization of <u>prefolded</u> monomers : Architecture 2

LD-TAPER: Protein dimerization By Small Interactive Protein Domains

Polarity considerations for parallel zippers

Parallel c-Jun tags

Antiparallel c-Jun tags

Fos-fusions with protein domain of interest

FKM-PEG3-NHS with side-chain click groups

FKM-PEG3-MTZ-NHS

FKM-PEG3-NHS with side-chain click groups

FKM-PEG3-TCO-NHS

1

2

3

4

(−) = Unconjugated thiol-oligonucleotide
(+) = Oligonucleotide after conjugation with MFL2

1

2

METHODS FOR DIRECTED FOLDING ASSEMBLY OR DIMERIZATION OF PROTEINS BY TEMPLATED ASSEMBLY REACTIONS

FIELD

The present disclosure is directed, in part, to nucleic acid molecules, compositions, and kits comprising the same, and methods for producing templated assembly products.

BACKGROUND

A goal of drug development is delivering potent bio-therapeutic interventions to pathogenic cells, such as virus infected cells, neoplastic cells, cells producing an autoimmune response, and other dysregulated or dysfunctional cells. Examples of potent bio-therapeutic interventions capable of combating pathogenic cells include toxins, pro-apoptotic agents, and immunotherapy approaches that re-direct immune cells to eliminate pathogenic cells. Unfortunately, developing these agents is extremely difficult because of the high risk of toxicity to adjacent normal cells or the overall health of the patient.

A method that has emerged to allow delivery of potent interventions to pathogenic cells while mitigating toxicity to normal cells is targeting of therapeutics by directing them against molecular markers specific for pathogenic cells. Targeted therapeutics have shown extraordinary clinical results in restricted cases, but are currently limited in their applicability due to a lack of accessible markers for targeted therapy. It is extremely difficult, and often impossible, to discover protein markers for many pathogenic cell types.

More recently, therapies targeted to nucleic acid targets specific to pathogenic cells have been developed. Existing nucleic acid-targeted therapies, such as siRNA, are able to down-modulate expression of potentially dangerous genes, but do not deliver potent cytotoxic or cytostatic interventions and thus are not particularly efficient at eliminating the dangerous cells themselves.

Hence, there exists a need to combat the poor efficacy and/or severe side effects of existing bio-therapeutic interventions. As described herein, proteins can be assembled via folding or dimerization using nucleic acid molecule templates which can be used to combat pathogenic or otherwise undesirable cells or cell products. Such templated assembly processes can be used to target the cell types of interest for destruction. Pairs of modified oligonucleotides carrying specially tailored and mutually reactive ligands can assemble proteins with predetermined functions following templated assembly as set forth herein.

SUMMARY

The present disclosure provides haplomer-ligand complexes comprising: a haplomer, wherein the haplomer comprises a polynucleotide that is substantially complementary to a target nucleic acid molecule; and a ligand linked to the 5' or 3' terminus of the haplomer, wherein the ligand comprises a ligand partner binding site.

The present disclosure also provides compositions or kits comprising a first haplomer-ligand complex described herein and a second haplomer-ligand complex described herein, wherein: the ligand of the first haplomer-ligand complex is linked to the 5' terminus of the polynucleotide of the first haplomer-ligand complex; and the ligand of the second haplomer-ligand complex is linked to the 3' terminus of the polynucleotide of the second haplomer-ligand complex.

The present disclosure also provides bottle haplomer-ligand complexes comprising: a bottle haplomer, wherein the bottle haplomer comprises a polynucleotide, wherein the polynucleotide comprises: a) a first stem portion comprising from about 10 to about 20 nucleotide bases; b) an anti-target loop portion comprising from about 16 to about 40 nucleotide bases and having a first end to which the first stem portion is linked, wherein the anti-target loop portion is substantially complementary to a target nucleic acid molecule; c) a second stem portion comprising from about 10 to about 20 nucleotide bases linked to a second end of the anti-target loop portion, wherein the first stem portion is substantially complementary to the second stem portion; and d) a ligand linked to the terminal end of either the first stem portion or the second stem portion, wherein the ligand comprises a ligand partner binding site; wherein the $T_m$ of the anti-target loop portion:target nucleic acid molecule is greater than the $T_m$ of the first stem portion:second stem portion.

The present disclosure also provides compositions or kits comprising: a bottle haplomer-ligand complex described herein; and a second haplomer-ligand complex comprising: a nucleotide portion comprising from about 6 to about 20 nucleotide bases that is substantially complementary to the stem portion of the bottle haplomer-ligand complex that is linked to the ligand of the bottle haplomer-ligand complex; and a ligand linked to the 5' or 3' terminus of the nucleotide portion of the second haplomer-ligand complex, wherein the ligand comprises a ligand partner binding site; wherein the $T_m$ of the second haplomer-ligand complex:first or second stem portion linked to the ligand of the bottle haplomer-ligand complex is less than or equal to the $T_m$ of the first stem portion:second stem portion of the bottle haplomer-ligand complex.

The present disclosure also provides compounds having the formula:

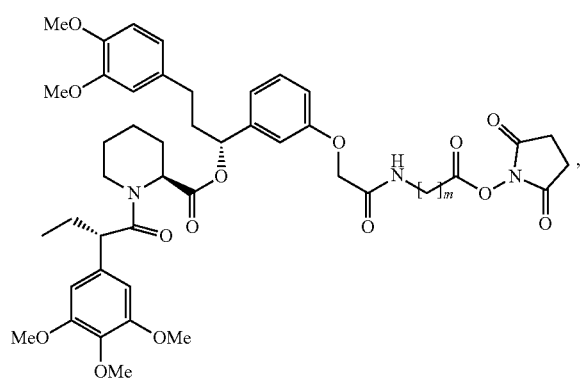

where m is from 3 to 6.

The present disclosure also provides compounds having the formula:
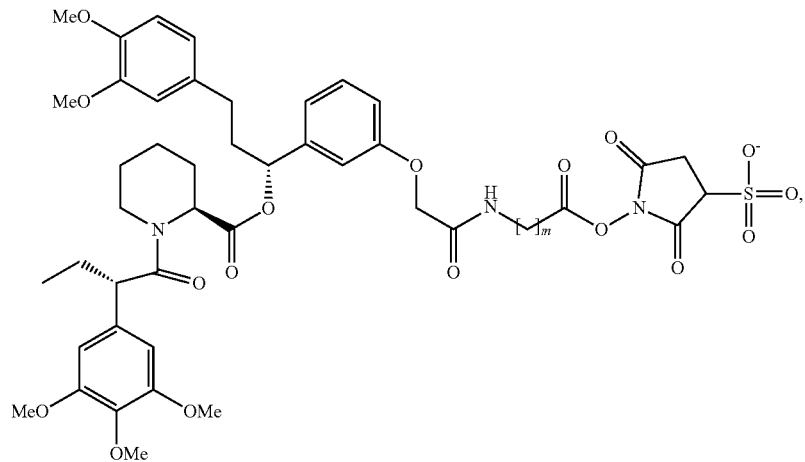
where m is from 3 to 6.
The present disclosure also provides compounds having the formula:
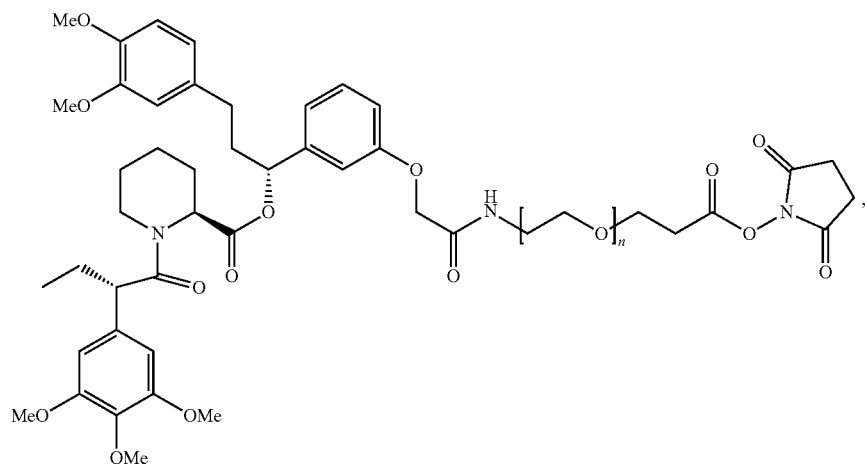
where n is from 1 to 6.

The present disclosure also provides compounds having the formula:

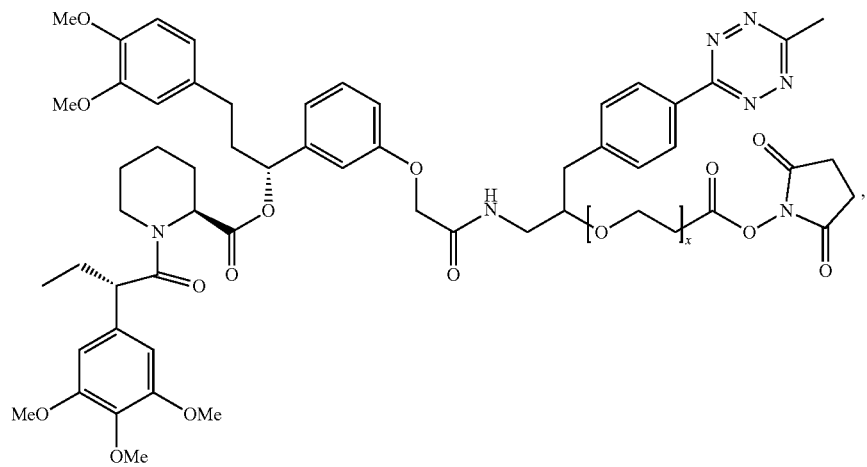

where x is from 1 to 6.

The present disclosure also provides compounds having the formula:

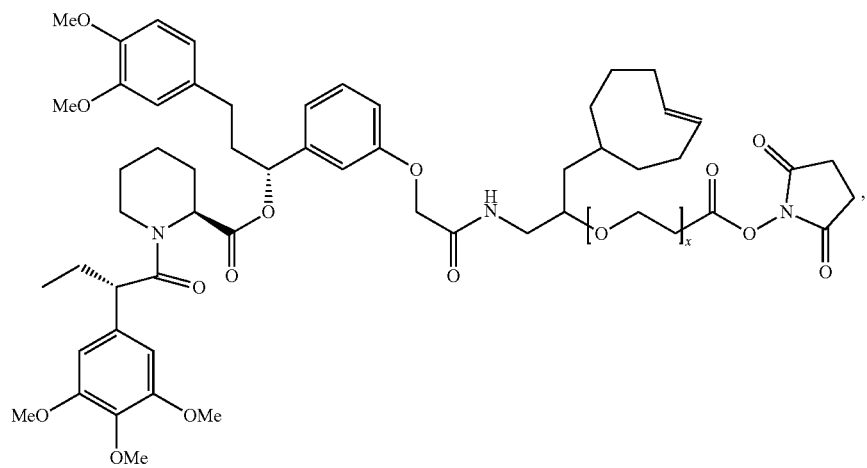

where x is from 1 to 6.

The present disclosure also provides compounds having the formula:

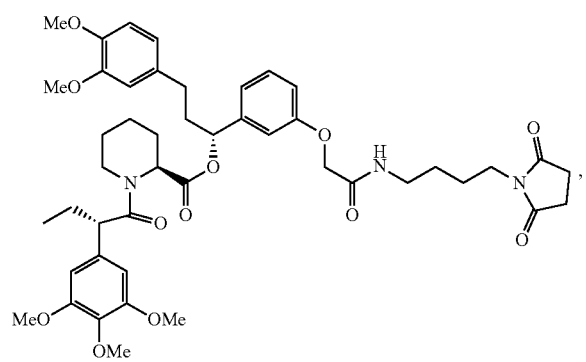 [SMILES: CC[C@H](C(=O)N1CCCC[C@H]1C(=O)O[C@H](CCc1ccc(OC)c(OC)c1)c1cccc(OCC(=O)NCCCCN2C(=O)CCC2=O)c1)c1cc(OC)c(OC)c(OC)c1]

which is also referred to herein as Monovalent FKBP Ligand-2 (MFL2).

The present disclosure also provides fusion proteins comprising a fragment of a protein of interest fused to a ligand binding domain, wherein: the ligand binding domain is a ligand binding domain for small molecule ligands; or the ligand binding domain is an interactive protein domain.

The present disclosure also provides compositions or kits comprising a first fusion protein described herein and a second fusion protein described herein, wherein the protein of interest of the first fusion protein and the protein of interest of the second fusion protein can dimerize or fold together.

The present disclosure also provides compositions or kits comprising: a first haplomer-ligand complex described herein: a second haplomer-ligand complex described herein; a first fusion protein described herein; and a second fusion protein described herein; wherein the ligand of the first haplomer-ligand complex is linked to the 5' terminus of the polynucleotide of the first haplomer-ligand complex; wherein the ligand of the second haplomer-ligand complex is linked to the 3' terminus of the polynucleotide of the second haplomer-ligand complex; wherein the polynucleotide of the first haplomer-ligand complex is substantially complementary to a target nucleic acid molecule; wherein the polynucleotide of the second haplomer-ligand complex is substantially complementary to the target nucleic acid molecule at a site in spatial proximity to the polynucleotide of the first haplomer-ligand complex: wherein the ligand of the first haplomer-ligand complex and the ligand binding domain of the first fusion protein can interact; wherein the ligand of the second haplomer-ligand complex and the ligand binding domain of the second fusion protein can interact; and wherein the fragment of the protein of interest of the first fusion protein and the fragment of the protein of interest of the second fusion protein can dimerize or fold together.

The present disclosure also provides compositions or kits comprising: a first haplomer-ligand complex described herein; a second haplomer-ligand complex described herein; a first fusion protein described herein; and a second fusion protein described herein; wherein the ligand of the first haplomer-ligand complex is linked to the 5' terminus of the polynucleotide of the first haplomer-ligand complex; wherein the ligand of the second haplomer-ligand complex is linked to the 3' terminus of the polynucleotide of the second haplomer-ligand complex; wherein the polynucleotide of the first haplomer-ligand complex is substantially complementary to a target nucleic acid molecule; wherein the polynucleotide of the second haplomer-ligand complex is substantially complementary to the target nucleic acid molecule at a site in spatial proximity to the polynucleotide of the first haplomer-ligand complex: wherein the ligand of the first haplomer-ligand complex and the ligand binding domain of the first fusion protein can interact; wherein the ligand of the second haplomer-ligand complex and the ligand binding domain of the second fusion protein can interact; and wherein the fragment of the protein of interest of the first fusion protein and the fragment of the protein of interest of the second fusion protein can dimerize or fold together.

The present disclosure also provides compositions or kits comprising: a first bottle haplomer-ligand complex described herein; a second haplomer-ligand complex described herein, wherein the second haplomer-ligand complex comprises a nucleotide portion that is substantially complementary to the stem portion of the bottle haplomer-ligand complex that is linked to the ligand of the bottle haplomer-ligand complex; a first fusion protein described herein; and a second fusion protein described herein; wherein the ligand of the first bottle haplomer-ligand complex and the ligand binding domain of the first fusion protein can interact; wherein the ligand of the second haplomer-ligand complex and the ligand binding domain of the second fusion protein can interact; and wherein the fragment of the protein of interest of the first fusion protein and the fragment of the protein of interest of the second fusion protein can dimerize or fold together.

The present disclosure also provides compositions or kits comprising: a first bottle haplomer-ligand complex described herein; a second haplomer-ligand complex described herein, wherein the second haplomer-ligand complex comprises a nucleotide portion that is substantially complementary to the stem portion of the bottle haplomer-ligand complex that is linked to the ligand of the bottle haplomer-ligand complex; a first fusion protein described herein; and a second fusion protein described herein; wherein the ligand of the first bottle haplomer-ligand complex and the ligand binding domain of the first fusion protein can interact; wherein the ligand of the second haplomer-ligand complex and the ligand binding domain of the second fusion protein can interact; and wherein the fragment of the protein of interest of the first fusion protein and the fragment of the protein of interest of the second fusion protein can dimerize or fold together.

The present disclosure also provides methods for the directed assembly of a protein comprising: contacting a target nucleic acid molecule with a first haplomer-ligand complex described herein; contacting the target nucleic acid with a second haplomer-ligand complex described herein; contacting the first haplomer-ligand complex with a first fusion protein described herein; and contacting the second haplomer-ligand complex with a second fusion protein described herein; wherein the ligand of the first haplomer-ligand complex is linked to the 5' terminus of the polynucleotide of the first haplomer-ligand complex; wherein the ligand of the second haplomer-ligand complex is linked to the 3' terminus of the polynucleotide of the second haplomer-ligand complex; wherein the polynucleotide of the first haplomer-ligand complex is substantially complementary to a target nucleic acid molecule; wherein the polynucleotide of the second haplomer-ligand complex is substantially complementary to the target nucleic acid molecule at a site in spatial proximity to the polynucleotide of the first haplomer-ligand complex; wherein the ligand of the first haplomer-ligand complex and the ligand binding domain of the first fusion protein can interact; and wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

The present disclosure also provides methods for the directed assembly of a protein comprising: contacting a target nucleic acid molecule with a first haplomer-ligand complex described herein; contacting the target nucleic acid with a second haplomer-ligand complex described herein; contacting the first haplomer-ligand complex with a first fusion protein described herein; and contacting the second haplomer-ligand complex with a second fusion protein described herein; wherein the ligand of the first haplomer-ligand complex is linked to the 5' terminus of the polynucleotide of the first haplomer-ligand complex; wherein the ligand of the second haplomer-ligand complex is linked to the 3' terminus of the polynucleotide of the second haplomer-ligand complex: wherein the polynucleotide of the first haplomer-ligand complex is substantially complementary to a target nucleic acid molecule; wherein the polynucleotide of the second haplomer-ligand complex is substantially complementary to the target nucleic acid molecule at a site in spatial proximity to the polynucleotide of the first haplomer-ligand complex; wherein the ligand of the first haplomer-ligand complex and the ligand binding domain of the first fusion protein can interact; and wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

The present disclosure also provides methods for the directed assembly of a protein comprising: contacting a target nucleic acid molecule with a complex formed by the interaction of a first haplomer-ligand complex described herein with a first fusion protein described herein, wherein the ligand of the first haplomer-ligand complex is linked to the 5' terminus of the polynucleotide of the first haplomer-ligand complex, and wherein the ligand of the first haplomer-ligand complex interacts with the ligand binding domain of the first fusion protein; and contacting the target nucleic acid molecule with a complex formed by the interaction of a second haplomer-ligand complex described herein with a second fusion protein described herein, wherein the ligand of the second haplomer-ligand complex is linked to the 5' terminus of the polynucleotide of the second haplomer-ligand complex, and wherein the ligand of the second haplomer-ligand complex interacts with the ligand binding domain of the second fusion protein; thereby resulting in the folding or dimerization of the fragment of the protein of interest of the first fusion protein with the fragment of the protein of interest of the second fusion protein.

The present disclosure also provides methods for the directed assembly of a protein comprising: contacting a target nucleic acid molecule with a complex formed by the interaction of a first haplomer-ligand complex described herein with a first fusion protein described herein, wherein the ligand of the first haplomer-ligand complex is linked to the 5' terminus of the polynucleotide of the first haplomer-ligand complex, and wherein the ligand of the first haplomer-ligand complex interacts with the ligand binding domain of the first fusion protein; and contacting the target nucleic acid molecule with a complex formed by the interaction of a second haplomer-ligand complex described herein with a second fusion protein described herein, wherein the ligand of the second haplomer-ligand complex is linked to the 5' terminus of the polynucleotide of the second haplomer-ligand complex, and wherein the ligand of the second haplomer-ligand complex interacts with the ligand binding domain of the second fusion protein; thereby resulting in the folding or dimerization of the fragment of the protein of interest of the first fusion protein with the fragment of the protein of interest of the second fusion protein.

The present disclosure also provides methods for the directed assembly of a protein comprising: contacting a target nucleic acid molecule with a bottle haplomer-ligand complex described herein; contacting the target nucleic acid with a second haplomer-ligand complex described herein, wherein the second haplomer-ligand complex comprises a nucleotide portion that is substantially complementary to the stem portion of the bottle haplomer-ligand complex that is linked to the ligand of the bottle haplomer-ligand complex; contacting the bottle haplomer-ligand complex with a first fusion protein described herein, wherein the ligand of the bottle haplomer-ligand complex and the ligand binding domain of the first fusion protein can interact; and contacting the second haplomer-ligand complex with a second fusion protein described herein, wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

The present disclosure also provides methods for the directed assembly of a protein comprising: contacting a target nucleic acid molecule with a bottle haplomer-ligand complex described herein; contacting the target nucleic acid with a second haplomer-ligand complex described herein, wherein the second haplomer-ligand complex comprises a nucleotide portion that is substantially complementary to the stem portion of the bottle haplomer-ligand complex that is linked to the ligand of the bottle haplomer-ligand complex; contacting the bottle haplomer-ligand complex with a first fusion protein described herein, wherein the ligand of the bottle haplomer-ligand complex and the ligand binding domain of the first fusion protein can interact; and contacting the second haplomer-ligand complex with a second fusion protein described herein, wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

The present disclosure also provides methods for the directed assembly of a protein comprising: contacting a target nucleic acid molecule with a bottle haplomer-ligand complex described herein; contacting the target nucleic acid molecule with a second haplomer-ligand complex described herein, wherein the second haplomer-ligand complex comprises a nucleotide portion that is substantially complementary to the stem portion of the bottle haplomer-ligand complex that is linked to the ligand of the bottle haplomer-ligand complex; contacting the bottle haplomer-ligand complex with a first fusion protein described herein, wherein the ligand of the bottle haplomer-ligand complex and the ligand binding domain of the first fusion protein can interact; and contacting the second haplomer-ligand complex with a second fusion protein described herein, wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

The templated assembly of functionally active proteins by dimerization or folding from protein fragments associated with modified oligonucleotides (haplomers) may be divided into a two-stage process. The first stage comprises the binding of haplomers to their complementary counterparts. The ligand-mediated second stage enables homo- or heterodimerization of protein fusions with appropriate ligand-binding domains. Template-mediated dimerization or folding is applicable to the activation of specific proteins in target pathological cells, for diagnostic or therapeutic purposes.

DESCRIPTION OF EMBODIMENTS

Figure 1:
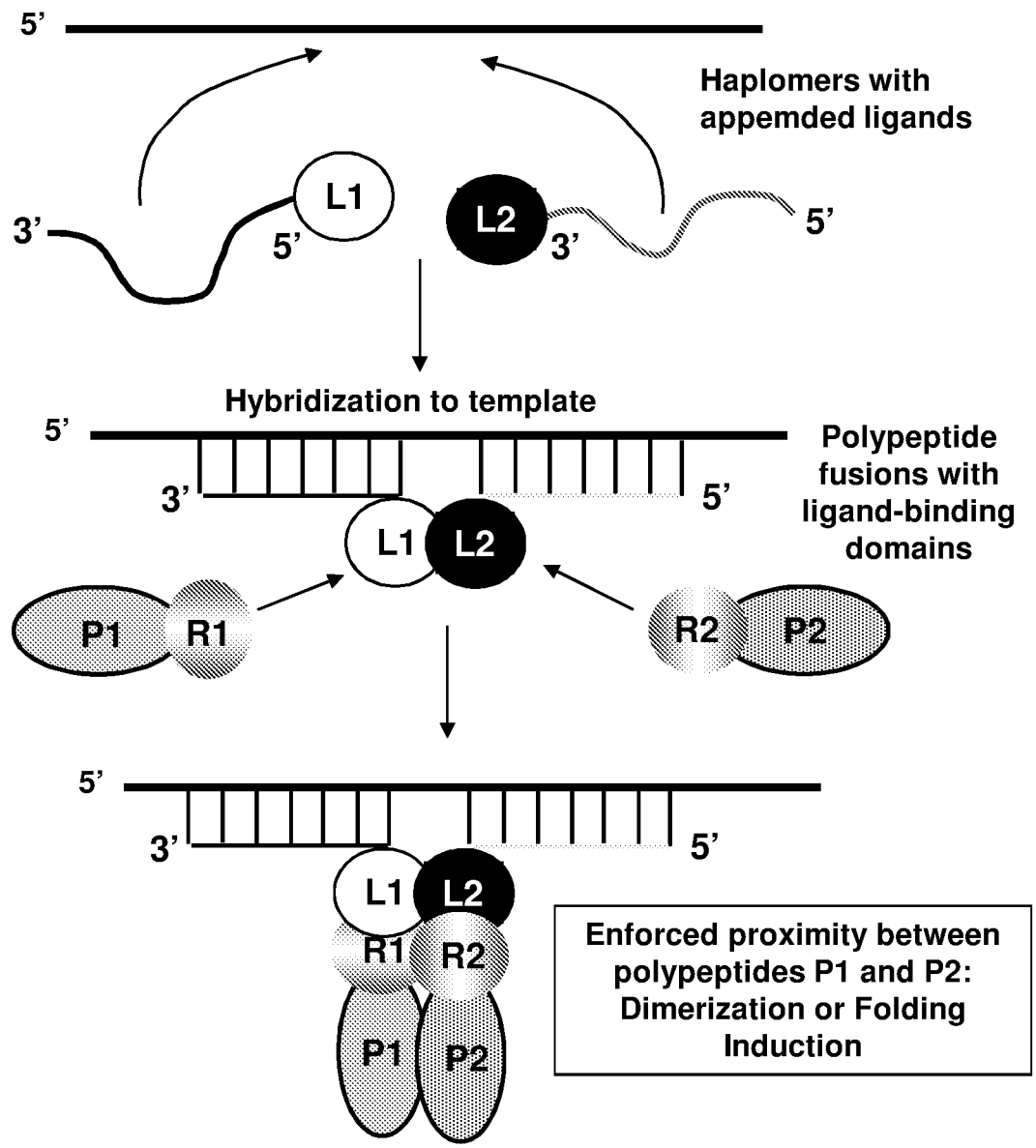
FIG. 1 shows an overview of a representative Ligand Directed Template Assembly by Proximity-Enhanced Reactivity (LD-TAPER) principle.

Certain exemplary embodiments will now be described to provide an overall understanding of the principles of the structure, function, manufacture, and use of the compositions and methods disclosed herein. One or more examples of these embodiments are illustrated in the accompanying drawings. Those skilled in the art will understand that the compositions and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

As used herein, the singular forms "a," "an," and "the" include plural references unless the content clearly dictates otherwise. The terms used in this disclosure adhere to standard definitions generally accepted by those having ordinary skill in the art. In case any further explanation might be needed, some terms have been further elucidated below.

As used herein, the phrase "anti-target loop portion" refers to a portion of a haplomer that facilitates sequence-specific binding to a target nucleic acid molecule.

As used herein, the term "base" refers to a molecule containing a purine or pyrimidine group, or an artificial analogue, that forms a binding pair with another corresponding base via Watson-Crick or Hoogsteen bonding interactions. Bases further contain groups that facilitate covalently joining multiple bases together in a polymer, such as an oligomer. Non-limiting examples include nucleotides, nucleosides, peptide nucleic acid residues, or morpholino residues.

As used herein, the terms "bind," "binds," "binding," and "bound" refer to a stable interaction between two molecules that are close to one another. The terms include physical interactions, such as chemical bonds (either directly linked or through intermediate structures), as well as non-physical interactions and attractive forces, such as electrostatic attraction, hydrogen bonding, and van der Waals/dispersion forces.

As used herein, the phrase "bioconjugation chemistry" refers to the chemical synthesis strategies and reagents that ligate common functional groups together under mild conditions, facilitating the modular construction of multi-moiety compounds.

As used herein, the phrase "chemical linker" refers to a molecule that binds one haplomer to another haplomer or one moiety to another moiety on different compounds. A linker may be comprised of branched or unbranched covalently bonded molecular chains.

As used herein, the phrase "dosage unit form" refers to physically discrete units suited as unitary dosages for the subjects to be treated.

As used herein, the term "haplomer" refers to nucleic acid molecules linked to a ligand that bind to a target nucleic acid molecule template in a sequence-specific manner and participate in protein formation during nucleic acid templated assembly. Also included herein are "derivatives" or "analogs" such as salts, hydrates, solvates thereof, or other molecules that have been subjected to chemical modification and maintain the same biological activity or lack of biological activity, and/or ability to act as a haplomer, or function in a manner consistent with a haplomer.

As used herein, the phrase "non-traceless bio-orthogonal chemistry" refers to a reaction involving selectively-reactive moieties in which part or all of the structure of the selectively-reactive moieties is retained in the product structure.

As used herein, the phrase "nucleic acid templated assembly" refers to the dimerization or folding of a protein on a target nucleic acid molecule, such that the protein formation can be facilitated by haplomers being assembled in proximity when bound to a target nucleic acid molecule.

As used herein, the terms "oligomer" and "oligo" refer to a molecule comprised of multiple units where some or all of the units are bases capable of forming Watson-Crick or Hoogsteen base-pairing interactions, allowing sequence-specific binding to nucleic acid molecules in a duplex or multiplex structure. Non-limiting examples include, but are not limited to, oligonucleotides, peptide nucleic acid oligomers, and morpholino oligomers.

As used herein, the phrase "pathogenic cell" can refer to a cell that is capable of causing or promoting a diseased or an abnormal condition, such as a cell infected with a virus, a tumor cell, and a cell infected with a microbe, or a cell that produces a molecule that induces or mediates diseases that include, but are not limited to allergy, anaphylaxis, inflammation and autoimmunity.

As used herein, the phrase "pharmaceutically acceptable" refers to a material that is not biologically or otherwise unacceptable, that can be incorporated into a composition and administered to a patient without causing unacceptable biological effects or interacting in an unacceptable manner with other components of the composition.

As used herein, the phrase "pharmaceutically acceptable salt" means a salt prepared from a base or an acid which is acceptable for administration to a patient, such as a mammal (e.g., salts having acceptable mammalian safety for a given dosage regime).

As used herein, the term "salt" can include salts derived from pharmaceutically acceptable inorganic acids and bases and salts derived from pharmaceutically acceptable organic acids and bases and their derivatives and variants thereof.

As used herein, the term "sample" refers to any system that haplomers can be administered into, where nucleic acid templated assembly may occur. Examples of samples include, but are not limited to, fixed or preserved cells, whole organisms, tissues, tumors, lysates, or in vitro assay systems.

As used herein, the phrases "set of corresponding reactants" or "corresponding haplomers" refer to haplomers that come together on a single target nucleic acid molecule to take part in a templated assembly reaction.

As used herein, the term "superantigen" refers to an antigen that binds to a broad subset of T cells that express a particular variable (V) region.

As used herein, the phrase "target compartment" refers to a cell, virus, tissue, tumor, lysate, other biological structure, spatial region, or sample that contains target nucleic acid molecule(s), or a different amount of target nucleic acid molecules than a non-target compartment.

As used herein, the phrases "target nucleic acid sequence" and "target nucleic acid molecule" are used interchangeably and refer to a sequence of units or nucleic acids which are intended to act as a template for nucleic acid templated assembly.

As used herein, the phrase "templated assembly product," refers to the protein formed by dimerization or folding of two fragments of a particular protein associated with the haplomers.

As used herein, the phrase "traceless bio-orthogonal chemistry" refers to a reaction involving haplomer ligands in which a naturally occurring bond, such as an amide, is formed by elimination of part or all of the bio-orthogonal moiety from the ligand structure thus produced.

Nucleic acid molecules that are specific to designated cells of interest (whether these are represented by pathological tumor cells, abnormal immune cells, or any other cellular types) can be used as templates for the generation of novel structures (e.g., effector structures) by means of proximity-induced enhancement of molecular interactions (see, for example, PCT Publication No. WO 2014/197547). Such templated products can be designed to trigger cell death in various ways, or to modulate cellular activities. Cell-type specific nucleic acids can be sourced from specific transcribed mRNAs, or via nucleic acid aptamers which can serve to adapt non-nucleic acid targets for the provision of a defined template sequence.

In the original process of templated assembly for diagnostic or therapeutic purposes described above, reactive groups are brought into spatial proximity by virtue of their linkage with oligonucleotides of predetermined sequence, which themselves co-hybridize in proximity on a target nucleic acid molecule template. The template-directed modified oligonucleotides bearing mutually reactive groups are termed "haplomers." Such enforced proximity of reactive groups greatly enhances product formation, and thus cell-type specific transcripts can direct the production of desired molecules in cells of interest. The general principle of TAPER can be altered to a two-level process, as described herein, by appending specific ligands to each haplomeric oligonucleotide instead of directly interactive functional groups. Thus, in the original configuration of TAPER (herein termed "conventional TAPER"), the process can be signified as occurring within a single reaction sequence, where the template can be considered functionally as a specific catalyst:

(Equation 1)

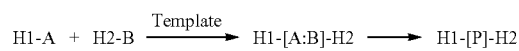

where H1 and H2 represent haplomers bearing reactive groups A and B, respectively. Upon hybridization to specific template, a proximity-driven reaction intermediate between A and B is formed [A:B], leading rapidly to the formation of product [P].

In a ligand-directed alternate of TAPER (i.e., LD-TAPER), the desired process occurs at two distinct levels:

(Equations 2.1 and 2.2)

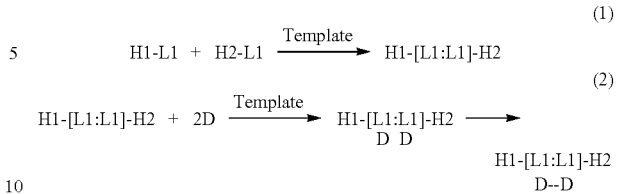

where H1 and H2 represent haplomers, L represents any form of ligand, and D indicates a protein binding domain or any other molecule capable of binding to the ligand in a specific manner. Here, the initial binding of two molecules of D to the two ligand molecules (displayed in spatial proximity via the haplomer template binding) is shown as a transitional state before the formation of a D-D dimer, which may or may not be thermodynamically reversible. In the second stage of LD-TAPER, the template is still required to enforce the ligand L-L spatial proximity. This is the case for all variant embodiments of LD-TAPER except where a proximity-enhanced covalent interaction is designed to occur between two modified L molecules, or modified L1 and L2 molecules, such that they become covalently linked and, thus, stabilized as a pair. Provided of course that their interactions with cognate binding domains is not affected by the ligand-ligand covalent joining (as a necessary precondition for this embodiment), then the subsequent stage two of the LD-TAPER process becomes template-independent. The generalizable nature of the two-stage LD-TAPER process is schematically depicted in FIG. 1. Referring to FIG. 1, haplomers with specific appended ligands (L1 and L2) bind to target nucleic acid molecule template such that the ligands fall into spatial proximity with each other. Proteins or polypeptides (P1 and P2) fused with binding domains for the ligands of interest (R1 and R2) are directed to the templated haplomer site by the interaction between the ligand and the corresponding ligand binding domain. The P1 and P2 segments brought into enforced spatial proximity, promoting dimerization or protein folding.

Although LD-TAPER is a two-stage process, it is not essential in principle that the haplomer/template hybridization comprises the first step (as portrayed in FIG. 1). In some embodiments, it may be desirable to initially pre-form each haplomer (bearing an appended ligand) with its designated cognate ligand binding domain, to form haplomer-fusion protein complexes. Subsequently, the hybridization step is performed, resulting in the desired molecular proximity of protein fragments fused with the ligand binding domains themselves. Using the above terminology, this may be represented as:

(Equations 3.1 and 3.2)

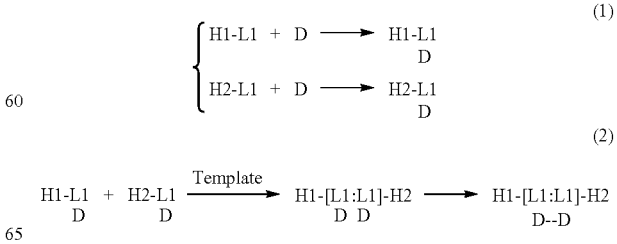

where the substituents are as described previously.

Various embodiments of LD-TAPER are possible, where H1 and H2 are appended with different ligands (L1 and L2), or where ligands can be bound by two separate binding domains (D1 and D2). If D1 and D2 are split-protein polypeptides, the second-level event can be comprised of mature protein folding between D1 and D2.

Figure 2:
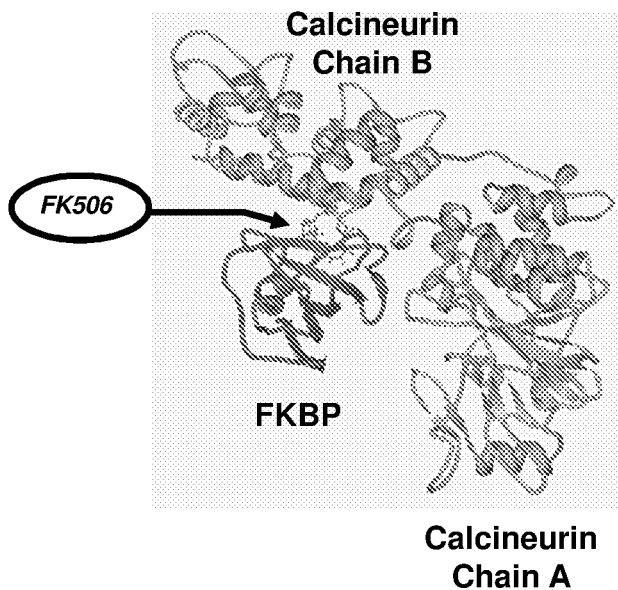
FIG. 2 shows representative ternary complex formation between FK506, FKBP, and calcineurin; and rapamycin and mTOR/FRB and calcineurin.
Figure 2:
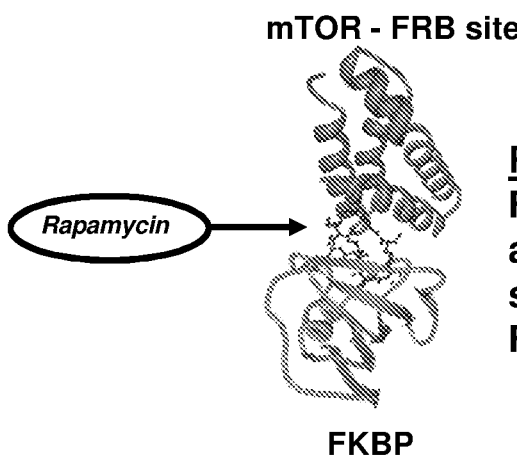

Evolution has provided important and very useful examples of natural small-molecule ligands, which can be exploited for biotechnological aims. In this respect, some natural small molecules can be noted that have had a major impact on both experimental and applied immunology. The natural product immunosuppressants Cyclosporin A and FK506 (from fungal and bacterial sources, respectively) have revolutionized organ transplantation through their blocking of T cell activation. These compounds bind different cellular proteins, cyclophilin and FK506-binding protein (FKBP) respectively, but they share a common target in the form of the protein phosphatase calcineurin, a calcium-responsive regulator of multiple signaling pathways. The cyclophilin-cyclosporin A and FK506-FKBP complexes, in turn, form ternary complexes with calcineurin and inhibit its role in T cell activation via transcription factors of the NFAT family. Rapamycin, another natural immunomodulatory molecule, binds the same FKBP as the FK506 molecule, but forms a ternary complex with the unrelated protein FRAP/mTOR with distinct signal pathway roles. The interactions between: a) FK506, calcineurin, and FKBP, and b) rapamycin, FKBP, and mTOR-FRB are depicted in FIG. 2.

The FK506/FKBP interaction has been exploited in many areas, further helped by the small size of the FKBP binding domain (about 100 amino acid residues). In order to enhance the potential therapeutic utility of this interaction and minimize binding to endogenous FKBP protein, mutant derivatives of FKBP have been derived which preferentially bind altered FK506 analogs. Thus, the F36V FKBP mutant binds a specific FK506 derivative much more strongly than the wild-type molecule itself.

Although small molecule ligands are one type of ligand for use in LD-TAPER, they are not the only type of ligands that can be used. There exist relatively small mutually interactive protein domains (e.g., fragments of proteins) that are applicable in this context, an example of which are leucine zippers. Suitable examples of interactive protein domains are the c-jun and c-fos zipper domains, which generally are polypeptides of less than 50 amino acid residues, including helix-initiating and helix-terminating segments. While c-jun can form homodimers, c-fos cannot; and c-fos:c-jun heterodimers are significantly more stable than c-jun:c-jun homodimers. Appending such zipper sequences to oligonucleotides for the purposes of creating LD-TAPER haplomers provides each haplomer, with the zipper acting as a ligand, to bind to fusion proteins of desired polypeptides with the complementary zipper as a ligand binding domain.

Figure 3:
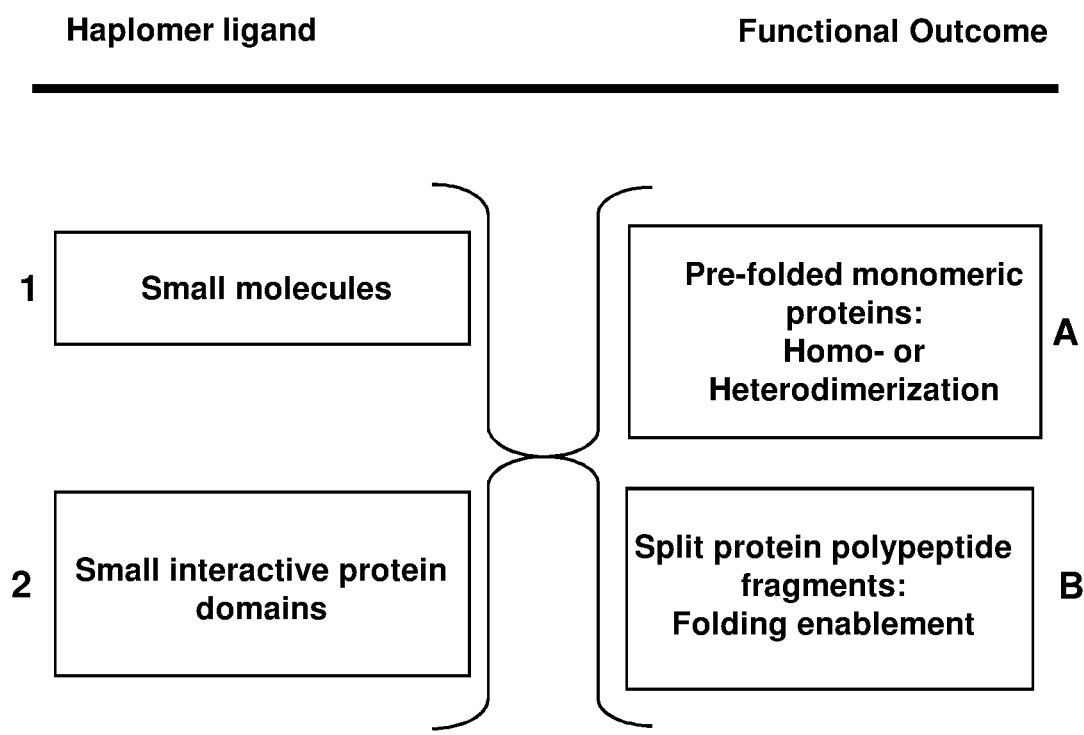
FIG. 3 shows a representative scope and range of LD-TAPER.

Whether the ligands used for LD-TAPER are small chemical entities or interactive protein domains, or any other structure for which a complementary binding element exists, the two-stage LD-TAPER process can be applied towards enforced dimerization of either the same partner protein fragments (homodimerization) or different partner protein fragments (heterodimerization). These multiple aspects of LD-TAPER are summarized in FIG. 3.

Figure 4:
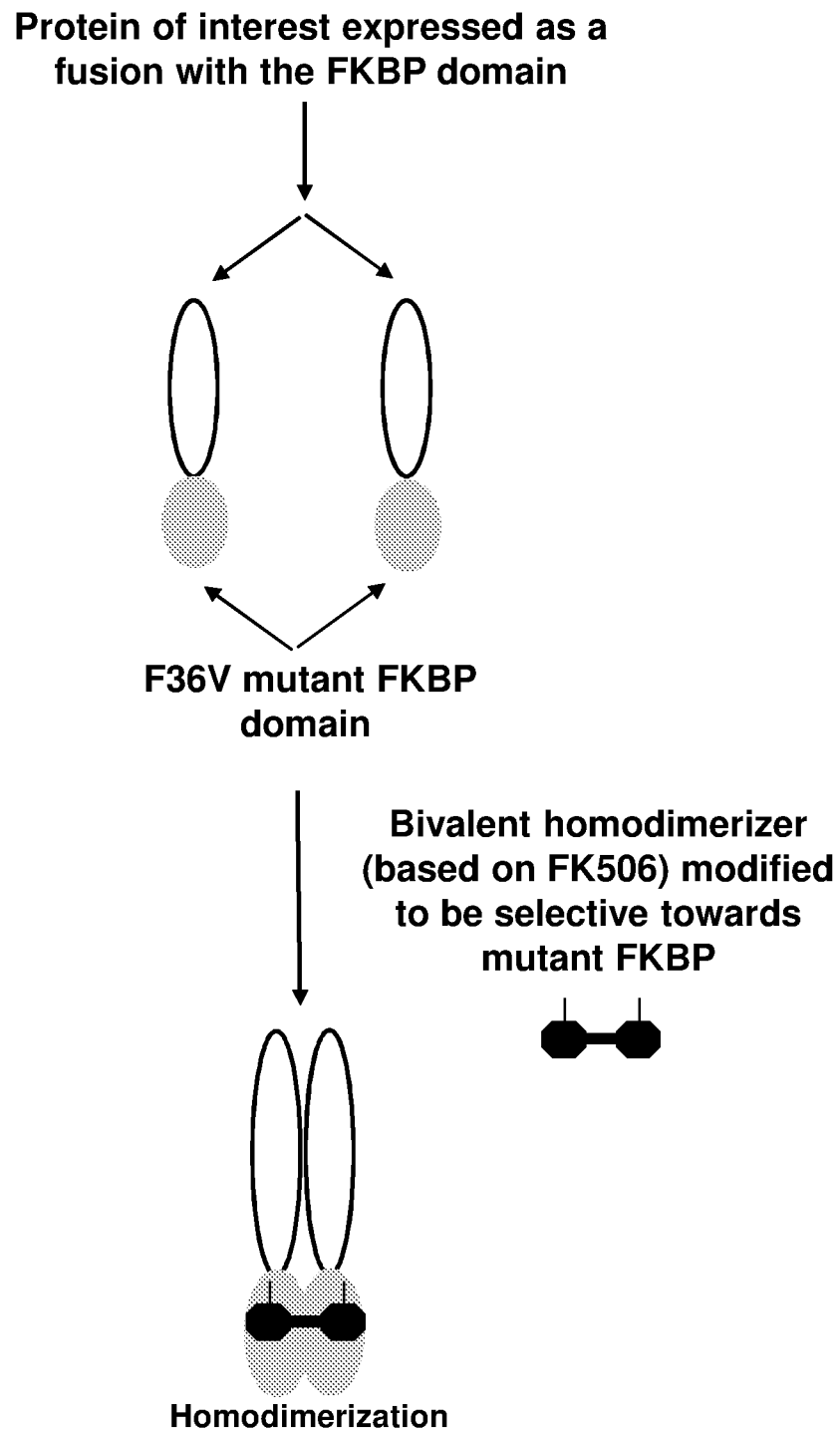
FIG. 4 shows a representative "enforced dimerization" of proteins of interest expressed as fusions with FKBP or FRB domains, mediated by compounds derived from FK506 or rapamycin.

The LD-TAPER processes and components thereof can be generally described by the following general representations. The embodiments of LD-TAPER using small molecule ligands may exploit, in a non-limiting example, the FKBP binding domain for FK506. It is known that bivalent analogs of FK506 can drive the dimerization of FKBP binding domains, or mutant derivatives of them. In turn, if such FKBP domains are fused with other proteins, the latter themselves undergo a forced dimerization event (see, FIG. 4), which in some cases may activate the proteins of interest towards potent biological activities.

Figure 5:
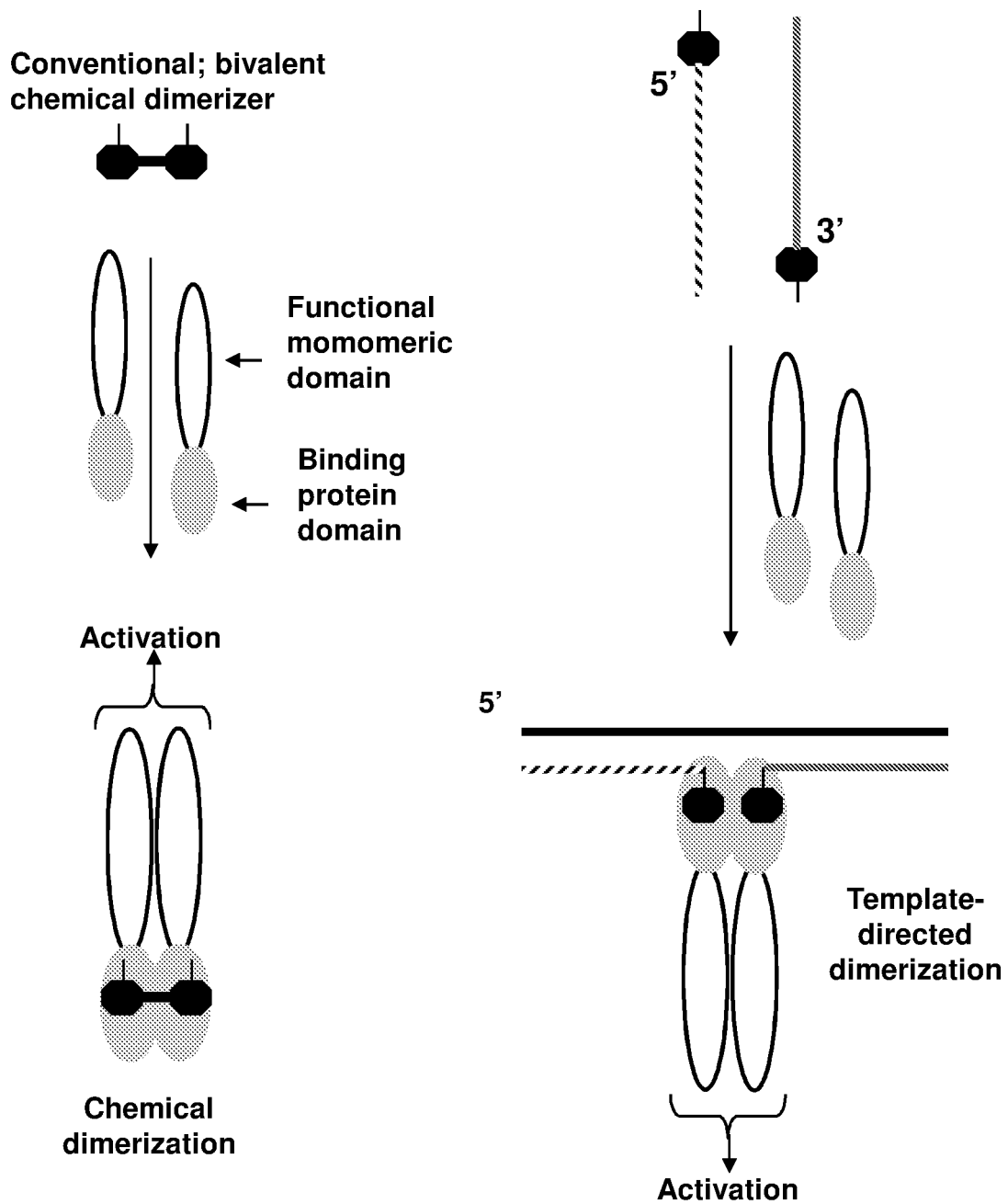
FIG. 5 shows a representative LD-TAPER: Protein dimerization by small molecule mediators.
Figure 9:
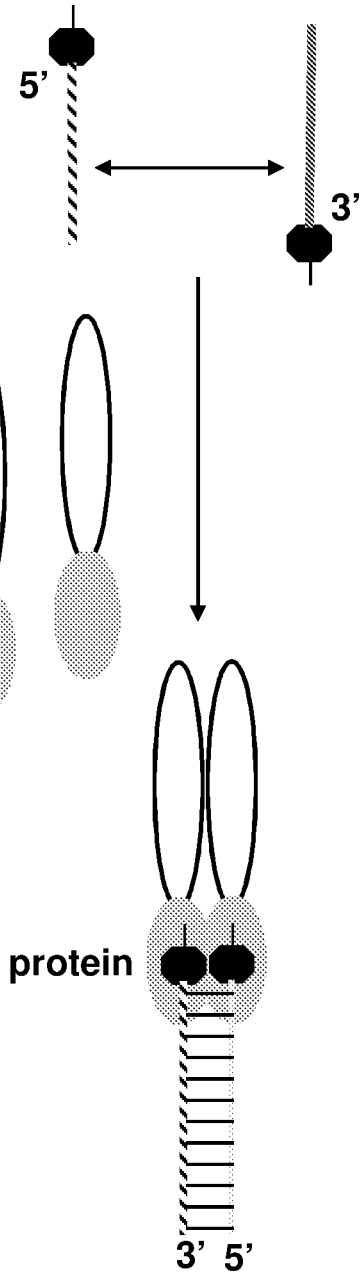
FIG. 9 shows a representative small molecule-mediated protein dimerization via LD-TAPER.
Figure 11:
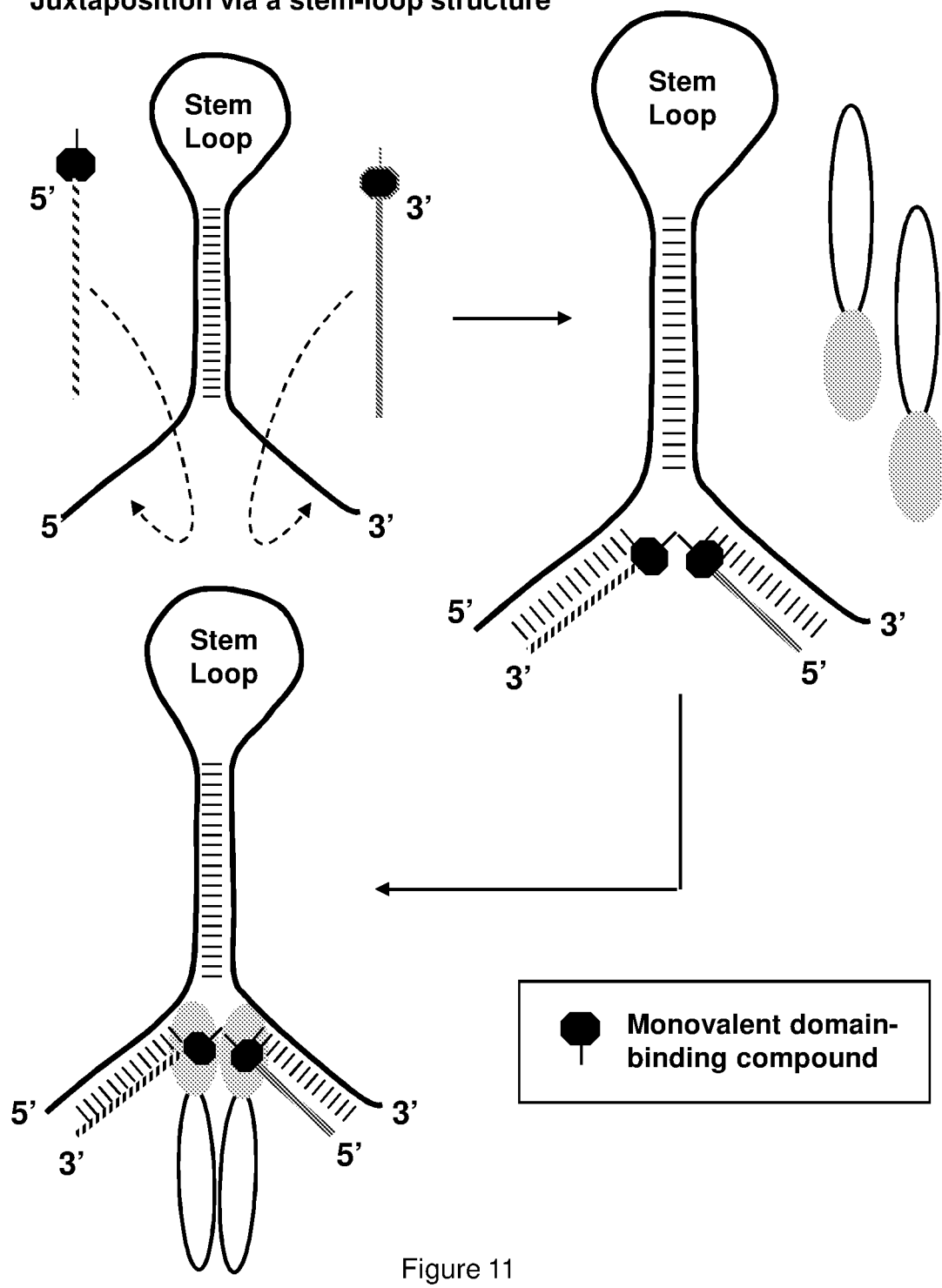
FIG. 11 shows another representative small molecule-mediated protein dimerization via LD-TAPER.
Figure 12:
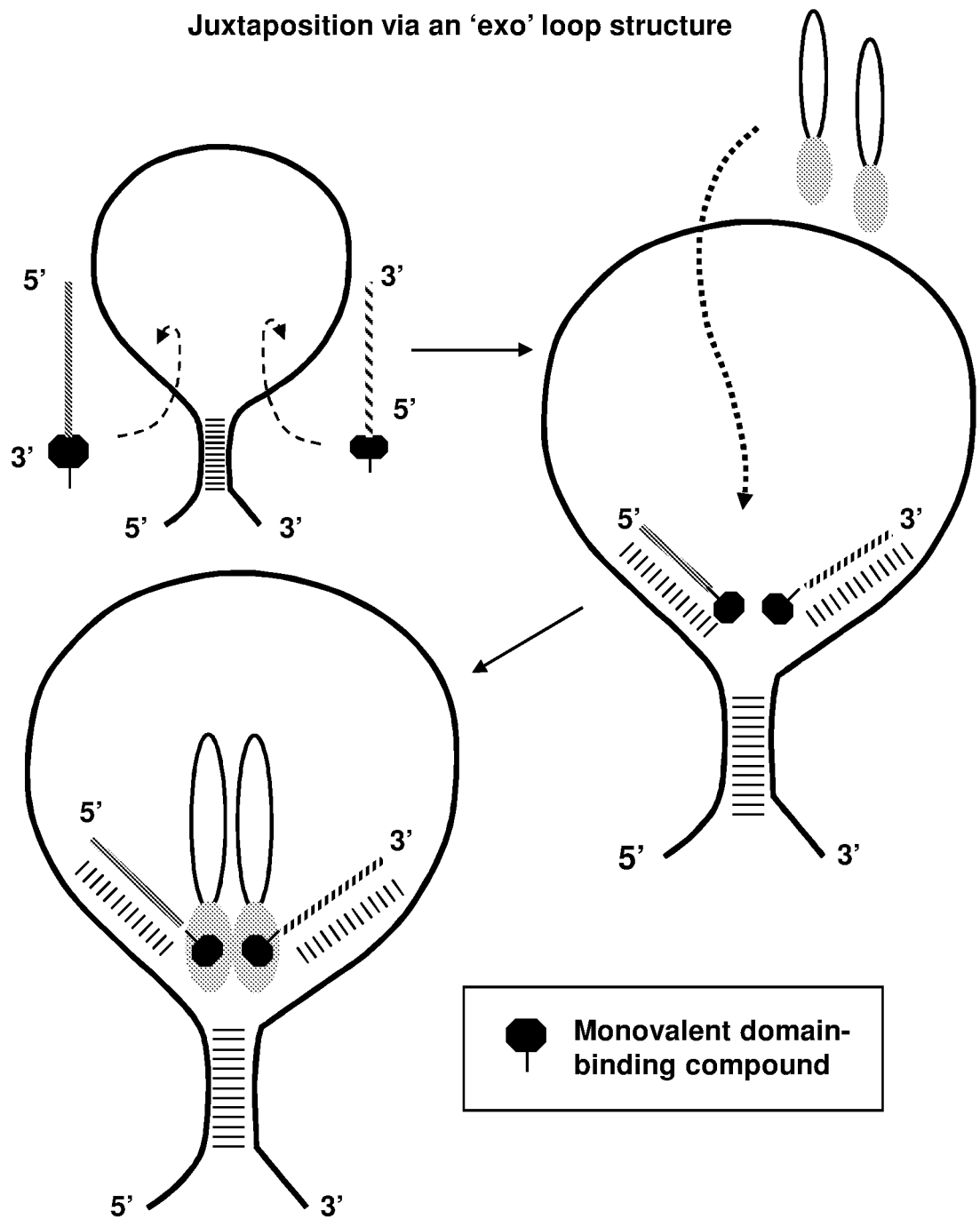
FIG. 12 shows another representative small molecule-mediated protein dimerization via LD-TAPER.

For the purposes of small molecule LD-TAPER, a monovalent domain binding compound is used, which is chemically appended to the 5' or 3' ends of short oligonucleotide strands, which comprise a portion of the resulting haplomers. When such haplomers are hybridized to a complementary target nucleic acid molecule template, the appended monovalent compounds are brought into spatial proximity (see, FIG. 5). Protein ligand binding domains which recognize and bind the monovalent compound (i.e., ligand) are likewise brought together close in spatial positioning, as are any other protein domains fused to the binding domains themselves (see, FIG. 5). Such enforced dimerization of the fusion domains of the proteins of interest leads to functional activation with measurable biological consequences.

Where LD-TAPER is mediated via small molecule ligands, the ligand identity may correspond to other low molecular weight defined compounds, or natural or artificial peptides, peptidomimetics, or any other molecule with a defined binding partner. Small molecule LD-TAPER can be designed with a number of distinct template:haplomer architectures. In some embodiments comprising the simplest arrangement, the haplomers are mutually complementary to each other, such that the resulting duplex enforces the desired spatial proximity of the ligand-interacting protein fusions. This configuration is herein referred to as Architecture 1 (see, FIG. 9). When the haplomers are not complementary to each other, but hybridize to spatially adjacent sites on a target nucleic molecule template, Architecture 2 is achieved (see, FIG. 5 and FIG. 10). Non-contiguous hybridization sites can still be LD-TAPER targets when suitable configurations exist. Thus, when LD-TAPER haplomers hybridize to the outer boundaries of a stem loop structure, spatial proximity is achieved, producing Architecture 3 (see, FIG. 11). Conversely, the inner region of a stem loop can be potentially targeted if haplomers anneal with the appropriate sites relative to each other, thus producing Architecture 4 (see, FIG. 12).

In some embodiments, the variation of TAPER referred to as "locked TAPER" is readily applicable to LD-TAPER. For locked LD-TAPER, the first bottle haplomer and second haplomers are conjugated with a predetermined ligand, in an analogous manner to other LD-TAPER architectures in the above embodiments. By the nature of the locked TAPER process, the hybridization site for the second haplomer-polypeptide conjugate is not accessible except in the presence of specific target, where hybridization occurs with the anti-target loop portion of the first bottle haplomer. Subsequently, the hybridization site for the second haplomer-polypeptide conjugate is rendered accessible, and in turn proximity-promoted ligand-mediated dimerization (see, FIG. 13).

Figure 6:
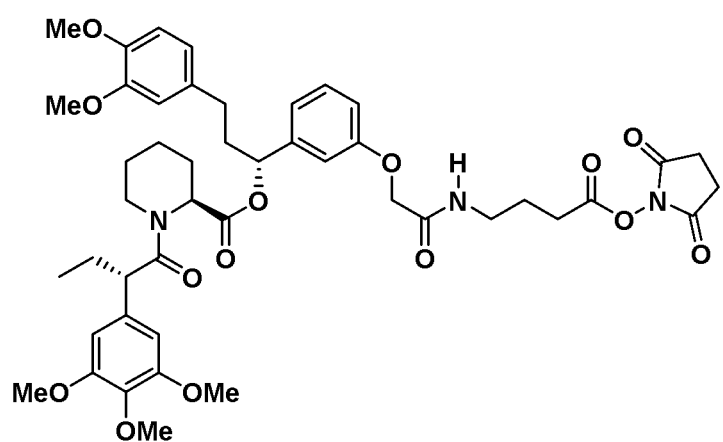
FIG. 6 shows a representative modified monovalent version of a mutant FKBP-binding compound, FKM-NHS.
Figure 7:
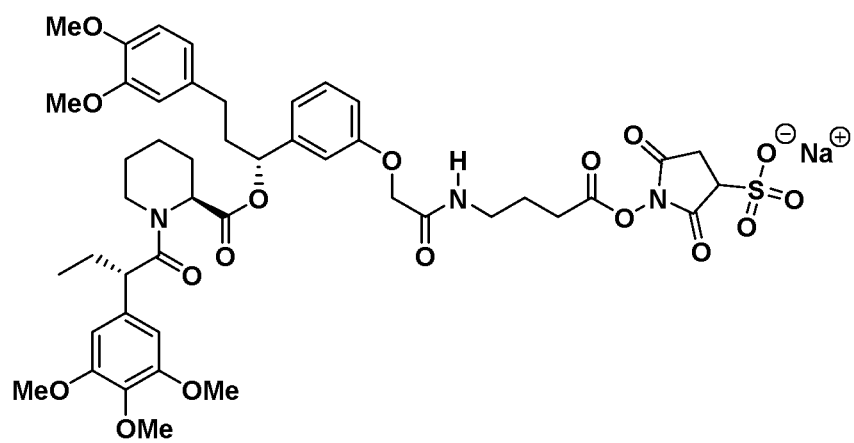
FIG. 7 shows a representative modified monovalent version of a mutant FKBP-binding compound, FKM-sulfo-NHS.

Within a locked-TAPER system, when two oligonucleotides bearing polypeptide conjugates are in hybridization-mediated spatial proximity (see, FIG. 13), the structure of the assembly pieces corresponds to Architecture 1 (see, FIG. 9), since the two derivatized oligonucleotides are complementary to each other, rather than complementary to a target nucleic acid molecule template as in Architectures 2-4. Nevertheless, since the anti-target loop portion of a locked-TAPER first bottle haplomer must hybridize to a target nucleic acid molecule template in order to expose the recognition site for the second haplomer, the anti-target loop portion binding to the target nucleic acid molecule itself can occur via different architectures. Thus, although the target hybridization of the locked TAPER oligonucleotide in FIG. 9 corresponds to Architecture 2 (see, FIG. 5), target hybridization by means of Architectures 3 and 4 (see, FIGS. 6 and 7, respectively) are equally possible. Locked TAPER accordingly has the unique feature whereby the TAPER assembly is always constant with Architecture 1, but target hybridization can assume variable architectures. In other words, for conventional TAPER, the target hybridization and assembly-directing hybridizations coincide, but for locked TAPER they are distinct and separable.

In some embodiments, the ligands for LD-TAPER are not small molecules in a conventional sense, but rather small interactive protein domains. These may include, but are not limited to, interacting leucine zipper motifs, which themselves may be comprised of, but not limited to, parallel zippers such as c-jun:c-fos; mad:max; and c-myc:max, or antiparallel zippers, such as that from *Thermus thermophilus* seryl-tRNA synthetase.

Figure 14:
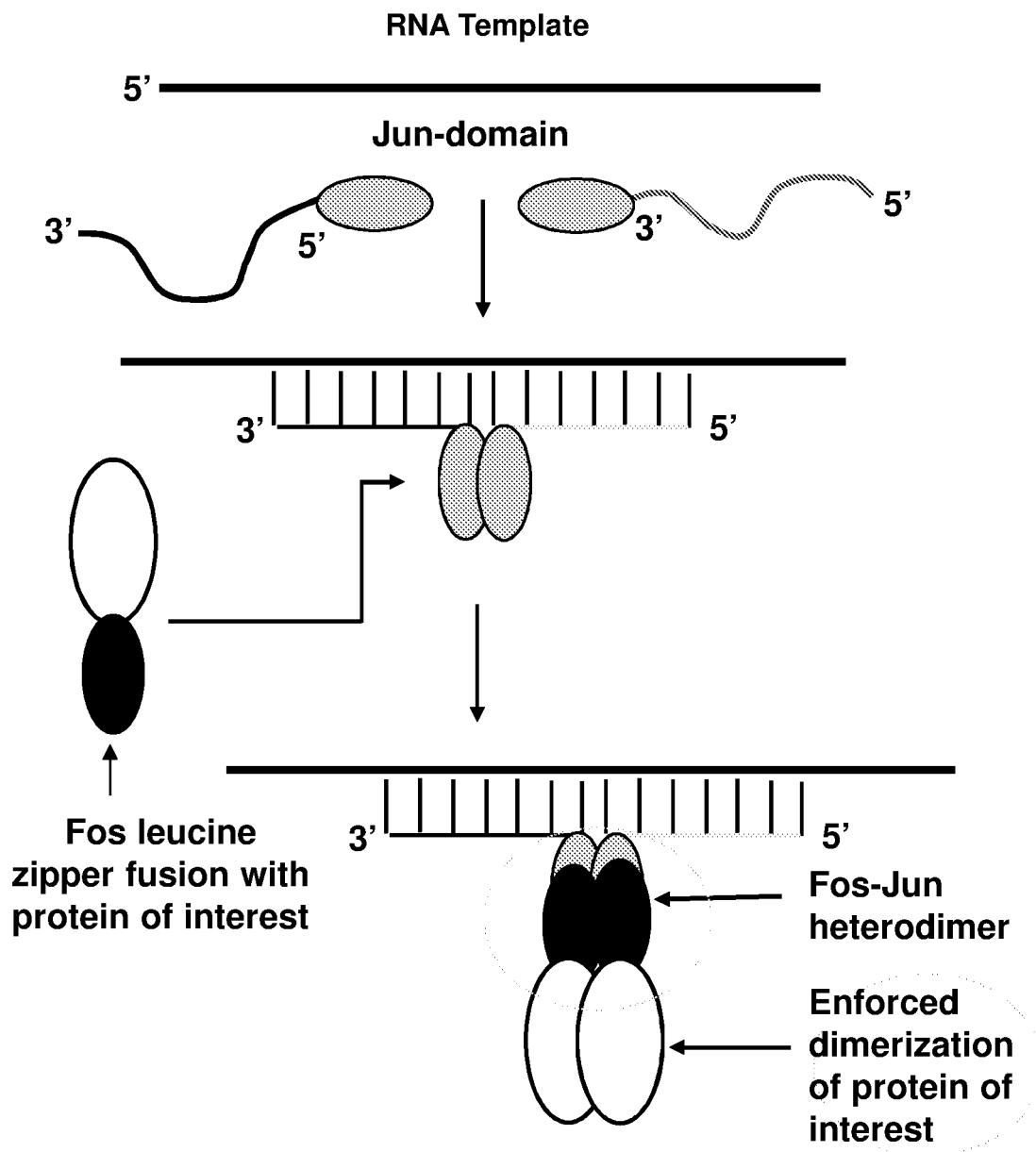
FIG. 14 shows a representative LD-TAPER:Protein dimerization by small interactive protein domains.

In some embodiments, when small interactive protein domains are used as ligands, the well-characterized c-jun: c-fos zipper pair is used, as depicted in FIG. 14. Haplomers comprised of oligonucleotide segments complementary to a target nucleic acid molecule template of interest may be conjugated with c-jun domains, and then hybridized with template. Subsequently, protein fragments of interest fused with c-fos domains are added, leading to complex formation and enforced dimerization of the protein fragment of interest. In the depiction of FIG. 14, which corresponds to the two-stage strategy generalized with Equation 2.1 and 2.2 above, the initial duplex may be further stabilized by the formation of c-jun homodimers. However, since c-jun:c-fos heterodimers are significantly more stable, the introduction of the fos-fusion protein results in the preferential formation of the desired heterodimeric complex (c-fos itself cannot form homodimers). In an alternate version of this embodiment, the haplomers bearing c-jun conjugated tags are pre-assembled with the fos-fusion protein of interest, before adding to the target system containing the template of interest. This alternate arrangement corresponds to the two-stage strategy generalized with Equation 3.1 and 3.2 above.

Figure 15:
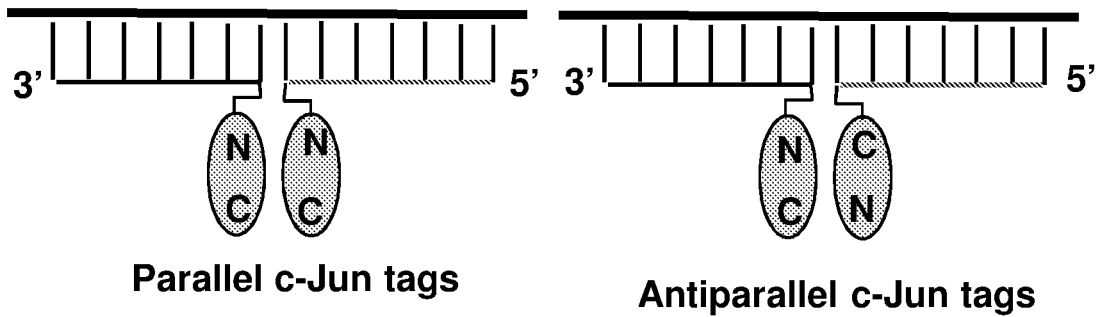
FIG. 15 shows representative polarity considerations for parallel leucine zippers.
Figure 15:
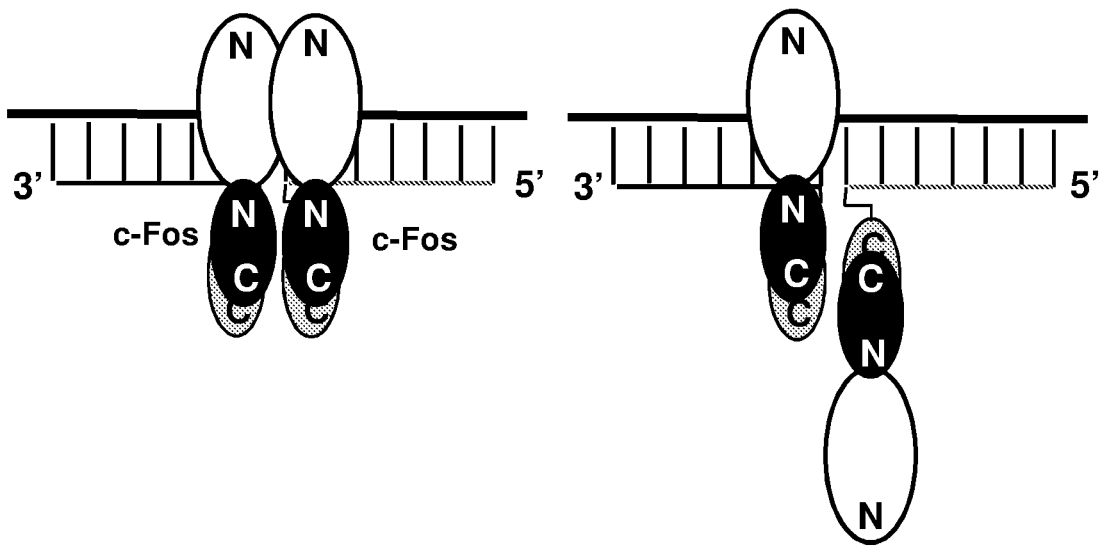

In embodiments using small interactive protein domains as ligands, the polarity of the conjugation of the small domain tag should be taken into account. This can be exemplified with the particular embodiments using fos-jun heterodimerization, where the leucine zipper interaction occurs with a parallel orientation. If haplomers have appended c-Jun tags such that their c-Jun helices are in a parallel orientation following hybridization (see, FIG. 15), then subsequent complex formation with c-fos fusion proteins will orient the fusion in a parallel sense; the reverse situation may disfavor dimerization between the protein segments of interest (see, FIG. 15). However, for certain other applications of LD-TAPER (most notably, for the assembly of split-protein fragments, as below), an antiparallel orientation may be beneficial. For this reason, it is advantageous if strategies exist for conjugating 5' or 3' oligonucleotide ends with small protein tags by either their N- or C-termini.

In embodiments using small interactive protein domains as ligands, c-jun and c-fos have significant advantages. In both cases, their alpha-helical zippers are fully defined by relatively short polypeptides, neither of which possess internal cysteine residues. These sequences can be readily produced by expression systems within *E. coli*, and are short enough that complete synthesis is feasible. This is useful for the c-Jun segment, since it renders thiol-mediated conjugation with oligonucleotides a facile approach. For c-jun tags, the sequence used herein for making N-terminal conjugates is a 47-mer, where the N-terminal cysteine is shown, and the bold sequences denote helical boundaries: CSGGASLERI-ARLEEKVKTLKAQNSELASTANMLRE QVAQLKQK-GAP (SEQ ID NO: 1). For c-jun tags, the sequence used herein for making C-terminal conjugates is a 49-mer, where the C-terminal cysteine is shown, and the bold sequences denote helical boundaries: SGASLERIAR-LEEKVKTLKAQNSELASTANMLREQVAQLKQK GAPSGGC (SEQ ID NO:2). The sequence of the fos zipper to be made as fusions with the protein fragment of interest is a 41-mer, where the bold sequences denote helical boundaries: ASRELTDTLQAETDQLEDEKSALQTE-IANLLKEKEKLEGAP (SEQ ID NO:3). Additional extended serine-glycine linkers can be inserted between the c-Fos sequence and the protein fragment of interest.

In some embodiments, mutants of c-Jun are used that cannot form homodimers, but which can still heterodimerize with c-Fos. Such modified sequences with N-terminal cysteine residues include, but are not limited to: CSGG ASLERIARLEEKVKSFKAQNSENASTAN MLREQVAQLKQKGAP (SEQ ID NO:4), where bold residues denote changes from wild-type, and double-underlined sequences denote helical boundaries. Such modified sequences with C-terminal cysteine residues include, but are not limited to: SGASLERIARLEEKVKSFKAQN SENAS-TANMLREQVAQLKQKQGAPSGGC (SEQ ID NO:5), where bold residues denote changes from wild-type, and double-underlined sequences denote helical boundaries.

In some embodiments of LD-TAPER using either small molecule ligands or small interactive domain ligands, the application may be aimed towards the assembly of split-protein fragments. In other LD-TAPER embodiments, the protein fragments fused with ligand binding domains are self-folding into well-ordered and stable structures, but this is not the case with LD-TAPER applied towards split-protein assembly. In the latter, the protein sequences appended to the ligand-binding domains only attain their mature folds when they are placed in close spatial proximity in the correct orientation.

Figure 8:
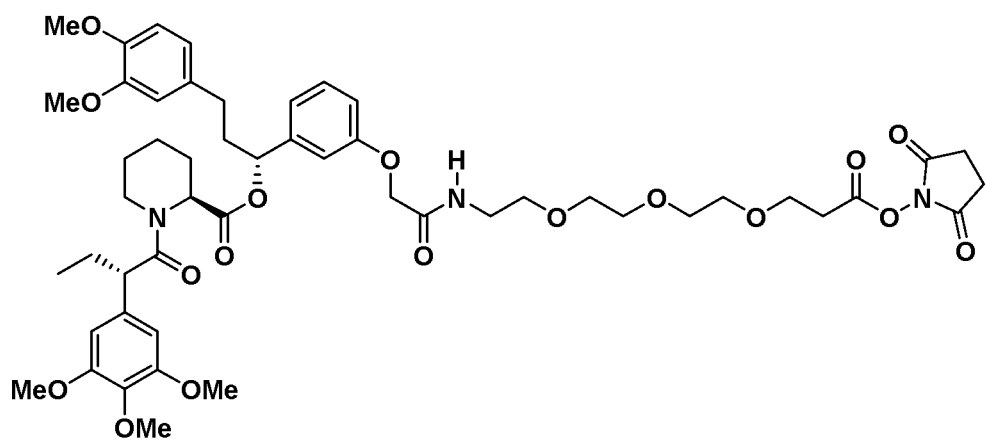
FIG. 8 shows a representative modified monovalent version of a mutant FKBP-binding compound, FKM-PEG3-NHS.
Figure 16:
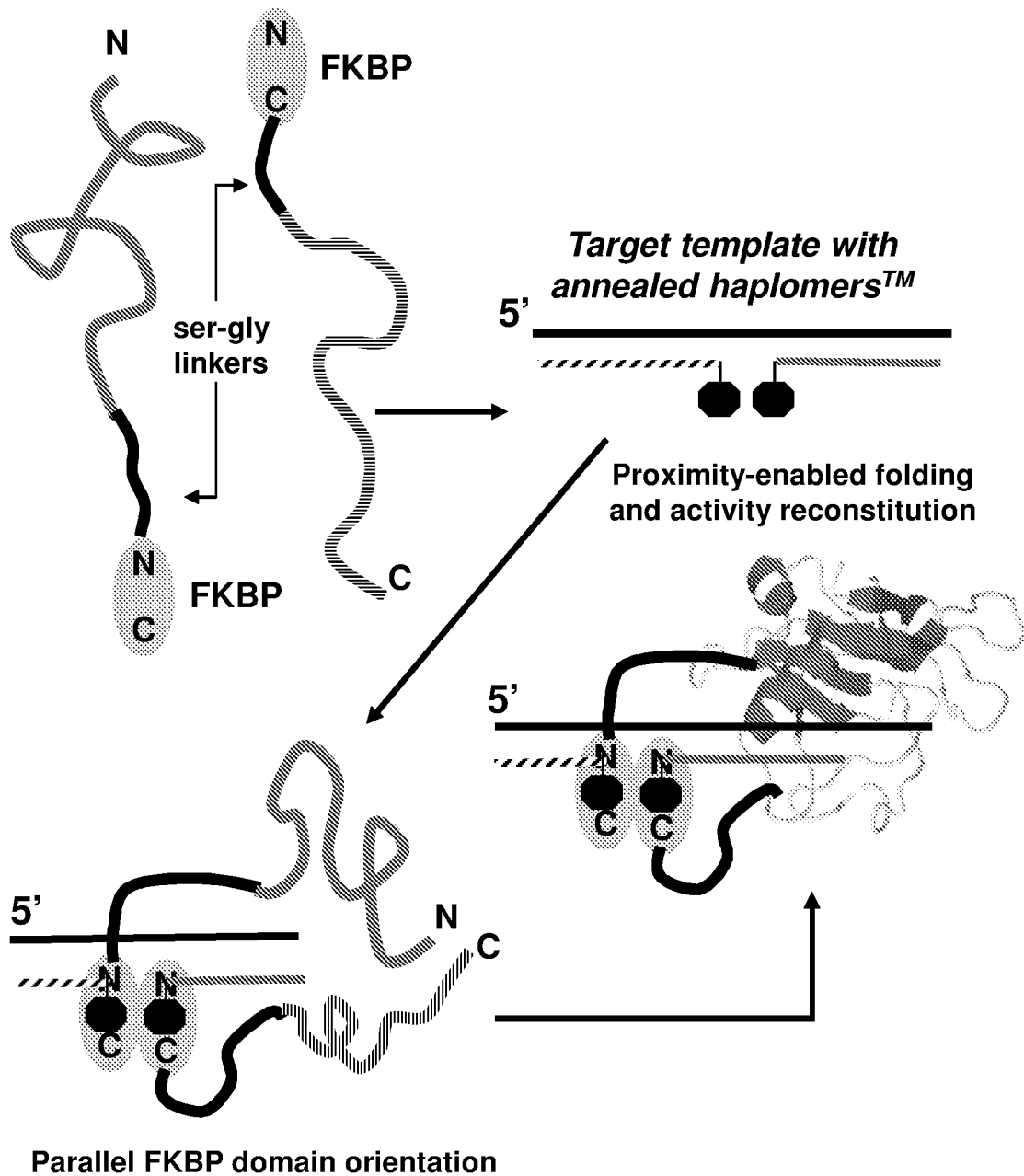
FIG. 16 shows a representative. LD-TAPER:Split-Protein Folding by small molecule ligand/ligand binding domain interactions.

In some embodiments of LD-TAPER for split protein refolding that utilize small molecule ligands, the split protein polypeptides are separately expressed as fusions with the FKBP FK506-binding domain. The N-terminal split protein fragment is expressed with a C-terminal FKBP segment, while the C-terminal split protein fragment is expressed with an N-terminal FKBP segment (see, FIG. 16). Upon binding of the FKBP domains to templated haplomeric conjugates bearing a monovalent FKBP-binder (see, FIGS. 6-8), proximity-enabled folding of the mature polypeptide is elicited (see, FIG. 16, depicted for template Architecture 2). Because the FKBP domains binding each haplomeric ligand are in the same (parallel) orientation, the split protein fragments are placed on opposite sides of the spatially proximal FKBP pair (see, FIG. 16). However, split protein refolding can still occur if the FKBP domains and the split protein polypeptides are separated by sufficiently long serine-glycine linkers.

Figure 17:
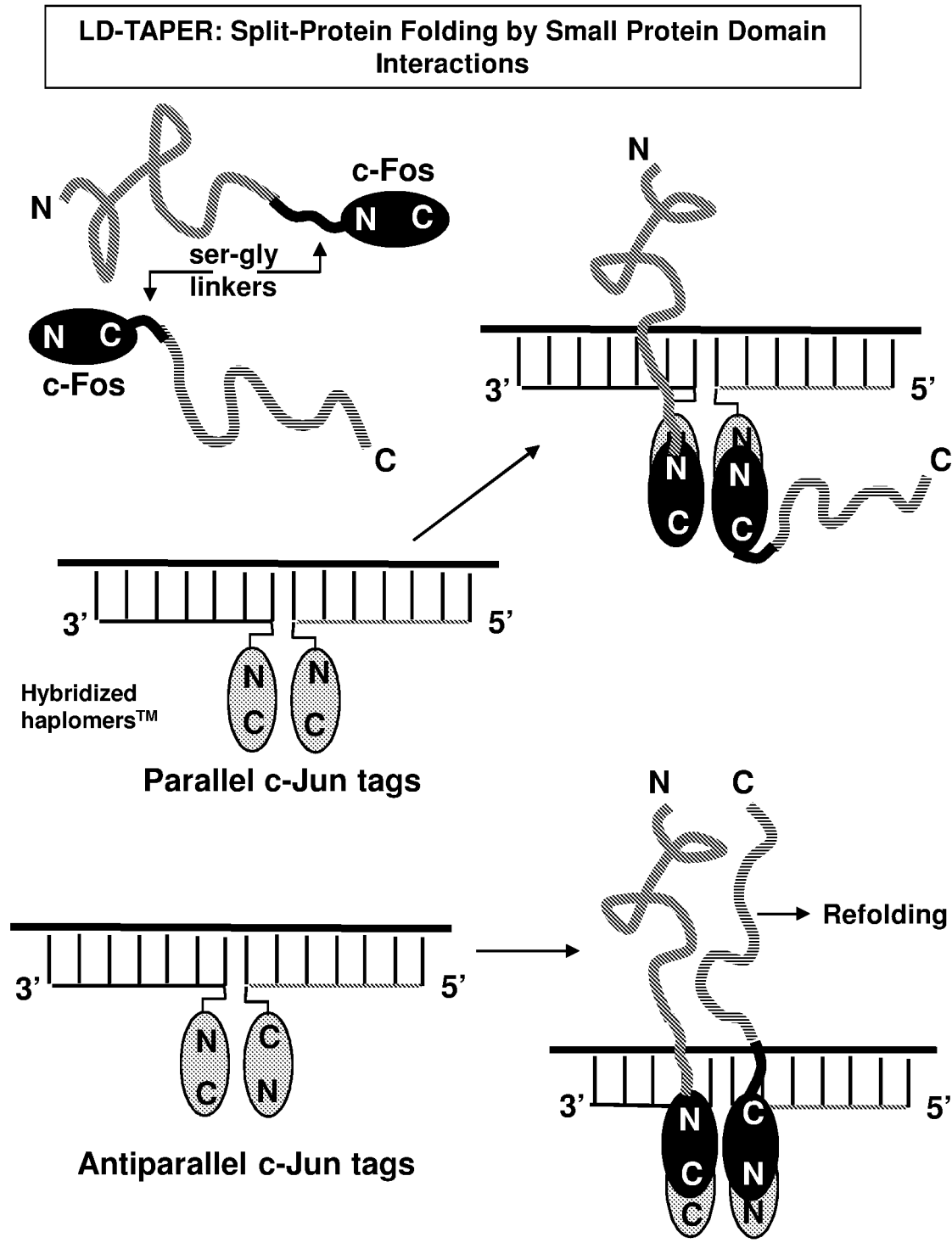
FIG. 17 shows a representative LD-TAPER:Split-Protein Folding by small protein domain interactions, and polarity effects.
Figure 18:
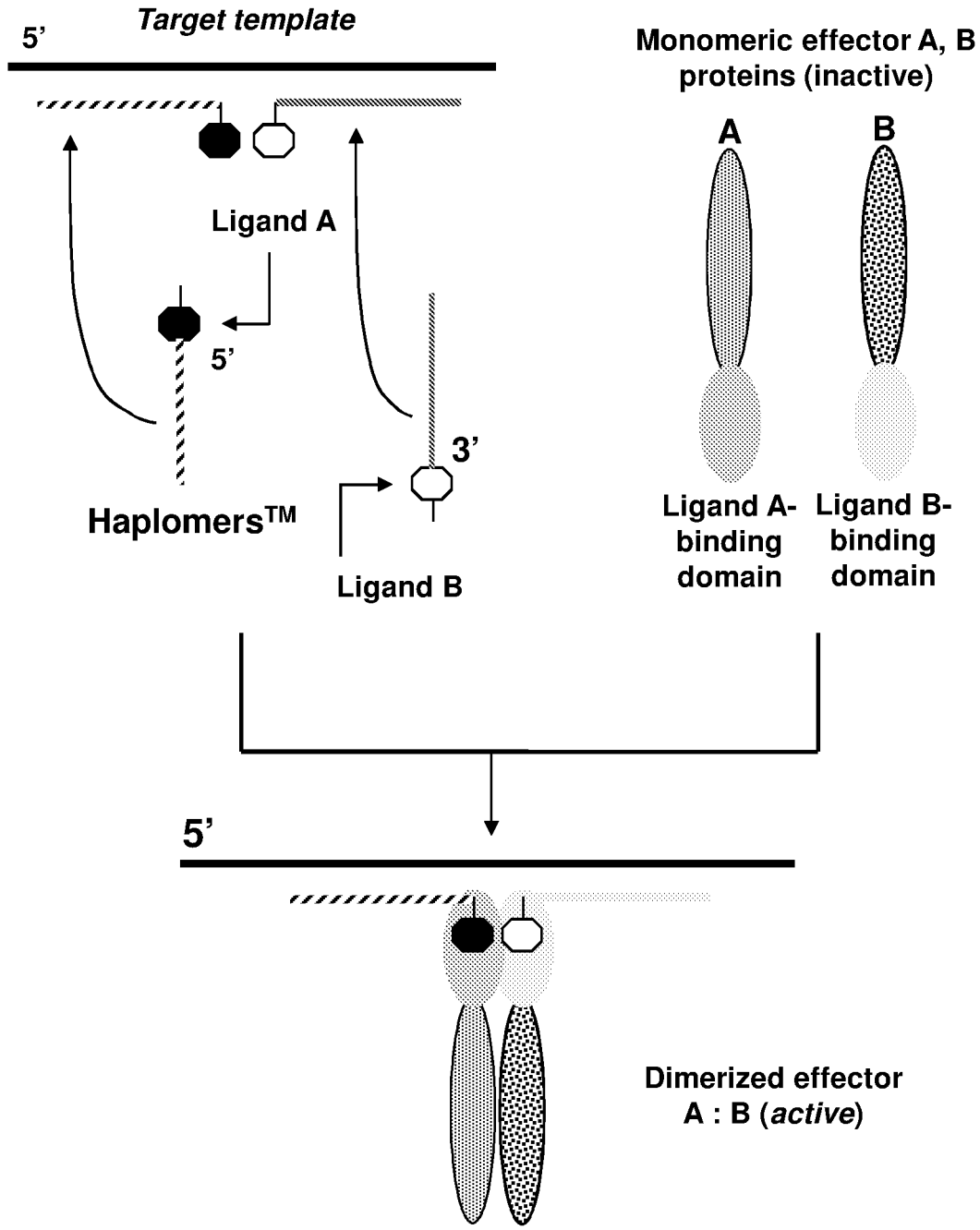
FIG. 18 shows representative heterocomponent systems for LD-TAPER.

Similar principles apply for embodiments of LD-TAPER for split protein refolding that utilize small interactive protein domains as ligands. In some embodiments using c-Jun: c-Fos interactions, the N-terminal split protein fragment is expressed as a C-terminal fusion with c-Fos, while the C-terminal split protein fragment is expressed as an N-terminal with c-Fos (see, FIG. 17). In these embodiments, an antiparallel arrangement of haplomers tagged with c-Jun can be readily accomplished, which is advantageous for placement of the protein fragments in juxtaposition on the same side of the c-Jun pair. Nevertheless, as for the split protein LD-TAPER mediated by small-molecule ligands (see, FIG. 16), parallel c-Jun tags can still be used if a serine-glycine linker of sufficient length is employed (see, FIG. 17). Although the depictions of split-protein embodiments of LD-TAPER use haplomer-template Architecture 2 (see, FIG. 10), Architectures 3 and 4 (see, FIGS. 11 and 12) are equally applicable. Architecture 1 (see, FIG. 9) in this context corresponds to locked TAPER (see, FIG. 13), also very compatible with split-protein embodiments of LD-TAPER.

In the above embodiments (as depicted in FIG. 5, and FIGS. 9-17) both haplomers bear a common ligand tag, and proteins or polypeptide fragments of interest are tagged with a common ligand binding domain. This arrangement is well-suited to systems featuring homodimerization, but is not ideal for heterodimerization, by its nature as a two-stage process. If a protein heterodimer A-B is to be assembled on a template with haplomers H-A and H-B where the first stage is haplomer-template binding (as in Equation 2.1 and 2.2 above), and a monoligand/binding domain system is used, then the protein segments A and B can assort in three possible ways, only one of which is the correct A-B:

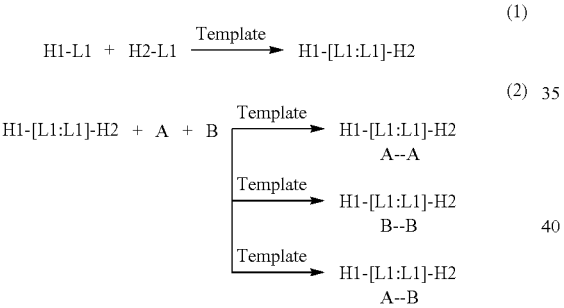

Equations 4.1, 4.2 (Only the Final Associative States of A and B are Shown for Simplicity)

Since the split-protein application of LD-TAPER involves two separate binding domain-polypeptide conjugates (see, FIGS. 16 and 17), the heterodimerization characteristics also apply in this case. While the use of a monoligand/binding domain system for hetero-components (as for A and B above) is not precluded, it may result in a very significant loss of activity if the two-stage procedure of Equations 4.1 and 4.2 are used. Nevertheless, this characteristic can be overcome in some embodiments by preparing the haplomer/ligand binding domain fusion complexes in advance of exposure to the nucleic acid molecule template. Pre-assembly of the haplomer-fusion protein complexes allows control over which ligand binding domain-fusion proteins form partners with a specific haplomer. By such means, a defined haplomer sequence carries a specific ligand binding domain complex of interest, in an analogous manner to Equations 3.1 and 3.2:

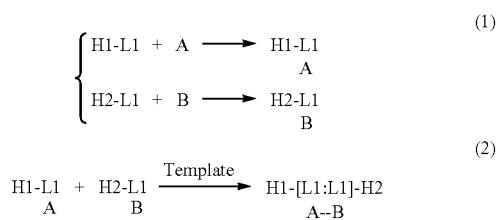

Equations 5.1, 5.2 (Only the Final Associative States of A and B are Shown for Simplicity)

In some embodiments of LD-TAPER, it may nonetheless be advantageous to be able to use a heterocomponent system with full efficiency, without the need for pre-assembly of haplomers and protein fusion domains. This can be achieved by using two distinct ligands, each with a distinct and specific partner ligand binding domain. Such an arrangement can be represented with the same symbology as above (where $L_A$ and $L_B$ represent two distinct ligands with different binding specificities, and A and B represent the corresponding ligand binding entities):

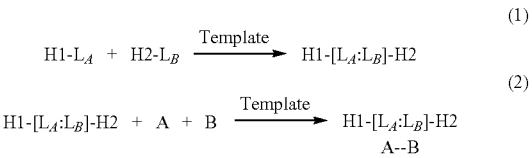

Equations 6.1, 6.2 (Only the Final Associative States of A and B are Shown for Simplicity)

Figure 19:
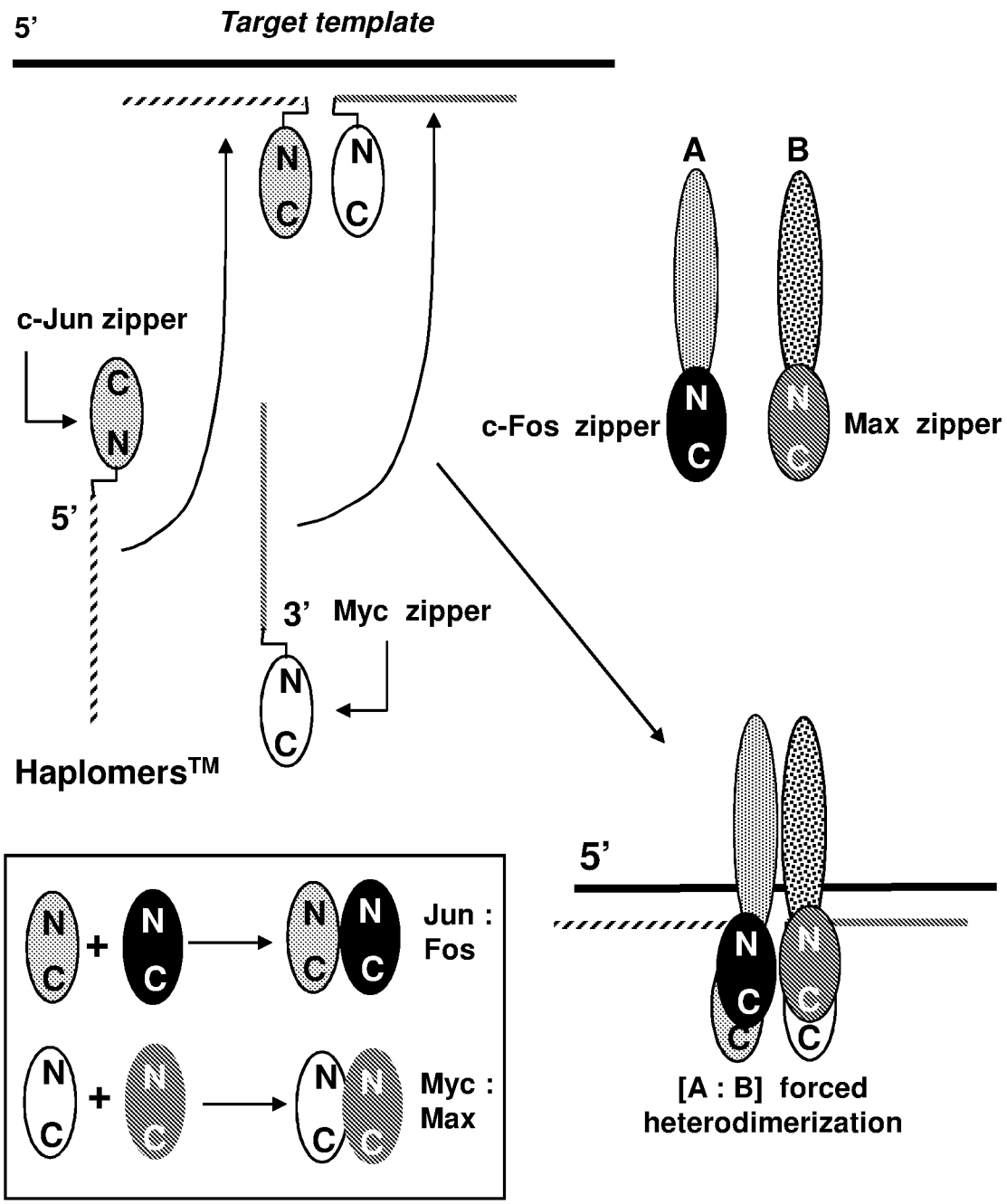
FIG. 19 shows representative heterocomponent systems for LD-TAPER:Specific embodiments with leucine zippers.

In some embodiments of heterocomponent LD-TAPER, the specificity of leucine zipper interactions is used. These include, but are not limited to, c-Jun:c-Fos, and c-Myc:Max heterodimer formation (see, FIG. 19). Thus, haplomers can be prepared with terminal conjugations with c-Jun and c-Myc zippers, and protein domains of interest (or split-protein polypeptide fragments) can be expressed as fusions with c-Fos and Max. The templated jun/myc haplomers direct the forced proximity of the two domains of interest (see, FIG. 19), for ensuing dimerization (pre-folded monomeric domains) or folding (split-protein polypeptide fragments).

Figure 20:
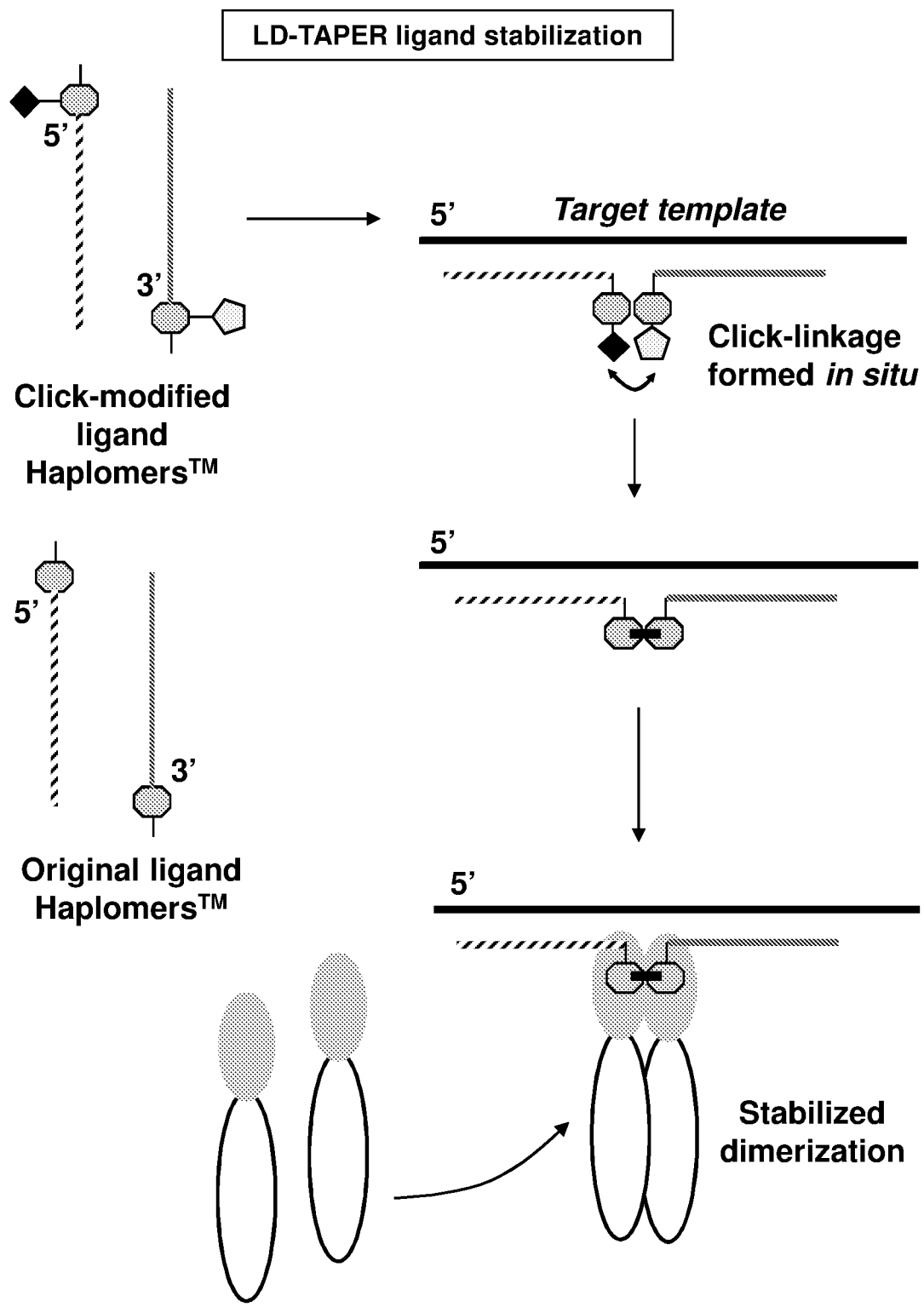
FIG. 20 shows a representative LD-TAPER ligand stabilization, by means of appending click groups onto haplomeric ligands for templated in situ joining.

In some embodiments of LD-TAPER, it may be beneficial to stabilize small molecule monovalent ligands as a linked pair after the desired haplomeric templating has taken place. Although in many cases, enforced dimerization of polypeptide folding by small-molecule LD-TAPER is either irreversible or slowly reversed, the template-mediated conversion of the monovalent ligands to bivalency enables the subsequent dimerization to become template-independent, just as it is for conventional bivalent chemical dimerizers in isolation. Cross-linking of haplomeric small molecule ligands is effected by equipping the monovalent ligand compounds with side chains corresponding to bio-orthogonal click groups, as schematically depicted in FIG. 20. Following the in situ templated click reaction, the initially monovalent ligands are converted in effect into a stable bivalent species, for subsequent interaction with appropriate ligand binding domains (see, FIG. 20).

Some embodiments of LD-TAPER involve homo- or hetero-dimerization of pre-folded proteins that perform important biological functions. Such proteins may be natural, or artificial constructs. These include, but are not limited to, the iCasp9 fusion protein (an artificial construct with a modified Caspase-9 sequence fused with a mutant FKBP sequence, proapoptotic proteins, or dimeric transcription factors. The effects of enforced dimerization mediated by LD-TAPER may be gauged, in various embodiments, by apoptotic assays, activation of reporter genes, or generation of specific fluorescence.

The LD-TAPER processes and components thereof can be generally described by the following more specific embodiments.

The present disclosure provides haplomer-ligand complexes comprising: a) a haplomer, wherein the haplomer comprises a polynucleotide that is substantially complementary to a target nucleic acid molecule; and b) a ligand linked to the 5' or 3' terminus of the haplomer, wherein the ligand comprises a ligand partner binding site. In some embodiments, the polynucleotide of the haplomer comprises from about 6 to about 20 nucleotide bases. In some embodiments, the the polynucleotide of the haplomer comprises from about 8 to about 15 nucleotide bases.

In some embodiments, a pair of haplomer-ligand complexes works in tandem. In some embodiments, the ligand of the first haplomer-ligand complex is linked to the 5' terminus of the polynucleotide of the first haplomer-ligand complex, and the ligand of the second haplomer-ligand complex is linked to the 3' terminus of the polynucleotide of the second haplomer-ligand complex.

In some embodiments, the polynucleotide of the first haplomer-ligand complex is substantially complementary to the polynucleotide of the second haplomer-ligand complex. In some embodiments, the polynucleotide of the first haplomer-ligand complex is substantially complementary to a target nucleic acid molecule, and the polynucleotide of the second haplomer-ligand complex is substantially complementary to the target nucleic acid molecule at a site in spatial proximity to the polynucleotide of the first haplomer-ligand complex.

In any of the embodiments described herein, the haplomer-ligand complexes are in spatial proximity (when bound to a target nucleic acid molecule) such that the ligands, and hence their respective ligand binding domains, can properly interact to induce the folding or dimerization of their respective fragments of the protein of interest. Thus, for any haplomer-ligand pairs, reactivity can occur where the gap N between the first and second haplomer-ligand complex binding to the target nucleic acid molecule is 0 (i.e., the haplomer-ligand complexes are immediately juxtaposed), and progressively greater gaps (N>0) will progressively diminish activity. Thus, in some embodiments, there is 0 nucleotides between the binding of a first haplomer-ligand complex and second haplomer-ligand complex to the target nucleic acid molecule. In some embodiments, there is less than 6 nucleotides between the binding of a first haplomer-ligand complex and second haplomer-ligand complex to the target nucleic acid molecule. In some embodiments, there is less than 5 nucleotides between the binding of a first haplomer-ligand complex and second haplomer-ligand complex to the target nucleic acid molecule. In some embodiments, there is less than 4 nucleotides between the binding of a first haplomer-ligand complex and second haplomer-ligand complex to the target nucleic acid molecule. In some embodiments, there is less than 3 nucleotides between the binding of a first haplomer-ligand complex and second haplomer-ligand complex to the target nucleic acid molecule. In some embodiments, there is less than 2 nucleotides between the binding of a first haplomer-ligand complex and second haplomer-ligand complex to the target nucleic acid molecule.

In some embodiments, both ligands are small molecule ligands or both ligands are interactive protein domains. In some embodiments, the ligand of the first haplomer-ligand complex further comprises a bio-orthogonal moiety, and the ligand of the second haplomer-ligand complex further comprises a bio-orthogonal moiety, wherein the bio-orthogonal moiety of the first haplomer-ligand complex is reactable with the bio-orthogonal moiety of the second haplomer-ligand complex.

The present disclosure also provides bottle haplomer-ligand complexes comprising: a) a bottle haplomer, wherein the bottle haplomer comprises a polynucleotide, wherein the polynucleotide comprises: i) a first stem portion comprising from about 10 to about 20 nucleotide bases; ii) an anti-target loop portion comprising from about 16 to about 40 nucleotide bases and having a first end to which the first stem portion is linked, wherein the anti-target loop portion is substantially complementary to a target nucleic acid molecule; and iii) a second stem portion comprising from about 10 to about 20 nucleotide bases linked to a second end of the anti-target loop portion, wherein the first stem portion is substantially complementary to the second stem portion; and b) a ligand linked to the terminal end of either the first stem portion or the second stem portion, wherein the ligand comprises a ligand partner binding site; wherein the $T_m$ of the anti-target loop portion:target nucleic acid molecule is greater than the $T_m$ of the first stem portion:second stem portion.

In some embodiments, the first stem portion that comprises from about 10 to about 20 nucleotide bases. In some embodiments, the first stem portion comprises from about 12 to about 18 nucleotide bases.

In some embodiments, the anti-target loop portion comprises from about 16 to about 40 nucleotide bases. In some embodiments, the anti-target loop portion comprises from about 18 to about 35 nucleotide bases. The anti-target loop portion has a first end to which the first stem portion is linked. The anti-target loop portion is substantially complementary to a target nucleic acid molecule. In some embodiments, a ligand is linked to the second stem portion.

In some embodiments, the anti-target loop portion can further comprise an internal hinge region, wherein the hinge region comprises one or more nucleotides that are not complementary to the target nucleic acid molecule. In some embodiments, the hinge region comprises from about 1 nucleotide to about 6 nucleotides, from about 1 nucleotide to about 5 nucleotides, from about 1 nucleotide to about 4 nucleotides, from about 1 nucleotide to about 3 nucleotides, or 1 or 2 nucleotides.

In some embodiments, the second stem portion comprises from about 10 to about 20 nucleotide bases. In some embodiments, the second stem portion comprises from about 12 to about 18 nucleotide bases. The second stem portion is linked to a second end of the anti-target loop portion. The first stem portion is substantially complementary to the second stem portion. In some embodiments, a ligand is linked to the second stem portion.

In some embodiments, the bottle haplomer comprises the nucleotide sequence 5'-ACTC GAGACGTCTCCTTGTCTTTGCTTTCTTCAGGACAC AGTGGCGAGACGGTGT-3' (SEQ ID NO:6) or 5'-ACTCGA-

GACGTCTCCTTCCTGCCCCTCCTCCTGCTCCGA-
GACGTC TCGAGT-3' (SEQ ID NO:7).

For the polynucleotides of the bottle haplomers described herein, the length of the particular polynucleotide or portion thereof is less important than the $T_m$ of the duplex formed by the interaction of the polynucleotide, or portion thereof, with another nucleic acid molecule, or portion thereof. For example, the $T_m$ of the duplex formed by the interaction of the anti-target loop portion with the target nucleic acid molecule (e.g., anti-target loop portion:target nucleic acid molecule) is greater than the $T_m$ of the duplex formed by the interaction of the first stem portion with the second stem portion (e.g., first stem portion:second stem portion). In some embodiments, the $T_m$ of the first stem portion:second stem portion subtracted from the $T_m$ of the anti-target loop portion:target nucleic acid molecule is from about 10° C. to about 40° C. In some embodiments, the $T_m$ of the first stem portion:second stem portion subtracted from the $T_m$ of the anti-target loop portion:target nucleic acid molecule is from about 10° C. to about 20° C. In some embodiments, the $T_m$ of the first stem portion:second stem portion is from about 40° C. to about 50° C. In some embodiments, the $T_m$ of the anti-target loop portion:target nucleic acid molecule is from about 60° C. to about 80° C.

In addition, translating the $T_m$ information above into specific lengths of the nucleic acid molecules described herein can also depend on the GC content of each nucleic acid molecule. For example, the length of a suitable HPV model target nucleic acid molecule is 30 bases (having a $T_m$ of 70° C.), while that for the EBV model target nucleic acid molecule is only 21 bases (having a $T_m$ of 69° C.), owing to its greater % GC.

In some embodiments, a bottle haplomer-ligand complex works in tandem with a second haplomer-ligand complex. In some embodiments, the bottle haplomer-ligand complex is any bottle haplomer-ligand complex described herein, and the second haplomer-ligand complex is any of the haplomer-ligand complexes described herein. In some embodiments, the second haplomer-ligand complex comprises: a) a nucleotide portion comprising from about 6 to about nucleotide bases that is substantially complementary to the stem portion of the bottle haplomer-ligand complex that is linked to the ligand of the bottle haplomer-ligand complex; and b) a ligand linked to the 5' or 3' terminus of the nucleotide portion of the second haplomer-ligand complex, wherein the ligand comprises a ligand partner binding site; wherein the $T_m$ of the second haplomer-ligand complex:first or second stem portion linked to the ligand of the bottle haplomer-ligand complex is less than or equal to the $T_m$ of the first stem portion:second stem portion of the bottle haplomer-ligand complex.

In some embodiments, the $T_m$ of the duplex formed by the interaction of the second haplomer-ligand complex with either the first stem portion or the second stem portion, whichever stem portion is linked to the ligand (e.g., second haplomer-ligand complex:first or second stem portion linked to the ligand), is less than or equal to the $T_m$ of the first stem portion:second stem portion. In some embodiments, the $T_m$ of the duplex formed by the second haplomer-ligand complex and the first or second stem portion linked to the ligand subtracted from the $T_m$ of the first stem portion:second stem portion is from about 0° C. to about 20° C. In some embodiments, the $T_m$ of the duplex formed by the second haplomer-ligand complex and the first or second stem portion linked to the ligand subtracted from the $T_m$ of the first stem portion:second stem portion is from about 5° C. to about 10° C. In some embodiments, the $T_m$ of the duplex formed by the second haplomer-ligand complex and the first or second stem portion linked to the ligand is from about 30° C. to about 40° C.

This structural arrangement is designed such that in the absence of target nucleic acid molecule template, the locked first haplomer bottle does not significantly hybridize to its complementary second haplomer and, thus, template-directed product assembly is not promoted under such conditions. When the specific target nucleic acid molecule template is present, on the other hand, the bottle haplomer-ligand complex is "unlocked" by the formation of a more stable hybrid between the anti-target loop region of the bottle haplomer and the target nucleic acid molecule itself. Once this occurs, the first stem portion of the bottle haplomer that is linked to the ligand is free to hybridize to the available second haplomer-ligand complex, with resulting proximity between the ligands on both.

In any of the haplomer polynucleotides described herein, or any portion thereof, the nucleotide bases are selected from the group consisting of DNA nucleotides, RNA nucleotides, phosphorothioate-modified nucleotides, 2-O-alkylated RNA nucleotides, halogenated nucleotides, locked nucleic acid nucleotides (LNA), peptide nucleic acids (PNA), morpholino nucleic acid analogues (morpholinos), pseudouridine nucleotides, xanthine nucleotides, hypoxanthine nucleotides, 2-deoxyinosine nucleotides, DNA analogs with L-ribose (L-DNA), Xeno nucleic acid (XNA) analogues, or other nucleic acid analogues capable of base-pair formation, or artificial nucleic acid analogues with altered backbones, or any combination or mixture thereof.

For any of the any of the haplomer polynucleotides described herein, the complementarity with another nucleic acid molecule can be 100%. In some embodiments, one particular nucleic acid molecule can be substantially complementary to another nucleic acid molecule. As used herein, the phrase "substantially complementary" means from 1 to 10 mismatched base positions, from 1 to 9 mismatched base positions, from 1 to 8 mismatched base positions, from 1 to 7 mismatched base positions, from 1 to 6 mismatched base positions, from 1 to 5 mismatched base positions, from 1 to 4 mismatched base positions, from 1 to 3 mismatched base positions, and 1 or 2 mismatched base positions. In some embodiments, it is desirable to avoid reducing the $T_m$ of the anti-target loop portion:target nucleic acid molecule by more than 10% via mismatched base positions. The bottle haplomer stem is designed with respect to a second haplomer, and its structure is deliberately arranged to be somewhat more stable than the formation of the second haplomer duplex.

In some embodiments, the portion of the bottle haplomer-ligand complex that is not linked to a ligand can have additional nucleotide bases that overhang and do not form a part of the stem structure. In some embodiments, the end of the second haplomer-ligand complex that is not linked to a ligand can have additional nucleotide bases that overhang and do not form a complementary part of the structure with the stem portion of the bottle haplomer-ligand complex. In addition, in some embodiments, the portion of the stem that is linked to the ligand can also have nucleotide bases that are not base paired with the first stem portion. Such an extension of the stem with a non-hybridized "arm" places the two ligands at a greater spatial distance, thus, tending to reduce their mutual reactivity. So, for a few nucleotide bases (less than or less than 5), enforced reactivity is still likely to occur, but will tend to diminish as the non-base paired segment grows in length.

In some embodiments, added nucleotide bases can be of indefinite length, as long as they did not: 1) have significant homologies with any of the other regions of the locked TAPER oligonucleotides, and thus tend to cross-hybridize and interfere; or 2) interfere non-specifically with any other features of the system. For example, a long appended sequence might reduce transformation efficiencies of locked TAPER oligonucleotides used in a therapeutic context. Also, appended sequences should be designed to avoid spurious hybridizations with other cellular transcripts. Appended non-homologous sequences of 20-30 nucleotide bases are suitable. The appended nucleic acid sequences may contain primer sequences commonly used in the art. Such examples may include, but are not limited to, M13, T3, T7, SP6, VF2, VR, modified versions thereof, complementary sequences thereof, and reverse sequences thereof. In addition, custom primer sequences are also included. Such primer sequences can be used, for example, the possible application of chemically-ligated oligonucleotides spatially elicited (CLOSE) to the locked TAPER strategy, (see, PCT Publication WO 2016/89958; which is incorporated herein by reference in its entirety).

In some embodiments, both ligands are small molecule ligands or both ligands are interactive protein domains. In some embodiments, the N-terminus of the interactive protein domain of the bottle haplomer-ligand complex is linked to the 5' terminus of the polynucleotide of the bottle haplomer-ligand complex, and the N-terminus of the interactive protein domain of the second haplomer-ligand complex is linked to the 3' terminus of the polynucleotide of the second haplomer-ligand complex. In some embodiments, the C-terminus of the interactive protein domain of the bottle haplomer-ligand complex is linked to the 5' terminus of the polynucleotide of the bottle haplomer-ligand complex, and the C-terminus of the interactive protein domain of the second haplomer-ligand complex is linked to the 3' terminus of the polynucleotide of the second haplomer-ligand complex.

In some embodiments, the C-terminus of the interactive protein domain of the bottle haplomer-ligand complex is linked to the 5' terminus of the polynucleotide of the bottle haplomer-ligand complex, and the N-terminus of the interactive protein domain of the second haplomer-ligand complex is linked to the 3' terminus of the polynucleotide of the second haplomer-ligand complex: or the N-terminus of the interactive protein domain of the bottle haplomer-ligand complex is linked to the 5' terminus of the polynucleotide of the bottle haplomer-ligand complex, and the C-terminus of the interactive protein domain of the second haplomer-ligand complex is linked to the 3' terminus of the polynucleotide of the second haplomer-ligand complex.

Any of the bottle haplomers described herein, or any portion thereof, can further comprise a linker between any one or more of the first stem portion and the anti-target loop portion, between the anti-target loop portion and the second stem portion, between the second stem portion and the ligand, between the first stem portion and the ligand, or between the second haplomer and its ligand. In some embodiments, the linker is selected from the group consisting of an alkyl group, an alkenyl group, an amide, an ester, a thioester, a ketone, an ether, a thioether, a disulfide, an ethylene glycol, a cycloalkyl group, a benzyl group, a heterocyclic group, a maleimidyl group, a hydrazone, a urethane, azoles, an imine, a haloalkyl, and a carbamate, or any combination thereof.

In some embodiments, the second haplomer-ligand complex comprises the nucleotide sequence 5'-AGCTCTCGAGT-3' (SEQ ID NO:8), or 5'-GACGTCTCGAGT-3' (SEQ ID NO:9).

In any of the embodiments described herein, the ligand is a small molecule ligand or an interactive protein domain.

In some embodiments, the ligand is a small molecule ligand. In some embodiments, the small molecule ligand is less than about 2500 Daltons. In some embodiments, the small molecule ligand is a small molecule, a peptide having less than about 20 amino acid residues, a naturally- or artificially-modified peptide, a peptidomimetic, a glycan, an organic enzyme cofactor, or an artificially-derived small molecular ligand. In some embodiments, the small molecule ligand is derived from compounds designed to target FKBP. In some embodiments, the small molecule ligand is an FKM monovalent ligand.

In some embodiments, the small molecule ligand is derived from compounds designed to target mutant versions of FKBP (Clackson et al., Proc. Natl. Acad. Sci. USA, 1998, 95, 103437-10432). One such modification is FKM-NHS, which comprises a modified monovalent mutant FKBP binding moiety with an appended amide, 3-carbon spacer, and a carboxylic acid group, esterified with N-hydroxysuccinimide (NHS) (see, FIG. 6), which can be used, for example, for coupling to amino-labeled oligonucleotides. The spacer moiety of FKM-NHS may comprise, but not limited to, 4, 5 or 6 carbon atoms in length. FKM-NHS may also be modified to enhance solubility.

In some embodiments, the small molecule ligand is FKM-sulfo-NHS (see, FIG. 7), which can be used, for example, for coupling to amino-labeled oligonucleotides, and with an additional sulfo-group for solubility enhancement. The NHS moeity carries a sulfo-group. The spacer moiety of FKM-sulfo-NHS may comprise, but not limited to, 4, 5 or 6 carbon atoms in length.

In some embodiments, the small molecule ligand is comprises another solubility-enhancing modification of FKM-NHS, where the spacer arm is converted into a short segment of polyethylene glycol (PEG) to provide FKM-PEG3-NHS (see, FIG. 8), which can be used, for example, for coupling to amino-labeled oligonucleotide, and with a PEG spacer for solubility enhancement. The spacer arm of FKM-PEG3-NHS may comprise, but not limited to, 1, 2, 4, 5, or 6 copies of the monomer ethylene glycol. FKM-NHS and all derivatives of it can be readily and directly coupled to amino-labeled oligonucleotides, at either 5' or 3' ends. In addition, the site of appending the reactive group to the PEG chain can be varied. Thus, if the carbon atoms in the PEG chain are numbered, the reactive group could be positioned at any of these sites.

In some embodiments, the FKM monovalent ligand is FKM-NHS, FKM-sulfo-NHS, FKM-PEG3-NHS, or monovalent FKBP Ligand-2 (MFL2), wherein: FKM-NHS is

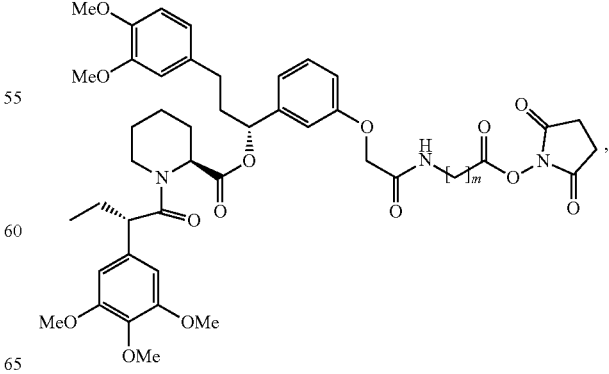

where m is from 3 to 6; FKM-sulfo-NHS is

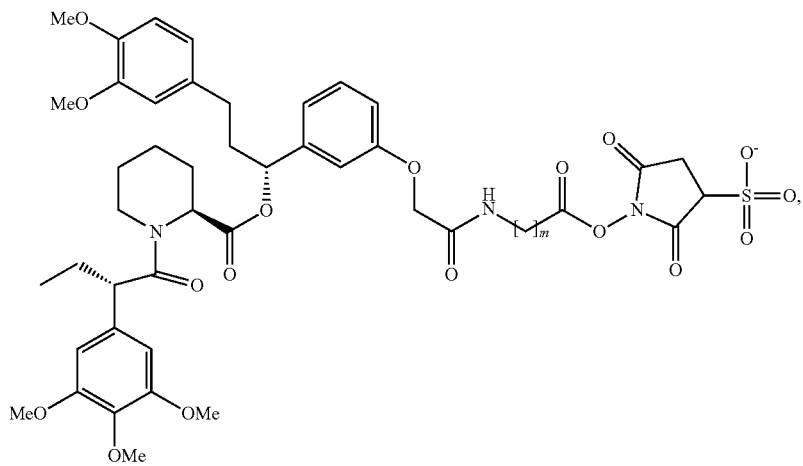

where m is from 3 to 6; FKM-PEG3-NHS is

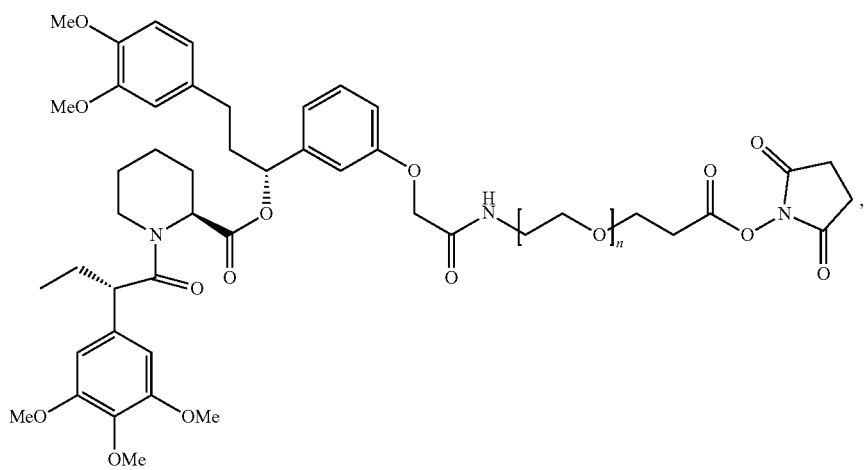

where n is from 1 to 6; and MFL2 is

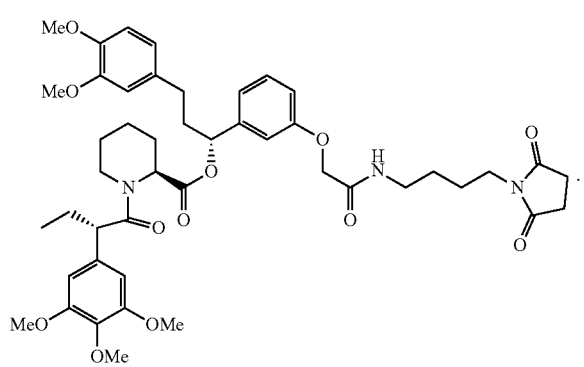 [SMILES: CC[C@H](C(=O)N1CCCC[C@H]1C(=O)O[C@H](CCc1ccc(OC)c(OC)c1)c1cccc(OCC(=O)NCCCCN2C(=O)CCC2=O)c1)c1cc(OC)c(OC)c(OC)c1]

In some embodiments, the ligand is an interactive protein domain. In some embodiments, the interactive protein domain comprises less than 100 amino acid residues. In some embodiments, the interactive protein domain is a leucine zipper domain. In some embodiments, the interactive protein domain is a c-jun domain, a c-fos domain, a c-myc domain, a c-max domain, an NZ domain, or a CZ domain.

In some embodiments, the NZ domain comprises the amino acid sequence ALKKELQ ANKKELAQLK-WELQALKKELAQ (SEQ ID NO:10), and the CZ domain comprises the amino acid sequence EQLEKKLQALEKKLAQLEWKNQALEKKLAQ (SEQ ID NO: 11).

In some embodiments, the N-terminus of the c-jun domain is linked to the 5' or 3' terminus of the polynucleotide of the haplomer. In some embodiments, the c-jun domain comprises the amino acid sequence CSGGASLE-RIARLEEKVKTLKAQNSELASTANMLR EQVAQLKQKGAP (SEQ ID NO:1). CSGGASLERIAR-LEEKVKSFKAQNSENASTAN MLREQVAQLKQKGAP (SEQ ID NO:4), or CSGASLERIAR-LEEKVKSFKAQNSENAS TANMLREQVAQLKQKG-AP (SEQ ID NO:12). In some embodiments, the C-terminus of the c-jun domain is linked to the 5' or 3' terminus of the polynucleotide of the haplomer. In some embodiments, the c-jun domain comprises the amino acid sequence SGASLE- RIARLEEKVK TLKAQNSELASTANML-
REQVAQLKQKGAPSGGC (SEQ ID NO:2), or SGASLE-
RIARLE
EKVKSFKAQNSENASTANMLREQVAQLKQK-
GAPSGGC (SEQ ID NO:5).

In some embodiments, the c-Fos domain comprises the amino acid sequence

```
                                         (SEQ ID NO: 3)
  ASRELTDTLQAETDQLEDEKSALQTEIANLLKEKEKLEGAP
or (SEQ ID NO: 13)
  SGASRELTDTLQAETDQLEDEKSALQTEIANLLKEKEKLEGAP.
```

In some embodiments where two haplomer-ligand complexes work in tandem, or where a bottle haplomer-ligand complexes work in tandem with a second haplomer-ligand complex, both ligands are either small molecule ligands or both ligands are interactive protein domains. In some embodiments, both interactive protein domains are leucine zipper domains.

In some embodiments, the N-terminus of the interactive protein domain of the first haplomer-ligand complex is linked to the 5' terminus of the polynucleotide of the first haplomer-ligand complex, and the N-terminus of the interactive protein domain of the second haplomer-ligand complex is linked to the 3' terminus of the polynucleotide of the second haplomer-ligand complex. In some embodiments, the C-terminus of the interactive protein domain of the first haplomer-ligand complex is linked to the 5' terminus of the polynucleotide of the first haplomer-ligand complex, and the C-terminus of the interactive protein domain of the second haplomer-ligand complex is linked to the 3' terminus of the polynucleotide of the second haplomer-ligand complex.

In some embodiments, the C-terminus of the interactive protein domain of the first haplomer-ligand complex is linked to the 5' terminus of the polynucleotide of the first haplomer-ligand complex, and the N-terminus of the interactive protein domain of the second haplomer-ligand complex is linked to the 3' terminus of the polynucleotide of the second haplomer-ligand complex; or the N-terminus of the interactive protein domain of the first haplomer-ligand complex is linked to the 5' terminus of the polynucleotide of the first haplomer-ligand complex, and the C-terminus of the interactive protein domain of the second haplomer-ligand complex is linked to the 3' terminus of the polynucleotide of the second haplomer-ligand complex.

In some embodiments, the C-terminus of the c-jun domain is linked to the 5' or 3' terminus of the polynucleotides of either or both of the first haplomer-ligand complex and second haplomer-ligand complex.

In some embodiments, the ligand linked to the polynucleotide of the first haplomer-ligand complex is a c-jun domain or a c-myc domain, and the ligand linked to the polynucleotide of the second haplomer-ligand complex is a c-jun domain or a c-myc domain. In some embodiments, the ligand linked to the polynucleotide of the first haplomer-ligand complex or second haplomer-ligand complex is a c-jun domain, and the ligand linked to the polynucleotide of the other of the first haplomer-ligand complex and second haplomer-ligand complex is a c-myc domain. In some embodiments, the ligand linked to the polynucleotide of the first haplomer-ligand complex is a c-jun domain, and the ligand linked to the polynucleotide of the second haplomer-ligand complex is a c-jun domain.

In some embodiments, the ligand linked to the polynucleotide of the bottle haplomer-ligand complex is a c-jun domain, and the ligand linked to the polynucleotide of the second haplomer-ligand complex is a c-jun domain. In some embodiments, the ligand linked to the polynucleotide of one of the bottle haplomer-ligand complex and second haplomer-ligand complex is a c-jun domain, and the ligand linked to the polynucleotide of the other of the bottle haplomer-ligand complex and second haplomer-ligand complex is a c-myc domain.

In some embodiments, the polynucleotide of the bottle haplomer-ligand complex comprises the nucleotide sequence of 5'-ACTCGA-GACGTCTCCTTGTCTTTGCTTTTCTT CAGGACACAGTGGCGAGACGTCTCGAGT-3' (SEQ ID NO:6), and the polynucleotide of the second haplomer-ligand complex comprises the nucleotide sequence of 5'-AGCTCTCGA GT-3' (SEQ ID NO:8); or the polynucleotide of the bottle haplomer-ligand complex comprises the nucleotide sequence of 5'-ACTCGA-GACGTCTCCTTCCTGCCCCTCCTCCTGCTCCGA GACGTCTCGAGT-3' (SEQ ID NO:7), and the polynucleotide of the second haplomer-ligand complex comprises the nucleotide sequence 5'-GACGTCTCGAGT-3' (SEQ ID NO:9).

The target nucleic acid molecules that serve as templates in the embodiments described herein can be comprised of any desired nucleic acid sequence capable of hybridizing with the polynucleotides of the haplomers or the anti-target loop portion of a bottle haplomer. Any single-stranded nucleic acid molecule with an accessible sequence is potentially targetable. These include, but are not limited to, cellular RNAs, mRNA, genomic or organellar DNA, episomal or plasmid DNA, viral DNA or RNA, miRNA, rRNA, snRNA, tRNA, short and long non-coding RNAs, and any artificial sequences used for templating purposes, or any other biological or artificial nucleic acid sequence. Artificial sequences include, but are not limited to, aptamers and macromolecular-nucleic acid conjugates. Aptamer templates are also included, where these are designed to convert a non-nucleic acid cellular product into a targetable sequence for any form of TAPER, including locked TAPER. In some embodiments, the target nucleic acid molecule hybridization site is kept as short as possible while: 1) maintaining specificity within a complex transcriptome or other complex targets; and 2) maintaining the locked TAPER design guidelines described herein.

Any cell, virus, tissues, spatial regions, lysate, or other subcomponent of a sample that contains a nucleic acid molecule can provide the target nucleic acid molecule. Target compartments that contain the target nucleic acid molecule can include, but are not limited to, pathogenic cells, cancer cells, viruses, host cells infected by a virus or other pathogen, or cells of the immune system that are contributing to autoimmunity such as cells of the adaptive or innate immune systems, transplant rejection, or an allergic response. In some embodiments, a target nucleic acid molecule can be present in a virus or cell infected by a virus, but absent in healthy cells. Examples of virus include, but are not limited to, DNA viruses, RNA viruses, or reverse transcribing viruses. In some embodiments, a target nucleic acid molecule can be present in a tumor or cancerous cell, but absent in healthy cells. Examples of cancers include, but are not limited to, those caused by oncoviruses, such as the human papilloma viruses, Epstein-Barr virus, hepatitis B virus, hepatitis C virus, human T-lymphotropic viruses, Merkel cell polyoma virus, and Kaposi's sarcoma-associated herpesvirus. In some embodiments, a target nucleic acid molecule can be present in an infectious agent or microbe, or a cell infected by an infectious agent or microbe but is absent in healthy cells. Examples of infectious agents or microbes include, but are not limited to, viruses, bacteria, fungi, protists, prions, or eukaryotic parasites.

The target nucleic acid molecule can also be a fragment, portion or part of a gene, such as an oncogene, a mutant gene, an oncoviral gene, a viral nucleic acid sequence, a microbial nucleic acid sequence, a differentially expressed gene, and a nucleic acid gene product thereof.

Examples of cancer-specific target nucleic acids include, but are not limited to, mutant oncogenes, such as mutated ras, HRAS, KRAS, NRAS, BRAF, EGFR, FLT1, FLT4, KDR, PDGFRA, PDGFRB, ABL1, PDGFB, MYC, CCND1, CDK2, CDK4, or SRC genes; mutant tumor suppressor genes, such as TP53, TP63, TP73, MDM1, MDM2, ATM, RB1, RBL1, RBL2, PTEN, APC, DCC, WT1, IRF1, CDK2API, CDKN1A, CDKN1B, CDKN2A, TRIM3, BRCA1, or BRCA2 genes; and genes expressed in cancer cells, where the gene may not be mutated or genetically altered, but is not expressed in healthy cells of a sample at the time of administration, such as carcinoembryonic antigen.

In some embodiments, the target nucleic acid molecule can be present in a differential amounts or concentrations in the target compartments as compared to the non-target compartments. Examples include, but are not limited to, genes expressed at a different level in cancer cells than in healthy cells, such as myc, telomerase, HER2, or cyclin-dependent kinases. In some embodiments, the target nucleic acid molecule can be a gene that is at least 1.5×-fold differentially expressed in the target versus the non-target compartments. Some examples of these include, but are not limited to, genes related to mediating Type I allergic responses, for which target RNA molecules contain immunoglobulin epsilon heavy chain sequences; genes expressed in T cell subsets, such as specific T cell receptors (TCRs) which recognize self-antigens in the context of particular major histocompatibility (MHC) proteins like proinsulin-derived peptide and clonally-specific mRNAs containing α or β variable-region sequences, derived from diabetogenic CD8+ T cells; and cytokines whose production may have adverse outcomes through exacerbation of inflammatory responses including, but not limited to, TNF-alpha, TNF-beta, IL-1, IL-2, IL-4, IL-6, IL-8, IL-10, IL-12, IL-15, IL-17, IL-18, IL-21, IL-22, IL-27, IL-31, IFN-gamma, OSM, and LIF.

In some embodiments, a target nucleic acid molecule is present in target compartments and an acceptable subgroup of non-target compartments, but not in a different or distinct subgroup of non-target compartments. Examples include, but are not limited to, genes expressed in cancer cells and limited to classes of healthy cells, such as cancer-testis antigens, survivin, prostate-specific antigen, carcinoembryonic antigen (CEA), alpha-fetoprotein and other oncofetal proteins. Also, many tissues and organs are not essential to otherwise healthy life in the face of serious disease. For example, melanocyte antigens, such as Melan-A/MART-1 and gp100 are expressed on many malignant melanomas as well as normal melanocytes, and therapies that target these antigens can destroy both tumors and normal melanocytes, resulting in vitiligo, but major tumor reduction. Likewise, the reproductive organs may be surgically removed, such as testis, ovary and uterus, as well as associated organs such as breast and prostate may be targeted when tumors of these tissues arise, and destruction of normal tissues within these organs may be a tolerable consequence of therapy. Furthermore, some cells that produce hormones, such as thyroxine and insulin can be replaced with the relevant protein, allowing potential targeting of normal cells that may exist in the presence of tumors of these origins.

Target nucleic acid molecules can also include novel sequences, not previously identified. In some embodiments, a sample or samples can be evaluated by sequence analysis, such as next-generation sequencing, whole-transcriptome (RNA-seq) or whole-genome sequencing, microarray profiling, serial analysis of gene expression (SAGE), to determine the genetic makeup of the sample. Target nucleic acid molecules can be identified as those present in target compartments, but not present in non-target compartments, or present in differential amounts or concentrations in target compartments as compared to non-target compartments. Sequences identified by these methods can then serve as target nucleic acid molecules.

In some embodiments, when the ligand is a small molecule ligand, the small molecule ligand may further comprise a bio-orthogonal moiety. In some embodiments where two haplomer-ligand complexes work in tandem, the ligand of the first haplomer-ligand complex further comprises a bio-orthogonal moiety, and the ligand of the second haplomer-ligand complex further comprises a bio-orthogonal moiety, wherein the bio-orthogonal moiety of the first haplomer-ligand complex is reactable with the bio-orthogonal moiety of the second haplomer-ligand complex. In some embodiments where a bottle haplomer-ligand complex work in tandem with a second haplomer-ligand complex, the ligand of the bottle haplomer-ligand complex further comprises a bio-orthogonal moiety, and the ligand of the second haplomer-ligand complex further comprises a bio-orthogonal moiety, wherein the bio-orthogonal moiety of the bottle haplomer-ligand complex is reactable with the bio-orthogonal moiety of the second haplomer-ligand complex.

A bio-orthogonal moiety includes those groups that can undergo "click" reactions between azides and alkynes, traceless or non-traceless Staudinger reactions between azides and phosphines, and native chemical ligation reactions between thioesters and thiols. Additionally, the bio-orthogonal moiety can be any of an azide, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, a quadricyclane, and derivatives thereof. Bio-orthogonal moieties of members of a set of corresponding haplomers are selected such that they will react with each other.

Multiple bio-orthogonal moieties can be used with the methods and compositions disclosed herein, some non-limiting examples include:

Azide-Alkyne "Click Chemistry"

Click chemistry is highly selective as neither azides nor alkynes react with common biomolecules under typical conditions. Azides of the form R—$N_3$ and terminal alkynes of the form R—C≡CH or internal alkynes of the form R—C≡C—R react readily with each other to produce Huisgen cycloaddition products in the form of 1,2,3-triazoles.

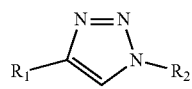

Azide-based haplomers have the substructure: R—N$_3$, where R is a chemical linker, nucleic acid recognition moiety (e.g. a portion of an oligonucleotide that is complementary to another portion of a nucleic acid molecule), or ligand. Azides and azide derivatives may be readily prepared from commercially available reagents.

Azides can also be introduced to a ligand during synthesis of the ligand. In some embodiments, an azide group is introduced into a peptide ligand by incorporation of a commercially available azide-derivatized standard amino acid or amino acid analogue during synthesis of the ligand using standard peptide synthesis methods. Amino acids may be derivatized with an azide replacing the α-amino group, affording a structure of the form:

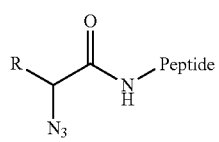

where R is a side chain of a standard amino acid or non-standard amino acid analogue.

Commercially available products can introduce azide functionality as amino acid side chains, resulting in a structure of the form:

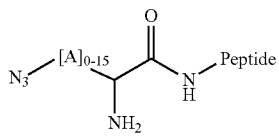

where A is any atom and its substituents in a side chain of a standard amino acid or non-standard amino acid analogue.

An azide may also be introduced into a peptide ligand after synthesis by conversion of an amine group on the peptide ligand to an azide by diazotransfer methods. Bioconjugate chemistry can also be used to join commercially available derivatized azides to chemical linkers, nucleic acid recognition moieties, or ligands that contain suitable reactive groups.

Standard alkynes can be incorporated into a haplomer by methods similar to azide incorporation. Alkyne-functionalized nucleotide analogues are commercially available, allowing alkyne groups to be directly incorporated at the time of nucleic acid recognition moiety synthesis. Similarly, alkyne-derivatized amino acid analogues may be incorporated into a ligand by standard peptide synthesis methods. Additionally, diverse functionalized alkynes compatible with bioconjugate chemistry approaches may be used to facilitate the incorporation of alkynes to other moieties through suitable functional or side groups.

Azide-Activated Alkyne "Click Chemistry"

Standard azide-alkyne chemistry reactions typically require a catalyst, such as copper(I). Since copper(I) at catalytic concentrations is toxic to many biological systems, standard azide-alkyne chemistry reactions have limited uses in living cells. Copper-free click chemistry systems based on activated alkynes circumvent toxic catalysts.

Activated alkynes often take the form of cyclooctynes, where incorporation into the cyclooctyl group introduces ring strain to the alkyne.

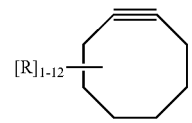

Heteroatoms or substituents may be introduced at various locations in the cyclooctyl ring, which may alter the reactivity of the alkyne or afford other alternative chemical properties in the compound. Various locations on the ring may also serve as attachment points for linking the cyclooctyne to a nucleic acid templated assembly moiety or linker. These locations on the ring or its substituents may optionally be further derivatized with accessory groups.

Multiple cyclooctynes are commercially available, including several derivatized versions suitable for use with standard bioconjugation chemistry protocols. Commercially available cyclooctyne derivatized nucleotides can aid in facilitating convenient incorporation of the ligand during nucleic acid recognition moiety synthesis.

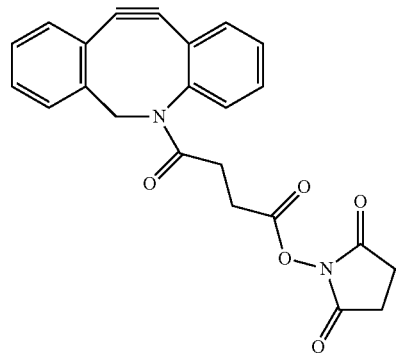 [SMILES: O=C(CCC(=O)N1Cc2ccccc2C#Cc2ccccc21)ON1C(=O)CCC1=O]

Cyclooctyne-azide based bio-orthogonal chemistry may produce templated assembly products of the general structure:

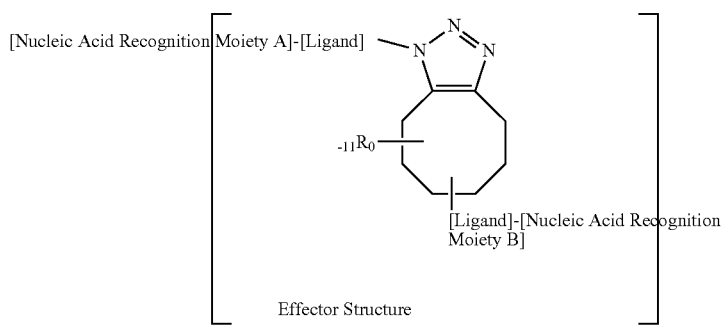

Another example:

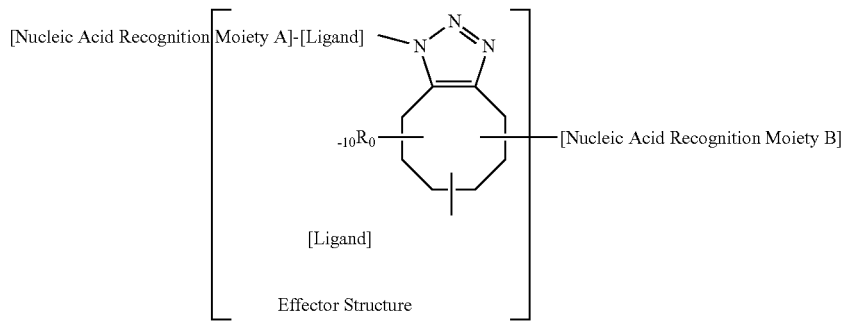

Azide-Phosphine Staudinger Chemistry

The Staudinger reduction, based on the rapid reaction between an azide and a phosphine or phosphite with loss of $N_2$, also represents a bio-orthogonal reaction. The Staudinger ligation, in which covalent links are formed between the reactants in a Staudinger reaction, is suited for use in nucleic acid templated assembly. Both non-traceless and traceless forms of the Staudinger ligation allow for a diversity of options in the chemical structure of products formed in these reactions.

Non-Traceless Staudinger Ligation

The standard Staudinger ligation is a non-traceless reaction between an azide and a phenyl-substituted phosphine such as triphenylphosphine, where an electrophilic trap substituent on the phosphine, such as a methyl ester, rearranges with the aza-ylide intermediate of the reaction to produce a ligation product linked by a phosphine oxide. An example of a Staudinger ligation product formed by haplomers A and B may have the structure:

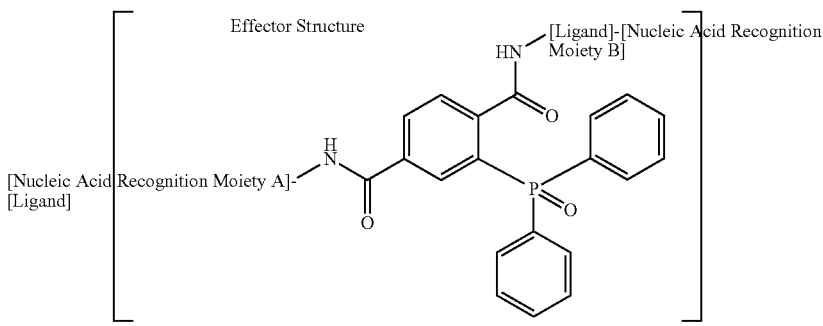

Phenyl-substituted phosphines carrying electrophilic traps can also be readily synthesized. Derivatized versions are available commercially and suitable for incorporation into haplomers:

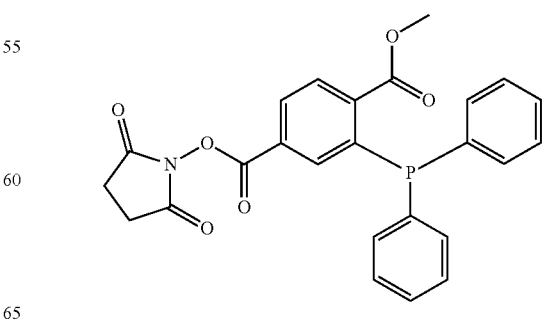

Traceless Staudinger Ligation

In some embodiments, phosphines capable of traceless Staudinger ligations may be utilized as bio-orthogonal moieties for ligands. In a traceless reaction, the phosphine serves as a leaving group during rearrangement of the aza-ylide intermediate, creating a ligation typically in the form of a native amide bond. Compounds capable of traceless Staudinger ligation generally take the form of a thioester derivatized phosphine or an ester derivatized phosphine: An exemplary ester-derivatized phosphine for traceless Staudinger ligation is:

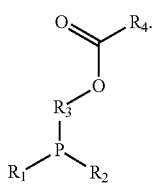

An exemplary thioester-derivatized phosphine for traceless Staudinger ligations is:

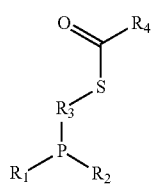

Chemical linkers or accessory groups may optionally be appended as substituents to the R groups in the above structures, providing attachment points for nucleic acid recognition moieties or for the introduction of additional functionality to the reactant.

Traceless Phosphinophenol Staudinger Ligation

Compared to the non-traceless Staudinger phenylphosphine compounds, the orientation of the electrophilic trap ester on a traceless phosphinophenol is reversed relative to the phenyl group. This enables traceless Staudinger ligations to occur in reactions with azides, generating a native amide bond in the product without inclusion of the phosphine oxide.

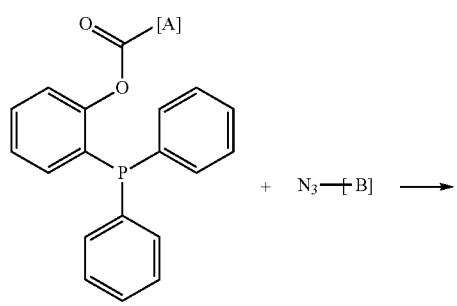

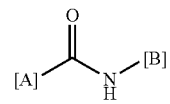

Traceless Ligation Product Effector Structure

+

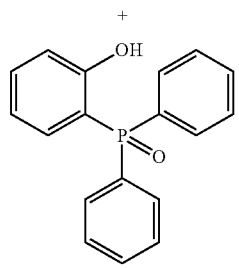

Phosphine Oxide Leaving Group

The traceless Staudinger ligation may be performed in aqueous media without organic co-solvents if suitable hydrophilic groups, such as tertiary amines, are appended to the phenylphosphine. Weisbrod and Marx describes preparation of water-soluble phosphinophenol, which may be loaded with a desired ligand containing a carboxylic acid (such as the C-terminus of a peptide) via the mild Steglich esterification using a carbodiimide such as dicyclohexylcarbodiimide (DCC) or N,N'-diisopropylcarbodiimide (DIC) and an ester-activating agent such as 1-hydroxybenzotriazole (HOBT). This approach facilitates synthesis of haplomers of the form:

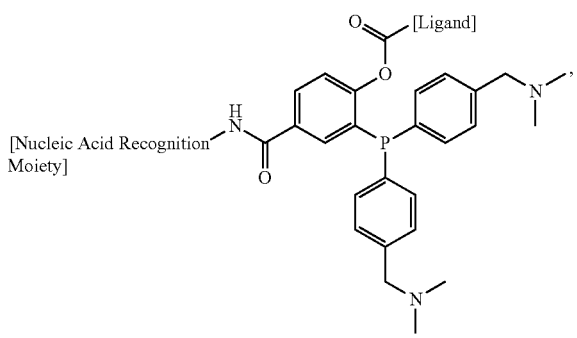

(Synlett, 2010, 5, 787-789).

Water-soluble phosphinophenol-based traceless haplomer structure.

Traceless Phosphinomethanethiol Staudinger Ligation

Phosphinomethanethiols represent an alternative to phosphinophenols for mediating traceless Staudinger ligation reactions. In general, phosphinomethanethiols possess favorable reaction kinetics compared with phosphinophenols in mediating traceless Staudinger reaction. U.S. Patent Application Publication 2010/0048866 and Tam et al., J. Am. Chem. Soc., 2007, 129, 11421-30 describe preparation of water-soluble phosphinomethanethiols of the form:

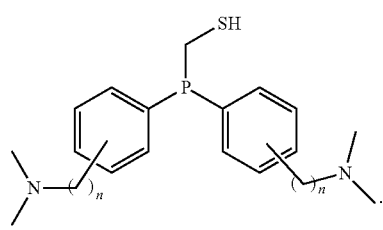

These compounds may be loaded with a peptide or other payload, in the form of an activated ester, to form a thioester suitable for use as a traceless bio-orthogonal reactive group:

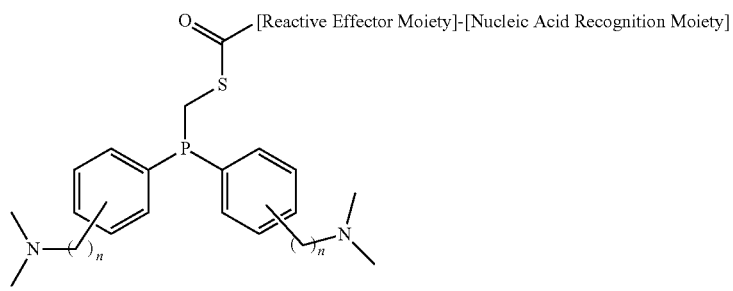

Haplomer structure based on water-soluble phosphinomethanethiol traceless Staudinger bio-orthogonal chemistry.

Native Chemical Ligation

Native chemical ligation is a bio-orthogonal approach based on the reaction between a thioester and a compound bearing a thiol and an amine. The classic native chemical ligation is between a peptide bearing a C-terminal thioester and another bearing an N-terminal cysteine, as seen below:

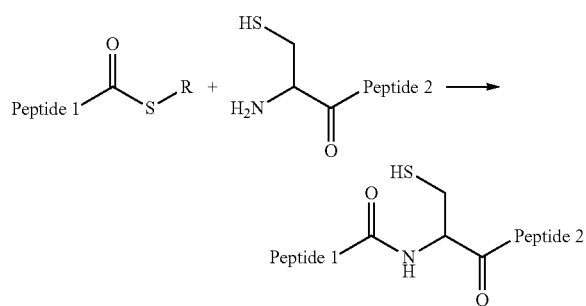

Native chemical ligation may be utilized to mediate traceless reactions producing a peptide or peptidomimetic containing an internal cysteine residue, or other thiol-containing residue if non-standard amino acids are utilized.

N-terminal cysteines may be incorporated by standard amino acid synthesis methods. Terminal thioesters may be generated by several methods known in the art, including condensation of activated esters with thiols using agents such as dicyclohexylcarbodiimide (DCC), or introduction during peptide synthesis via the use of "Safety-Catch" support resins.

Other Selectively Reactive Moieties

Any suitable bio-orthogonal reaction chemistry may be utilized for synthesis of haplomer-ligand complexes, as long as it efficiently mediates a reaction in a highly selective manner in complex biologic environments. A recently developed non-limiting example of an alternative bio-orthogonal chemistry that may be suitable is reaction between tetrazine and various alkenes such as norbornene and trans-cyclooctene, which efficiently mediates bio-orthogonal reactions in aqueous media.

Chemical linkers or accessory groups may optionally be appended as substituents to the above structures, providing attachment points for nucleic acid recognition moieties or ligands, or for the introduction of additional functionality to the reactant.

The configurations involving the ligands depicted in the Examples and Figures could be reversed. In other words, the ligand could be linked to the 3' end of the bottle haplomer-ligand complex, as long as the second haplomer-ligand complex accordingly had its ligand linked to its 5' end. The Examples provided below have the bottle haplomer-ligand complex with a 5'-linked ligand and the second haplomer-ligand complex with a 3'-linked ligand. Likewise, in this system, the bio-orthogonal moieties can be switched around. For example, instead of using the bottle haplomer-ligand complex with a 5'-hexynyl and the second haplomer-ligand complex with a 3'-azide, the bottle haplomer-ligand complex could bear the azide, and the second haplomer-ligand complex the hexynyl group.

In some embodiments, the bio-orthogonal moiety is chosen from an azide, an alkyne, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, or a quadricyclane, or any derivative thereof. In some embodiments, the bio-orthogonal moiety of the first haplomer is hexynyl and the bio-orthogonal moiety of the second haplomer is azide. In some embodiments, the bio-orthogonal moiety of the first haplomer is azide and the bio-orthogonal moiety of the second haplomer is hexynyl.

Figure 21:
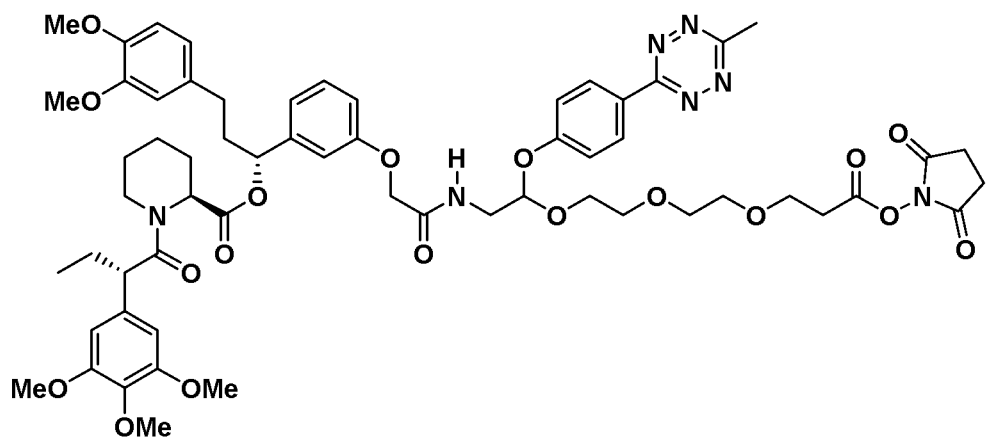
FIG. 21 shows a representative click-modified monovalent ligand with a methyltetrazine (MTZ) side-chain for mutant FKBP and oligonucleotide derivatization.
Figure 22:
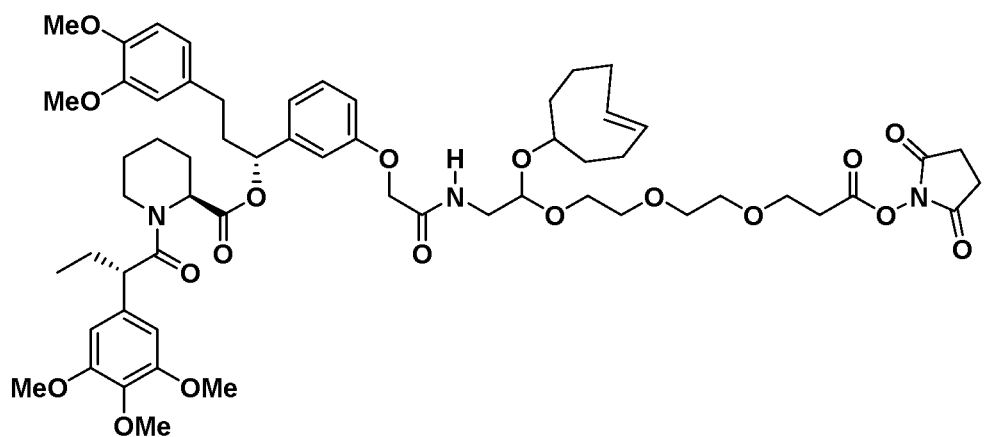
FIG. 22 shows a representative click-modified monovalent ligand with a trans-cyclooctene (TCO) side chain for mutant FKBP and oligonucleotide derivatization.

For example, some embodiments use modifications of the FKM-NHS series of compounds (FIGS. 6-8) with click-group side chains. In some embodiments, FKM-PEG3-NHS is modified at the C2 position of the PEG chain with a methyltetrazine group (FKM-PEG3-MTZ-NHS) (see, FIG. 21), or a trans-cyclooctene group (FKM-PEG3-TCO-NHS) (see, FIG. 22). When these compounds are appended to amino-labeled oligonucleotides via standard NHS chemistry to form click-modified ligand haplomers (see, FIG. 20), they can react with each other in a bio-orthogonal fashion after templating places them in close spatial proximity. FKM-PEG3-MTZ-NHS is:

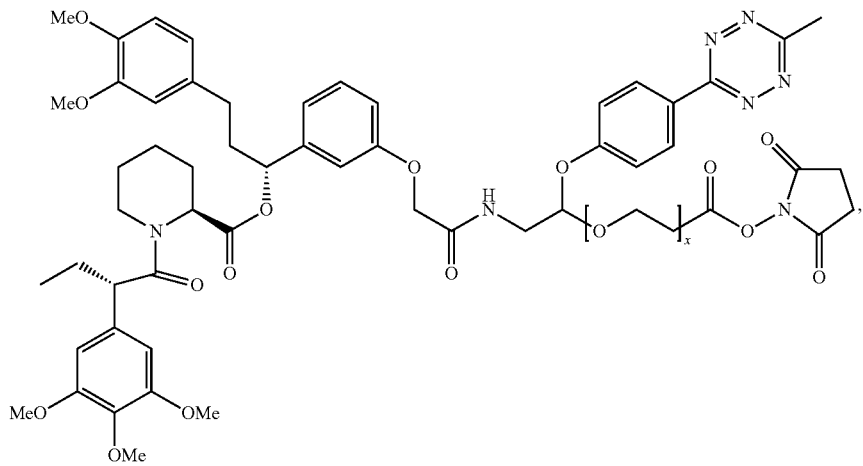

where x is from 1 to 6; and FKM-PEG3-TCO-NHS is

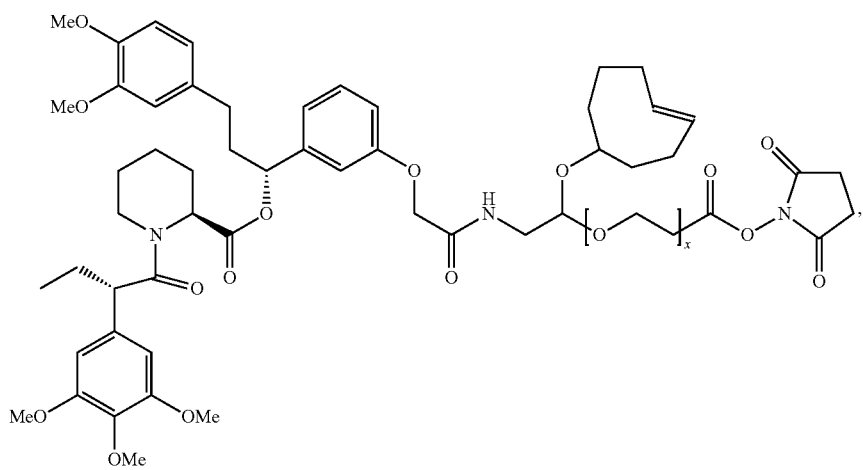

where x is from 1 to 6.

In some embodiments, the ligand of one of the first haplomer-ligand complex or second haplomer-ligand complex is an FKM monovalent ligand that is FKM-PEG3-MTZ-NHS and the ligand of the other of the first haplomer-ligand complex or second haplomer-ligand complex is an FKM monovalent ligand that is FKM-PEG3-TCO-NHS. In some embodiments, the ligand of one of the bottle haplomer-ligand complex and second haplomer-ligand complex is an FKM monovalent ligand that is FKM-PEG3-MTZ-NHS and the ligand of the other of the bottle haplomer-ligand complex and second haplomer-ligand complex is an FKM monovalent ligand that is FKM-PEG3-TCO-NHS.

The present disclosure also provides a compound having the formula:

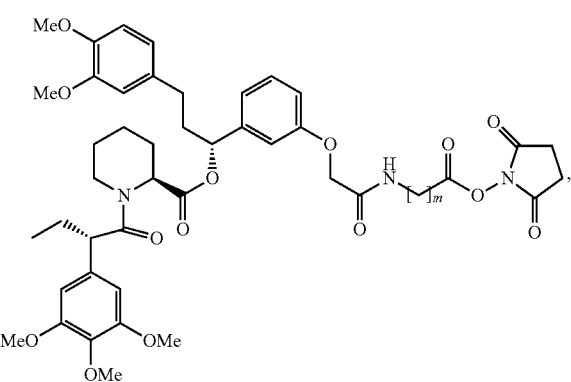

where m is from 3 to 6.

The present disclosure also provides a compound having the formula:
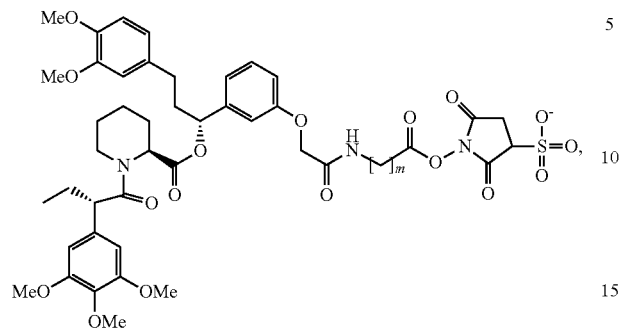
where m is from 3 to 6.
The present disclosure also provides a compound having the formula:
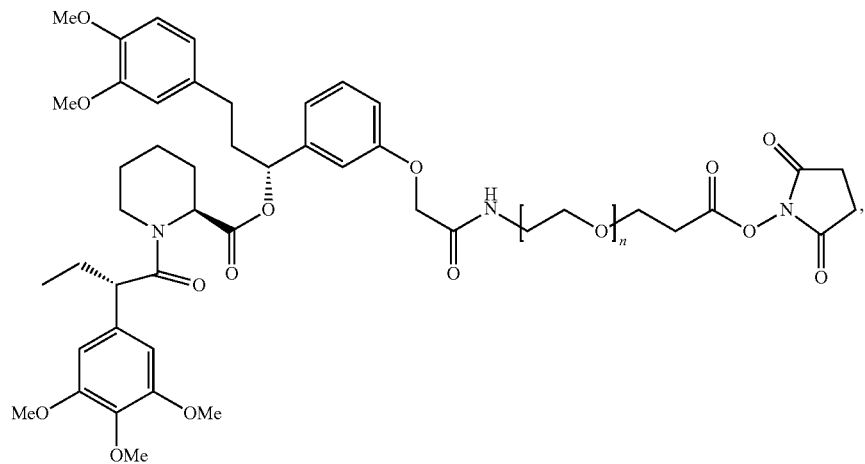
where n is from 1 to 6.
The present disclosure also provides a compound having the formula:
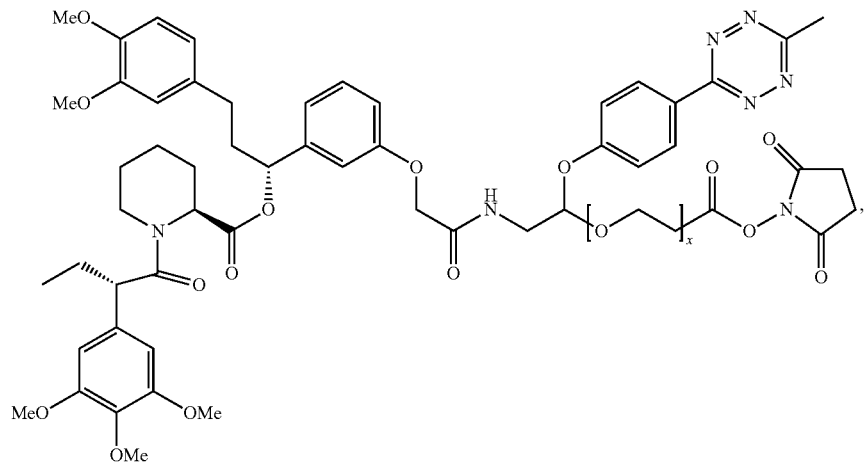
where x is from 1 to 6.

The present disclosure also provides a compound having the formula:

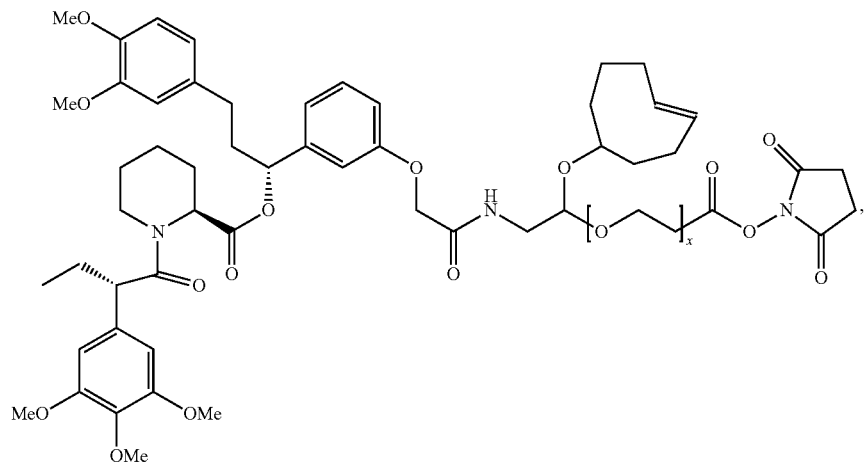

where x is from 1 to 6.

The present disclosure also provides a compound having the formula:

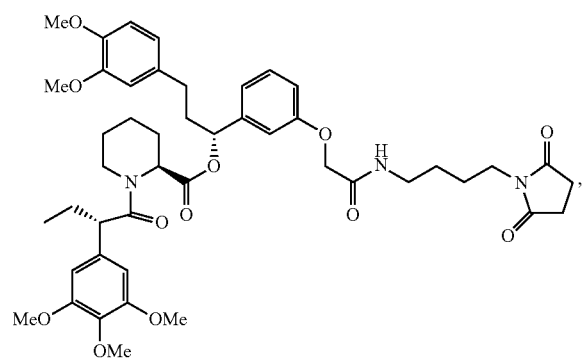 [SMILES: CC[C@H](C(=O)N1CCCC[C@H]1C(=O)O[C@H](CCc1ccc(OC)c(OC)c1)c1cccc(OCC(=O)NCCCCN2C(=O)CCC2=O)c1)c1cc(OC)c(OC)c(OC)c1]

which is MFL2.

The present disclosure also provides fusion proteins comprising a fragment of a protein of interest fused to a ligand binding domain, wherein the ligand binding domain is a ligand binding domain for small molecule ligands, or the ligand binding domain is an interactive protein domain.

In some embodiments, the ligand binding domain is a ligand binding domain for small molecule ligands. In some embodiments, the ligand binding domain is an FKBP domain or an FRB domain. In some embodiments, the FKBP domain is a mutant FKBP domain. In some embodiments, the mutant FKBP domain is the F36V FKBP mutant domain comprising the amino acid sequence GVQVETISPGDGRTFPKRGQTCVVHYTGMLEDGKK VDSSRDRNKP FKFMLGKQEVIR-GWEEGVAQMSVGQRAKLTISPDYAYGATGHPGIIP-PHATLVFDVELL KLE (SEQ ID NO:14) or MGVQVETISPGDGRTFPKRGQTCVVHYTGMLEDGK KVDSSRD RNKPFKFMLGKQEVIR-GWEEGVAQMSVGQRAKLTISPDYAYGATGHPGIIP-PHATLVFD VELLKLE (SEQ ID NO:15).

In some embodiments, the ligand binding domain is an interactive protein domain. In some embodiments, the interactive protein domain comprises less than 100 amino acid residues. In some embodiments, the interactive protein domain is a leucine zipper domain. In some embodiments, the interactive protein domain is a c-jun domain, a c-fos domain, a c-myc domain, a c-max domain, an NZ domain, or a CZ domain.

In some embodiments, the interactive protein domain is fused to the N-terminus of the protein of interest. In some embodiments, the interactive protein domain is fused to the C-terminus of the protein of interest.

In some embodiments, the NZ domain comprises the amino acid sequence ALKKELQANKKELAQLK-WELQALKKELAQ (SEQ ID NO:10), and the CZ domain comprises the amino acid sequence EQLEKKLQALEKKLAQLEWKNQALEKKLAQ (SEQ ID NO:11).

In some embodiments, the c-jun domain comprises the amino acid sequence

```
                                           (SEQ ID NO: 1)
CSGGASLERIARLEEKVKTLKAQNSELASTANMLREQVAQLKQKGAP, (SEQ ID NO: 4)
CSGGASLERIARLEEKVKSFKAQNSENASTANMLREQVAQLKQKGAP,
or (SEQ ID NO: 16)
ASLERIARLEEKVKSFKAQNSENASTANMLREQVAQLKQKGAP.
```

In some embodiments, the c-jun domain comprises the amino acid sequence

```
                                           (SEQ ID NO: 2)
SGASLERIARLEEKVKTLKAQNSELASTANMLREQVAQLKQKGAPSGGC
or (SEQ ID NO: 5)
SGASLERIARLEEKVKSFKAQNSENASTANMLREQVAQLKQKGAPSGGC.
```

In some embodiments, the c-Fos domain comprises the amino acid sequence

```
                                          (SEQ ID NO: 3)
   ASRELTDTLQAETDQLEDEKSALQTEIANLLKEKEKLEGAP
   or
```

(SEQ ID NO: 13)
SGASRELTDTLQAETDQLEDEKSALQTEIANLLKEKEKLEGAP.

In some embodiments, the fusion protein comprises a linker between the protein of interest and the ligand binding domain. In some embodiments, the linker is a Ser/Gly linker, a Poly-Asparagine linker, or a linker comprising the amino acid sequence AGSSAAGSGS (SEQ ID NO: 17). In some embodiments, the Poly-Asparagine linker comprises from about 8 to about 16 asparagine residues. In some embodiments, the Ser/Gly linker comprises GGGSGGGSGGGS GGGSGGG (SEQ ID NO:18), GGSGGGSGGGSGGGSGGGSGGG (SEQ ID NO:19), GGSGGGSGGGSGGGSGGGSGGGSGGG (SEQ ID NO:20), SGGGGSGGGGSGGGG (SEQ ID NO:21), SGGGGSGGGGSGGGGSGGGG (SEQ ID NO:22), SGGGGSGGGGSGGGGSGG GGSGGGG (SEQ ID NO:23), SGGGS (SEQ ID NO:24), SGSG (SEQ ID NO:25), SGGGGS (SEQ ID NO:26), or SGSGG (SEQ ID NO:27).

The protein of interest, whose fragments are brought together via their respective fusion to the respective ligand binding domain, can be any desired protein capable of folding together or dimerization.

In some embodiments, the protein of interest may trigger activity by acting within a target compartment (for example, within a cell), at the surface of a target compartment (for example, at the cell surface), in the vicinity of the target compartment (for example, when the effector structure is actively exported from the cell, leaks from the cell, or released upon cell death), or diffuse or be carried to a distant region of the sample to trigger a response. In some embodiments, the protein of interest can be targeted to their active sites by incorporation of targeting groups in the templated assembly product. Examples of targeting groups include, but are not limited to, endoplasmic reticulum transport signals, golgi apparatus transport signals, nuclear transport signals, mitochondrial transport signals, ubiquitination motifs, other proteosome targeting motifs, or glycosylphosphatidylinositol anchor motifs. Targeting groups may be introduced by their incorporation into a haplomer moiety, chemical linker, or accessory group during synthesis, or may be generated during the ligation reaction.

In some embodiments, the protein of interest can be presented on the surface of a target compartment. In some embodiments, the protein of interest can be presented on the surface of a cell as a ligand bound to a major histocompatibility complex molecule.

In some embodiments, the protein of interest can be an endogenous peptide, and their analogue, or a completely synthetic structure which is a target for agents such as antibodies. Because the availability of target nucleic acid molecules can limit production of active proteins of interest, it may be desirable to have proteins of interest that exert activity when present at low levels.

In some embodiments, killing or growth inhibition of target cells can be induced by direct interaction with cytotoxic, microbicidal, or virucidal effector structures. Numerous toxic molecules known in the art can be produced. In some embodiments, the protein of interest is a toxic peptide. Examples of toxic peptides include, but are not limited to, bee melittin, conotoxins, cathelicidins, defensins, protegrins, and NK-lysin.

In some embodiments, killing or growth inhibition of target cells can be induced by pro-apoptotic proteins of interest. For example, proteins of interest include pro-apoptotic peptides, including but not limited to, prion protein fragment 106-126 (PrP 106-126), Bax-derived minimum poropeptides associated with the caspase cascade including Bax 106-134, and pro-apoptotic peptide (KLAK-LAKKLAKLAK; SEQ ID NO:28).

In some embodiments, the protein of interest can be thrombogenic, in that it induces activation of various components of the clotting cascade of proteins, or activation of proteins, or activation and/or aggregation of platelets, or endothelial damage that can lead to a biologically active process in which a region containing pathogenic cells can be selectively thrombosed to limit the blood supply to a tumor or other pathogenic cell. These types of proteins of interest can also induce clotting, or prevent clotting, or prevent platelet activation and aggregation in and around targeted pathogenic cells.

In some embodiments, proteins of interest can mediate killing or growth inhibition of target cells or viruses by activating molecules, pathways, or cells associated with the immune system. Proteins of interest may engage the innate immune system, the adaptive immune system, and/or both.

In some embodiments, proteins of interest can mediate killing or growth inhibition of cells or viruses by stimulation of the innate immune system. In some embodiments, proteins of interest include pathogen-associated molecular patterns (PAMPs), damage-associated molecular patterns (DAMPs), and synthetic analogues thereof.

In some embodiments, the innate immune system can be engaged by proteins of interest that activate the complement system. A non-limiting example of a complement activating effector structures can be the C3a fragment of complement protein C3.

In some embodiments, proteins of interest can be natural or synthetic ligands of Toll-Like Receptors (TLR). Examples of such proteins of interest include peptide fragments of heat shock proteins (hsp) known to be TLR agonists.

In some embodiments, traceless bio-orthogonal chemistry may be used to produce the muramyl dipeptide agonist of the NOD2 receptor to activate an inflammatory response.

In some embodiments, proteins of interest can mediate killing or growth inhibition of cells or viruses by activating molecules or cells of the adaptive immune system. Unique to the adaptive immune system, molecules or cells can be engineered to recognize an extraordinary variety of structures, thus removing the constraint that the proteins of interest must be intrinsically active or bind to an endogenous protein.

In some embodiments, proteins of interest can be a ligand for an antibody or antibody fragment (including but not limited to Fab, Fv, and scFv). Traceless bio-orthogonal approaches can be used to produce a peptide or other epitope that is bound by an existing antibody, or an antibody can be developed to recognize proteins of interest created.

In some embodiments, the protein of interest is a fragment of: a cytotoxic protein, a microbicidal protein, a virucidal protein, a pro-apoptotic protein, a thrombogenic protein, a complement activating protein, a Toll-Like Receptor protein, a NOD2 receptor agonist protein, or an antibody or fragment thereof, wherein the first fragment and the second fragment dimerize or fold together.

In some embodiments, the cytotoxic protein is a bee melittin, a conotoxin, a cathelicidin, a defensin, a protegrin, or NK-lysin. In some embodiments, the pro-apoptotic protein is prion protein, a Bax-derived minimum poropeptide associated with the caspase cascade, or a pro-apoptotic peptide (KLAKLAKKLAKLAK) (SEQ ID NO:28). In some embodiments, the innate immune system stimulation protein is a pathogen-associated molecular pattern (PAMP) or a damage-associated molecular pattern (DAMP). In some embodiments, the complement activating protein is a C3a fragment of complement protein C3. In some embodiments, the Toll-Like Receptor (TLR) protein is a heat shock protein (hsp). In some embodiments, the NOD2 receptor agonist protein is muramyl dipeptide agonist. In some embodiments, the antibody fragment is an Fab, Fv, or scFv.

In some embodiments, the protein of interest is a fragment of: superfolder GFP (sfGFP), Renilla luciferase, murine dihydrofolate reductase (DHFR), S. cerevisiae ubiquitin, β-lactamase, or Herpes simplex virus type 1 thymidine kinase, wherein one fragment of the protein of interest dimerizes or folds together with the other fragment of the protein of interest.

In some embodiments, the fragment of superfolder GFP (sfGFP) comprises MRKGEELFTGVVPIL-VELDGDVNGHKFSVRGEGEGDATNGKLTLK-FICTTGKLPVPWPT LVTTLTYGVQC-FARYPDHMKQHDFFKSAMPEGYVQERTISFKDDGT YKTRAEVKFEGD TLVNRIELKGIDFKEDGNILGHK-LEYNFNSHNVYITADKQ (SEQ ID NO:29) or KNGIKAN FKIRHNVEDGSVQLADHYQQNTPIGDGPVLLPDN-HYLSTQSVLSKDPNEKRDHMVLLEF VTAAGITHGMDELYK (SEQ ID NO:30), wherein one fragment dimerizes or folds together with the other fragment.

In some embodiments, the fragment of Renilla luciferase comprises MASKVYDPEQR KRMITGPQWWARCKQMNVLDSFINYYDSEKHAE-NAVIFLHGNAASSYLWRHVPHIEP VARCI-IPDLIGMGKSGKSGNGSYRLLDHYKYLTAW-FELLNLPKKIIFVGHDWGACLAFH YSYEHQDKIKAIVHAESVVDVIESWDEWPDIEEDI-ALIKSEEGEKMVLENNFFVETMLPS KIMRKLE-PEEFAAYLEPFKEKGEVRRFTLSWPREIPLVKGG (SEQ ID NO:31) or KPDVVQIVRNYNAYLRASDDLPKM-FIESDPGFFSNAIVEGAKKFPNTEFVKVKGLHFSQ EDAPDEMGKYIKSFVERVLKNEQ (SEQ ID NO:32), wherein one fragment dimerizes or folds together with the other fragment.

In some embodiments, the fragment of murine dihydrofolate reductase (DHFR) comprises amino acids 1-105 or 106-186 thereof, wherein one fragment dimerizes or folds together with the other fragment.

In some embodiments, the fragment of S. cerevisiae ubiquitin comprises amino acids 1-34 (MQIFVKTLTGKTI-TLEVESSDTIDNVKSKIQDKE; SEQ ID NO:33) or 35-76 (GIPPDQQ RLIFAGKQLEDGRTLSDY-NIQKESTLHLVLRLRGG; SEQ ID NO:34) thereof, wherein one fragment dimerizes or folds together with the other fragment.

In some embodiments, the fragment of β-lactamase comprises amino acids 25-197 or 198-286 thereof, wherein one fragment dimerizes or folds together with the other fragment.

In some embodiments, the fragment of Herpes simplex virus type 1 thymidine kinase comprises amino acids 1-265 or 266-376 thereof, wherein one fragment dimerizes or folds together with the other fragment.

In some embodiments, there may be no pre-existing information regarding where a protein of interest may be divided for general split-protein analyses, including LD-TAPER. In such cases, inspection of the three-dimensional crystal structure of the protein may provide a number of candidate targets within surface loops and turns, away from regions directly concerned with the protein's function. Fragments arising from cleavage at a predicted target site may be screened by separate expression as fusion proteins with suitable mutually interactive leucine zippers, where protein activity is restored upon mixing of fusion proteins if the split protein targeting is successful. More rapid assays for empirically flagging suitable cleavage sites are available, including solubility assays (see, Chen et al., Protein Science, 2009, 18, 399-409), or the preferred circular permutation assay (see, Massoud et al., Nature Medicine, 2010, 16, 921-926). These assays are applicable even in the absence of structural information, but can be guided and made more efficient by structural knowledge where available. For the circular permutation assay, a tandem in-frame continuous dimer of the coding sequence of interest is initially generated, with a serine-glycine linker (such as SGGGGSGGGGSGGGG; SEQ ID NO:21) positioned between the two copies. Circularly permuted coding sequence blocks for expression are then generated from the dimer by amplification using suitable primers.

In some embodiments, the fragment of the protein of interest of a first fusion protein and the fragment of the protein of interest of a second fusion protein can dimerize or fold together. In some embodiments, a first fusion protein comprises a fragment of a protein of interest fused to a ligand binding domain for a small molecule ligand, and a second fusion protein comprises a fragment of a protein of interest fused to a ligand binding domain for a small molecule ligand. In some embodiments, a first fusion protein comprises a fragment of a protein of interest fused to an interactive protein domain, and a second fusion protein comprises a fragment of a protein of interest fused to an interactive protein domain.

In some embodiments, the interactive protein domain of a first fusion protein is fused to the N-terminus of the fragment of the protein of interest, and the interactive protein domain of a second fusion protein is fused to the N-terminus of the fragment of the protein of interest; or the interactive protein domain of a first fusion protein is fused to the C-terminus of the fragment of the protein of interest, and the interactive protein domain of a second fusion protein is fused to the C-terminus of the fragment of the protein of interest; or the interactive protein domain of one of the first fusion protein and second fusion protein is fused to the N-terminus of the fragment of the protein of interest, and the interactive protein domain of the other of the first fusion protein and second fusion protein is fused to the C-terminus of the fragment of the protein of interest.

In some embodiments, both the first fusion protein and second fusion protein comprise a linker between the protein of interest and the ligand binding domain. In some embodiments, each linker is, independently, a Ser/Gly linker, a Poly-Asparagine linker, or a linker comprising the amino acid sequence AGSSAAGSGS (SEQ ID NO:17), as described herein.

The present disclosure also provides compositions or kits comprising any one or more of: the haplomer-ligand complexes, the bottle haplomer-ligand complexes, and the fusion proteins described herein.

In some embodiments, the composition or kit comprises: a first haplomer-ligand complex described herein comprising a small molecule ligand; a second haplomer-ligand complex described herein comprising a small molecule ligand; a first fusion protein comprising a fragment of a protein of interest fused to a ligand binding domain for a small molecule ligand; and a second fusion protein comprising a fragment of a protein of interest fused to a ligand binding domain for a small molecule ligand; wherein: i) the ligand of the first haplomer-ligand complex is linked to the 5' terminus of the polynucleotide of the first haplomer-ligand complex; ii) the ligand of the second haplomer-ligand complex is linked to the 3' terminus of the polynucleotide of the second haplomer-ligand complex; iii) the polynucleotide of the first haplomer-ligand complex is substantially complementary to a target nucleic acid molecule; iv) the polynucleotide of the second haplomer-ligand complex is substantially complementary to the target nucleic acid molecule at a site in spatial proximity to the polynucleotide of the first haplomer-ligand complex; v) the ligand of the first haplomer-ligand complex and the ligand binding domain of the first fusion protein can interact; vi) the ligand of the second haplomer-ligand complex and the ligand binding domain of the second fusion protein can interact; and vii) the fragment of the protein of interest of the first fusion protein and the fragment of the protein of interest of the second fusion protein can dimerize or fold together.

In some embodiments, the composition or kit comprises: a first haplomer-ligand complex comprising of a ligand that is an interactive protein domain, a second haplomer-ligand complex comprising of a ligand that is an interactive protein domain: a first fusion protein comprising a fragment of a protein of interest fused to an interactive protein domain; and a second fusion protein comprising a fragment of a protein of interest fused to an interactive protein domain; wherein: i) the ligand of the first haplomer-ligand complex is linked to the 5' terminus of the polynucleotide of the first haplomer-ligand complex; ii) the ligand of the second haplomer-ligand complex is linked to the 3' terminus of the polynucleotide of the second haplomer-ligand complex; iii) the polynucleotide of the first haplomer-ligand complex is substantially complementary to a target nucleic acid molecule; iv) the polynucleotide of the second haplomer-ligand complex is substantially complementary to the target nucleic acid molecule at a site in spatial proximity to the polynucleotide of the first haplomer-ligand complex; v) the ligand of the first haplomer-ligand complex and the ligand binding domain of the first fusion protein can interact; vi) the ligand of the second haplomer-ligand complex and the ligand binding domain of the second fusion protein can interact; and vii) the fragment of the protein of interest of the first fusion protein and the fragment of the protein of interest of the second fusion protein can dimerize or fold together.

In some embodiments, the composition or kit comprises: a first bottle haplomer-ligand complex as described herein comprising a small molecule ligand; a second haplomer-ligand complex described herein comprising a small molecule ligand, wherein the second haplomer-ligand complex comprises a nucleotide portion that is substantially complementary to the stem portion of the bottle haplomer-ligand complex that is linked to the ligand of the bottle haplomer-ligand complex; a first fusion protein a fragment of a protein of interest fused to a ligand binding domain for a small molecule ligand; and a second fusion protein a fragment of a protein of interest fused to a ligand binding domain for a small molecule ligand; wherein: i) the ligand of the first bottle haplomer-ligand complex and the ligand binding domain of the first fusion protein can interact; ii) the ligand of the second haplomer-ligand complex and the ligand binding domain of the second fusion protein can interact; and iii) the fragment of the protein of interest of the first fusion protein and the fragment of the protein of interest of the second fusion protein can dimerize or fold together.

In some embodiments, the composition or kit comprises: a first bottle haplomer-ligand complex described herein comprising a ligand that is an interactive protein domain; a second haplomer-ligand complex comprising of a ligand that is an interactive protein domain, wherein the second haplomer-ligand complex comprises a nucleotide portion that is substantially complementary to the stem portion of the bottle haplomer-ligand complex that is linked to the ligand of the bottle haplomer-ligand complex; a first fusion protein comprising a fragment of a protein of interest fused to an interactive protein domain; and a second fusion protein comprising a fragment of a protein of interest fused to an interactive protein domain; wherein: i) the ligand of the first bottle haplomer-ligand complex and the ligand binding domain of the first fusion protein can interact; ii) the ligand of the second haplomer-ligand complex and the ligand binding domain of the second fusion protein can interact; and iii) the fragment of the protein of interest of the first fusion protein and the fragment of the protein of interest of the second fusion protein can dimerize or fold together.

The present disclosure also provides methods of using the any of the haplomer-ligand complexes described herein in combination with the fusion proteins described herein to produce a dimerized or folded protein.

In some embodiments, the method comprises: a) contacting a target nucleic acid molecule with a first haplomer-ligand complex comprising a small molecule ligand; b) contacting the target nucleic acid with a second haplomer-ligand complex comprising a small molecule ligand; c) contacting the first haplomer-ligand complex with a first fusion protein that comprises a ligand binding domain for a small molecule ligand; and d) contacting the second haplomer-ligand complex with a second fusion protein that comprises a ligand binding domain for a small molecule ligand; wherein: i) the ligand of the first haplomer-ligand complex is linked to the 5' terminus of the polynucleotide of the first haplomer-ligand complex; ii) the ligand of the second haplomer-ligand complex is linked to the 3' terminus of the polynucleotide of the second haplomer-ligand complex; iii) the polynucleotide of the first haplomer-ligand complex is substantially complementary to a target nucleic acid molecule; iv) the polynucleotide of the second haplomer-ligand complex is substantially complementary to the target nucleic acid molecule at a site in spatial proximity to the polynucleotide of the first haplomer-ligand complex; v) the ligand of the first haplomer-ligand complex and the ligand binding domain of the first fusion protein can interact; and vi) the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

In some embodiments, the method comprises: a) contacting a target nucleic acid molecule with a first haplomer-ligand complex comprising a ligand that is an interactive protein domain; b) contacting the target nucleic acid with a second haplomer-ligand complex comprising a ligand that is an interactive protein domain; c) contacting the first haplomer-ligand complex with a first fusion protein that comprises a fragment of a protein of interest fused to an interactive protein domain; and d) contacting the second haplomer-ligand complex with a second fusion protein that comprises a fragment of a protein of interest fused to an interactive protein domain; wherein: i) the ligand of the first haplomer-ligand complex is linked to the 5' terminus of the polynucleotide of the first haplomer-ligand complex; ii) the ligand of the second haplomer-ligand complex is linked to the 3' terminus of the polynucleotide of the second haplomer-ligand complex: iii) the polynucleotide of the first haplomer-ligand complex is substantially complementary to a target nucleic acid molecule; iv) the polynucleotide of the second haplomer-ligand complex is substantially complementary to the target nucleic acid molecule at a site in spatial proximity to the polynucleotide of the first haplomer-ligand complex; v) the ligand of the first haplomer-ligand complex and the ligand binding domain of the first fusion protein can interact; and vi) the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

In some embodiments, the polynucleotide of the first haplomer-ligand complex is complementary to the polynucleotide of the second haplomer-ligand complex. In some embodiments, the polynucleotide of the first haplomer-ligand complex binds to the target nucleic acid molecule in spatial proximity to the binding of the polynucleotide of the second haplomer-ligand complex to the target nucleic acid molecule. In some embodiments, the ligand of the first haplomer-ligand complex is linked to the 5' terminus of the polynucleotide of the first haplomer-ligand complex, and the polynucleotide of the first haplomer-ligand complex is complementary to a portion of the nucleic acid target 5' adjacent to a stem-loop structure; and the ligand of the second haplomer-ligand complex is linked to the 3' terminus of the polynucleotide of the second haplomer-ligand complex, and the polynucleotide of the second haplomer-ligand complex is complementary to a portion of the nucleic acid target 3' adjacent to the stem-loop structure. In some embodiments, the ligand of the first haplomer-ligand complex is linked to the 3' terminus of the polynucleotide of the first haplomer-ligand complex, and the polynucleotide of the first haplomer-ligand complex is complementary to a 5' portion of a loop structure of a stem-loop structure of the nucleic acid target, wherein the 5' portion of the loop structure is adjacent to the stem region of the stem-loop structure; and the ligand of the second haplomer-ligand complex is linked to the 5' terminus of the polynucleotide of the second haplomer-ligand complex, and the polynucleotide of the second haplomer-ligand complex is complementary to a 3' portion of the loop structure of the stem-loop structure of the nucleic acid target, wherein the 3' portion of the loop structure is adjacent to the stem region of the stem-loop structure.

In some embodiments, the method comprises: a) contacting a target nucleic acid molecule with a complex formed by the interaction of a first haplomer-ligand complex comprising a small molecule ligand with a first fusion protein that comprises a ligand binding domain for a small molecule ligand, wherein the ligand of the first haplomer-ligand complex is linked to the 5' terminus of the polynucleotide of the first haplomer-ligand complex, and wherein the ligand of the first haplomer-ligand complex interacts with the ligand binding domain of the first fusion protein; and b) contacting the target nucleic acid molecule with a complex formed by the interaction of a second haplomer-ligand complex comprising a small molecule ligand with a second fusion protein that comprises a ligand binding domain for a small molecule ligand, wherein the ligand of the second haplomer-ligand complex is linked to the 5' terminus of the polynucleotide of the second haplomer-ligand complex, and wherein the ligand of the second haplomer-ligand complex interacts with the ligand binding domain of the second fusion protein; thereby resulting in the folding or dimerization of the fragment of the protein of interest of the first fusion protein with the fragment of the protein of interest of the second fusion protein.

In some embodiments, the method comprises: a) contacting a target nucleic acid molecule with a complex formed by the interaction of a first haplomer-ligand complex comprising a ligand that is an interactive protein domain with a first fusion protein that comprises a fragment of a protein of interest fused to an interactive protein domain, wherein the ligand of the first haplomer-ligand complex is linked to the 5' terminus of the polynucleotide of the first haplomer-ligand complex, and wherein the ligand of the first haplomer-ligand complex interacts with the ligand binding domain of the first fusion protein; and b) contacting the target nucleic acid molecule with a complex formed by the interaction of a second haplomer-ligand complex comprising a ligand that is an interactive protein domain with a second fusion protein that comprises a fragment of a protein of interest fused to an interactive protein domain, wherein the ligand of the second haplomer-ligand complex is linked to the 5' terminus of the polynucleotide of the second haplomer-ligand complex, and wherein the ligand of the second haplomer-ligand complex interacts with the ligand binding domain of the second fusion protein; thereby resulting in the folding or dimerization of the fragment of the protein of interest of the first fusion protein with the fragment of the protein of interest of the second fusion protein.

In some embodiments, the polynucleotide of the first haplomer-ligand complex is complementary to the polynucleotide of the second haplomer-ligand complex. In some embodiments, the polynucleotide of the first haplomer-ligand complex binds to the target nucleic acid molecule in spatial proximity to the binding of the polynucleotide of the second haplomer-ligand complex to the target nucleic acid molecule. In some embodiments, the ligand of the first haplomer-ligand complex is linked to the 5' terminus of the polynucleotide of the first haplomer-ligand complex, and the polynucleotide of the first haplomer-ligand complex is complementary to a portion of the nucleic acid target 5' adjacent to a stem-loop structure; and the ligand of the second haplomer-ligand complex is linked to the 3' terminus of the polynucleotide of the second haplomer-ligand complex, and the polynucleotide of the second haplomer-ligand complex is complementary to a portion of the nucleic acid target 3' adjacent to the stem-loop structure. In some embodiments, the ligand of the first haplomer-ligand complex is linked to the 3' terminus of the polynucleotide of the first haplomer-ligand complex, and the polynucleotide of the first haplomer-ligand complex is complementary to a 5' portion of a loop structure of a stem-loop structure of the nucleic acid target, wherein the 5' portion of the loop structure is adjacent to the stem region of the stem-loop structure; and the ligand of the second haplomer-ligand complex is linked to the 5' terminus of the polynucleotide of the second haplomer-ligand complex, and the polynucleotide of the second haplomer-ligand complex is complementary to a 3' portion of the loop structure of the stem-loop structure of the nucleic acid target, wherein the 3' portion of the loop structure is adjacent to the stem region of the stem-loop structure.

In some embodiments, the method comprises: a) contacting a target nucleic acid molecule with a bottle haplomer-ligand complex described herein comprising a small molecule ligand; b) contacting the target nucleic acid with a second haplomer-ligand complex comprising a small molecule ligand, wherein the second haplomer-ligand complex comprises a nucleotide portion that is substantially complementary to the stem portion of the bottle haplomer-ligand complex that is linked to the ligand of the bottle haplomer-ligand complex; c) contacting the bottle haplomer-ligand complex with a first fusion protein that comprises a ligand binding domain for a small molecule ligand, wherein the ligand of the bottle haplomer-ligand complex and the ligand binding domain of the first fusion protein can interact; and d) contacting the second haplomer-ligand complex with a second fusion protein that comprises a ligand binding domain for a small molecule ligand, wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

In some embodiments, the method comprises: a) contacting a target nucleic acid molecule with a bottle haplomer-ligand complex comprising a ligand that is an interactive protein domain; b) contacting the target nucleic acid with a second haplomer-ligand complex comprising a ligand that is an interactive protein domain, wherein the second haplomer-ligand complex comprises a nucleotide portion that is substantially complementary to the stem portion of the bottle haplomer-ligand complex that is linked to the ligand of the bottle haplomer-ligand complex; c) contacting the bottle haplomer-ligand complex with a first fusion protein that comprises a fragment of a protein of interest fused to an interactive protein domain, wherein the ligand of the bottle haplomer-ligand complex and the ligand binding domain of the first fusion protein can interact; and d) contacting the second haplomer-ligand complex with a second fusion protein that comprises a fragment of a protein of interest fused to an interactive protein domain, wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

In some embodiments, the method comprises: a) contacting a target nucleic acid molecule with a bottle haplomer-ligand complex comprising a small molecule ligand; b) contacting the target nucleic acid molecule with a second haplomer-ligand complex comprising a small molecule ligand, wherein the second haplomer-ligand complex comprises a nucleotide portion that is substantially complementary to the stem portion of the bottle haplomer-ligand complex that is linked to the ligand of the bottle haplomer-ligand complex; c) contacting the bottle haplomer-ligand complex with a first fusion protein that comprises a ligand binding domain for a small molecule ligand, wherein the ligand of the bottle haplomer-ligand complex and the ligand binding domain of the first fusion protein can interact; and d) contacting the second haplomer-ligand complex with a second fusion protein that comprises a ligand binding domain for a small molecule ligand, wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

In some embodiments, the method comprises: a) contacting a target nucleic acid molecule with a bottle haplomer-ligand complex comprising a ligand that is an interactive protein domain; b) contacting the target nucleic acid molecule with a second haplomer-ligand complex comprising a ligand that is an interactive protein domain, wherein the second haplomer-ligand complex comprises a nucleotide portion that is substantially complementary to the stem portion of the bottle haplomer-ligand complex that is linked to the ligand of the bottle haplomer-ligand complex; c) contacting the bottle haplomer-ligand complex with a first fusion protein that comprises a fragment of a protein of interest fused to an interactive protein domain, wherein the ligand of the bottle haplomer-ligand complex and the ligand binding domain of the first fusion protein can interact; and d) contacting the second haplomer-ligand complex with a second fusion protein that comprises a fragment of a protein of interest fused to an interactive protein domain, wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

The present disclosure also provides methods of using any of the haplomer-ligand complexes, bottle haplomer-ligand complexes, and fusion proteins described herein to modulate a cell or cell target molecule. Administration of sets of corresponding haplomer-ligand complexes along with their corresponding fusion proteins to a mammal, or to a human, may vary according to the nature of the disease, disorder or condition sought to be treated. In some embodiments, the haplomer-ligand complexes, bottle haplomer-ligand complexes, and fusion proteins can be dispensed into a sample within a suitable vessel or chamber. In some embodiments, the sample may be dispensed into a vessel already containing the haplomer-ligand complexes, bottle haplomer-ligand complexes, and fusion proteins. In some embodiments, the haplomer-ligand complexes, bottle haplomer-ligand complexes, and fusion proteins can used in vitro or in situ. In some embodiment, the human will be in need of such treatment.

In some embodiments, the haplomer-ligand complexes, bottle haplomer-ligand complexes, and fusion proteins can be administered for templated assembly in vivo. To facilitate such treatment, prepared haplomer-ligand complexes, bottle haplomer-ligand complexes, and fusion proteins may be administered in any suitable buffer or formulation, optionally incorporating a suitable delivery agent, and contacted with the mammal or human, or sample thereof for ex vivo methods. Concentrated forms of haplomer-ligand complexes, bottle haplomer-ligand complexes, and fusion proteins may be handled separate from its counterpart haplomer-ligand complexes, bottle haplomer-ligand complexes, and fusion proteins, as product-generating reactions may occur in the absence of target nucleic acid molecule template at high concentrations. Table 1 provides guidelines for maximum acceptable concentrations of gymnotic (no delivery agent) haplomers comprised of various haplomer-ligand complexes, bottle haplomer-ligand complexes, and fusion proteins. If the haplomer-ligand complexes, bottle haplomer-ligand complexes, and fusion proteins are contacted at concentrations above these thresholds, non-templated background reactions may occur.

TABLE 1

Maximum concentrations for contact of haplomers, above which non-templated reaction levels may occur

| Bioorthogonal Reactive Chemistry | Maximum Concentration |
|---|---|
| Azide-Alkyne | <50 µM |
| Azide-Phosphine | <50 µM |
| Native Chemical Ligation | <1 mM |

Threshold concentrations of other haplomer-ligand complexes, bottle haplomer-ligand complexes, and fusion proteins may be determined empirically utilizing the templated assembly diagnostic evaluation assay disclosed.

In some embodiments, the likelihood of non-templated reactions may be reduced by administering a set of corresponding haplomer-ligand complexes, bottle haplomer-ligand complexes, and fusion proteins such that one haplomer-ligand complex is administered first, then a time delay is observed before the corresponding haplomer-ligand complex is administered. This time delay may range from one minute to days, depending on the persistence of the haplomer-ligand complex in the system.

Certain delivery agents, such as transfection reagents such as cationic lipids, polyethyleneimine, dextran-based transfectants, or others known in the art, may cause condensation of the haplomer-ligand complex. Under these circumstances, haplomer-ligand complex may be prepared separate from the corresponding reactive haplomer-ligand complex and administered to the sample separately. haplomer-ligand complex may also be administered gymnotically, dissolved in an appropriate buffer without addition of any additional delivery agent.

The haplomer-ligand complexes, bottle haplomer-ligand complexes, and fusion proteins may also be administered after formulation with a suitable delivery agent. A suitable delivery agent may enhance the stability, bioavailability, biodistribution, cell permeability, or other desirable pharmacologic property of the haplomer-ligand complexes, bottle haplomer-ligand complexes, and fusion proteins, or a combination of these properties. Delivery agents known in the art include, but are not limited to, polycationic transfection reagents, polyethyleneimine and its derivatives, DEAE-Dextran, other transfection reagents, salts, ions, buffers, solubilization agents, various viral vectors, liposomes, targeted liposomes, nanoparticles, carrier polymers, endosome disruptors, permeabilization agents, lipids, steroids, surfactants, dispersants, stabilizers, or any combination thereof.

Delivery of haplomer-ligand complexes, bottle haplomer-ligand complexes, and fusion proteins to target compartments may also be enhanced by covalent attachment of accessory groups to haplomer-ligand complexes, bottle haplomer-ligand complexes, and fusion proteins. Accessory groups that may enhance delivery may include compounds known to enhance the stability and biodistribution of compounds, such as polyethylene glycol (PEG); and enhance cell permeability of haplomers, including, but not limited to, cholesterol derivatives known in the art, endosome-disrupting agents known in the art, and cell-penetrating peptides, such as poly-cations such as poly-arginine or polylysine, peptides derived from the HIV tat protein, transportan, and peptides derived from the antennapedia protein (penetratin).

Administration of effector protein product-triggered agents, such as an antibody or other effector protein product-detecting molecule, or effector protein product-detecting cell, may also be included. The administration can be part of the templated assembly procedure. It may be administered before, during, or after administration of the haplomer-ligand complexes, bottle haplomer-ligand complexes, and fusion proteins, and by any method appropriate to the agent. In some embodiments, the effector protein product-triggered agent is administered prior to administration of the haplomer-ligand complexes, bottle haplomer-ligand complexes, and fusion proteins to facilitate triggering of activity by effector proteins as soon as they are formed and available for agent binding.

In some embodiments, multiple sets of corresponding haplomer-ligand complexes, bottle haplomer-ligand complexes, and fusion proteins may be administered in parallel. These sets of reactants may bind to multiple hybridization sites on a single target nucleic acid, or bind to different target nucleic acids, or a combination thereof. The different sets of haplomer-ligand complexes, bottle haplomer-ligand complexes, and fusion proteins may produce the same protein structure, thus increasing the level of activity generated by that protein structure by boosting its production, or the different sets of haplomer-ligand complexes, bottle haplomer-ligand complexes, and fusion proteins may produce different protein structures, thus producing multivalent activity in the sample, or a combination thereof. When multiple sets of haplomer-ligand complexes, bottle haplomer-ligand complexes, and fusion proteins are administered in parallel, ligands from different sets of haplomer-ligand complexes that have the same bio-orthogonal reactive group (or groups that do not react with each other, if different bio-orthogonal chemistries are employed for different sets of haplomer-ligand complexes) may be administered together, even at high concentrations, since they will not be reactive with each other. For example, if an azide-alkyne bio-orthogonal reactive system is employed for each set of corresponding haplomer-ligand complexes, all of the azide-containing haplomer-ligand complexes may be formulated and administered together, and all of the alkyne-containing haplomer-ligand complexes may be formulated and administered together after sufficient dilution of the azides in the sample.

Production of effector proteins by the methods described herein can yield activities, such as, inducing an immune response, programmed cell death, apoptosis, necrosis, lysis, growth inhibition, inhibition of viral infection, inhibition of viral replication, inhibition of oncogene expression, modification of gene expression, inhibition of microbial infection, and inhibition of microbe replication, as well as combinations of these biological activities.

In some embodiments, the composition administered can include two or more sets of corresponding haplomer-ligand complexes, bottle haplomer-ligand complexes, and fusion proteins that target two or more target nucleic acid molecules. Two or more target nucleic acid molecules may be found within the same gene transcript, or alternatively on distinct and separate transcripts. Two or more sets of corresponding haplomer-ligand complexes, bottle haplomer-ligand complexes, and fusion proteins recognizing distinct nucleic acid target molecules within the same cellular transcript may independently produce the same or different proteins.

The abundance of target nucleic acid molecules may also limit the amount of active protein produced by templated assembly. In some embodiments, there is an average of at least 5 copies of target nucleic acid molecules per target compartment. The dosage and concentration of the composition administered can take the availability of the target nucleic acid molecules into account.

In some embodiments, methods of delivering haplomer-ligand complexes, bottle haplomer-ligand complexes, and fusion proteins or a composition comprising one or more sets of the same to a pathogenic cell is disclosed. The methods can include administering a therapeutically effective amount of a set or multiple sets of corresponding haplomer-ligand complexes, bottle haplomer-ligand complexes, and fusion proteins compositions to the pathogenic cell. In some embodiments, the methods can also include detecting the presence or absence of the target nucleic acid molecule prior to administering the haplomer-ligand complexes, bottle haplomer-ligand complexes, and fusion proteins composition.

Pharmaceutical compositions may be administered by one of the following routes: oral, topical, systemic (e.g. transdermal, intranasal, or by suppository), or parenteral (e.g. intramuscular, subcutaneous, or intravenous injection). Compositions may take the form of tablets, pills, capsules, semisolids, powders, sustained release formulations, solutions, suspensions, elixirs, aerosols, or any other appropriate compositions; and comprise at least one compound in combination with at least one pharmaceutically acceptable excipient. Suitable excipients are well known to persons of ordinary skill in the art, and they, and the methods of formulating the compositions, may be found in such standard references as Remington: The Science and Practice of Pharmacy, A. Gennaro, ed., 20th edition, Lippincott, Williams & Wilkins, Philadelphia, Pa. Suitable liquid carriers, especially for injectable solutions, include water, aqueous saline solution, aqueous dextrose solution, and glycols.

Pharmaceutical compositions suitable for injection may include sterile aqueous solutions (where water soluble) or dispersions and sterile powders for the extemporaneous preparation of sterile injectable solutions or dispersion. In all cases, the composition should be sterile and should be fluid to the extent that easy syringeability exists. The composition should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents. In many cases, isotonic agents can be included, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the composition containing the haplomer-ligand complexes, bottle haplomer-ligand complexes, and fusion proteins in a suitable amount in an appropriate solvent with one or a combination of ingredients enumerated above. Generally, dispersions are prepared by incorporating the composition into a sterile vehicle which contains a basic dispersion medium and the required other ingredients from those enumerated above When the composition containing the haplomer-ligand complexes, bottle haplomer-ligand complexes, and fusion proteins is suitably protected, as described above, the composition can be formulated for oral administration, for example, with an inert diluent or an assimilable edible carrier. The composition and other ingredients can also be enclosed in a hard or soft shell gelatin capsule, compressed into tablets, or incorporated directly into the subject's diet. For oral therapeutic administration, the composition can be incorporated with excipients and used in the form of ingestible tablets, buccal tablets, troches, capsules, elixirs, suspensions, syrups, wafers, and the like. The percentage of the compositions and preparations can, of course, be varied. The amount of haplomer-ligand complexes, bottle haplomer-ligand complexes, and fusion proteins in such therapeutically useful compositions is such that a suitable dosage will be obtained.

It may be advantageous to formulate compositions in dosage unit form for ease of administration and uniformity of dosage. Each dosage unit form contains a predetermined quantity of the haplomer-ligand complexes, bottle haplomer-ligand complexes, and fusion proteins calculated to produce the amount of active effector product in association with a pharmaceutical carrier. The specification for the novel dosage unit forms is dependent on the unique characteristics of the targeted templated assembly composition, and the particular therapeutic effect to be achieved. Dosages are determined by reference to the usual dose and manner of administration of the ingredients.

The haplomer-ligand complexes, bottle haplomer-ligand complexes, and fusion proteins compositions may comprise pharmaceutically acceptable carriers, such that the carrier can be incorporated into the composition and administered to a patient without causing unacceptable biological effects or interacting in an unacceptable manner with other components of the composition. Such pharmaceutically acceptable carriers typically have met the required standards of toxicological and manufacturing testing, and include those materials identified as suitable inactive ingredients by the U.S. Food and Drug Administration.

The haplomer-ligand complexes, bottle haplomer-ligand complexes, and fusion proteins can also be prepared as pharmaceutically acceptable salts. Such salts can be, for example, a salt prepared from a base or an acid which is acceptable for administration to a patient, such as a mammal (e.g., salts having acceptable mammalian safety for a given dosage regime). However, it is understood that the salts covered herein are not required to be pharmaceutically acceptable salts, such as salts of the haplomers that are not intended for administration to a patient. Pharmaceutically acceptable salts can be derived from pharmaceutically acceptable inorganic or organic bases and from pharmaceutically acceptable inorganic or organic acids. In addition, when a haplomer contains both a basic moiety, such as an amine, and an acidic moiety such as a carboxylic acid, zwitterions may be formed and are included within the term "salt" as used herein. Salts derived from pharmaceutically acceptable inorganic bases can include ammonium, calcium, copper, ferric, ferrous, lithium, magnesium, manganic, manganous, potassium, sodium, and zinc salts, and the like. Salts derived from pharmaceutically acceptable organic bases can include salts of primary, secondary and tertiary amines, including substituted amines, cyclic amines, naturally-occurring amines and the like, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable inorganic acids can include salts of boric, carbonic, hydrohalic (hydrobromic, hydrochloric, hydrofluoric or hydroiodic), nitric, phosphoric, sulfamic and sulfuric acids. Salts derived from pharmaceutically acceptable organic acids can include salts of aliphatic hydroxyl acids (e.g., citric, gluconic, glycolic, lactic, lactobionic, malic, and tartaric acids), aliphatic monocarboxylic acids (e.g., acetic, butyric, formic, propionic and trifluoroacetic acids), amino acids (e.g., aspartic and glutamic acids), aromatic carboxylic acids (e.g., benzoic, p-chlorobenzoic, diphenylacetic, gentisic, hippuric, and triphenylacetic acids), aromatic hydroxyl acids (e.g., o-hydroxybenzoic, p-hydroxybenzoic, 1-hydroxynaphthalene-2-carboxylic and 3-hydroxynaphthalene-2-carboxylic acids), ascorbic, dicarboxylic acids (e.g., fumaric, maleic, oxalic and succinic acids), glucoronic, mandelic, mucic, nicotinic, orotic, pamoic, pantothenic, sulfonic acids (e.g., benzenesulfonic, camphorsulfonic, edisylic, ethanesulfonic, isethionic, methanesulfonic, naphthalenesulfonic, naphthalene-1,5-disulfonic, naphthalene-2,6-disulfonic and p-toluenesulfonic acids), xinafoic acid, and the like.

The effector proteins generated by the processes described herein (via dimerization or folding) is the trigger that drives a desired action. Some examples of desired protein activity can include, but are not limited to, inducing an immune response, programmed cell death, apoptosis, non-specific or programmed necrosis, lysis, growth inhibition, inhibition of viral infection, inhibition of viral replication, inhibition of oncogene expression, modification of gene expression, inhibition of microbial infection, and inhibition of microbe replication, as well as combinations of these biological activities. In some embodiments, the protein produced can serve as a ligand for an antibody to induce an immune response at the site of the pathogenic cells, or to localize antibody-directed therapies, such as an antibody bearing a therapeutic payload, to the site of the pathogenic cells. In some embodiments, the protein produced can modulate expression of a target gene. In some embodiments, the protein produced can regulate enzyme activity, gene/protein expression, molecular signaling, and molecular interactions.

In some embodiments involving the use of the dimerization domains FKBP or FRB, the domains were altered in specific ways to improve their performances when expressed as fusion proteins with protein fragments of interest. In particular, it was observed that both FKBP and FRB possess single cysteine residues. Many of the protein fragments of interest, including but not limited to Gaussia luciferase and heavy and light chains of immunoglobulins, themselves possess multiple cysteines which in some cases are structurally important for the formation of disulfide bonds and folding. Since only single cysteines were present in both FKBP and FRB, it could not the case that disulfide bonds were essential for the folding of the dimerization domains themselves. Accordingly, it was considered possible that the FKBP and FRB cysteines could potentially interfere with folding maturation of desired fusion proteins by formation of structurally incorrect internal cross-disulfide bonds. In turn, conservative replacement of the FKBP and FRB cysteines with alternative amino acid residues could be beneficial, provided the changes were compatible with the stabilities and ligand-binding activities of these domains. Therefore, in some embodiments, mutants of FKBP, in addition to the F36V mutation, also contained a cysteine to serine mutation (C22S). In certain other embodiments, a cysteine to alanine mutation (C22A) or a cysteine to valine mutation (C22V) may also be used. In an analogous manner, in some embodiments mutants of FRB are used with a cysteine to serine mutation (C61S), or in certain other embodiments, a cysteine to alanine mutation (C61A) or a cysteine to valine mutation (C61V).

In all cases, mutagenesis was effected in a standard fashion by amplifications of two overlapping blocks of coding sequences where one of the primers specified the desired coding sequence changes. A subsequent round of PCR enabled precise fusion of the sequence blocks, confirmed by sequencing.

The following representative embodiments are presented:

Embodiment 1

A haplomer-ligand complex comprising: a haplomer, wherein the haplomer comprises a polynucleotide that is substantially complementary to a target nucleic acid molecule; and a ligand linked to the 5' or 3' terminus of the haplomer, wherein the ligand comprises a ligand partner binding site.

Embodiment 2

The haplomer-ligand complex of embodiment 1 wherein the polynucleotide comprises DNA nucleotides, RNA nucleotides, phosphorothioate-modified nucleotides, 2-O-alkylated RNA nucleotides, halogenated nucleotides, locked nucleic acid nucleotides (LNA), peptide nucleic acids (PNA), morpholino nucleic acid analogues (morpholinos), pseudouridine nucleotides, xanthine nucleotides, hypoxanthine nucleotides, 2-deoxyinosine nucleotides, DNA analogs with L-ribose (L-DNA), Xeno nucleic acid (XNA) analogues, or other nucleic acid analogues capable of base-pair formation, or artificial nucleic acid analogues with altered backbones, or any combination thereof.

Embodiment 3

The haplomer-ligand complex of embodiment 1 or embodiment 2 wherein the ligand is a small molecule ligand or an interactive protein domain.

Embodiment 4

The haplomer-ligand complex of embodiment 3 wherein the small molecule ligand is less than about 2500 Daltons.

Embodiment 5

The haplomer-ligand complex of embodiment 4 wherein the small molecule ligand is a small molecule, a peptide having less than about 20 amino acid residues, a naturally- or artificially-modified peptide, a peptidomimetic, a glycan, an organic enzyme cofactor, or an artificially-derived small molecular ligand.

Embodiment 6

The haplomer-ligand complex of embodiment 3 wherein the small molecule ligand is an FKM monovalent ligand.

Embodiment 7

The haplomer-ligand complex of embodiment 6 wherein the FKM monovalent ligand is FKM-NHS, FKM-sulfo-NHS, FKM-PEG3-NHS, or MFL2, wherein:

FKM-NHS is

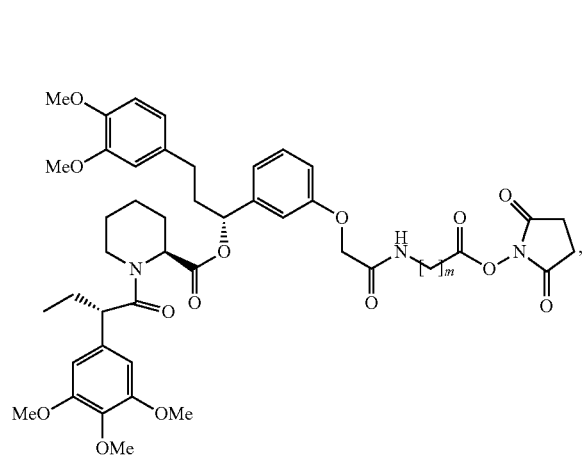

where m is from 3 to 6; FKM-sulfo-NHS is

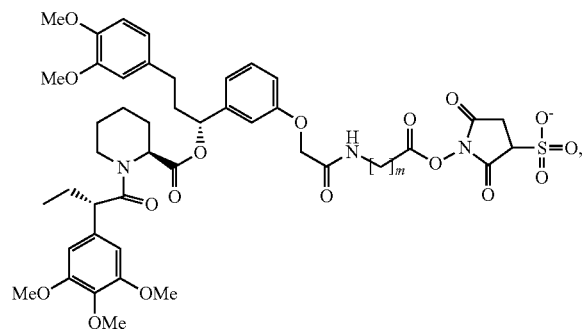

where m is from 3 to 6; FKM-PEG3-NHS is

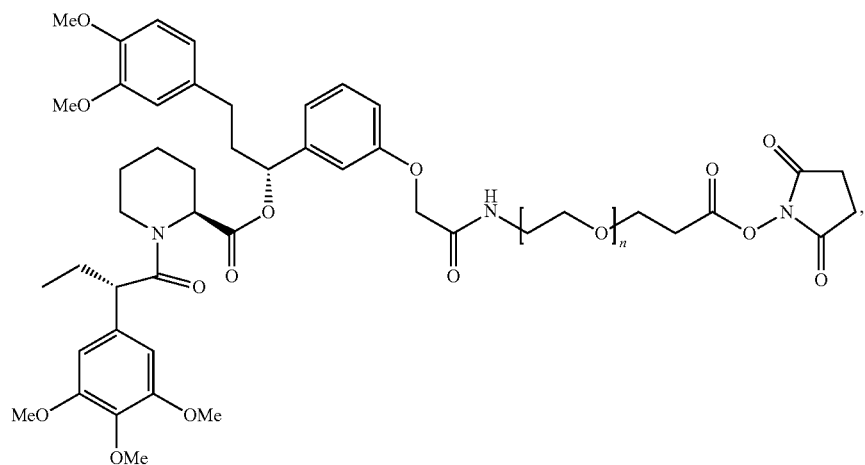

where n is from to 6; and MFL2

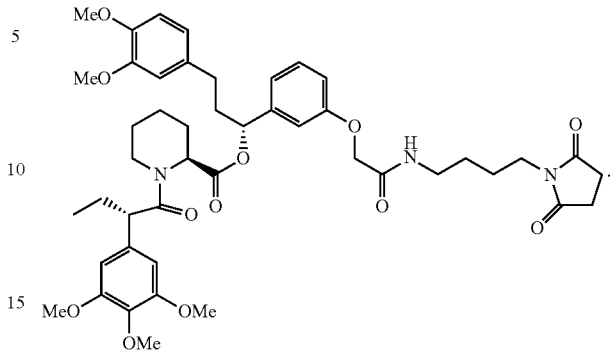

Embodiment 8

The haplomer-ligand complex of any one of embodiments 1 to 7 wherein the ligand further comprises a bio-orthogonal moiety.

Embodiment 9

The haplomer-ligand complex of embodiment 8 wherein the bio-orthogonal moiety is an azide, an alkyne, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, or a quadricyclane, or any derivative thereof.

Embodiment 10

The haplomer-ligand complex of embodiment 8 wherein the ligand is an FKM monovalent ligand chosen from FKM-PEG3-MTZ-NHS and FKM-PEG3-TCO-NHS, wherein: FKM-PEG3-MTZ-NHS is

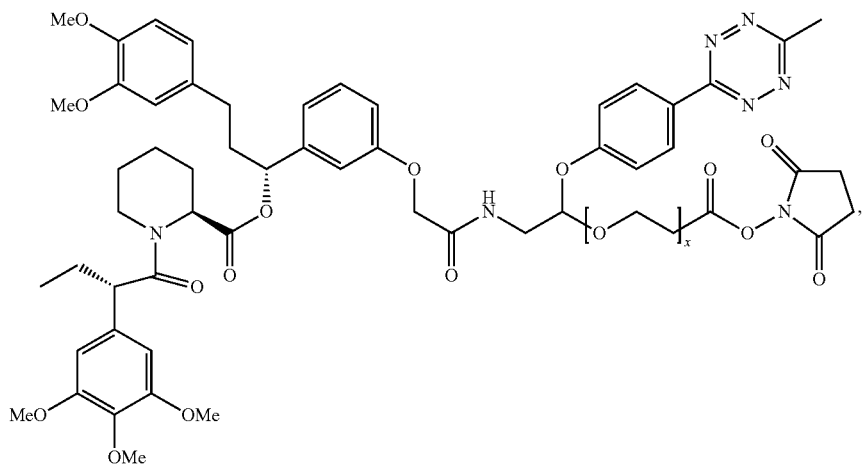

where x is from 1 to 6; and FKM-PEG3-TCO-NHS is

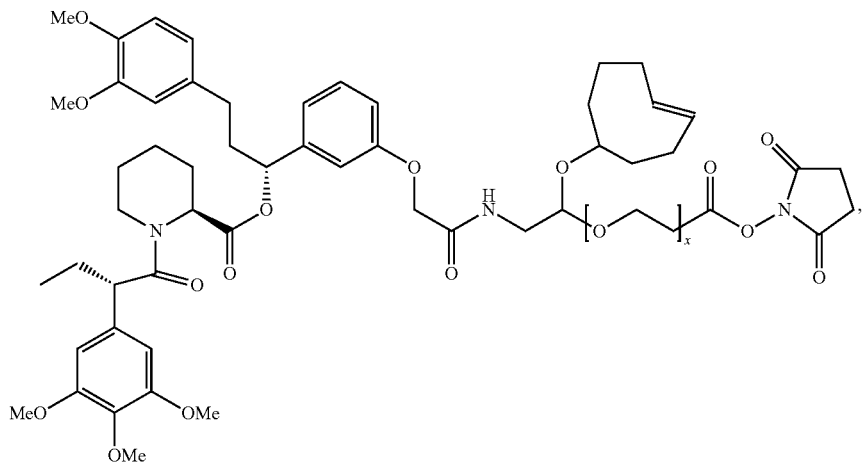

where x is from 1 to 6.

Embodiment 11

The haplomer-ligand complex of embodiment 3 wherein the interactive protein domain comprises less than 100 amino acid residues.

Embodiment 12

The haplomer-ligand complex of embodiment 11 wherein the interactive protein domain is a leucine zipper domain.

Embodiment 13

The haplomer-ligand complex of embodiment 12 wherein the interactive protein domain is a c-jun domain, a c-fos domain, a c-myc domain, a c-max domain, an NZ domain, or a CZ domain.

Embodiment 14

The haplomer-ligand complex of embodiment 13 wherein the NZ domain comprises the amino acid sequence ALKKELQANKKELAQLKWELQALKKELAQ (SEQ ID NO:10), and the CZ domain comprises the amino acid sequence EQLEKKLQALEKK LAQLEW-KNQALEKKLAQ (SEQ ID NO: 11).

Embodiment 15

The haplomer-ligand complex of embodiment 12 wherein the N-terminus of the c-jun domain is linked to the 5' or 3' terminus of the polynucleotide of the haplomer.

Embodiment 16

The haplomer-ligand complex of embodiment 15 wherein the c-jun domain comprises the amino acid sequence CSGASLERIARLEEKVKTLKAQNSELAST ANML-REQVAQLKQKGAP (SEQ ID NO:1), CSGGASLERIAR-LEEKVKSFKAQNSENAST ANMLREQVAQLKQKGAP (SEQ ID NO:4), or CSGASLERIAR-LEEKVKSFKAQNSENAST ANMLREQVAQLKQKGAP (SEQ ID NO:12).

Embodiment 17

The haplomer-ligand complex of embodiment 12 wherein the C-terminus of the c-jun domain is linked to the 5' or 3' terminus of the polynucleotide of the haplomer.

Embodiment 18

The haplomer-ligand complex of embodiment 17 wherein the c-jun domain comprises the amino acid sequence SGASLERIARLEEKVKTLKAQNSELASTANM LREQVAQLKQKGAPSGGC (SEQ ID NO:2) or SGASLE-RIARLEEKVKSFKAQNSENASTA NML-REQVAQLKQKGAPSGGC (SEQ ID NO:5).

Embodiment 19

A composition or kit comprising a first haplomer-ligand complex of embodiment 1 and a second haplomer-ligand complex of embodiment 1, wherein: the ligand of the first haplomer-ligand complex is linked to the 5' terminus of the polynucleotide of the first haplomer-ligand complex: and the ligand of the second haplomer-ligand complex is linked to the 3' terminus of the polynucleotide of the second haplomer-ligand complex.

Embodiment 20

The composition or kit of embodiment 19, wherein the polynucleotide of the first haplomer-ligand complex is substantially complementary to the polynucleotide of the second haplomer-ligand complex.

Embodiment 21

The composition or kit of embodiment 19, wherein the polynucleotide of the first haplomer-ligand complex is substantially complementary to a target nucleic acid molecule, and the polynucleotide of the second haplomer-ligand complex is substantially complementary to the target nucleic acid molecule at a site in spatial proximity to the polynucleotide of the first haplomer-ligand complex.

Embodiment 22

The composition or kit of any one of embodiments 19 to 21, wherein the polynucleotides of the first haplomer-ligand complex and second haplomer-ligand complex comprise DNA nucleotides, RNA nucleotides, phosphorothioate-modified nucleotides, 2-O-alkylated RNA nucleotides, halogenated nucleotides, locked nucleic acid nucleotides (LNA), peptide nucleic acids (PNA), morpholino nucleic acid analogues (morpholinos), pseudouridine nucleotides, xanthine nucleotides, hypoxanthine nucleotides, 2-deoxyinosine nucleotides, DNA analogs with L-ribose (L-DNA), Xeno nucleic acid (XNA) analogues, or other nucleic acid analogues capable of base-pair formation, or artificial nucleic acid analogues with altered backbones, or any combination thereof.

Embodiment 23

The composition or kit of any one of embodiments 19 to 22, wherein both ligands are small molecule ligands or both ligands are interactive protein domains.

Embodiment 24

The composition or kit of embodiment 23 wherein both small molecule ligands are less than about 2500 Daltons.

Embodiment 25

The composition or kit of embodiment 24 wherein both small molecule ligands are small molecules, peptides having less than about 20 amino acid residues, naturally- or artificially-modified peptides, peptidomimetics, glycans, organic enzyme cofactors, or artificially-derived small molecular ligands.

Embodiment 26

The composition or kit of embodiment 23 wherein both small molecule ligands are FKM monovalent ligands.

Embodiment 27

The composition or kit of embodiment 26 wherein each FKM monovalent ligand is, independently, FKM-NHS, FKM-sulfo-NHS, FKM-PEG3-NHS, or MFL2, wherein: FKM-NHS is

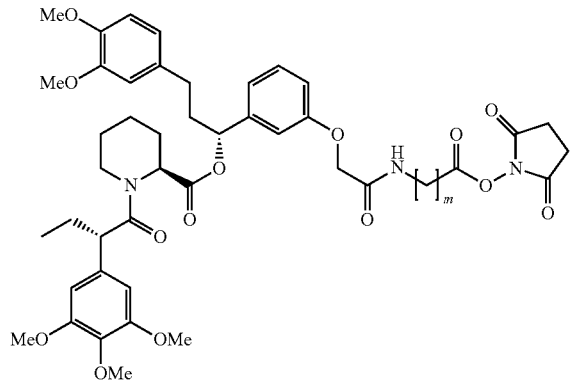

, where m is from 3 to 6; FKM-sulfo-NHS is

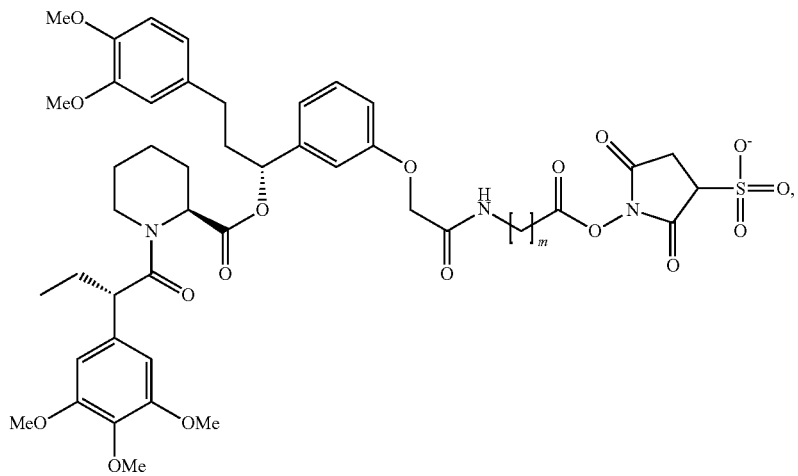

where m is from 3 to 6;
FKM-PEG3-NHS is

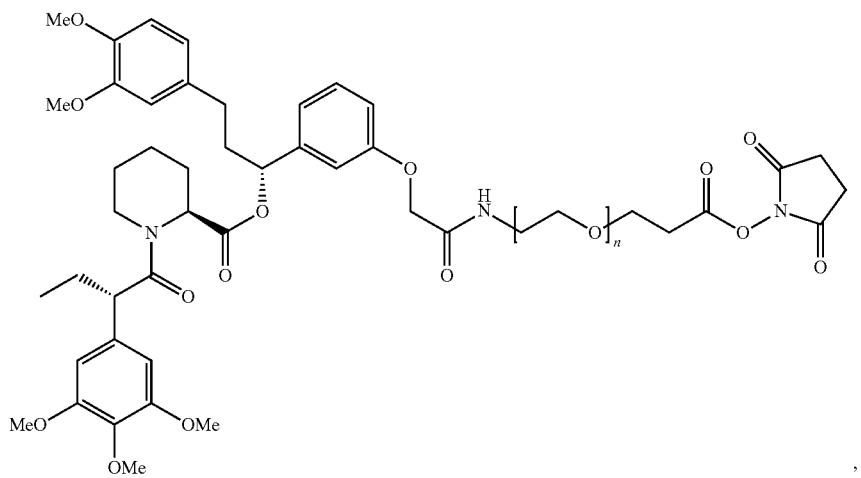

where n is from 1 to 6; and MFL2 is

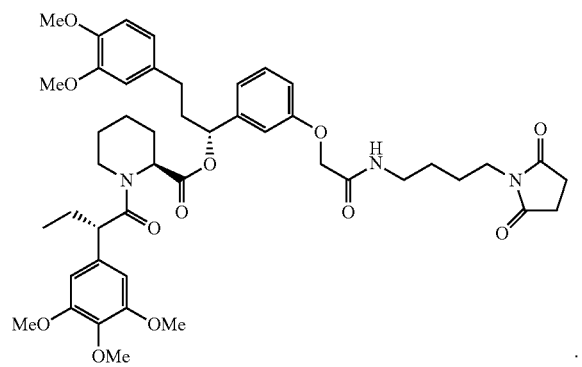 [SMILES: CC[C@H](C(=O)N1CCCC[C@H]1C(=O)O[C@H](CCc1ccc(OC)c(OC)c1)c1cccc(OCC(=O)NCCCCN2C(=O)CCC2=O)c1)c1cc(OC)c(OC)c(OC)c1]

Embodiment 28

The composition or kit of any one of embodiments 19 to 27 wherein: the ligand of the first haplomer-ligand complex further comprises a bio-orthogonal moiety; and the ligand of the second haplomer-ligand complex further comprises a bio-orthogonal moiety; wherein the bio-orthogonal moiety of the first haplomer-ligand complex is reactable with the bio-orthogonal moiety of the second haplomer-ligand complex.

Embodiment 29

The composition or kit of embodiment 28 wherein the reactable bio-orthogonal moietys are chosen from an azide, an alkyne, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, or a quadricyclane, or any derivative thereof.

Embodiment 30

The composition or kit of embodiment 28 wherein the ligand of one of the first haplomer-ligand complex or second haplomer-ligand complex is an FKM monovalent ligand that is FKM-PEG3-MTZ-NHS and the ligand of the other of the first haplomer-ligand complex or second haplomer-ligand complex is an FKM monovalent ligand that is FKM-PEG3-TCO-NHS, wherein: FKM-PEG3-MTZ-NHS is

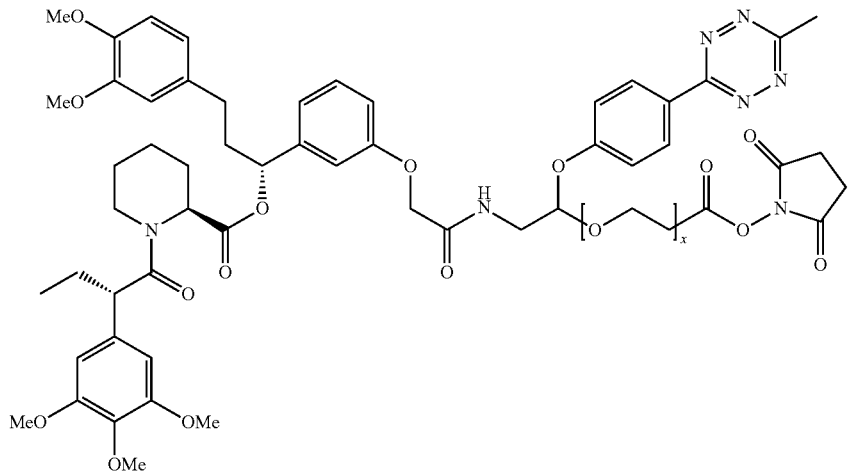

where x is from 1 to 6; and FKM-PEG3-TCO-NHS is

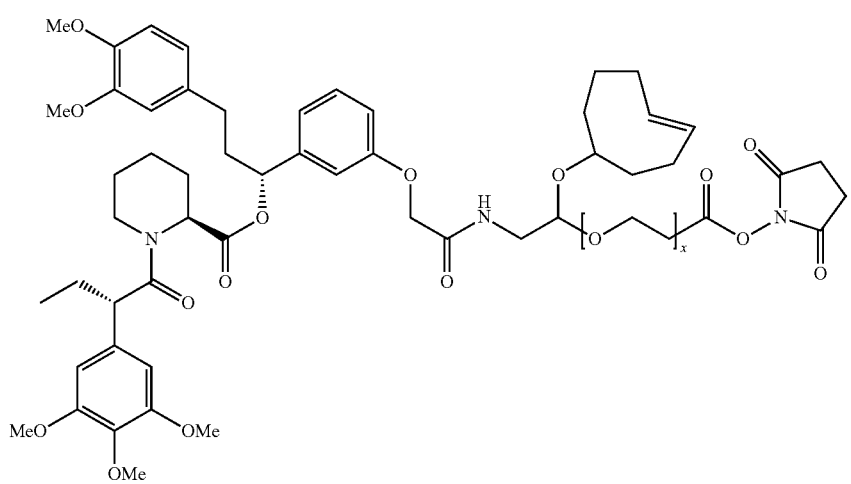

where x is from 1 to 6.

Embodiment 31

The composition or kit of embodiment 23 wherein both interactive protein domains each comprise less than 100 amino acid residues.

Embodiment 32

The composition or kit of embodiment 31 wherein both interactive protein domains are leucine zipper domains.

Embodiment 33

The composition or kit of embodiment 32 wherein each interactive protein domain is, independently, a c-jun domain, a c-fos domain, a c-myc domain, a c-max domain, an NZ domain, or a CZ domain.

Embodiment 34

The composition or kit of embodiment 33 wherein the N-terminus of the interactive protein domain of the first haplomer-ligand complex is linked to the 5' terminus of the polynucleotide of the first haplomer-ligand complex, and the N-terminus of the interactive protein domain of the second haplomer-ligand complex is linked to the 3' terminus of the polynucleotide of the second haplomer-ligand complex.

Embodiment 35

The composition or kit of embodiment 33 wherein the C-terminus of the interactive protein domain of the first haplomer-ligand complex is linked to the 5' terminus of the polynucleotide of the first haplomer-ligand complex, and the C-terminus of the interactive protein domain of the second haplomer-ligand complex is linked to the 3' terminus of the polynucleotide of the second haplomer-ligand complex.

Embodiment 36

The composition or kit of embodiment 33 wherein: the C-terminus of the interactive protein domain of the first haplomer-ligand complex is linked to the 5' terminus of the polynucleotide of the first haplomer-ligand complex, and the N-terminus of the interactive protein domain of the second haplomer-ligand complex is linked to the 3' terminus of the polynucleotide of the second haplomer-ligand complex; or the N-terminus of the interactive protein domain of the first haplomer-ligand complex is linked to the 5' terminus of the polynucleotide of the first haplomer-ligand complex, and the C-terminus of the interactive protein domain of the second haplomer-ligand complex is linked to the 3' terminus of the polynucleotide of the second haplomer-ligand complex.

Embodiment 37

The composition or kit of any one of embodiments 33 to 36 wherein the NZ domain comprises the amino acid sequence ALKKELQANKKELAQLKWELQALKKE LAQ (SEQ ID NO:10), and the CZ domain comprises the amino acid sequence EQLEKKLQAL EKKLAQLEW-KNQALEKKLAQ (SEQ ID NO: 11).

Embodiment 38

The composition or kit of any one of embodiments 33 to 36 wherein the ligand linked to the polynucleotide of the first haplomer-ligand complex is a c-jun domain, and the ligand linked to the polynucleotide of the second haplomer-ligand complex is a c-jun domain.

Embodiment 39

The composition or kit of any one of embodiments 33 to 36 wherein the c-jun domain comprises the amino acid sequence CSGGASLERIARLEEKVKTLKAQNS ELASTANMLREQVAQLKQKGAP (SEQ ID NO: 1), CSGGASLERIARLEEKVKSFKAQNS ENASTANML-REQVAQLKQKGAP (SEQ ID NO:4), or ASLERIAR-LEEKVKSFKAQNSEN ASTANMLREQVAQLKQKGAP (SEQ ID NO:16).

Embodiment 40

The composition or kit of embodiment 35 or embodiment 36 wherein the C-terminus of the c-jun domain is linked to the 5' or 3' terminus of the polynucleotides of either or both of the first haplomer-ligand complex and second haplomer-ligand complex.

Embodiment 41

The composition or kit of embodiment 40 wherein the c-jun domain comprises the amino acid sequence SGASLE-RIARLEEKVKTLKAQNSELASTANMLREQ VAQLKQKGAPSGGC (SEQ ID NO:2) or GASLERIAR-LEEKVKSFKAQNSENASTANML REQVAQLKQK-GAPSGGC (SEQ ID NO:5).

Embodiment 42

The composition or kit of any one of embodiments 33 to 36 wherein the ligand linked to the polynucleotide of the first haplomer-ligand complex is a c-jun domain or a c-myc domain, and the ligand linked to the polynucleotide of the second haplomer-ligand complex is a c-jun domain or a c-myc domain.

Embodiment 43

The composition or kit of embodiment 42 wherein the ligand linked to the polynucleotide of the first haplomer-ligand complex or second haplomer-ligand complex is a c-jun domain, and the ligand linked to the polynucleotide of the other of the first haplomer-ligand complex and second haplomer-ligand complex is a c-myc domain.

Embodiment 44

A bottle haplomer-ligand complex comprising: a) a bottle haplomer, wherein the bottle haplomer comprises a polynucleotide, wherein the polynucleotide comprises: i) a first stem portion comprising from about 10 to about 20 nucleotide bases; ii) an anti-target loop portion comprising from about 16 to about 40 nucleotide bases and having a first end to which the first stem portion is linked, wherein the anti-target loop portion is substantially complementary to a target nucleic acid molecule; and iii) a second stem portion comprising from about 10 to about 20 nucleotide bases linked to a second end of the anti-target loop portion, wherein the first stem portion is substantially complementary to the second stem portion; and b) a ligand linked to the terminal end of either the first stem portion or the second stem portion, wherein the ligand comprises a ligand partner binding site; wherein the $T_m$ of the anti-target loop portion: target nucleic acid molecule is greater than the $T_m$ of the first stem portion:second stem portion.

Embodiment 45

The bottle haplomer-ligand complex of embodiment 44 wherein the $T_m$ of the first stem portion:second stem portion subtracted from the $T_m$ of the anti-target loop portion:target nucleic acid molecule is from about 10° C. to about 40° C.

Embodiment 46

The bottle haplomer-ligand complex of embodiment 44 or embodiment 45 wherein the $T_m$ of the first stem portion: second stem portion is from about 40° C. to about 50° C.

Embodiment 47

The bottle haplomer-ligand complex of any one of embodiments 44 to 46 wherein the $T_m$ of the anti-target loop portion:target nucleic acid molecule is from about 60° C. to about 80° C.

Embodiment 48

The bottle haplomer-ligand complex of any one of embodiments 44 to 47 wherein the $T_m$ of the first stem portion:second stem portion subtracted from the $T_m$ of the anti-target loop portion:target nucleic acid molecule is from about 10° C. to about 20° C.

Embodiment 49

The bottle haplomer-ligand complex of any one of embodiments 44 to 48 wherein the first stem portion comprises from about 12 to about 18 nucleotide bases.

Embodiment 50

The bottle haplomer-ligand complex of any one of embodiments 44 to 49 wherein the anti-target loop portion comprises from about 18 to about 35 nucleotide bases.

Embodiment 51

The bottle haplomer-ligand complex of any one of embodiments 44 to 50 wherein the second stem portion comprises from about 12 to about 18 nucleotide bases.

Embodiment 52

The bottle haplomer-ligand complex of any one of embodiments 44 to 51 wherein the nucleotide bases of any one or more of the first stem portion, anti-target loop portion, and second stem portion are selected from the group consisting of DNA nucleotides, RNA nucleotides, phosphorothioate-modified nucleotides, 2-O-alkylated RNA nucleotides, halogenated nucleotides, locked nucleic acid nucleotides (LNA), peptide nucleic acids (PNA), morpholino nucleic acid analogues (morpholinos), pseudouridine nucleotides, xanthine nucleotides, hypoxanthine nucleotides, 2-deoxyinosine nucleotides, DNA analogs with L-ribose (L-DNA), Xeno nucleic acid (XNA) analogues, or other nucleic acid analogues capable of base-pair formation, or artificial nucleic acid analogues with altered backbones, or any combination thereof.

Embodiment 53

The bottle haplomer-ligand complex of any one of embodiments 44 to 52 further comprising a linker between any one or more of the first stem portion and the anti-target loop portion, between the anti-target loop portion and the second stem portion, and between the second stem portion and the reactive effector moiety.

Embodiment 54

The bottle haplomer-ligand complex of embodiment 53 wherein the linker is selected from the group consisting of an alkyl group, an alkenyl group, an amide, an ester, a thioester, a ketone, an ether, a thioether, a disulfide, an ethylene glycol, a cycloalkyl group, a benzyl group, a heterocyclic group, a maleimidyl group, a hydrazone, a urethane, azoles, an imine, a haloalkyl, and a carbamate, or any combination thereof.

Embodiment 55

The bottle haplomer-ligand complex of any one of embodiments 44 to 54 wherein the anti-target loop portion further comprises an internal hinge region, wherein the hinge region comprises one or more nucleotides that are not complementary to the target nucleic acid molecule.

Embodiment 56

The bottle haplomer-ligand complex of embodiment 55 wherein the hinge region comprises from about 1 nucleotide to about 6 nucleotides.

Embodiment 57

The bottle haplomer-ligand complex of any one of embodiments 44 to 56 which comprises the nucleotide sequence 5'-ACTCGAGACGTCTCCTTGTCTTTGCTTTT CTTCAGGACACAGTGGCGAGACGTCTCGAGT-3' (SEQ ID NO:6) or 5'-ACTCGAGACG TCTCCTTCCTGCCCCTCCTCCGCTCCGA- GACGTCTCGAGT-3' (SEQ ID NO:7).

Embodiment 58

The bottle haplomer-ligand complex of any one of embodiments 44 to 57 wherein the ligand is a small molecule ligand or an interactive protein domain.

Embodiment 59

The bottle haplomer-ligand complex of embodiment 58 wherein the small molecule ligand is less than about 2500 Daltons.

Embodiment 60

The bottle haplomer-ligand complex of embodiment 59 wherein the small molecule ligand is a small molecule, a peptide having less than about 20 amino acid residues, a naturally- or artificially-modified peptide, a peptidomimetic, a glycan, an organic enzyme cofactor, or an artificially-derived small molecular ligand.

Embodiment 61

The bottle haplomer-ligand complex of embodiment 58 wherein the small molecule ligand is an FKM monovalent ligand.

Embodiment 62

The bottle haplomer-ligand complex of embodiment 61 wherein the FKM monovalent ligand is FKM-NHS, FKM-sulfo-NHS, FKM-PEG3-NHS, MFL2, wherein: FKM-NHS is

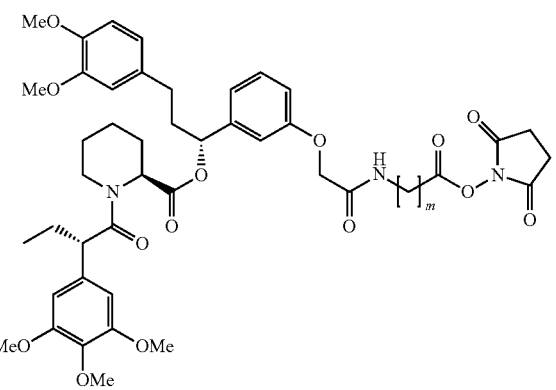

where m is from 3 to 6; FKM-sulfo-NHS is

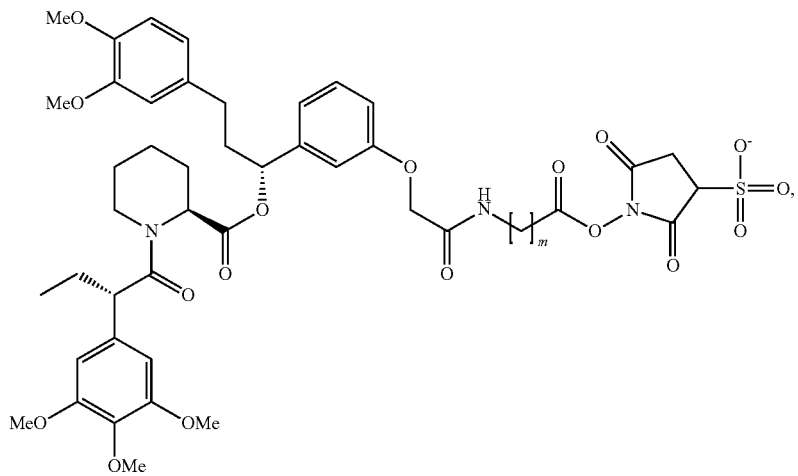

where m is from 3 to 6; FKM-PEG3-NHS is

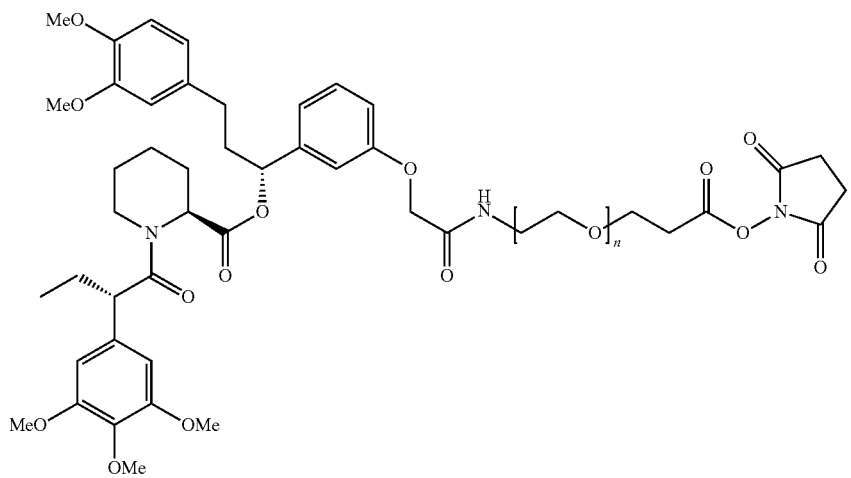

where n is from 1 to 6; and MFL2 i

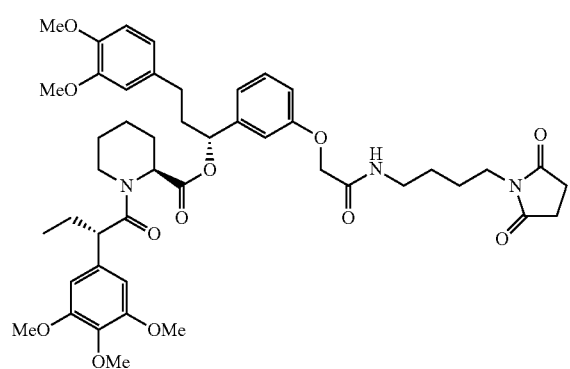

Embodiment 63

The bottle haplomer-ligand complex of any one of embodiments 44 to 62 wherein the ligand further comprises a bio-orthogonal moiety.

Embodiment 64

The bottle haplomer-ligand complex of embodiment 63 wherein the bio-orthogonal moiety is an azide, an alkyne, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, or a quadricyclane, or any derivative thereof.

Embodiment 65

The bottle haplomer-ligand complex of embodiment 63 wherein the ligand is an FKM monovalent ligand chosen from FKM-PEG3-MTZ-NHS and FKM-PEG3-TCO-NHS, wherein: FKM-PEG3-MTZ-NHS is

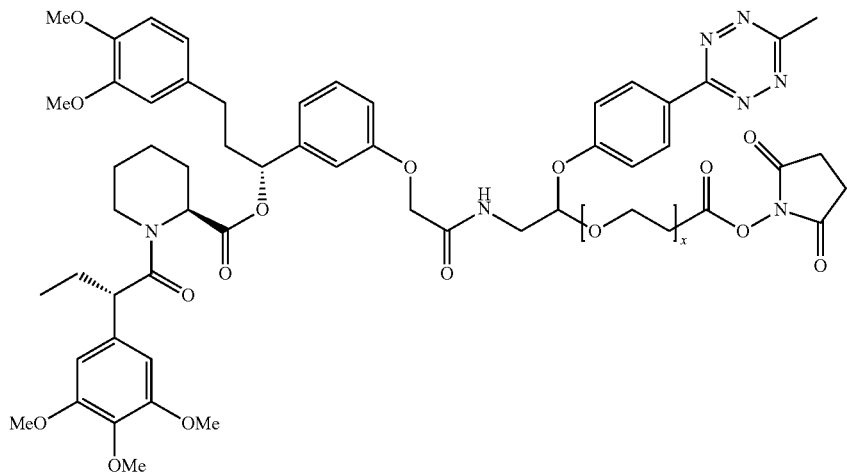

where x is from 1 to 6; and FKM-PEG3-TCO-NHS is

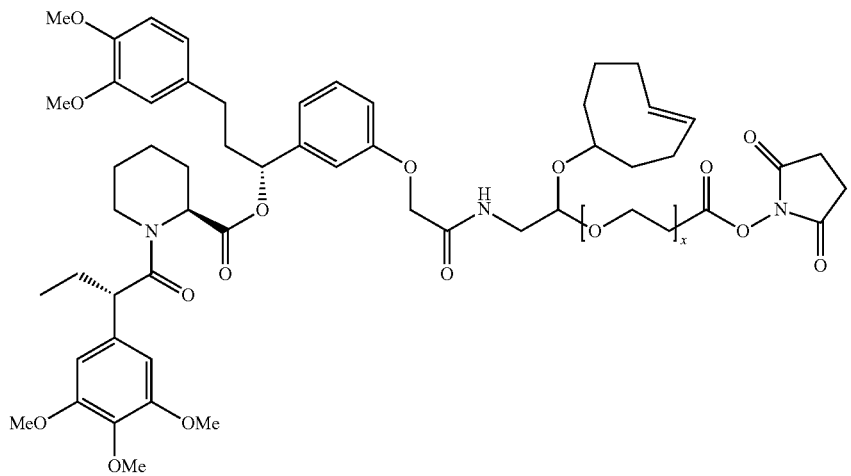

where x is from 1 to 6.

Embodiment 66

The bottle haplomer-ligand complex of embodiment 58 wherein the interactive protein domain comprises less than 100 amino acid residues.

Embodiment 67

The bottle haplomer-ligand complex of embodiment 66 wherein the interactive protein domain is a leucine zipper domain.

Embodiment 68

The bottle haplomer-ligand complex of embodiment 67 wherein the interactive protein domain is a c-jun domain, a c-fos domain, a c-myc domain, a c-max domain, an NZ domain, or a CZ domain.

Embodiment 69

The bottle haplomer-ligand complex of embodiment 68 wherein the NZ domain comprises the amino acid sequence ALKKELQANKKELAQLKWELQALKKEL AQ (SEQ ID NO:10), and the CZ domain comprises the amino acid sequence EQLEKKLQALE KKLAQLEW-KNQALEKKLAQ (SEQ ID NO: 11).

Embodiment 70

The bottle haplomer-ligand complex of embodiment 67 wherein the N-terminus of the c-jun domain is linked to the 5' or 3' terminus of the polynucleotide of the bottle haplomer.

Embodiment 71

The bottle haplomer-ligand complex of embodiment 70 wherein the c-jun domain comprises the amino acid sequence CSGGASLERIARLEEKVKTLKAQNSELAST ANMLREQVAQLKQKGAP (SEQ ID NO:1), CSG-GASLERIARLEEKVKSFKAQNSEN ASTANML-REQVAQLKQKGAP (SEQ ID NO:4), or CSGASLERIAR-LEEKVKSFKAQNSE NASTANMLREQVAQLKQKGAP (SEQ ID NO:12).

Embodiment 72

The bottle haplomer-ligand complex of embodiment 67 wherein the C-terminus of the c-jun domain is linked to the 5' or 3' terminus of the polynucleotide of the bottle haplomer.

Embodiment 73

The bottle haplomer-ligand complex of embodiment 72 wherein the c-jun domain comprises the amino acid sequence SGASLERIARLEEKVKTLKAQNSELASTAN MLREQVAQLKQKGAPSGGC (SEQ ID NO:2) or SGASLERIARLEEKVKSFKAQNSENAST ANML-REQVAQLKQKGAPSGGC (SEQ ID NO:5).

Embodiment 74

A composition or kit comprising: a bottle haplomer-ligand complex of any one of embodiments 44 to 73; and a second haplomer-ligand complex comprising: a nucleotide portion comprising from about 6 to about 20 nucleotide bases that is substantially complementary to the stem portion of the bottle haplomer-ligand complex that is linked to the ligand of the bottle haplomer-ligand complex; and a ligand linked to the 5' or 3' terminus of the nucleotide portion of the second haplomer-ligand complex, wherein the ligand comprises a ligand partner binding site; wherein the $T_m$ of the second haplomer-ligand complex:first or second stem portion linked to the ligand of the bottle haplomer-ligand complex is less than or equal to the $T_m$ of the first stem portion:second stem portion of the bottle haplomer-ligand complex.

Embodiment 75

The composition or kit of embodiment 74 wherein the $T_m$ of the duplex formed by the second haplomer-ligand complex and the first or second stem portion of the bottle haplomer-ligand complex linked to the ligand subtracted from the $T_m$ of the first stem portion:second stem portion of the bottle haplomer-ligand complex is from about 0° C. to about 20° C.

Embodiment 76

The composition or kit of embodiment 74 or embodiment 75 wherein the $T_m$ of the duplex formed by the second haplomer-ligand complex and the first or second stem portion of the bottle haplomer-ligand complex linked to the ligand is from about 30° C. to about 40° C.

Embodiment 77

The composition or kit of any one of embodiments 74 to 76 wherein the $T_m$ of the duplex formed by the second haplomer-ligand complex and the first or second stem portion of the bottle haplomer-ligand complex linked to the ligand subtracted from the $T_m$ of the first stem portion:second stem portion of the bottle haplomer-ligand complex is from about 5° C. to about 10° C.

Embodiment 78

The composition or kit of any one of embodiments 74 to 77 wherein the polynucleotide of the second haplomer-ligand complex comprises from about 8 to about 15 nucleotide bases.

Embodiment 79

The composition or kit of any one of embodiments 74 to 78, wherein the polynucleotides of the bottle haplomer-ligand complex and the second haplomer-ligand complex comprise DNA nucleotides, RNA nucleotides, phosphorothioate-modified nucleotides, 2-O-alkylated RNA nucleotides, halogenated nucleotides, locked nucleic acid nucleotides (LNA), peptide nucleic acids (PNA), morpholino nucleic acid analogues (morpholinos), pseudouridine nucleotides, xanthine nucleotides, hypoxanthine nucleotides, 2-deoxyinosine nucleotides, DNA analogs with L-ribose (L-DNA), Xeno nucleic acid (XNA) analogues, or other nucleic acid analogues capable of base-pair formation, or artificial nucleic acid analogues with altered backbones, or any combination thereof.

Embodiment 80

The composition or kit of any one of embodiments 74 to 79, wherein both ligands are small molecule ligands or both ligands are interactive protein domains.

Embodiment 81

The composition or kit of embodiment 80 wherein both small molecule ligands are less than about 2500 Daltons.

Embodiment 82

The composition or kit of embodiment 81 wherein both small molecule ligands are small molecules, peptides having less than about 20 amino acid residues, naturally- or artificially-modified peptides, peptidomimetics, glycans, organic enzyme cofactors, or artificially-derived small molecular ligands.

Embodiment 83

The composition or kit of embodiment 80 wherein both small molecule ligands are FKM monovalent ligands.

Embodiment 84

The composition or kit of embodiment 83 wherein each FKM monovalent ligand is, independently, FKM-NHS. FKM-sulfo-NHS. FKM-PEG3-NHS, or MFL2, wherein: FKM-NHS is

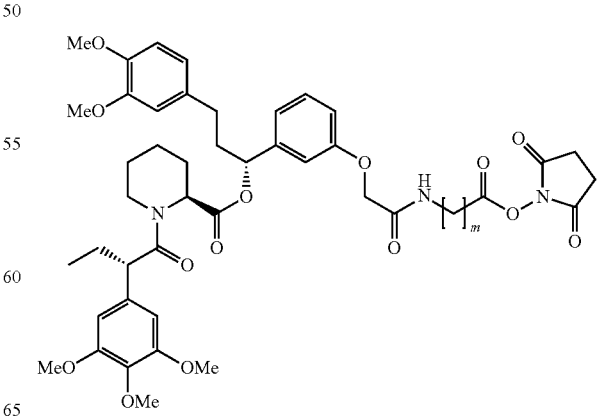

where m is from 3 to 6; FKM-sulfo-NHS is

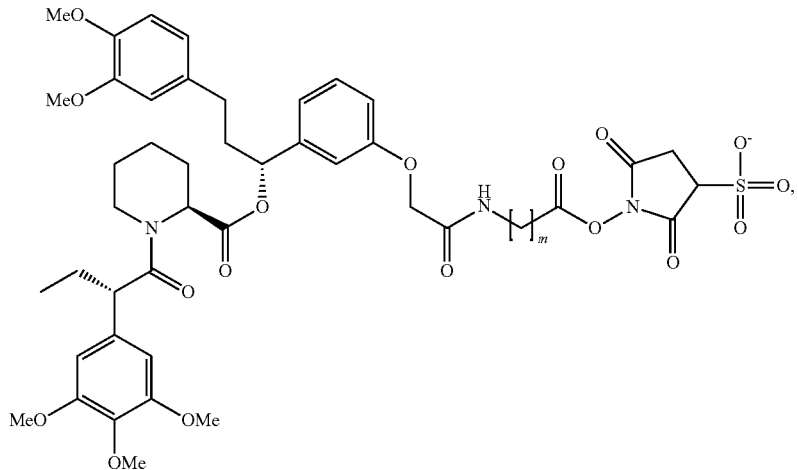

where m is from 3 to 6;
FKM-PEG3-NHS is

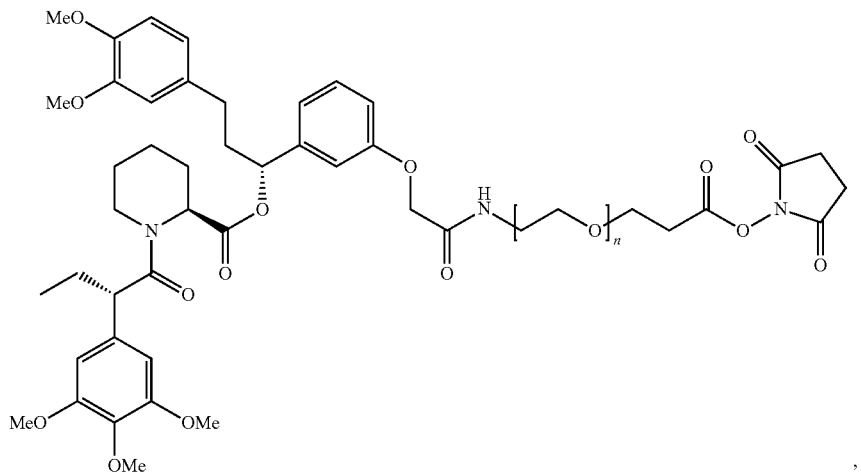

where n is from 1 to 6; and MFL2 is

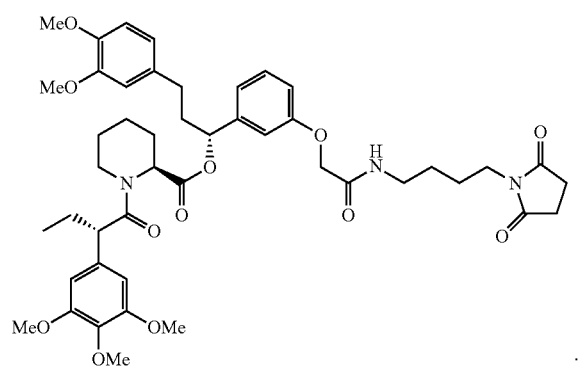

Embodiment 85

The composition or kit of any one of embodiments 74 to 84 wherein: the ligand of the bottle haplomer-ligand complex further comprises a bio-orthogonal moiety; and the ligand of the second haplomer-ligand complex further comprises a bio-orthogonal moiety; wherein the bio-orthogonal moiety of the bottle haplomer-ligand complex is reactable with the bio-orthogonal moiety of the second haplomer-ligand complex.

Embodiment 86

The composition or kit of embodiment 85 wherein the reactable bio-orthogonal moietys are chosen from an azide, an alkyne, a cyclooctyne, a nitrone, a norbornene, an oxanorbornadiene, a phosphine, a dialkyl phosphine, a trialkyl phosphine, a phosphinothiol, a phosphinophenol, a cyclooctene, a nitrile oxide, a thioester, a tetrazine, an isonitrile, a tetrazole, or a quadricyclane, or any derivative thereof.

Embodiment 87

The composition or kit of embodiment 85 wherein the ligand of one of the bottle haplomer-ligand complex and second haplomer-ligand complex is an FKM monovalent ligand that is FKM-PEG3-MTZ-NHS and the ligand of the other of the bottle haplomer-ligand complex and second haplomer-ligand complex is an FKM monovalent ligand that is FKM-PEG3-TCO-NHS, wherein: FKM-PEG3-MTZ-NHS is

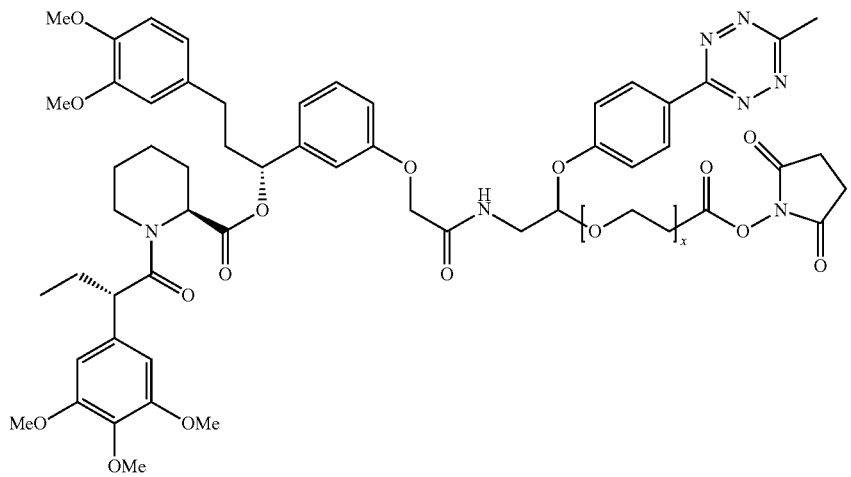

where x is from 1 to 6; and FKM-PEG3-TCO-NHS is

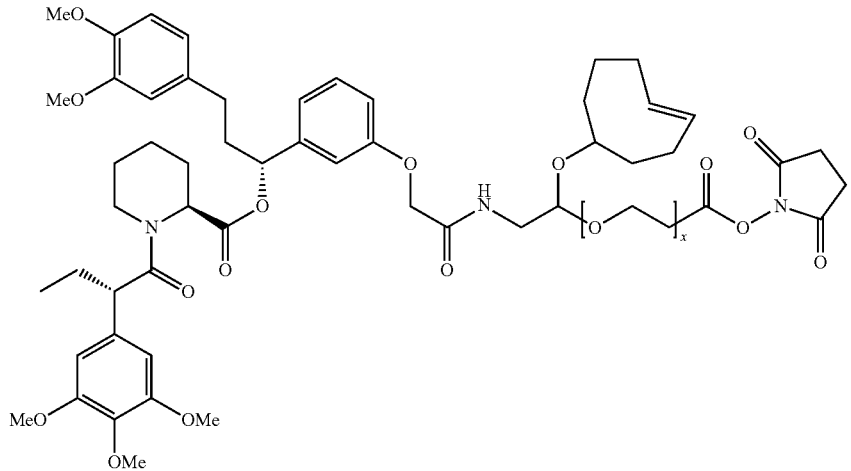

where x is from 1 to 6.

Embodiment 88

The composition or kit of embodiment 80 wherein both interactive protein domains each comprise less than 100 amino acid residues.

Embodiment 89

The composition or kit of embodiment 88 wherein both interactive protein domains are leucine zipper domains.

Embodiment 90

The composition or kit of embodiment 89 wherein each interactive protein domain is, independently, a c-jun domain, a c-fos domain, a c-myc domain, a c-max domain, an NZ domain, or a CZ domain.

Embodiment 91

The composition or kit of embodiment 90 wherein the N-terminus of the interactive protein domain of the bottle haplomer-ligand complex is linked to the 5' terminus of the polynucleotide of the bottle haplomer-ligand complex, and the N-terminus of the interactive protein domain of the second haplomer-ligand complex is linked to the 3' terminus of the polynucleotide of the second haplomer-ligand complex.

Embodiment 92

The composition or kit of embodiment 90 wherein the C-terminus of the interactive protein domain of the bottle haplomer-ligand complex is linked to the 5' terminus of the polynucleotide of the bottle haplomer-ligand complex, and the C-terminus of the interactive protein domain of the second haplomer-ligand complex is linked to the 3' terminus of the polynucleotide of the second haplomer-ligand complex.

Embodiment 93

The composition or kit of embodiment 90 wherein: the C-terminus of the interactive protein domain of the bottle haplomer-ligand complex is linked to the 5' terminus of the polynucleotide of the bottle haplomer-ligand complex, and the N-terminus of the interactive protein domain of the second haplomer-ligand complex is linked to the 3' terminus of the polynucleotide of the second haplomer-ligand complex; or the N-terminus of the interactive protein domain of the bottle haplomer-ligand complex is linked to the 5' terminus of the polynucleotide of the bottle haplomer-ligand complex, and the C-terminus of the interactive protein domain of the second haplomer-ligand complex is linked to the 3' terminus of the polynucleotide of the second haplomer-ligand complex.

Embodiment 94

The composition or kit of any one of embodiments 90 to 93 wherein the NZ domain comprises the amino acid sequence ALKKELQANKKELAQLKWELQALKK ELAQ (SEQ ID NO:10), and the CZ domain comprises the amino acid sequence EQLEKKLQALEKKLAQLEW-KNQALEKKLAQ (SEQ ID NO: 11).

Embodiment 95

The composition or kit of any one of embodiments 90 to 93 wherein the ligand linked to the polynucleotide of the bottle haplomer-ligand complex is a c-jun domain, and the ligand linked to the polynucleotide of the second haplomer-ligand complex is a c-jun domain.

Embodiment 96

The composition or kit of any one of embodiments 90 to 93 wherein the c-jun domain comprises the amino acid sequence CSGGASLERIARLEEKVKTLKAQNSE LAST-ANMLREQVAQLKQKGAP (SEQ ID NO: 1), CSG-GASLERIARLEEKVKSFKAQNSE NASTANML-REQVAQLKQKGAP (SEQ ID NO:4), or ASLERIARLEEKVKSFKAQNSENAS TANML-REQVAQLKQKGAP (SEQ ID NO:12).

Embodiment 97

The composition or kit of embodiment 92 or embodiment 93 wherein the C-terminus of the c-jun domain is linked to the 5' or 3' terminus of the polynucleotides of either or both of the bottle haplomer-ligand complex and second haplomer-ligand complex.

Embodiment 98

The composition or kit of embodiment 97 wherein the c-jun domain comprises the amino acid sequence SGASLE-RIARLEEKVKTLKAQNSELASTANMLREQV AQLKQKGAPSGGC (SEQ ID NO:2) or SGASLERIAR-LEEKVKSFKAQNSENASTANML REQVAQLKQK-GAPSGGC (SEQ ID NO:5).

Embodiment 99

The composition or kit of any one of embodiments 90 to 93 wherein the ligand linked to the polynucleotide of the bottle haplomer-ligand complex is a c-jun domain or a c-myc domain, and the ligand linked to the polynucleotide of the second haplomer-ligand complex is a c-jun domain or a c-myc domain.

Embodiment 100

The composition or kit of embodiment 99 wherein the ligand linked to the polynucleotide of one of the bottle haplomer-ligand complex and second haplomer-ligand complex is a c-jun domain, and the ligand linked to the polynucleotide of the other of the bottle haplomer-ligand complex and second haplomer-ligand complex is a c-myc domain.

Embodiment 101

The kit of any one of embodiments 74 to 100 wherein: the polynucleotide of the bottle haplomer-ligand complex comprises the nucleotide sequence of 5'-ACTCGA-GACGTCTCCTTGTCTTGCTTCTTCAGGACACAGTG GCGAGACGT CTCGAGT-3' (SEQ ID NO:6), and the polynucleotide of the second haplomer-ligand complex comprises the nucleotide sequence of 5'-AGCTCTCGAGT-3' (SEQ ID NO:8); or the polynucleotide of the bottle haplomer-ligand complex comprises the nucleotide sequence of 5'-ACTCGA-GACGTCTCCTTCCTGCCCCTCCTCCTGCTCCGA-GACGTCTCGAGT-3' (SEQ ID NO:7), and the polynucleotide of the second haplomer-ligand complex comprises the nucleotide sequence 5'-GACGTCTCGAGT-3' (SEQ ID NO:9).

Embodiment 102

A compound having the formula:

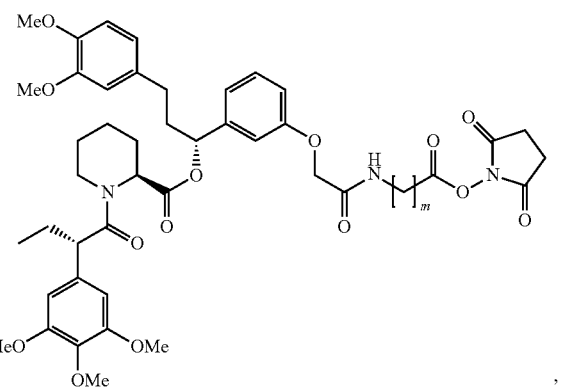

where m is from 3 to 6.

Embodiment 103
A compound having the formula:
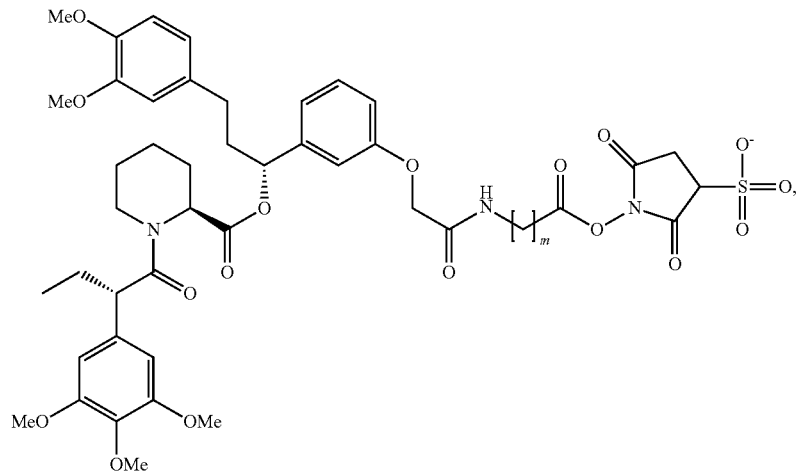
where m is from 3 to 6.
Embodiment 104
A compound having the formula:
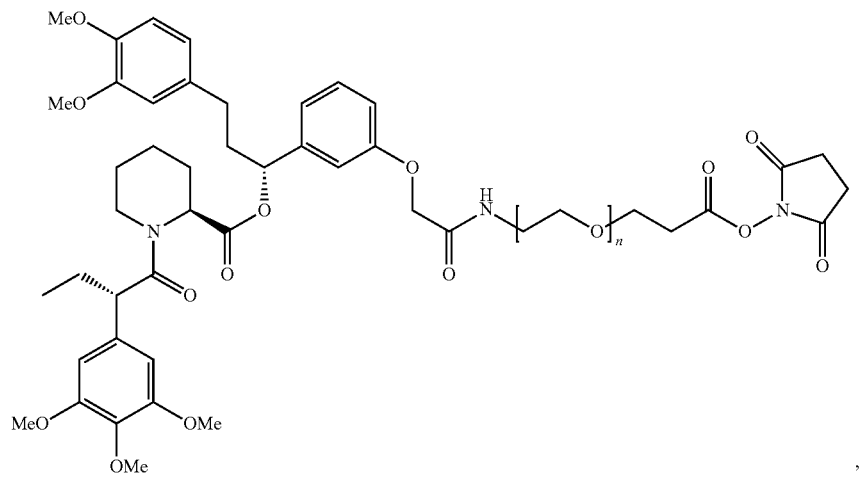
where n is from 1 to 6.

Embodiment 105
A compound having the formula:
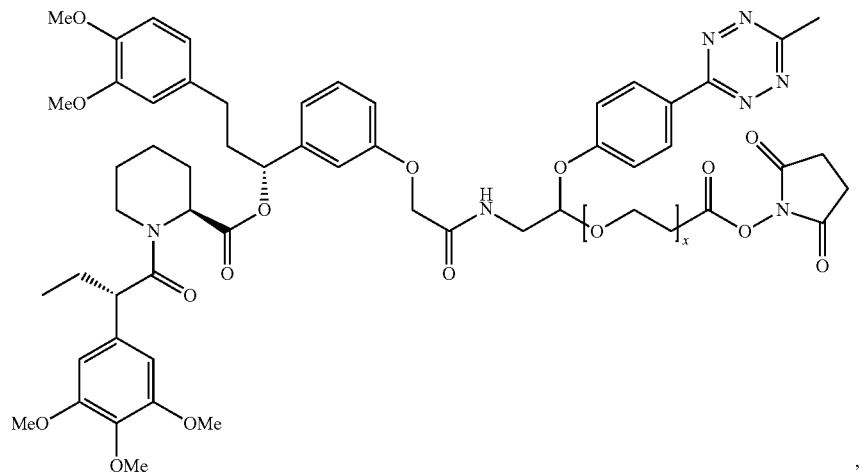
where x is from 1 to 6.
Embodiment 106
A compound having the formula:
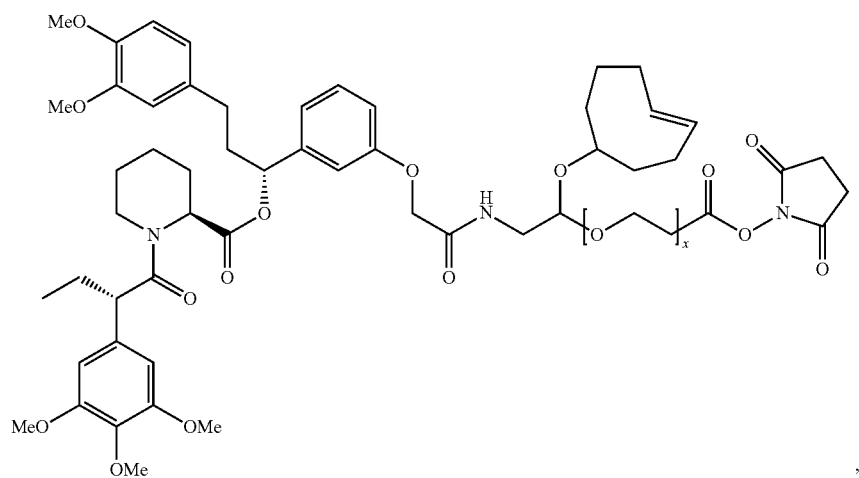
where x is from 1 to 6.

Embodiment 106B

A compound having the formula:

[chemical structure]

Embodiment 107

A fusion protein comprising a fragment of a protein of interest fused to a ligand binding domain, wherein: the ligand binding domain is a ligand binding domain for small molecule ligands; or the ligand binding domain is an interactive protein domain.

Embodiment 108

The fusion protein of embodiment 107 wherein the ligand binding domain is a ligand binding domain for small molecule ligands.

Embodiment 109

The fusion protein of embodiment 108 wherein the ligand binding domain is an FKBP domain or an FRB domain.

Embodiment 110

The fusion protein of embodiment 109 wherein the FKBP domain is a mutant FKBP domain.

Embodiment 110B

The fusion protein of embodiment 108 wherein the FKBP domain comprises a C22S, C22A, or C22V substitution, or wherein the FRB domain comprises a C61S, C61A, or C61V substitution.

Embodiment 111

The fusion protein of embodiment 110 wherein the mutant FKBP domain is the F36V FKBP mutant domain comprising the amino acid sequence GVQVETISPGDGRTFPKRGQTCVVHYTGMLEDGKKVDSSRDRNKPFKFMLGKQEVIRGWEEGVAQM SVGQRAKLTISPDYAYGATGHPGIIPPHATLVFDVELLKLE (SEQ ID NO:14) or MGVQVETISPGDGRTFPKRGQTCVVHYTGMLEDGKKVDSSRDRNKPFKFMLGKQEVIRGWEE GVAQMSVGQRAKLTISPDYAYGATGHPGIIPPHATLVFDVELLKLE (SEQ ID NO:15).

Embodiment 112

The fusion protein of embodiment 107 wherein the ligand binding domain is an interactive protein domain.

Embodiment 113

The fusion protein of embodiment 112 wherein the interactive protein domain comprises less than 100 amino acid residues.

Embodiment 114

The fusion protein of embodiment 112 wherein the interactive protein domain is a leucine zipper domain.

Embodiment 115

The fusion protein of embodiment 114 wherein the interactive protein domain is a c-jun domain, a c-fos domain, a c-myc domain, a c-max domain, an NZ domain, or a CZ domain.

Embodiment 116

The fusion protein of embodiment 115 wherein the interactive protein domain is fused to the N-terminus of the protein of interest.

Embodiment 117

The fusion protein of embodiment 115 wherein the interactive protein domain is fused to the C-terminus of the protein of interest.

Embodiment 118

The fusion protein of any one of embodiments 115 to 117 wherein the NZ domain comprises the amino acid sequence ALKKELQANKKELAQLKWELQALKKE LAQ (SEQ ID NO:10), and the CZ domain comprises the amino acid sequence EQLEKKLQAL EKKLAQLEWKNQALEKKLAQ (SEQ ID NO: 11).

Embodiment 119

The fusion protein of any one of embodiments 115 to 117 wherein the c-jun domain comprises the amino acid sequence CSGGASLERIARLEEKVKTLKAQNSEL ASTANMLREQVAQLKQKGAP (SEQ ID NO:1), CSG-GASLERIARLEEKVKSFKAQNSEN ASTANMLREQVAQLKQKGAP (SEQ ID NO:4), or ASLERIARLEEKVKSFKAQNSENAST ANMLREQVAQLKQKGAP (SEQ ID NO:12).

Embodiment 120

The fusion protein of any one of embodiments 115 to 117 wherein the c-jun domain comprises the amino acid sequence SGASLERIARLEEKVKTLKAQNSEL ASTANMLREQVAQLKQKGAPSGGC (SEQ ID NO:2), SGASLERIARLEEKVKSFKAQN SENASTANMLREQVAQLKQKGAPSGGC (SEQ ID NO:5).

Embodiment 121

The fusion protein of any one of embodiments 115 to 117 wherein the c-Fos domain comprises the amino acid sequence ASRELTDTLQAETDQLEDEKSALQTE IANLLKEKEKLEGAP (SEQ ID NO:3) or SGAS-RELTDTLQAETDQLEDEKSALQTEIANLL KEKEKLE-GAP (SEQ ID NO:13).

Embodiment 122

The fusion protein of any one of embodiments 107 to 121 wherein the fusion protein comprises a linker between the protein of interest and the ligand binding domain.

Embodiment 123

The fusion protein of embodiment 122 wherein the linker is a Ser/Gly linker, a Poly-Asparagine linker, or a linker comprising the amino acid sequence AGSSAAGS GS (SEQ ID NO:17).

Embodiment 124

The fusion protein of embodiment 123 wherein the Poly-Asparagine linker comprises from about 8 to about 16 asparagine residues.

Embodiment 125

The fusion protein of embodiment 123 wherein the Ser/Gly linker comprises GGSGGGSGGGSGGGSGGG (SEQ ID NO:18), GGSGGGSGGGSGGGSGGGSG GG (SEQ ID NO:19), GGSGGGSGGGSGGGSGGGSGGGSGGG (SEQ ID NO:20), SGGGG SGGGGSGGGG (SEQ ID NO:21), SGGGGSGGGGSGGGGSGGGG (SEQ ID NO:22), SGGG GSGGGGSGGGGSGGGGSGGGG (SEQ ID NO:23), SGGGS (SEQ ID NO:24), SGSG (SEQ ID NO:25), SGGGGS (SEQ ID NO:26), or SGSGG (SEQ ID NO:27).

Embodiment 126

The fusion protein of any one of embodiments 107 to 125 wherein the protein of interest is a fragment of: a cytotoxic protein, a microbicidal protein, a virucidal protein, a pro-apoptotic protein, a thrombogenic protein, a complement activating protein, a Toll-Like Receptor protein, a NOD2 receptor agonist protein, or an antibody or fragment thereof.

Embodiment 127

The fusion protein of embodiment 126 wherein: the cytotoxic protein is a bee melittin, a conotoxin, a cathelicidin, a defensin, a protegrin, or NK-lysin; the pro-apoptotic protein is prion protein, a Bax-derived minimum poropeptide associated with the caspase cascade, or a pro-apoptotic peptide (KLAKLAK)$_2$ (SEQ ID NO:28); the innate immune system stimulation protein is a pathogen-associated molecular pattern (PAMP) or a damage-associated molecular pattern (DAMP); the complement activating protein is a C3a fragment of complement protein C3; the Toll-Like Receptor (TLR) protein is a heat shock protein (hsp); the NOD2 receptor agonist protein is muramyl dipeptide agonist; and the antibody fragment is an Fab, Fv, or scFv.

Embodiment 128

The fusion protein of any one of embodiments 107 to 125 wherein the protein of interest is a fragment of: superfolder GFP (sfGFP), Renilla luciferase, murine dihydrofolate reductase (DHFR), S. cerevisiae ubiquitin, β-lactamase, or Herpes simplex virus type 1 thymidine kinase.

Embodiment 129

The fusion protein of embodiment 128 wherein: the fragment of superfolder GFP (sfGFP) comprises MRK-GEELFTGVVPILVELDGDVNGHKFSVRGEGE GDATNGKLTLKFICTTGKLPVPWPTLVTTLTYGVQC-FARYPDHMKQHDFFKSAMPEGY VQERTIS-FKDDGTYKTRAEVKFEGDTLVNRIELKGIDFKEDG-NILGHKLEYNFNSHNVYI TADKQ (SEQ ID NO:29) or KNGIKANFKIRHNVEDGSVQLADHYQQNT-PIGDGPVLLPD NHYLSTQSVLSKDP-NEKRDHMVLLEFVTAAGITHGMDELYK (SEQ ID NO:30); the fragment of Renilla luciferase comprises MASKVYDPEQRKRMITGPQWWARCKQMNVLD SFINYYDSEKHAENAVIFLHGNAASSYLWRHVVPHI-EPVARCIIPDLIGMKSGKSGNGS YRLLDHYKYL-TAWFELLNLPKKIIFVGHDWGACLAFHYSYEHQD-KIKAIVHAESVVDVI ESWDEWPDIEEDIALIK-SEEGEKMVLENNFFVETMLPSKIMRKLEPEEFAAY-LEPFKEKG EVRRPTLSWPREIPLVKGG (SEQ ID NO:31) or KPDVVQIVRNYNAYLRASDDLPKMFIES DPGFFSNAIVEGAKKFPNTEFVKVKGLHFSQEDAP-DEMGKYIKSFVERVLKNEQ (SEQ ID NO:32); the fragment of murine dihydrofolate reductase (DHFR) comprises amino acids 1-105 or 106-186 thereof; the fragment of S. cerevisiae ubiquitin comprises amino acids 1-34 (MQIFVKTLTGKTITLEVESSDTIDNVKSKIQDKE; SEQ ID NO:33) or 35-76 (GIPPDQQ RLIFAGKQLEDGRTLS-DYNIQKESTLHLVLRLRGG; SEQ ID NO:34) thereof; the fragment of f-lactamase comprises amino acids 25-197 or 198-286 thereof; and the fragment of Herpes simplex virus type 1 thymidine kinase comprises amino acids 1-265 or 266-376 thereof.

Embodiment 130

A composition or kit comprising a first fusion protein of embodiment 107 and a second fusion protein of embodiment 107, wherein the protein of interest of the first fusion protein and the protein of interest of the second fusion protein can dimerize or fold together.

Embodiment 131

The composition or kit of embodiment 130 wherein: the first fusion protein comprises a protein of interest fused to a ligand binding domain for a small molecule ligand; the second fusion protein comprises a protein of interest fused to a ligand binding domain for a small molecule ligand.

Embodiment 132

The composition or kit of embodiment 131 wherein the ligand binding domain of both the first fusion protein and the second fusion protein are an FKBP domain or an FRB domain.

Embodiment 133

The composition or kit of embodiment 132 wherein the FKBP domain is a mutant FKBP domain.

Embodiment 133B

The fusion protein of embodiment 132 wherein the FKBP domain comprises a C22S, C22A, or C22V substitution, or wherein the FRB domain comprises a C61S, C61A, or C61V substitution.

Embodiment 134

The composition or kit of embodiment 133 wherein the mutant FKBP domain is the F36V FKBP mutant domain comprising the amino acid sequence GVQVETISPGDGRTFPKRGQTCVVHYTGMLEDGKKVDSSRDRNKPFKFMLGKQEVIRGWEEGVAQMS VGQRAKLTISPDYAYGATGHPGIIPPHATLVFDVELLKLE (SEQ ID NO:14) or MGVQVETISPGDGRTFPKRGQTCVVHYTGMLEDGKKVDSSRDRNKPFKFMLGKQEVIRGWEEGVA QMSVGQRAKLTISPDYAYGATGHPGIIPPHATLVFDVELLKLE (SEQ ID NO:15).

Embodiment 135

The composition or kit of embodiment 130 wherein: the first fusion protein comprises a protein of interest fused to an interactive protein domain; the second fusion protein comprises a protein of interest fused to an interactive protein domain.

Embodiment 136

The composition or kit of embodiment 135 wherein the interactive protein domain of both fusion proteins comprises less than 100 amino acid residues.

Embodiment 137

The composition or kit of embodiment 135 wherein the interactive protein domain of both fusion proteins is a leucine zipper domain.

Embodiment 138

The composition or kit of embodiment 114 wherein the interactive protein domain of the first fusion protein and the second fusion protein is, independently, an NZ domain, a CZ domain, a c-jun domain, a c-fos domain, a c-myc domain, or a c-max domain.

Embodiment 139

The composition or kit of any one of embodiments 135 to 138 wherein: the interactive protein domain of the first fusion protein is fused to the N-terminus of the protein of interest, and the interactive protein domain of the second fusion protein is fused to the N-terminus of the protein of interest; the interactive protein domain of the first fusion protein is fused to the C-terminus of the protein of interest, and the interactive protein domain of the second fusion protein is fused to the C-terminus of the protein of interest; or the interactive protein domain of one of the first fusion protein and second fusion protein is fused to the N-terminus of the protein of interest, and the interactive protein domain of the other of the first fusion protein and second fusion protein is fused to the C-terminus of the protein of interest.

Embodiment 140

The composition or kit of any one of embodiments 135 to 139 wherein the NZ domain comprises the amino acid sequence ALKKELQANKKELAQLKWELQ ALKKELAQ (SEQ ID NO:10), and the CZ domain comprises the amino acid sequence EQLEKKLQALEKKLAQLEWKNQALEKKLAQ (SEQ ID NO: 11).

Embodiment 141

The composition or kit of any one of embodiments 135 to 139 wherein the c-jun domain comprises the amino acid sequence CSGGASLERIARLEEKVKTL KAQNSELASTANMLREQVAQLKQKGAP (SEQ ID NO:1), CSGGASLERIARLEEKVKSFK AQNSENASTANMLREQVAQLKQKGAP (SEQ ID NO:4), or ASLERIARLEEKVKSFKAQ NSENASTANMLREQVAQLKQKGAP (SEQ ID NO:16).

Embodiment 142

The composition or kit of any one of embodiments 135 to 139 wherein the c-jun domain comprises the amino acid sequence SGASLERIARLEEKVKTLK AQNSELASTANMLREQVAQLKQKGAPSGGC (SEQ ID NO:2) or SGASLERIARLEEKV KSFKAQNSENASTANMLREQVAQLKQKGAPSGGC (SEQ ID NO:5).

Embodiment 143

The composition or kit of any one of embodiments 135 to 139 wherein the c-Fos domain comprises the amino acid sequence ASRELTDTLQAETDQLEDE KSALQTEIANLLKEKEKLEGAP (SEQ ID NO:3) or SGASRELTDTLQAETDQLEDEKS ALQTEIANLLKEKEKLEGAP (SEQ ID NO:13).

Embodiment 144

The composition or kit of any one of embodiments 130 to 143 wherein both the first fusion protein and second fusion protein comprise a linker between the protein of interest and the ligand binding domain.

Embodiment 145

The composition or kit of embodiment 144 wherein each linker is, independently, a Ser/Gly linker, a Poly-Asparagine linker, or a linker comprising the amino acid sequence AGSSAAGSGS (SEQ ID NO:17).

Embodiment 146

The composition or kit of embodiment 145 wherein each Poly-Asparagine linker, independently, comprises from about 8 to about 16 asparagine residues.

Embodiment 147

The composition or kit of embodiment 145 wherein each Ser/Gly linker, independently, comprises GGSGGGSGGGSGGGSGGG (SEQ ID NO:18), GGSGG GSGGGSGGGSGGGSGGG (SEQ ID NO:19), GGSGGGSGGGSGGGSGGGSGGGSGGG (SEQ ID NO:20), SGGGGSGGGGSGGGG (SEQ ID NO:21), SGGGGSGGGGSGGGGSGG GG (SEQ ID NO:22), SGGGGSGGGGSGGGGSGGGGSGGGG (SEQ ID NO:23), SGGGS (SEQ ID NO:24), SGSG (SEQ ID NO:25), SGGGGS (SEQ ID NO:26), or SGSGG (SEQ ID NO:27).

Embodiment 148

The composition or kit of any one of embodiments 130 to 147 wherein: the protein of interest of the first fusion protein is a first fragment of a cytotoxic protein, and the protein of interest of the second fusion protein is a second fragment of a cytotoxic protein, wherein the first fragment of the cytotoxic protein and the second fragment of the cytotoxic protein dimerize or fold together; the protein of interest of the first fusion protein is a first fragment of a microbicidal protein, and the protein of interest of the second fusion protein is a second fragment of a microbicidal protein, wherein the first fragment of the microbicidal protein and the second fragment of the microbicidal protein dimerize or fold together; the protein of interest of the first fusion protein is a first fragment of a virucidal protein, and the protein of interest of the second fusion protein is a second fragment of a virucidal protein, wherein the first fragment of the virucidal protein and the second fragment of the virucidal protein dimerize or fold together; the protein of interest of the first fusion protein is a first fragment of a pro-apoptotic protein, and the protein of interest of the second fusion protein is a second fragment of a pro-apoptotic protein, wherein the first fragment of the pro-apoptotic protein and the second fragment of the pro-apoptotic protein dimerize or fold together; the protein of interest of the first fusion protein is a first fragment of a thrombogenic protein, and the protein of interest of the second fusion protein is a second fragment of a thrombogenic protein, wherein the first fragment of the thrombogenic protein and the second fragment of the thrombogenic protein dimerize or fold together; the protein of interest of the first fusion protein is a first fragment of a complement activating protein, and the protein of interest of the second fusion protein is a second fragment of a complement activating protein, wherein the first fragment of the complement activating protein and the second fragment of the complement activating protein dimerize or fold together; the protein of interest of the first fusion protein is a first fragment of a Toll-Like Receptor protein, and the protein of interest of the second fusion protein is a second fragment of a Toll-Like Receptor protein, wherein the first fragment of the Toll-Like Receptor protein and the second fragment of the Toll-Like Receptor protein dimerize or fold together; the protein of interest of the first fusion protein is a first fragment of a NOD2 receptor agonist protein, and the protein of interest of the second fusion protein is a second fragment of a NOD2 receptor agonist protein, wherein the first fragment of the NOD2 receptor agonist protein and the second fragment of the NOD2 receptor agonist protein dimerize or fold together; or the protein of interest of the first fusion protein is a first fragment of an antibody or fragment thereof, and the protein of interest of the second fusion protein is a second fragment of an antibody or fragment thereof, wherein the first fragment of the antibody or fragment thereof and the second fragment of the antibody or fragment thereof dimerize or fold together.

Embodiment 149

The composition or kit of embodiment 148 wherein: the cytotoxic protein is a bee melittin, a conotoxin, a cathelicidin, a defensin, a protegrin, or NK-lysin; the pro-apoptotic protein is prion protein, a Bax-derived minimum poropeptide associated with the caspase cascade, or a pro-apoptotic peptide (KLAKLAK)$_2$ (SEQ ID NO:28); the innate immune system stimulation protein is a pathogen-associated molecular pattern (PAMP) or a damage-associated molecular pattern (DAMP); the complement activating protein is a C3a fragment of complement protein C3; the Toll-Like Receptor (TLR) protein is a heat shock protein (hsp); the NOD2 receptor agonist protein is muramyl dipeptide agonist; and the antibody fragment is an Fab, Fv, or scFv.

Embodiment 150

The composition or kit of any one of embodiments 130 to 147 wherein: the protein of interest of the first fusion protein is a first fragment of superfolder GFP (sfGFP), and the protein of interest of the second fusion protein is a second fragment of sfGFP, wherein the first fragment of the sfGFP and the second fragment of the sfGFP dimerize or fold together; the protein of interest of the first fusion protein is a first fragment of Renilla luciferase, and the protein of interest of the second fusion protein is a second fragment of Renilla luciferase, wherein the first fragment of the Renilla luciferase and the second fragment of the Renilla luciferase dimerize or fold together; the protein of interest of the first fusion protein is a first fragment of murine dihydrofolate reductase (DHFR), and the protein of interest of the second fusion protein is a second fragment of DHFR, wherein the first fragment of the DHFR and the second fragment of the DHFR dimerize or fold together; the protein of interest of the first fusion protein is a first fragment of *S. cerevisiae* ubiquitin, and the protein of interest of the second fusion protein is a second fragment of *S. cerevisiae* ubiquitin, wherein the first fragment of the *S. cerevisiae* ubiquitin and the second fragment of the *S. cerevisiae* ubiquitin dimerize or fold together; the protein of interest of the first fusion protein is a first fragment of β-lactamase, and the protein of interest of the second fusion protein is a second fragment of β-lactamase, wherein the first fragment of the β-lactamase and the second fragment of the β-lactamase dimerize or fold together; or the protein of interest of the first fusion protein is a first fragment of Herpes simplex virus type 1 thymidine kinase, and the protein of interest of the second fusion protein is a second fragment of Herpes simplex virus type 1 thymidine kinase, wherein the first fragment of the Herpes simplex virus type 1 thymidine kinase and the second fragment of the Herpes simplex virus type 1 thymidine kinase dimerize or fold together.

Embodiment 151

The composition or kit of embodiment 150 wherein: the first fragment or second fragment of sfGFP comprises the amino acid sequence MRKGEELFTGVV PIL-VELDGDVNGHKFSVRGEGEGDATNGKLTLK-FICTTGKLPVPWPFLVTTLTYGVQCF ARYPDHMKQHDFFKSAMPEGYVQERTIS-FKDDGTYKTRAEVKFEGDTLVNRIELKGIDF KEDG-NILGHKLEYNFNSHNVYITADKQ (SEQ ID NO:29), and the other of the first fragment or second fragment of sfGFP comprises the amino acid sequence KNGIKANFKIRHN-VEDGSV QLADHYQQNTPIGDGPVLLPDNHYL-STQSVLSKDPNEKRDHMVLLEFVTAAGITHGMD ELYK (SEQ ID NO:30); the first fragment or second fragment of Renilla luciferase comprises the amino acid sequence MASKVYDPEQRKR-MITGPQWWARCKQMNVLDSFINYYDSEKH AENAVI-FLHGNAASSYLWRHVVPHIEPVARCI-IPDLIGMGKSGKSGNGSYRLLDHYKYL TAWFELLNLPKKIIFVGHDWGACLAFHYSYEHQD-KIKAIVHAESVVDVIESWDEWPDIE EDIALIK-SEEGEKMVLENNFFVETMLPSKIMRKLEPEEFAAY- LEPFKEKGEVRRPTLSWP REIPLVKGG (SEQ ID NO:31), and the other of the first fragment or second fragment of Renilla luciferase comprises the amino acid sequence KPDVVQIVRNYNAYLRASDDLPKM-FIESDPG FFSNAIVEG-AKKFPNTEFVKVKGLHFSQEDAP-DEMGKYIKSFVERVLKNEQ (SEQ ID NO:32); the first fragment or second fragment of DHFR comprises amino acids 1-105 thereof, and the other of the first fragment or second fragment of DHFR comprises amino acids 106-186 thereof; the first fragment or second fragment of S. cerevisiae ubiquitin comprises the amino acid sequence MQIFVKTLTGKTITLEVESSDTIDNVKSKIQDKE (SEQ ID NO:33), and the other of the first fragment or second fragment of S. cerevisiae ubiquitin comprises the amino acid sequence GIPPDQQRLIFAGKQLEDGRTLSDY-NIQKESTLHLVLRLRGG (SEQ ID NO:34); the first fragment or second fragment of f-lactamase comprises amino acids 25-197 thereof, and the other of the first fragment or second fragment of f-lactamase comprises amino acids 198-286 thereof; and the first fragment or second fragment of Herpes simplex virus type 1 thymidine kinase comprises amino acids 1-265 thereof, and the other of the first fragment or second fragment of Herpes simplex virus type 1 thymidine kinase comprises amino acids 266-376 thereof.

Embodiment 152

A composition or kit comprising: a first haplomer-ligand complex of any one of embodiments 1, 2, or 3 to 10; a second haplomer-ligand complex of any one of embodiments 1, 2, or 3 to 10; a first fusion protein of any one of embodiments 107 to 111 or 122 to 129; and a second fusion protein of any one of embodiments 107 to 111 or 122 to 129; wherein the ligand of the first haplomer-ligand complex is linked to the 5' terminus of the polynucleotide of the first haplomer-ligand complex: wherein the ligand of the second haplomer-ligand complex is linked to the 3' terminus of the polynucleotide of the second haplomer-ligand complex; wherein the polynucleotide of the first haplomer-ligand complex is substantially complementary to a target nucleic acid molecule; wherein the polynucleotide of the second haplomer-ligand complex is substantially complementary to the target nucleic acid molecule at a site in spatial proximity to the polynucleotide of the first haplomer-ligand complex; wherein the ligand of the first haplomer-ligand complex and the ligand binding domain of the first fusion protein can interact; wherein the ligand of the second haplomer-ligand complex and the ligand binding domain of the second fusion protein can interact; and wherein the fragment of the protein of interest of the first fusion protein and the fragment of the protein of interest of the second fusion protein can dimerize or fold together.

Embodiment 153

A composition or kit comprising: a first haplomer-ligand complex of any one of embodiments 1, 2, or 1 to 18; a second haplomer-ligand complex of any one of embodiments 1, 2, or 11 to 18; a first fusion protein of any one of embodiments 107 or 112 to 129; and a second fusion protein of any one of embodiments 107 or 112 to 129; wherein the ligand of the first haplomer-ligand complex is linked to the 5' terminus of the polynucleotide of the first haplomer-ligand complex; wherein the ligand of the second haplomer-ligand complex is linked to the 3' terminus of the polynucleotide of the second haplomer-ligand complex; wherein the polynucleotide of the first haplomer-ligand complex is substantially complementary to a target nucleic acid molecule; wherein the polynucleotide of the second haplomer-ligand complex is substantially complementary to the target nucleic acid molecule at a site in spatial proximity to the polynucleotide of the first haplomer-ligand complex; wherein the ligand of the first haplomer-ligand complex and the ligand binding domain of the first fusion protein can interact; wherein the ligand of the second haplomer-ligand complex and the ligand binding domain of the second fusion protein can interact; and wherein the fragment of the protein of interest of the first fusion protein and the fragment of the protein of interest of the second fusion protein can dimerize or fold together.

Embodiment 154

A composition or kit comprising: a first bottle haplomer-ligand complex of any one of embodiments 44 to 65; a second haplomer-ligand complex of any one of embodiments 1, 2, or 3 to 10, wherein the second haplomer-ligand complex comprises a nucleotide portion that is substantially complementary to the stem portion of the bottle haplomer-ligand complex that is linked to the ligand of the bottle haplomer-ligand complex; a first fusion protein of any one of embodiments 107 to 111 or 122 to 129; and a second fusion protein of any one of embodiments 107 to 111 or 122 to 129; wherein the ligand of the first bottle haplomer-ligand complex and the ligand binding domain of the first fusion protein can interact; wherein the ligand of the second haplomer-ligand complex and the ligand binding domain of the second fusion protein can interact; and wherein the fragment of the protein of interest of the first fusion protein and the fragment of the protein of interest of the second fusion protein can dimerize or fold together.

Embodiment 155

A composition or kit comprising: a first bottle haplomer-ligand complex of any one of embodiments 44 to 57 or 66 to 73; a second haplomer-ligand complex of any one of embodiments 1, 2, or 11 to 18, wherein the second haplomer-ligand complex comprises a nucleotide portion that is substantially complementary to the stem portion of the bottle haplomer-ligand complex that is linked to the ligand of the bottle haplomer-ligand complex; a first fusion protein of any one of embodiments 107 or 112 to 129; and a second fusion protein of any one of embodiments 107 or 112 to 129; wherein the ligand of the first bottle haplomer-ligand complex and the ligand binding domain of the first fusion protein can interact; wherein the ligand of the second haplomer-ligand complex and the ligand binding domain of the second fusion protein can interact; and wherein the fragment of the protein of interest of the first fusion protein and the fragment of the protein of interest of the second fusion protein can dimerize or fold together.

Embodiment 156

A method for the directed assembly of a protein comprising: contacting a target nucleic acid molecule with a first haplomer-ligand complex of any one of embodiments 1, 2, or 3 to 10; contacting the target nucleic acid with a second haplomer-ligand complex of any one of embodiments 1, 2, or 3 to 10; contacting the first haplomer-ligand complex with a first fusion protein of any one of embodiments 107 to 111 or 122 to 129; and contacting the second haplomer-ligand complex with a second fusion protein of any one of embodiments 107 to 111 or 122 to 129; wherein the ligand of the first haplomer-ligand complex is linked to the 5' terminus of the polynucleotide of the first haplomer-ligand complex; wherein the ligand of the second haplomer-ligand complex is linked to the 3' terminus of the polynucleotide of the second haplomer-ligand complex; wherein the polynucleotide of the first haplomer-ligand complex is substantially complementary to a target nucleic acid molecule; wherein the polynucleotide of the second haplomer-ligand complex is substantially complementary to the target nucleic acid molecule at a site in spatial proximity to the polynucleotide of the first haplomer-ligand complex; wherein the ligand of the first haplomer-ligand complex and the ligand binding domain of the first fusion protein can interact; and wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

Embodiment 157

A method for the directed assembly of a protein comprising: contacting a target nucleic acid molecule with a first haplomer-ligand complex of any one of embodiments 1, 2, or 11 to 18; contacting the target nucleic acid with a second haplomer-ligand complex of any one of embodiments 1, 2, or 11 to 18; contacting the first haplomer-ligand complex with a first fusion protein of any one of embodiments 107 or 112 to 129; and contacting the second haplomer-ligand complex with a second fusion protein of any one of embodiments 107 or 112 to 129; wherein the ligand of the first haplomer-ligand complex is linked to the 5' terminus of the polynucleotide of the first haplomer-ligand complex; wherein the ligand of the second haplomer-ligand complex is linked to the 3' terminus of the polynucleotide of the second haplomer-ligand complex; wherein the polynucleotide of the first haplomer-ligand complex is substantially complementary to a target nucleic acid molecule; wherein the polynucleotide of the second haplomer-ligand complex is substantially complementary to the target nucleic acid molecule at a site in spatial proximity to the polynucleotide of the first haplomer-ligand complex; wherein the ligand of the first haplomer-ligand complex and the ligand binding domain of the first fusion protein can interact; and wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

Embodiment 158

The method of embodiment 156 or embodiment 157 wherein the polynucleotide of the first haplomer-ligand complex is complementary to the polynucleotide of the second haplomer-ligand complex.

Embodiment 159

The method of embodiment 156 or embodiment 157 wherein the polynucleotide of the first haplomer-ligand complex binds to the target nucleic acid molecule in spatial proximity to the binding of the polynucleotide of the second haplomer-ligand complex to the target nucleic acid molecule.

Embodiment 160

The method of embodiment 156 or embodiment 157 wherein: the ligand of the first haplomer-ligand complex is linked to the 5' terminus of the polynucleotide of the first haplomer-ligand complex, and the polynucleotide of the first haplomer-ligand complex is complementary to a portion of the nucleic acid target 5' adjacent to a stem-loop structure; and the ligand of the second haplomer-ligand complex is linked to the 3' terminus of the polynucleotide of the second haplomer-ligand complex, and the polynucleotide of the second haplomer-ligand complex is complementary to a portion of the nucleic acid target 3' adjacent to the stem-loop structure.

Embodiment 161

The method of embodiment 156 or embodiment 157 wherein: the ligand of the first haplomer-ligand complex is linked to the 3' terminus of the polynucleotide of the first haplomer-ligand complex, and the polynucleotide of the first haplomer-ligand complex is complementary to a 5' portion of a loop structure of a stem-loop structure of the nucleic acid target, wherein the 5' portion of the loop structure is adjacent to the stem region of the stem-loop structure; and the ligand of the second haplomer-ligand complex is linked to the 5' terminus of the polynucleotide of the second haplomer-ligand complex, and the polynucleotide of the second haplomer-ligand complex is complementary to a 3' portion of the loop structure of the stem-loop structure of the nucleic acid target, wherein the 3' portion of the loop structure is adjacent to the stem region of the stem-loop structure.

Embodiment 162

A method for the directed assembly of a protein comprising: contacting a target nucleic acid molecule with a complex formed by the interaction of a first haplomer-ligand complex of any one of embodiments 1, 2, or 3 to 10 with a first fusion protein of any one of embodiments 107 to 111 or 122 to 129, wherein the ligand of the first haplomer-ligand complex is linked to the 5' terminus of the polynucleotide of the first haplomer-ligand complex, and wherein the ligand of the first haplomer-ligand complex interacts with the ligand binding domain of the first fusion protein; and contacting the target nucleic acid molecule with a complex formed by the interaction of a second haplomer-ligand complex of any one of embodiments 1, 2, or 3 to 10 with a second fusion protein of any one of embodiments 107 to 111 or 122 to 129, wherein the ligand of the second haplomer-ligand complex is linked to the 5' terminus of the polynucleotide of the second haplomer-ligand complex, and wherein the ligand of the second haplomer-ligand complex interacts with the ligand binding domain of the second fusion protein; thereby resulting in the folding or dimerization of the fragment of the protein of interest of the first fusion protein with the fragment of the protein of interest of the second fusion protein.

Embodiment 163

A method for the directed assembly of a protein comprising: contacting a target nucleic acid molecule with a complex formed by the interaction of a first haplomer-ligand complex of any one of embodiments 1, 2, or 11 to 18 with a first fusion protein of any one of embodiments 107 or 112 to 129, wherein the ligand of the first haplomer-ligand complex is linked to the 5' terminus of the polynucleotide of the first haplomer-ligand complex, and wherein the ligand of the first haplomer-ligand complex interacts with the ligand binding domain of the first fusion protein; and contacting the target nucleic acid molecule with a complex formed by the interaction of a second haplomer-ligand complex of any one of embodiments 1, 2, or 11 to 18 with a second fusion protein of any one of embodiments 107 or 112 to 129, wherein the ligand of the second haplomer-ligand complex is linked to the 5' terminus of the polynucleotide of the second haplomer-ligand complex, and wherein the ligand of the second haplomer-ligand complex interacts with the ligand binding domain of the second fusion protein; thereby resulting in the folding or dimerization of the fragment of the protein of interest of the first fusion protein with the fragment of the protein of interest of the second fusion protein.

Embodiment 164

The method of embodiment 162 or embodiment 163 wherein the polynucleotide of the first haplomer-ligand complex is complementary to the polynucleotide of the second haplomer-ligand complex.

Embodiment 165

The method of embodiment 162 or embodiment 163 wherein the polynucleotide of the first haplomer-ligand complex binds to the target nucleic acid molecule in spatial proximity to the binding of the polynucleotide of the second haplomer-ligand complex to the target nucleic acid molecule.

Embodiment 166

The method of embodiment 162 or embodiment 163 wherein: the ligand of the first haplomer-ligand complex is linked to the 5' terminus of the polynucleotide of the first haplomer-ligand complex, and the polynucleotide of the first haplomer-ligand complex is complementary to a portion of the nucleic acid target 5' adjacent to a stem-loop structure; and the ligand of the second haplomer-ligand complex is linked to the 3' terminus of the polynucleotide of the second haplomer-ligand complex, and the polynucleotide of the second haplomer-ligand complex is complementary to a portion of the nucleic acid target 3' adjacent to the stem-loop structure.

Embodiment 167

The method of embodiment 162 or embodiment 163 wherein: the ligand of the first haplomer-ligand complex is linked to the 3' terminus of the polynucleotide of the first haplomer-ligand complex, and the polynucleotide of the first haplomer-ligand complex is complementary to a 5' portion of a loop structure of a stem-loop structure of the nucleic acid target, wherein the 5' portion of the loop structure is adjacent to the stem region of the stem-loop structure; and the ligand of the second haplomer-ligand complex is linked to the 5' terminus of the polynucleotide of the second haplomer-ligand complex, and the polynucleotide of the second haplomer-ligand complex is complementary to a 3' portion of the loop structure of the stem-loop structure of the nucleic acid target, wherein the 3' portion of the loop structure is adjacent to the stem region of the stem-loop structure.

Embodiment 168

A method for the directed assembly of a protein comprising: contacting a target nucleic acid molecule with a bottle haplomer-ligand complex of any one of embodiments 44 to 57 or 58 to 65; contacting the target nucleic acid with a second haplomer-ligand complex of any one of embodiments 1, 2, or 3 to 10, wherein the second haplomer-ligand complex comprises a nucleotide portion that is substantially complementary to the stem portion of the bottle haplomer-ligand complex that is linked to the ligand of the bottle haplomer-ligand complex; contacting the bottle haplomer-ligand complex with a first fusion protein of any one of embodiments 107 to 111 or 122 to 129, wherein the ligand of the bottle haplomer-ligand complex and the ligand binding domain of the first fusion protein can interact; and contacting the second haplomer-ligand complex with a second fusion protein of any one of embodiments 107 to 111 or 122 to 129, wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

Embodiment 169

A method for the directed assembly of a protein comprising: contacting a target nucleic acid molecule with a bottle haplomer-ligand complex of any one of embodiments 44 to 57 or 66 to 73; contacting the target nucleic acid with a second haplomer-ligand complex of any one of embodiments 1, 2, or 11 to 18, wherein the second haplomer-ligand complex comprises a nucleotide portion that is substantially complementary to the stem portion of the bottle haplomer-ligand complex that is linked to the ligand of the bottle haplomer-ligand complex: contacting the bottle haplomer-ligand complex with a first fusion protein of any one of embodiments 107 or 112 to 129, wherein the ligand of the bottle haplomer-ligand complex and the ligand binding domain of the first fusion protein can interact; and contacting the second haplomer-ligand complex with a second fusion protein of any one of embodiments 107 or 112 to 129, wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

Embodiment 170

A method for the directed assembly of a protein comprising: contacting a target nucleic acid molecule with a bottle haplomer-ligand complex of any one of embodiments 44 to 65; contacting the target nucleic acid molecule with a second haplomer-ligand complex of any one of embodiments 1, 2, or 3 to 10, wherein the second haplomer-ligand complex comprises a nucleotide portion that is substantially complementary to the stem portion of the bottle haplomer-ligand complex that is linked to the ligand of the bottle haplomer-ligand complex; contacting the bottle haplomer-ligand complex with a first fusion protein of any one of embodiments 107 to 111 or 122 to 129, wherein the ligand of the bottle haplomer-ligand complex and the ligand binding domain of the first fusion protein can interact; and contacting the second haplomer-ligand complex with a second fusion protein of any one of embodiments 107 to 111 or 122 to 129, wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

Embodiment 171

A method for the directed assembly of a protein comprising: contacting a target nucleic acid molecule with a bottle haplomer-ligand complex of any one of embodiments 44 to 57 or 66 to 73; contacting the target nucleic acid molecule with a second haplomer-ligand complex of any one of embodiments 1, 2, or 11 to 18, wherein the second haplomer-ligand complex comprises a nucleotide portion that is substantially complementary to the stem portion of the bottle haplomer-ligand complex that is linked to the ligand of the bottle haplomer-ligand complex; contacting the bottle haplomer-ligand complex with a first fusion protein of any one of embodiments 107 or 112 to 129, wherein the ligand of the bottle haplomer-ligand complex and the ligand binding domain of the first fusion protein can interact; and contacting the second haplomer-ligand complex with a second fusion protein of any one of embodiments 107 or 112 to 129, wherein the ligand of the second haplomer-ligand complex and the ligand binding domain of the second fusion protein can interact; thereby resulting in the folding or dimerization of the fragment of the protein of interest of the first fusion protein with the fragment of the protein of interest of the second fusion protein.

In order that the subject matter disclosed herein may be more efficiently understood, examples are provided below. It should be understood that these examples are for illustrative purposes only and are not to be construed as limiting the claimed subject matter in any manner.

EXAMPLES

Example 1. Expression of c-Jun Leucine Zipper Domains Via the Maltose-Binding Protein System, and Conjugation with Specific Oligonucleotides to Form an LD-TAPER Haplomer c-Jun fragments for conjugation with oligonucleotides to form small protein interactive domain LD-TAPER haplomers were expressed as fusion proteins in the maltose-binding protein (MBP) system, before release from the MBP fusion protein with enterokinase.

Coding sequences for each c-Jun segment (bearing either an N-terminal cysteine or a C-terminal cysteine, as above) were equipped with an enterokinase recognition signal (codons for DDDDK; SEQ ID NO:35), such that after expression, the C-terminal MBP fragments could be cleaved from the maltose binding carrier protein. Assembled sequences were cloned between XmnI and SbfI sites of pMALc5x (New England Biolabs), and the structure of candidate clones confirmed by sequencing. Verified clones were transformed into the strain NEB-express (New England Biolabs), and propagated in liquid culture (50 ml) under short-term growth conditions at 37° C. for 1.5 hours, before induction with 300 µM IPTG for a further 2 hours. Samples ("direct lysates"; 200 µl) were taken, pelleted in 1.5 ml tubes at 1000×g, washed once with 200 µl of IX PBS, and re-suspended in 50 µl of PBS. The remainder of the 50 ml growths were pelleted (10 minutes/3000 rpm in a Sorvall benchtop centrifuge), and re-suspended in 2.0 ml Eppendorf tubes in 1.5 ml of ice-cold maltose-binding protein system column buffer (MC-buffer: 20 mM Tris (pH 7.4), 200 mM NaCl, 1 mM EDTA, and 1 mM DTT) also containing 1% protease inhibitor cocktail (Sigma P3840). Cell suspensions were then sonicated (6×5 second pulses, 5-setting, Branson 450 Sonifier, with chilling between each sonication round), centrifuged for 5 minutes at 14000 rpm (benchtop microfuge), and the supernatants were transferred to a fresh tube.

Polypeptides expressed as fusions with maltose-binding protein were affinity purified on amylose magnetic beads (A-MBs; New England Biolabs). Suitable samples of A-MBs (usually equivalent to 250 µl of the original slurries per 1 ml of supernatant) were washed twice with 1 ml of cold MC-buffer (using magnetic separation to pull down the A-MBs), and re-suspended in the original volume. Sonicated supernatants from induced plasmid cultures were mixed with the A-MBs for 1 hour at 4° C., with frequent tube inversion to re-suspend the beads. The supernatants were then magnetically removed, and the beads washed four times with 0.5 ml of cold MC-buffer before resuspension in 150 µl of the same buffer/250 µl of original beads.

Figure 23:
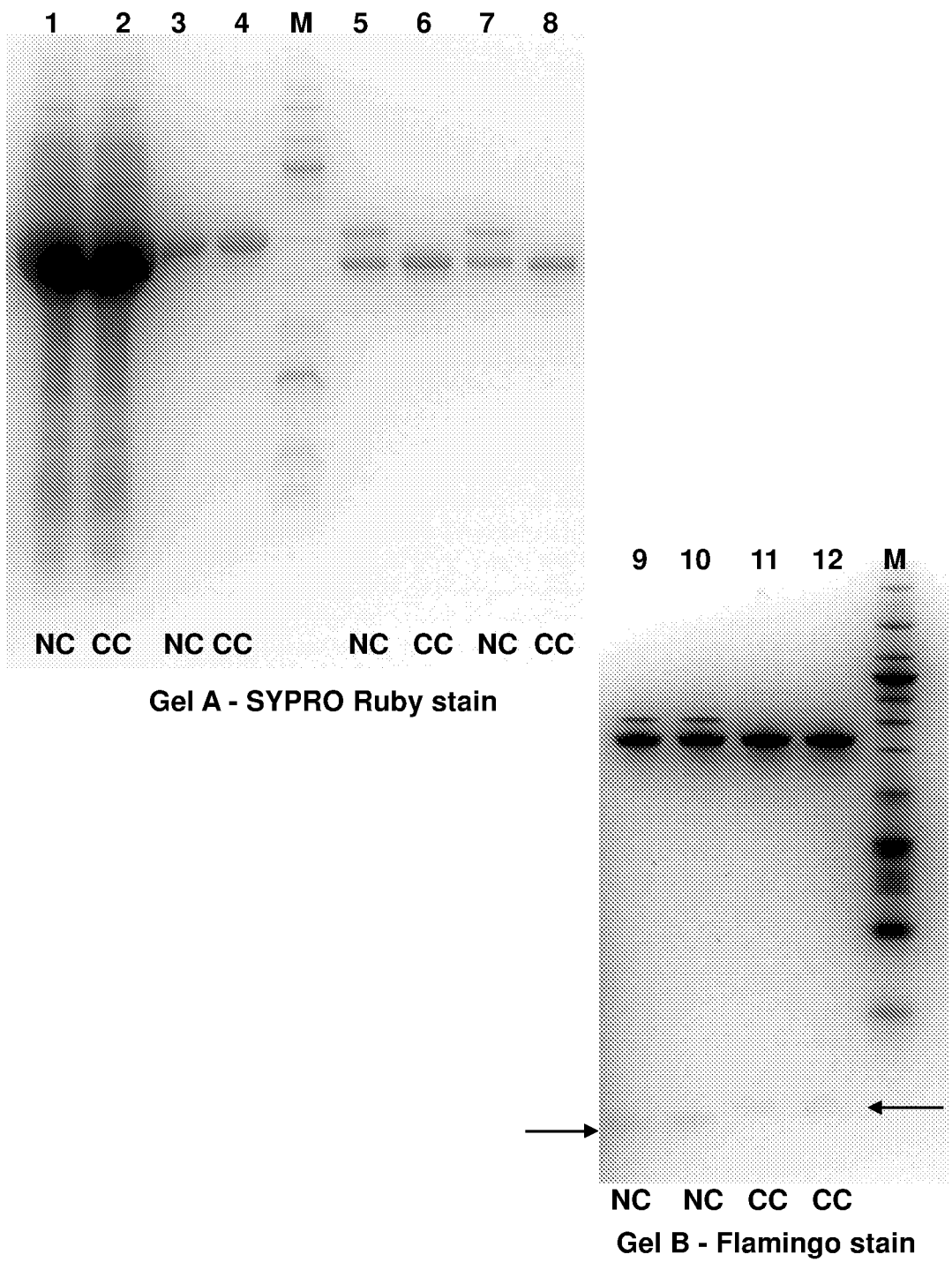
FIG. 23 shows a representative testing expression of c-Jun fragments as fusion proteins with Maltose-Binding Protein (MBP), and demonstration of production of free c-Jun products after enterokinase cleavage of the fusion.

Bound proteins were eluted with a final concentration of 10 mM maltose. The elution and enterokinase treatments were performed simultaneously by the addition of 2 mM calcium chloride to the MC-buffer containing the maltose. After 3 hours of elution/digestion, supernatants were magnetically separated, the pellets treated with 75 µl of MC-buffer, and the soluble phase combined with the first supernatant. A portion of this product was then subjected to an agarose affinity treatment to remove enterokinase (EMD-Millipore), and the non-binding flow-through retained. Samples were analyzed initially on a TGX any-kD gel (BioRad), and stained with SYPRO-Ruby (ThermoFisher). Expression of both c-Jun MBP fusions as soluble proteins occurred at very high levels (see, lanes 1 and 2, FIG. 23), considerably in excess of the maximal retainable by the amount of A-MBs used (see, lanes 1 and 2 vs. lanes 3 and 4, FIG. 23). Enterokinase cleavage of co-eluted fusion protein went to completion in the case of the C-terminal cysteine c-Jun fragment (see, lane 6, FIG. 23), and was approximately 80% complete for the N-terminal cysteine fusion (see, lane 5, FIG. 23). Recovery of the products following enterokinase removal was on the order of 75% (see, lanes 7 and 8 vs. lanes 5 and 6, FIG. 23). In both cases, enterokinase cleavage produced the expected MBP cleavage band, but under conditions used, the small c-Jun bands were not visible. Subsequently, samples of cleaved products were run on a 16% Tris-Tricine gel (ThermoFisher) and stained with Flamingo stain (BioRad), after which the expected 5.0 and 5.2 kD bands for the N-terminal and C-terminal cysteine c-Jun fragments (respectively) could be visualized (see, lanes 9-12, FIG. 23).

Since both c-Jun fragments lack internal cysteines, they are readily amenable to conjugation with thiol-labeled oligonucleotides via bifunctional maleimide reagents. The conjugation process using bis-maleimide linkers is performed in two stages. Initially, oligonucleotides bearing a 5' or 3' terminal disulfide modification are treated with 100-fold molar excess of TCEP for at least 4 hours at 25° C., and then desalted into 10 mM Tris (pH 7.4) to remove the TCEP and low-molecular weight products. The resulting —SH oligonucleotides are then treated with a molar excess (500-fold)

of 1,8-bis(maleimido) diethylene glycol (BMP2, Sigma) in sodium phosphate buffer pH 7.1 for 4 hours at 25° C. The preparations are then desalted once more to remove excess BMP2. Samples of the modified oligonucleotides are run on 8 M urea gels to examine the success of the process, in comparison to the original —SS-oligonucleotides and the corresponding derived —SH oligonucleotides.

The second stage uses the BMP2-derivatized oligonucleotide to cross-link to the c-Jun fragments with N- and C-terminal cysteine residues. Before treatment, the cleaved fragment -MBP preparations are treated with a 10-fold molar excess of TCEP to ensure that the cysteine —SH groups are reduced, and then desalted into phosphate buffer (pH 7.1) with 100 mM sodium chloride.

Fragments are incubated in the same buffer with a large molar excess of BMP2-derivatized oligonucleotide to drive the reaction, for 4 hours at 25° C. Excess oligonucleotides (bearing unreacted maleimide groups) are then removed by treatment with sulfhydryl magnetic beads (Bioclone). Polypeptide conjugates are then dialyzed against PBSM and stored in 50% glycerol at −20° C.

Example 2: Use of c-Jun Haplomers with c-Fos Polypeptide Fusions for Split-Protein LD-TAPER (Prophetic)

Where c-Jun zipper fragments are used to implement LD-TAPER (by constructing haplomers with 5' and 3' c-Jun tags; see, Example 1), after hybridization of haplomers to target templates, the second stage uses fusion proteins with complementary c-Fos zippers. Thus, for the application of split-protein technology with small interactive protein domains to LD-TAPER, suitable protein fragments are expressed as N- or C-terminal c-Fos fusions. Superfolder GFP (sfGFP) and Renilla luciferase fragments are used.

Figure 24:
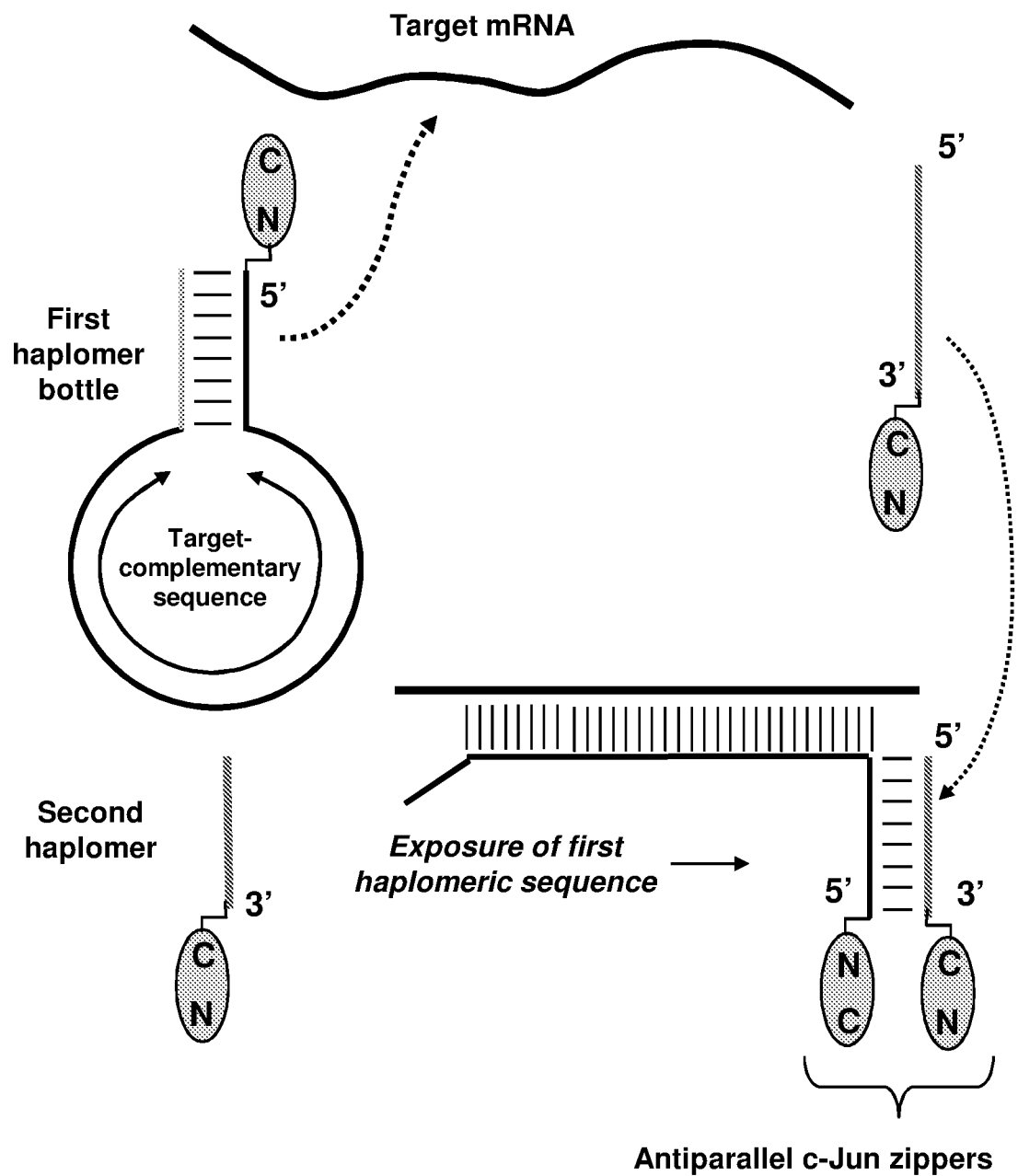
FIG. 24 shows a representative Locked TAPER c-Jun oligonucleotides for split-protein folding by LD-TAPER, using an antiparallel zipper configuration.

Locked TAPER (see, FIG. 13) is used with c-Jun tags, instead of small-molecule ligands (see, FIG. 24). The 5' end of the first bottle haplomer is conjugated by thiol-maleimide chemistry with the c-Jun fragment with an N-terminal cysteine, and the 3' end of the second haplomer is conjugated with the c-Jun fragment with a C-terminal cysteine (sequences as above).

With this arrangement, the zippers are aligned in an antiparallel orientation following "unlocking" of the initial first bottle haplomer anti-target loop portion in the presence of specific template (see, FIG. 24).

Fos-fusion protein sequences are as follows (c-Fos sequence are in bold, including helix boundary signals; double underlined segments indicate serine-glycine linkers):

N-terminal sfGFP/C-terminal Fos:
(SEQ ID NO: 36)
MSKGEELFTGVVPILVELDGDVNGHKFSVRGEGEGDATNGKLTLKFICTT

GKLPVPWPTLVTTLTYGVQCFSRYPDHMKRHDFFKSAMPEGYVQERTISF

KDDGTYKTRAVVKFEGDTLVNRIELKGTDFKEDGNILGHKLEYNFNSHNV

YITADKQ<u>GGSGGGSGGGSGGGSGGG</u>ASRELTDTLQAETDQLEDEKSALQT

EIANLLKEKEKLEGAP\*;

N-terminal Fos/C-terminal sfGFP:
(SEQ ID NO: 37)
SGASRELTDTLQAETDQLEDEKSALQTEIANLLKEKEKLEGAP<u>GGSGGGS</u>

<u>GGGSGGGSGGG</u>KNGIKANFTVRHNVEDGSVQLADHYQQNTPIGDPVLLP

-continued
DNHYLSTQTVLSKDPNEKRDHMVLHEYVNAAGITLGMDELYK\*;

N-terminal Renilla/C-terminal Fos:
(SEQ ID NO: 38)
MASKVYDPEQRKRMITGPQWWARCKQMNVLDSFINYYDSEKHAENAVIFL

HGNAASSYLWRHVVPHIEPVARCIIPDLIGMGKSGKSGNGSYRLLDHYKY

LTAWFELLNLPKKIIFVGHDWGACLAFHYSYEHQDKIKAIVHAESVVDVI

ESWDEWPDIEEDIALIKSEEGEKMVLENNFFVETMLPSKIMRKLEPEEFA

AYLEPFKEKGEVRRPTLSWPREIPLVKGG<u>GGSGGGSGGGSGGGSGGG</u>AS

RELTDTLQAETDQLEDEKSALQTEIANLLKEKEKLEGAP\*;

N-terminal Fos/C-terminal Renilla:
(SEQ ID NO: 39)
SGASRELTDTLQAETDQLEDEKSALQTEIANLLKEKEKLEGAP<u>GGSGGG</u>

<u>SGGGSGGGSGGG</u>KPDVVQIVRNYNAYLRASDDLPKMFIESDPGFFSNAI

VEGAKKFPNTEFVKVKGLHFSQEDAPDEMGKYIKSFVERVLKNEQ\*.

For expression purposes, all protein codons are optimized for *E. coli* K12. All proteins are expressed as maltose-binding protein (MBP) fusions (see, Example 1), and released from the MBP carrier by treatment with enterokinase.

Figure 25:
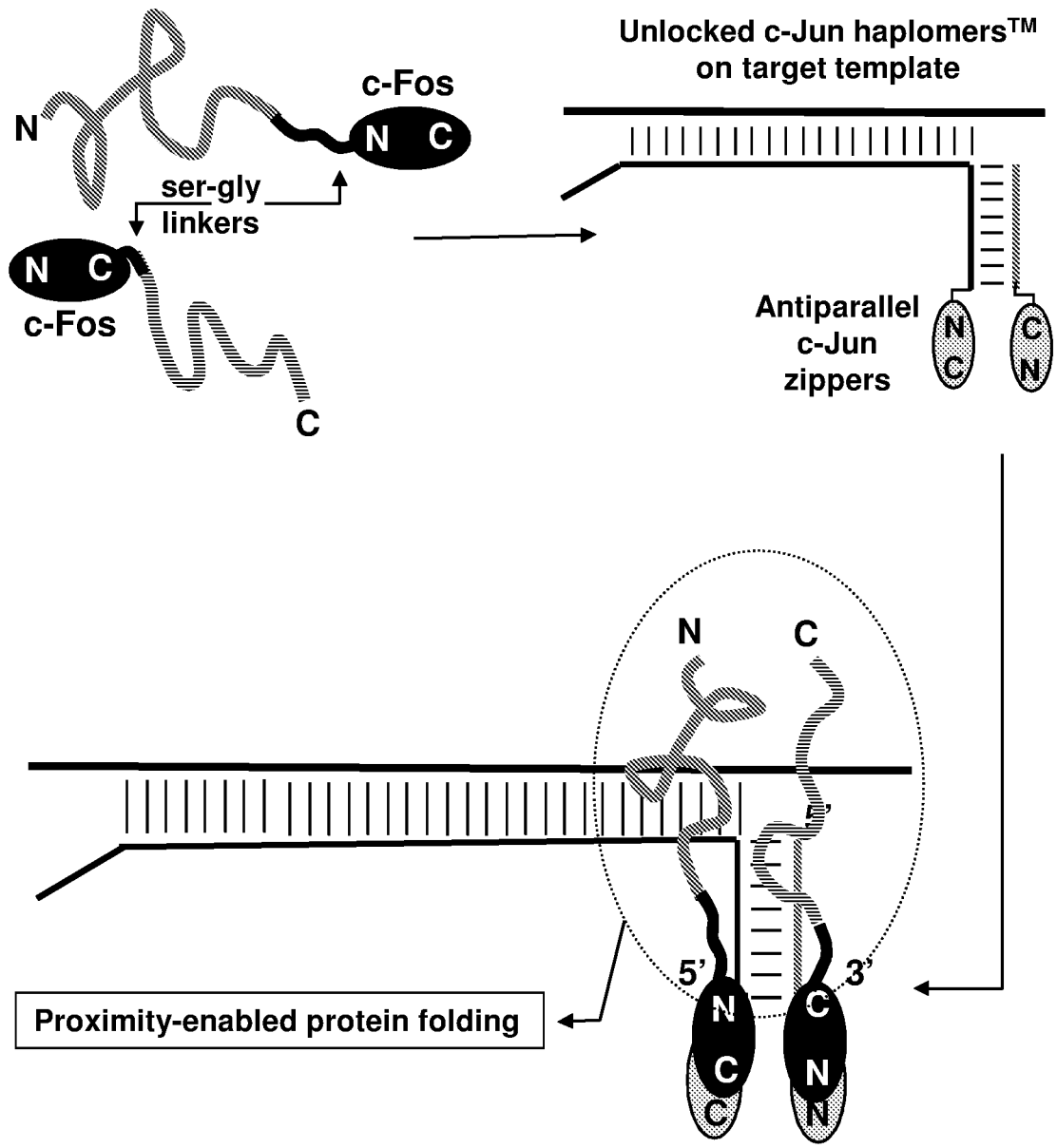
FIG. 25 shows a representative Locked TAPER split-protein folding by LD-TAPER with c-Jun:c-Fos interactions.

In the initial experimental approach "A", to implement the experimental process, the c-Jun first bottle haplomer is incubated with specific target template (complementary to its anti-target loop portion), allowing "unlocking" of this first bottle haplomer, and exposure of the hybridization site for the second haplomer. After duplex formation with the second haplomer, the preparations of c-Fos fusions of sfGFP and Renilla N- and C-terminal fragments (as above) are added. This allows the second stage of the LD-TAPER process to proceed, with c-Fos:c-Jun zippers pairing, and thereby juxtaposing the polypeptide split-protein pair for mature folding (see, FIG. 25). The antiparallel orientation of the haplomer c-Jun tags (see, FIG. 24) facilitates the positioning and orientation of the polypeptides (see, FIG. 25).

The sfGFP signal is fluorescence at the same emission maximum as for fluorescein, and is monitored by means of a spectrophotometer with fluorescent reading facility (Tecan). The enzymatic activity of Renilla luciferase is assessed by means of commercial kits for this enzyme (Promega), using coelenterazine substrate, and purified Renilla luciferase (RayBiotech) as a positive control. Luminescence is quantified by means of a standard luminometer (Berthold).

In a dose-response experimental design, equimolar amounts of sfGFP N- and C-terminal Fos-fusions are mixed with first-stage haplomers "unlocked" in the presence of specific target template as above. Ratios of the N- and C-terminal Fos fusions to haplomer range from 1:1 to 10:1. Analogous experiments are established with Renilla N- and C-terminal Fos-fusions. After a 16 hour incubation at 25° C., reporter signals are assayed as appropriate for both sfGFP and Renilla luciferase.

Since homoligand LD-TAPER for split-protein folding has an efficiency limitation if the haplomer/template hybridizations are performed as the first step (as shown with Equations 4.1, 4.2), in addition to experimental approach "A," a second ("B") protocol is also followed, in accord with Equations 5.1 and 5.2. Here the locked-TAPER first bottle haplomer bearing a c-Jun tag (see, FIG. 24) is hybridized to template as before, but then treated with the N-terminal sfGFP or Renilla C-terminal Fos fusions. In a separate reaction, the second haplomer is treated with the C-terminal sfGFP or Renilla N-terminal fusions. After 2 hours at 25° C., each pre-assembled c-Jun haplomer/template/c-Fos-polypeptide is mixed in equimolar amounts. After a 16 hour incubation at 25° C., reporter signals are assayed as appropriate for both sfGFP and Renilla luciferase.

For both experimental designs "A" and "B", comparable time-course experiments are also performed after the two-stage assembly of all LD-TAPER components has been completed. In protocol "A", this corresponds to the initial hybridizations for both Jun-haplomers; followed by the addition of the split-protein Fos-polypeptides; for protocol "B", this corresponds to the separate pre-assembly of Jun-haplomers with specific split-protein Fos-polypeptides, followed by combination of the two haplomeric complexes. For each arrangement, assayable samples taken at a series of time points: 15, 30, 45, and 60 minutes; and 1, 2, 4, 6, 8, and 16 hours.

Specificity of the template-mediated LD-TAPER assembly may be demonstrated by the use of a blocking oligonucleotide that corresponds to the same sequence as the second haplomer, but lacking any appended tag. A molar excess of such an oligonucleotide effectively inhibits the assembly reaction, whereas the assembly process is unaffected by excess oligonucleotide of the same length but with scrambled sequence.

Example 3: Use of Oligonucleotide Conjugates with Mutant FKBP-Binding Monovalent Compounds in LD-TAPER for Split-Protein LD-TAPER (Prophetic)

This Example describes the derivatization of amino-labeled oligonucleotides with mutant FKBP-binding monovalent compounds, and their application in LD-TAPER for small-molecule ligand-directed split-protein folding. Compounds, such as FKM-NHS (see, FIG. 6), are solubilized in DMSO to 10 mM and incubated in a 100-fold molar excess in sodium phosphate buffer (pH 7.4) with oligonucleotides to be used as haplomers, where either the 5' or 3' ends of the oligonucleotides are modified with a commercially available aminolinker. After 2 hours at 25° C., excess unreacted compound is removed by desalting columns, after which the resulting FKM-haplomers are stored in (10/1.0) TE buffer. The success of the formation of the oligonucleotide:FKM adducts is confirmed by testing product mobility on 15% 8 M urea gels, relative to untreated parental oligonucleotide.

Figure 13:
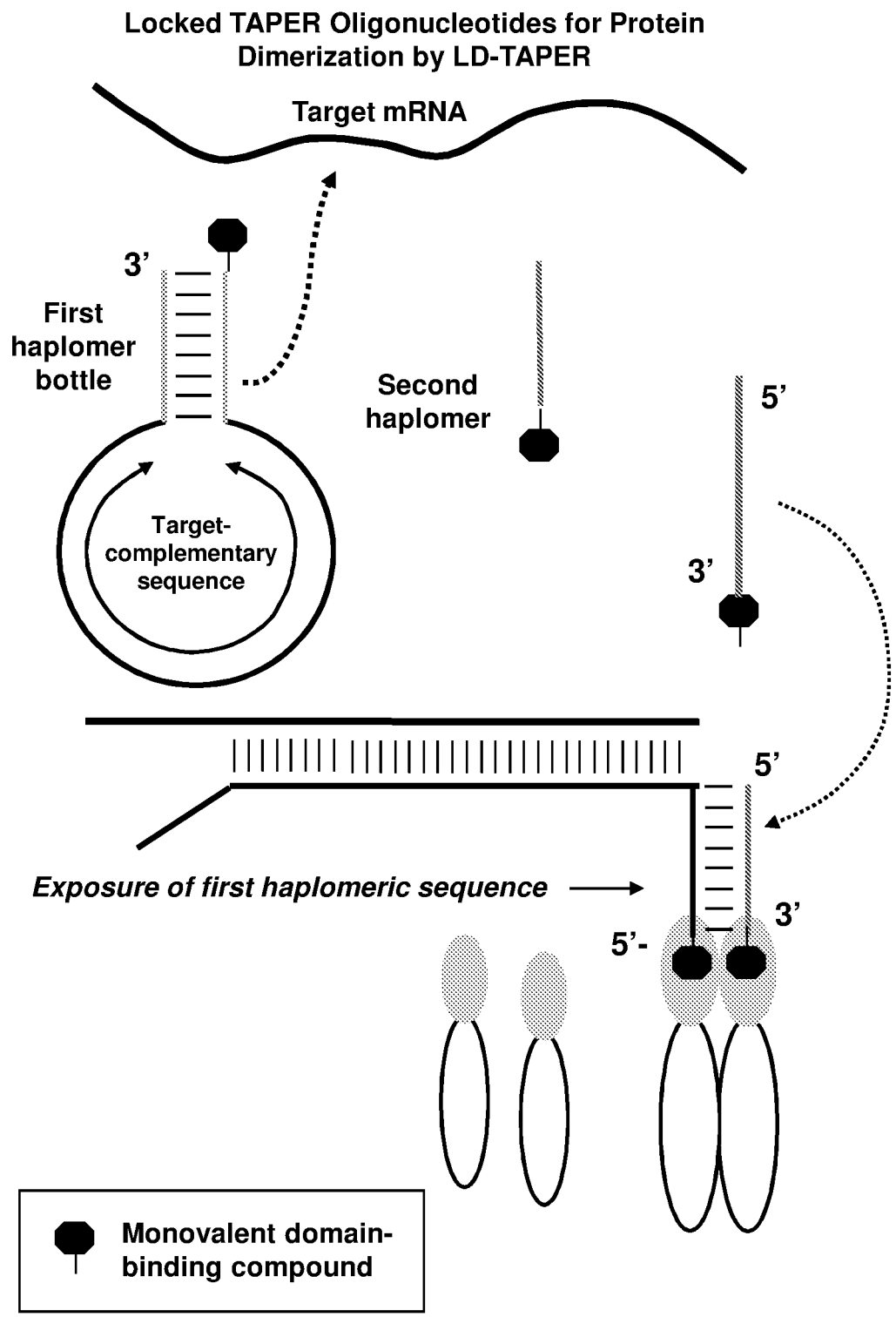
FIG. 13 shows representative structures of locked TAPER oligonucleotides for small molecule-mediated protein dimerization via LD-TAPER, using small-molecule ligands.
Figure 26:
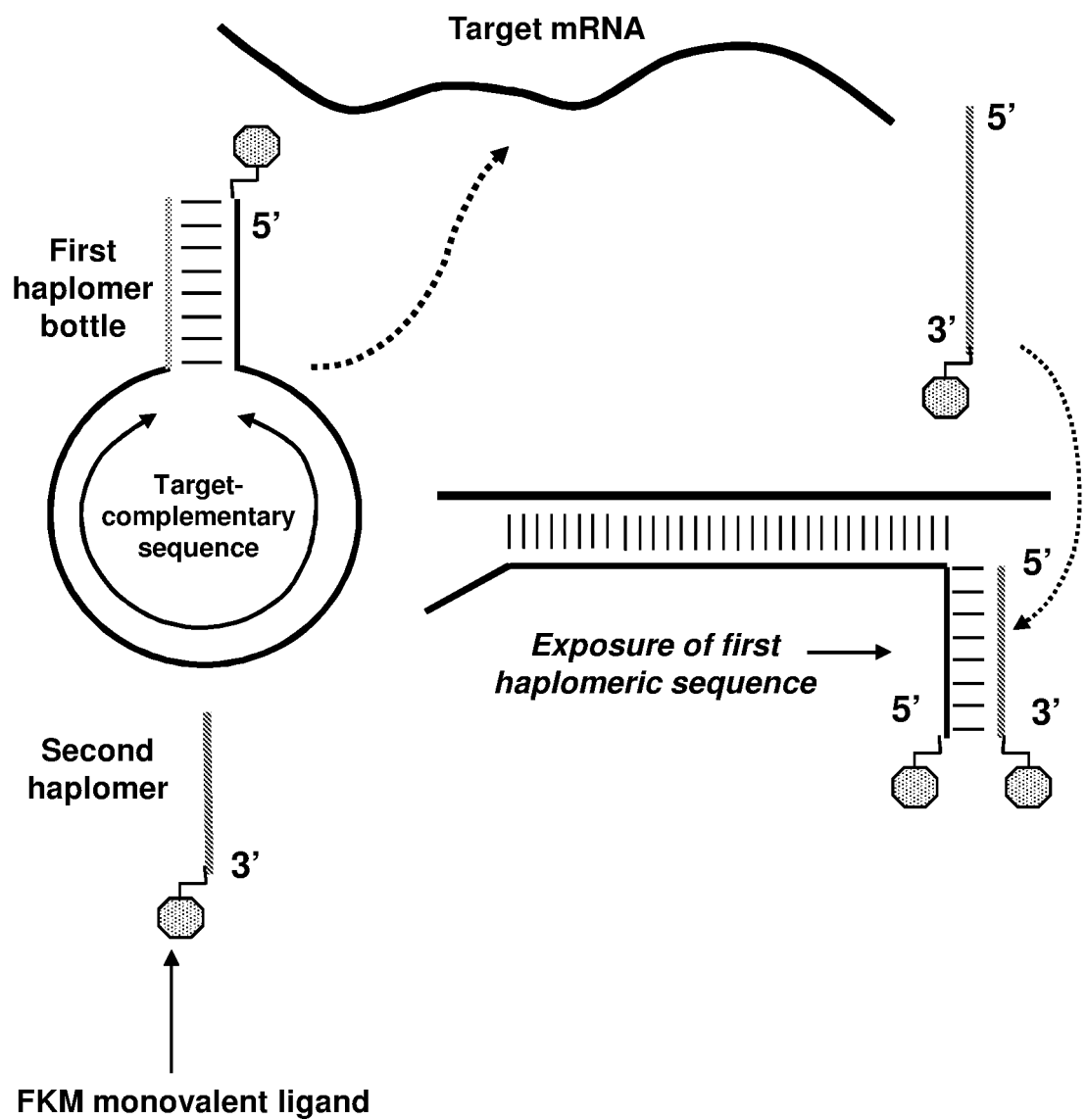
FIG. 26 shows a representative Locked TAPER compound FKM-oligonucleotides for split-protein folding by LD-TAPER.

Haplomers bearing FKM as small-molecule ligands are then amenable to split-protein studies. In this Example, Locked TAPER is used, as depicted in FIG. 13. Polypeptide split-protein targets are rendered as fusion proteins with the F36V mutant of FKBP-1A. For the application of split-protein technology with small molecule ligands to LD-TAPER, suitable protein fragments are expressed as N- or C-terminal mutant FKBP (F36V) fusions. Superfolder GFP (sfGFP) and Renilla luciferase fragments are used. For haplomer construction, Locked TAPER (see, FIG. 13) is used with FKM serving as the small molecule ligand (see, FIG. 26), with its conjugation to the haplomeric oligonucleotides performed as described above.

Mutant FKBP (mFKBP)-fusion protein sequences are as follows (FKBP sequence is in bold, except for the F36V mutation, in small letters; double underlined segments indicate serine-glycine linkers):

N-terminal sfGFP/C-terminal mFKBP:
(SEQ ID NO: 40)
MSKGEELFTGVVPILVELDGDVNGHKFSVRGEGEGDATNGKLTLKFICTT
GKLPVPWPTLVTTLTYGVQCFSRYPDHMKRHDFFKSAMPEGYVQERTISF
KDDGTYKTRAVVKFEGDTLVNRIELKGTDFKEDGNILGHKLEYNFNSHNV
YITADKQ<u>GGSGGGSGGGSGGGSGGG</u>**GVQVETISPGDGRTFPKRGQTCVVH
YTGMLEDGKKv DSSRDRNKPFKFMLGKQEVIRGWEEGVAQMSVGQRAKLT
ISPDYAYGATGHPGIIPPHATLVFDVELLKLE**;

N-terminal mFKBP/C-terminal sfGFP:
(SEQ ID NO: 41)
**MGVQVETISPGDGRTFPKRGQTCVVHYTGMLEDGKKv DSSRDRNKPFKFM
LGKQEVIRGWEEGVAQMSVGQRAKLTISPDYAYGATGHPGIIPPHATLVF
DVELLKLE**<u>GGSGGGSGGGSGGGSGGG</u>KNGIKANFTVRHNVEDGSVQLADH
YQQNTPIGDGPVLLPDNHYLSTQTVLSKDPNEKRDHMVLHEYVNAAGITL
GMDELYK*;

N-terminal Renilla/C-terminal mFKBP:
(SEQ ID NO: 42)
MASKVYDPEQRKRMITGPQWWARCKQMNVLDSFINYYDSEKHAENAVIFL
HGNAASSYLWRHVVPHIEPVARCIIPDLIGMGKSGKSGNGSYRLLDHYKY
LTAWFELLNLPKKIIFVGHDWGACLAFHYSYEHQDKIKAIVHAESVVDVI
ESWDEWPDIEEDIALIKSEEGEKMVLENNFFVETMLPSKIMRKLEPEEFA
AYLEPFKEKGEVRRPTLSWPREIPLVKGG<u>GGSGGGSGGGSGGGSGGG</u>**GVQ
VETISPGDGRTFPKRGQTCVVHYTGMLEDGKKv DSSRDRNKPFKFMLGKQ
EVIRGWEEGVAQMSVGQRAKLTISPDYAYGATGHPGIIPPHATLVFDVEL
LKLE**;

N-terminal mFKBP/C-terminal Renilla:
(SEQ ID NO: 43)
**MGVQVETISPGDGRTFPKRGQTCVVHYTGMLEDGKKv DSSRDRNKPFKFM
LGKQEVIRGWEEGVAQMSVGQRAKLTISPDYAYGATGHPGIIPPHATLVF
DVELLKLE**<u>GGSGGGSGGGSGGGSGGG</u>KPDVVQIVRNYNAYLRASDDLPKM
FIESDPGFFSNAIVEGAKKFPNTEFVKVKGLHFSQEDAPDEMGKYIKSFV
ERVLKNEQ*.

For expression purposes, all protein codons are optimized for *E. coli* K12. All proteins are expressed as maltose-binding protein (MBP) fusions (see, Example 1), and released from the MBP carrier by treatment with enterokinase.

Figure 27:
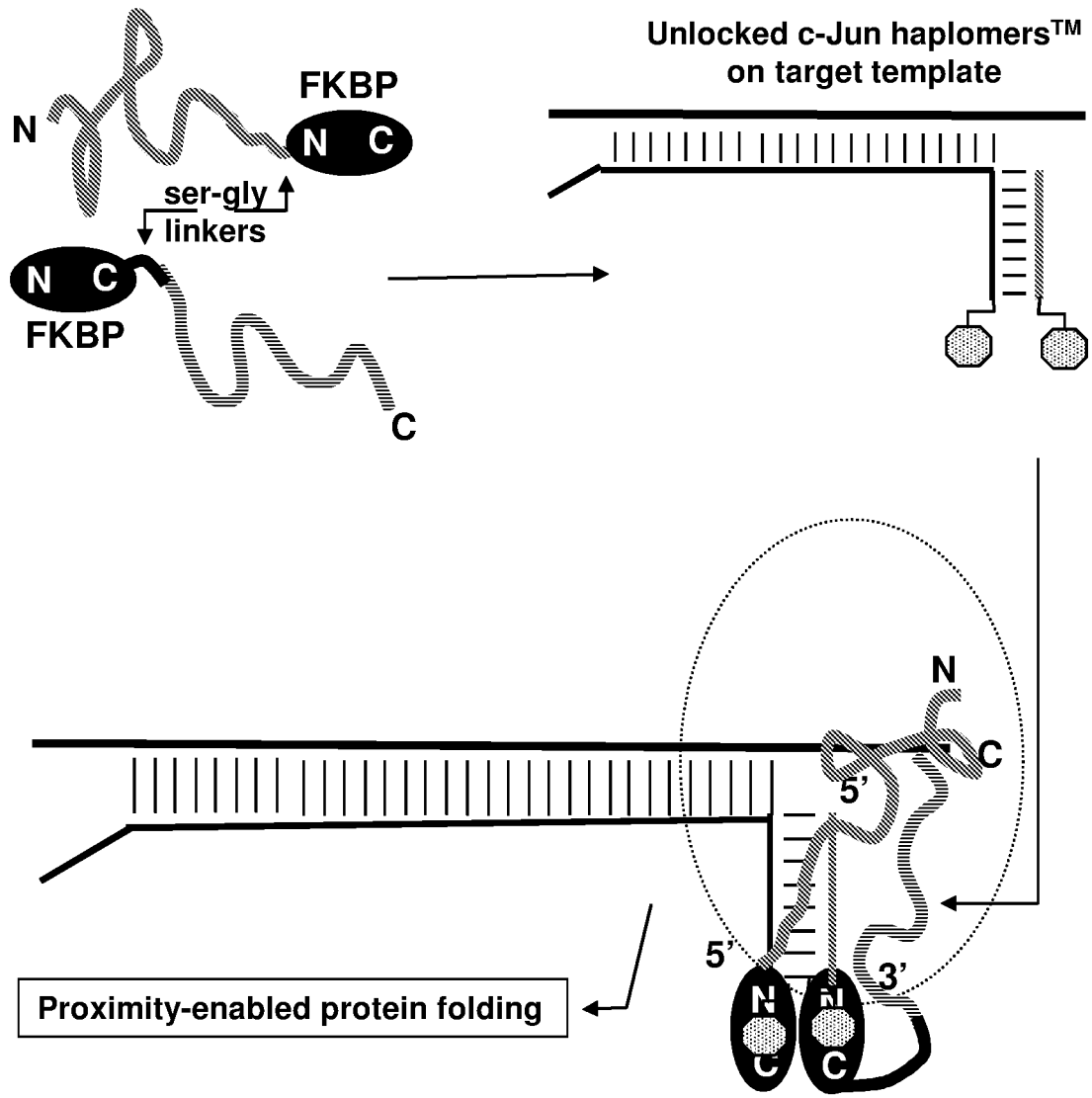
FIG. 27 shows a representative Locked TAPER split-protein folding by LD-TAPER with FKM-FKBP binding.

In the initial experimental approach "A", to implement the experimental process, the FKM-first bottle haplomer is incubated with specific target template (complementary to its loop region), allowing "unlocking" of this first haplomer, and exposure of the hybridization site for the second haplomer. After duplex formation with the second FKM-haplomer (see, FIG. 26), the preparations of mFKBP fusions of sfGFP and Renilla N- and C-terminal fragments (as above) are added. This allows the second stage of the LD-TAPER process to proceed, with FKM-mFKBP binding, and thereby juxtaposing the polypeptide split-protein pair for mature folding (see FIG. 27).

The sfGFP signal is fluorescence at the same emission maximum as for fluorescein, and is monitored by means of a spectrophotometer with fluorescent reading facility (Tecan). The enzymatic activity of Renilla luciferase is assessed by means of commercial kits for this enzyme (Promega), using coelenterazine substrate, and purified Renilla luciferase (RayBiotech) as a positive control. Luminescence is quantified by means of a standard luminometer (Berthold).

In a dose-response experimental design, equimolar amounts of sfGFP N- and C-terminal mFKBP-fusions are mixed with first-stage FKM-haplomers "unlocked" in the presence of specific target template as above. Ratios of the N- and C-terminal mFKBP fusions to FKM-haplomer range from 1:1 to 10:1. Analogous experiments are established with Renilla N- and C-terminal mFKBP fusions. After a 16 hour incubation at 25° C., reporter signals are assayed as appropriate for both sfGFP and Renilla luciferase.

Since homoligand LD-TAPER for split-protein folding has an efficiency limitation if the haplomer/template hybridizations are performed as the first step (as shown with Equations 4.1, 4.2), in addition to experimental approach "A" a second ("B") protocol is also followed, in accord with Equations 5.1 and 5.2. Here the locked-TAPER first bottle haplomer bearing its FKM tag (see, FIG. 26) is hybridized to template as before, but then treated with the N-terminal sfGFP or Renilla C-terminal mFKBP fusions. In a separate reaction, the second FKM-haplomer is treated with the C-terminal sfGFP or Renilla N-terminal mFKBP fusions. After 2 hours at 25° C., each pre-assembled FKM-haplomer/template/mFKBP-polypeptide is mixed in equimolar amounts. After a 16 hour incubation at 25° C., reporter signals are assayed as appropriate for both sfGFP and Renilla luciferase. During the incubation time, mature protein folding is enable. Note that long serine-glycine linkers are used to accommodate the orientation of the mFKBP domain binding to its cognate FKM monovalent ligand (see, FIG. 27).

For both experimental designs "A" and "B", comparable time-course experiments are also performed after the two-stage assembly of all LD-TAPER components has been completed. In protocol "A", this corresponds to the initial hybridizations for both FKM-haplomers; followed by the addition of the split-protein mFKBP-polypeptides; for protocol "B", this corresponds to the separate pre-assembly of FKM-haplomers with specific split-protein mFKBP-polypeptides, followed by combination of the two haplomeric complexes. For each arrangement, assayable samples taken at a series of time points: 15, 30, 45, and 60 minutes; and 1, 2, 4, 6, 8, and 16 hours.

Specificity of the template-mediated LD-TAPER assembly may be demonstrated by the use of a blocking oligonucleotide that corresponds to the same sequence as the second haplomer, but lacking any appended tag. A molar excess of such an oligonucleotide effectively inhibits the assembly reaction, whereas the assembly process is unaffected by excess oligonucleotide of the same length but with scrambled sequence.

Example 4: Improved Responses with Cysteine Mutants of FKBP and FRB Dimerization Domains with Gaussia Luciferase Split-Protein Assays This example describes the application of cysteine mutants of FKBP and FRB dimerization domains, C22S and C61S, respectively, in split-protein assays with Gaussia luciferase. In this case, the homodimerization agent AP20187 (Clontech Labs) was used to dimerize N-terminal Gaussia split-protein fragment-FKBP and FKBP-C-terminal Gaussia split-protein fragment fusions, and thus greatly accelerate Gaussia split-protein assembly. In a likewise fashion, the heterodimerization agent rapamycin (Sigma) was used to dimerize N-terminal Gaussia split-protein fragment-FKBP and FRB-C-terminal Gaussia split-protein fragment fusions, with a concomitant Gaussia assembly rate increase. For the FKBP domain, the C22S cysteine mutation was introduced in the context of the additional F36V mutation, as described above.

Figure 28:
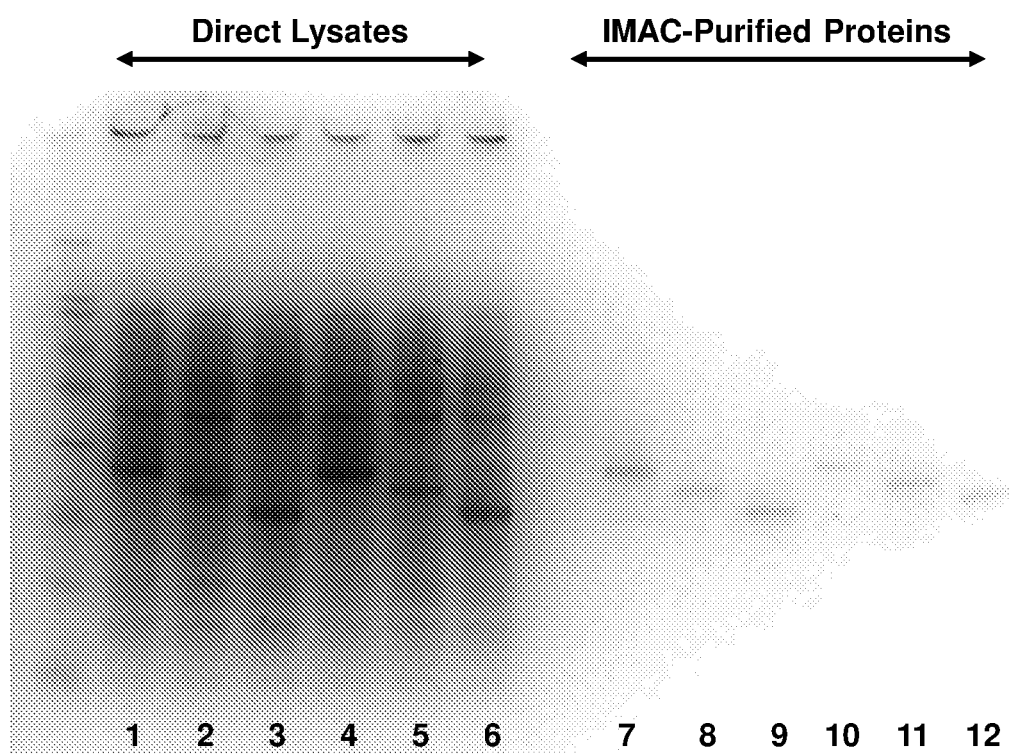
FIG. 28 shows expressed Gaussia split-protein FKBP and FRB fusion proteins, with and without respective C22S and C61S mutations, tested on 16% Tricine gel; shown are expressed samples post-induction with IPTG, where 'Direct Lysates' refers to whole cell samples taken and lysed in standard Laemmli SDS buffer before gel loading, and 'IMAC Purified Proteins' refers to samples after elution with imidazole from hexahistidine affinity-magnetic beads; lanes: 1 & 7, N-terminal Gaussia segment-FKBP(F36V); 2 & 8, FKBP(F36V)-C-terminal Gaussia segment; 3 & 9, FRB-C-terminal Gaussia segment; 4 & 10, N-terminal Gaussia segment-FKBP(F36V/C22S); 5 & 11, FKBP(F36V/C22S)-C-terminal Gaussia segment; 6 & 12, FRB(C61S)-C-terminal Gaussia segment.

Protein fragments with and without the cysteine mutations were expressed in *E. coli* in standard fashion, such that their purifications could be effected by means of hexhistidine affinity tags, on solid-phase immobilized metal affinity chromatography (IMAC) beads (IMAC-Dynabeads, Thermofisher Scientific). Proteins purified in this manner were visualized on 16% Tricine gels (FIG. 28).

The sequence of the N-terminal Gaussia split-protein fragment-FKBP single F36V mutant fusion protein is: MKPTENNEDFNIVAVASNFATTTDL-DADRGKLPGKKLPLEVLK EMEANARKAGCTRGCLI-CLSHIKCTPKMKKFIPGRCHTYEGDKESAQGGIG-GSGGGG SSGGG-GVQVETISPGDGRTFPKRGQTCVVHYTGMLEDGKK VDSSRDRNKPFKFMLGK QEVIR-GWEEGVAQMSVGQRAKLTISPDYAYGATGHPGIIP-PHATLVFDVELLKLEGGSG-HHHHHH (SEQ ID NO:47), where hyphens demarcate (in order) the N-terminal Gaussia segment, a serine-glycine linker segment, the C-terminal FKBP F36V mutant, and the hexahistidine tag, with the mutant valine residue (F36V) in bold.

The sequence of the N-terminal Gaussia split-protein fragment-FKBP C22S/F36V double mutant fusion protein is likewise: MKPTENNEDFNIVAVASNFATTTDL-DADRGKLP GKKLPLEVLKEMEANARKAGCTRGCLI-CLSHIKCTPKMKKFIPGRCHTYEGDKESAQGG IG-GSGGGGSSGGG-GVQVETISPGDGRTFPKRGQTSVVHYTGMLEDGK KVDSSRDRNK PFKFMLGKQEVIR-GWEEGVAQMSVGQRAKLTISPDYAYGATGHPGIIP-PHATLVFDVEL LKLEGGSG-HHHHHH (SEQ ID NO:48), where the mutant valine (F36V) residue is in bold, and mutant serine (C22S) residue is underlined.

The sequence of the FKBP-C-terminal Gaussia split-protein fragment single FKBP F36V mutant fusion protein is: MHHHHHH-GGSG-GVQVETISPGDGRTFPKRGQTCVVHYT GMLEDGKKVDSSRDRNKPFKFMLGKQEVIR-GWEEGVAQMSVGQRAKLTISPDYAYGA TGHPGIIP-PHATLVFDVELLKLE-GSGGGGSSGGG-EAIVDI-PEIPGFKDLEPMEQFIAQV DLCVDCTTGCLKGLANVQCSDLLKKWLPQR-CATFASKIQGQVDKIKGAGGD (SEQ ID NO:49), where hyphens demarcate (in order) the hexahistidine tag, a short serine glycine linker, the N-terminal FKBP segment, a longer serine-glycine linker segment, and the C-terminal Gaussia sequence, with the mutant FKBP valine residue (F36V) in bold.

The sequence of the FKBP-C-terminal Gaussia split-protein fragment double FKBP C22S/F36V mutant fusion protein is likewise: MHHHHHH-GGSG-GVQVETISPGDGRTFPK RGQTSVVHYTGMLEDGKKVDSSRDRNKPFKFMLG KQEVIRGWEEGVAQMSVGQRAK LTISPDYAY-GATGHPGIIPPHATLVFDVELLKLE-GSGGGGSSGGG-EAIVDIPEIPGFKDLE PMEQFIAQVDLCVDC-TIGCLKGLANVQCSDLLKKWLPQRCATFASKIQGQ VDKIKGAG GD (SEQ ID NO:50), where the FKBP mutant valine (F36V) residue is in bold, and mutant serine (C22S) residue is underlined.

The sequence of the wild-type FRB-C-terminal Gaussia split-protein fragment mutant C61S mutant fusion protein is: MHHHHHH-GGSG-EMWHEGLEEASR-LYFGERNVKGMFEV LEPLHAM-MERGPQTLKETSFNQAYGRDLMEAQEWCR-KYMKSGNVKDLTQAWDLYYH VFRRISKQ-GSGGGGSSGG-GEAIVDIPEIPGFKDLEPMEQFIAQVDLCVDCTIGCL KGLA NVQCSDLLKKWLPQRCATFASKIQGQVDKIK-GAGGD (SEQ ID NO:51), where hyphens demarcate (in order) the hexahistidine tag, a short serine glycine linker, the N-terminal FRB segment, a longer serine-glycine linker segment, and the C-terminal Gaussia sequence.

The sequence of the C61S mutant FRB-C-terminal Gaussia split-protein fragment fusion protein is likewise: MHHHHHH-GGSG-EMWHEGLEEASR-LYFGERNVKGMFEVLE PLHAM-MERGPQTLKETSFNQAYGRDLMEAQEWSR-KYMKSGNVKDLTQAWDLYYHVF RRISKQ-GSGGGGSSGG-GEAIVDIPEIPGFKDLEPMEQFIAQVDLCVDCTIGCL KGLANV QCSDLLKKWLPQRCATFASKIQGQVDKIK-GAGGD (SEQ ID NO:52), where the mutant serine (C61 S) residue is underlined.

After expression and elution from IMAC magnetic beads with imidazole, proteins were assayed (Bradford reagent) and visualized on 16% Tricine gels (Thermofisher).

Figure 29:
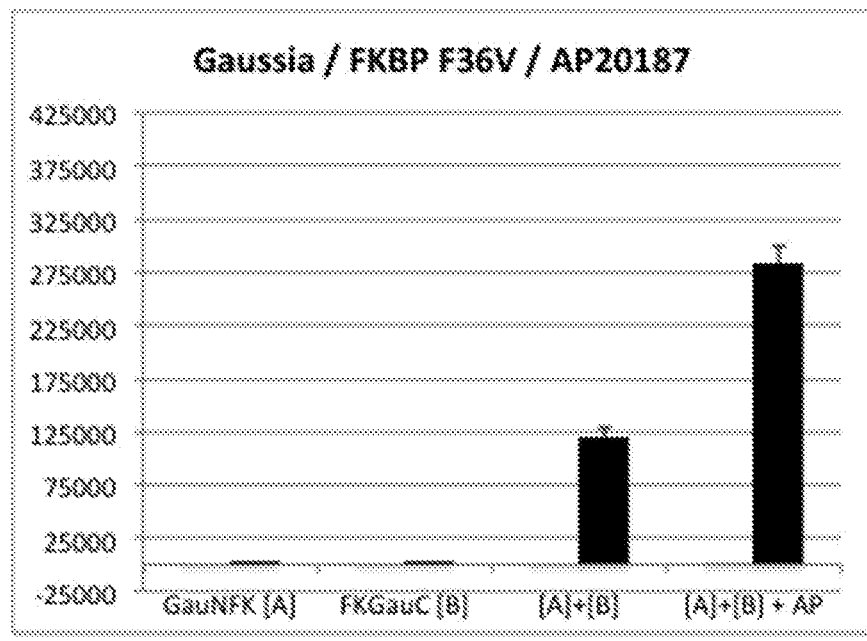
FIG. 29 (panels 1, 2, 3, and 4) shows dimerization responses of split-protein Gaussia fragments fused with either the FKBP-F36V domain, with or without additional C22S mutations, or the FRB domain, with or without additional C61S mutations; data shows luminescence responses for proteins with and without dimerizers, all at 4 hours from start of the test; 1: Gaussia N-terminal-FKBP-F36V fusion (A), FKBP-F36V-C-terminal Gaussia fusion (B), combination (A)+(B), and (A)+(B) with 0.15 µM AP20187 (AP); 2: Gaussia N-terminal-FKBP-F36V-C22S fusion (C), FKBP-F36V-C22S-C-terminal Gaussia fusion (D), combination (C)+(D), and (C)+(D) with 0.15 µM AP20187 (AP); 3: Gaussia N-terminal-FKBP-F36V fusion (A), FRB-C-terminal Gaussia fusion (V), (A)+(V), and (A)+(V) with 0.15 µM rapamycin (RAP); 4: Gaussia N-terminal-FKBP-F36V-C22S fusion (CO, FRB-C61S-C-terminal Gaussia fusion (W), (C)+(W), and (C)+(W) with 0.15 µM rapamycin (RAP).
Figure 29:
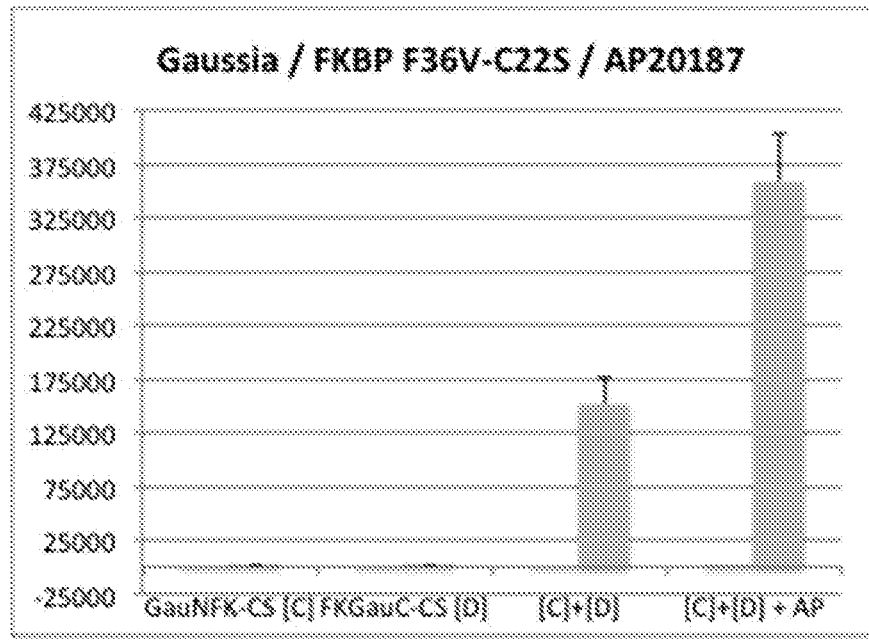
Figure 29:
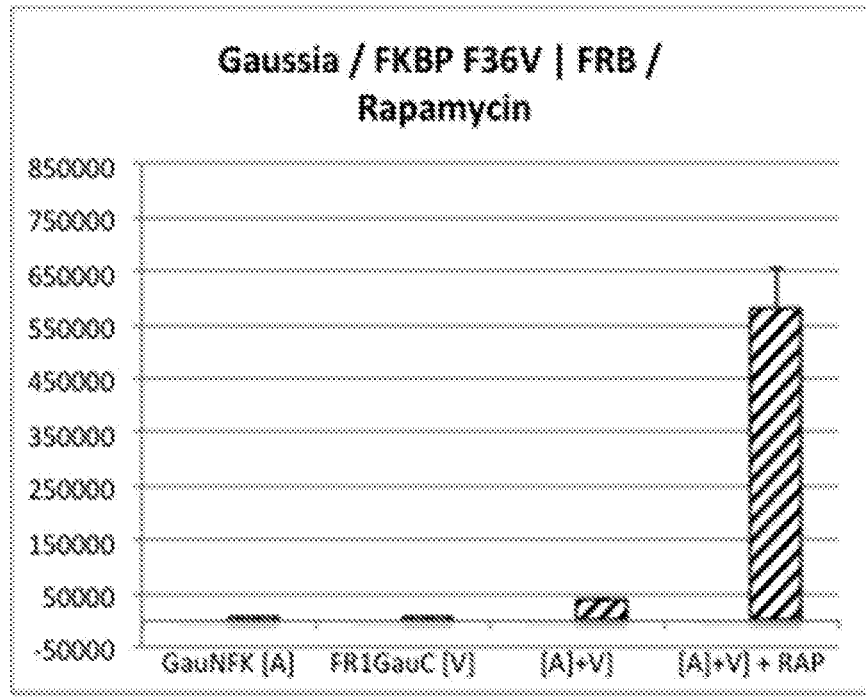
Figure 29:
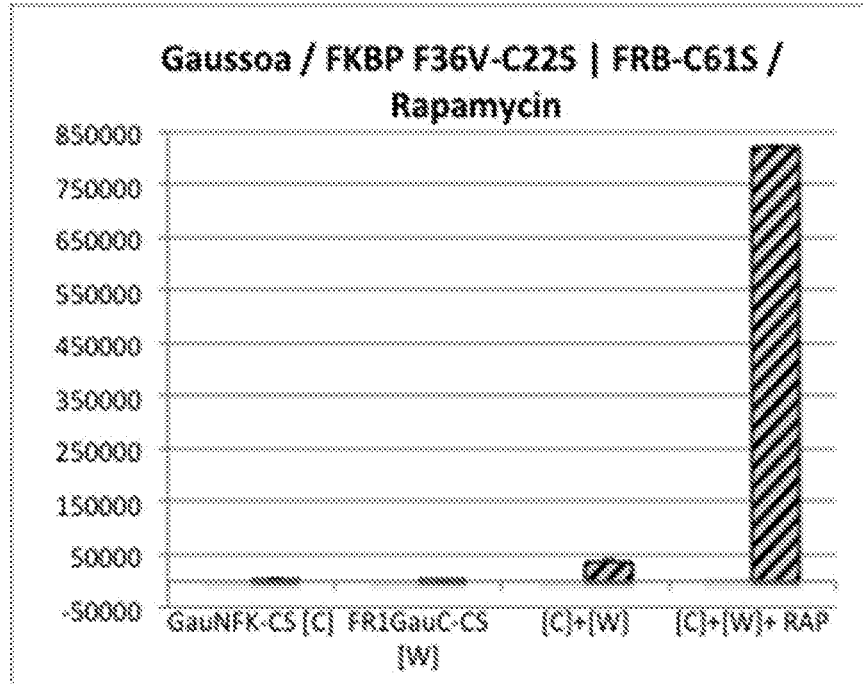

Assays were set up in 20 µl volumes with protein fragments (single or in paired mixes) at a final concentration 0.3 µM, with or without AP20187 or rapamycin as appropriate (both at 0.15 µM final). At suitable time-points, 2 µl samples were taken and assayed for luminescence in a Berthold luminometer, in tubes with coelenterazine (2.5 µM final) in 50 µl PBS with 5 mM sodium bromide. Representative data are shown in FIG. 29. Co-incubated preparations of N-terminal Gaussia segment-FKBP-F36V fusion and FKBP-F36V-C-terminal Gaussia segment fusion showed enhanced responses in the presence of the homodimerizer AP20187 (FIG. 29, Panel 1), while greater equivalent responses were seen with the use of corresponding fusions with the FKBP-F36V-C22S double mutations (FIG. 29, Panel 2). Co-incubated preparations of N-terminal Gaussia segment-FKBP-F36V fusion and wild-type FRB-C-terminal Gaussia segment fusion showed marked enhancement with the heterodimerizer rapamycin (FIG. 29, Panel 3), which was further promoted in the context of the FKBP-F36V-C22S double mutation in combination with the FRB C61S mutation (FIG. 29, Panel 4). Results demonstrated both the efficacy of dimerizers in this context, and functionality of the FKBP and FRB cysteine-serine mutations.

Figure 30:
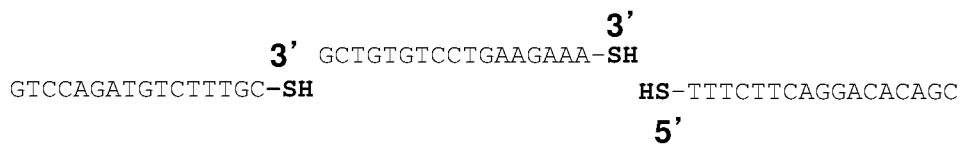
FIG. 30 shows conjugate formation via reaction between 5'- or 3'-thiol-modified oligonucleotides and monovalent FKBP-F36V Ligand MFL2; each thiol group on the modified oligonucleotides is separated from the nearest base by a 6C spacer; 33 pmol of unmodified thiol-oligonucleotides or corresponding MFL2 conjugates were tested on a 15% denaturing 8M urea gel, and stained with SYBR-Gold. The three nucleic acid sequences present from left to right are SEQ ID NOs: 44-46.
Figure 30:
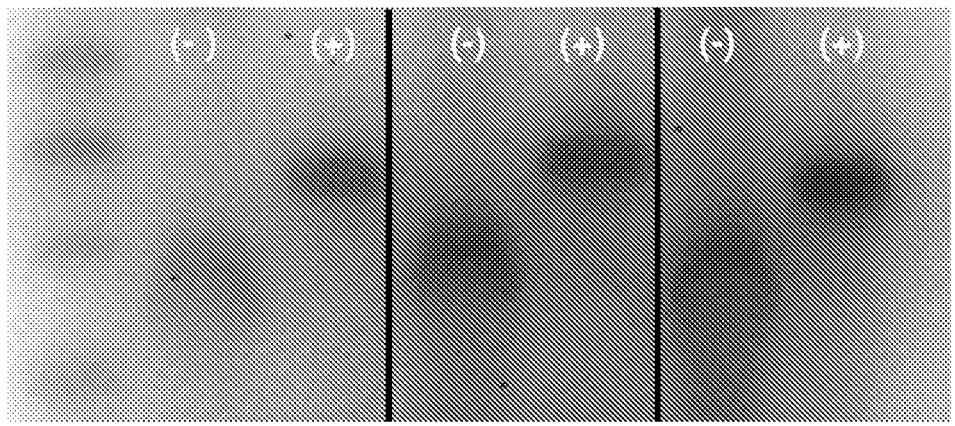
Figure 30:
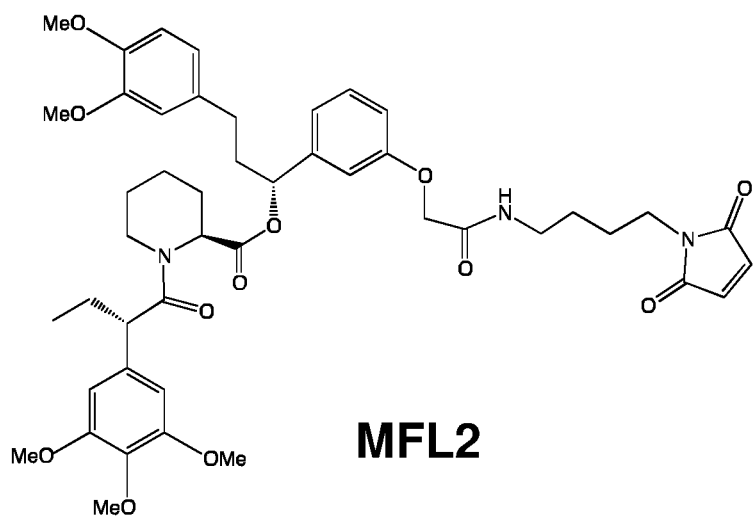

Example 5: Demonstration of Oligonucleotide Conjugate Formation with the MFL2 Monovalent FKBP Ligand This example describes the derivatization of thiol-labeled oligonucleotides specifically with MFL2, the monovalent ligand for the F36V mutant form of FKBP. MFL2 was solubilized in DMSO at a concentration of 100 mM. To prepare for conjugation, 5 nmol of oligonucleotides modified at their 5'- or 3'-ends with disulfide moieties (IDT Corp.) were treated with 1 mM tris-carboxyethylphosphine (TCEP) for 12-16 hours in 50 µl PBS to reduce the disulfides and produce free thiol groups. Following this, the reduced oligonucleotides were desalted on Micro-Biospin P6 columns (Bio-Rad) into 10 mM Tris pH 7.4, and then used immediately for conjugation. Conjugation reactions were performed in 100 µl volumes, in 50 mM phosphate buffer pH 7.0/100 mM NaCl, with 4 nmol of reduced thiol-oligonucleotides, 2 mM TCEP and 400 nmol MFL2, all with a final concentration of 50% DMSO. The 100-fold molar excess of MFL2 was used to drive the reaction between the MFL2 maleimido moiety and the thiol group on the relevant oligonuclotides towards completion; the indicated DMSO level was necessary to maintain solubility of the hydrophobic MFL2 molecule at the desired concentration. Reactions were allowed to proceed for 12-16 hours at room temperature, and then free MFL2 was removed from the preparations by two successive rounds of buffer exchange through Micro-Biospin P6 columns equilibrated with PBS. Conjugate preparations were compared with corresponding unmodified thiol-oligonucleotides on denaturing 15% urea gels. It was apparent that under the conditions used, the conjugation reaction progressed essentially towards completion (FIG. 30).

The conjugates produced in this Example were: #407-MFL2 (3' conjugation) GTCCAG ATGTCTTTGC-MFL2 (SEQ ID NO:44); #408-MFL2 (3' conjugation) GCTGTGTCCTGAAG AAA-MFL2 (SEQ ID NO:45); #409-MFL2 (5' conjugation) MFL2-TTTTCTTCAGGACACA GC (SEQ ID NO:46).

Example 6: Use of Oligonucleotide Conjugates with Mutant FKBP-Binding Monovalent Compounds in LD-TAPER for Split-Protein LD-TAPER In this Example, LD-TAPER is demonstrated both with Architecture 1, and two approaches to demonstrating it with Architecture 2.

Architecture 1

Figure 31:
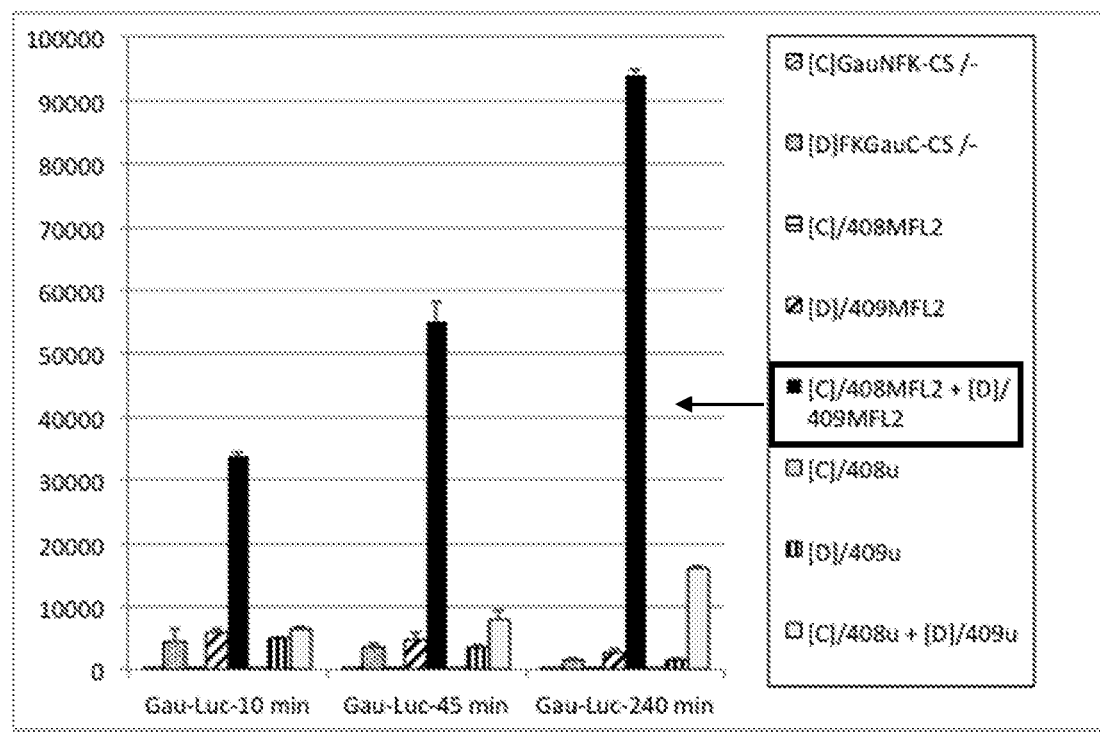
FIG. 31 shows LD-TAPER demonstration with Gaussia luciferase split-protein fusions with FKBP-F36V-C22S, mediated via MFL2-oligonucleotide conjugates in Architecture 1; luminescence readings are shown in the Y-axis; the preparation of mutually complementary LD-TAPER haplomers giving time-dependent positive signals is boxed in the Legend.

In this case, mutually complementary oligonucleotides bearing 5' (#409) or 3' (#408) thiol modifications were reacted with the compound MFL2 (Example 5), and desalted/buffer exchanged into PBS by two rounds of passage through Micro-Biospin P6 columns (Bio-Rad) previously PBS-equilibrated. Resulting conjugates were then incubated for 1 hour at room temperature with purified Gaussia split-protein segments fused with the FKBP-F36V-C22S double mutant domain (FIG. 28), with the corresponding unconjugated oligos used as controls. The N-terminal Gaussia-FKBP-F36V-C22S fusion (code (C) in this Example) was thus incubated with conjugate #408-MFL2 (Example 5) or control #408 alone, while the FKBP-F36V-C22S-C-terminal Gaussia fusion (code (D) in this Example) was incubated with conjugate #409-MFL2 (Example 5) or control #409 alone. Each preparation (15 µl PBS final) contained 60 pmol of protein fragments, and 30 pmol of conjugate or oligonucleotide alone. The interaction products of FKBP domain protein fusions and MFL2 conjugates constitute a particular class of LD-TAPER haplomers. Following this, 5 µl samples of these pre-incubations were used in isolation or as appropriate mixtures, with volumes adjusted to a final 20 µl. At suitable time-points, 2 µl samples were then taken and assayed for luminescence in a Berthold luminometer, in tubes with coelenterazine (2.5 µM final) in 50 µl PBS with 5 mM sodium bromide. Data for three time points are shown in FIG. 31. Markedly increased luminescence over time was observed where the mutually complementary LD-TAPER haplomers (C)-#408MFL2 and (D)-#409MFL2 were co-incubated together, but no such effect was seen with equivalent co-incubations with the unconjugated oligos alone, nor any haplomer in isolation (FIG. 31).

Architecture 2—Solid-Phase Capture

Figure 10:
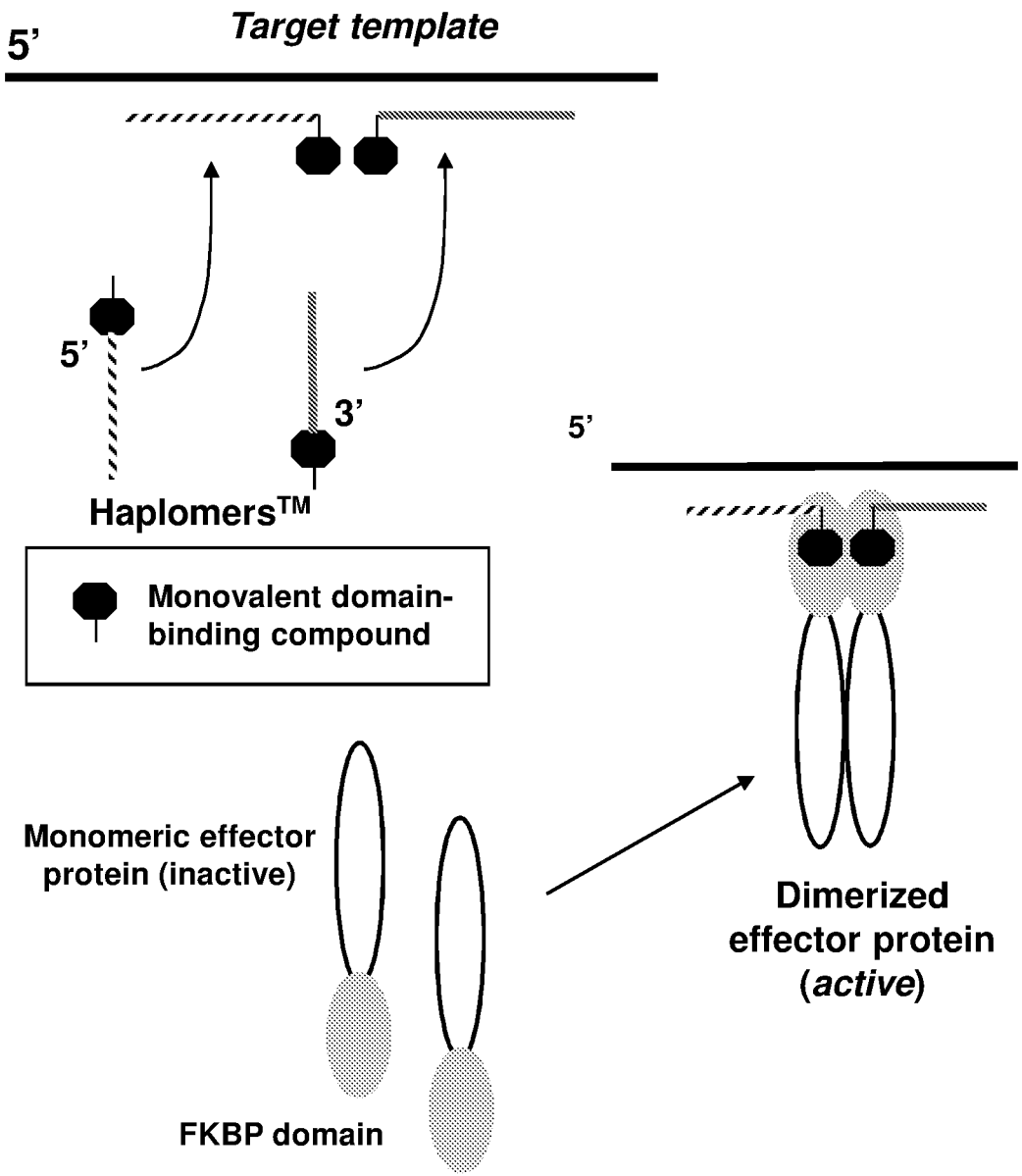
FIG. 10 shows another representative small molecule-mediated protein dimerization via LD-TAPER.
Figure 32:
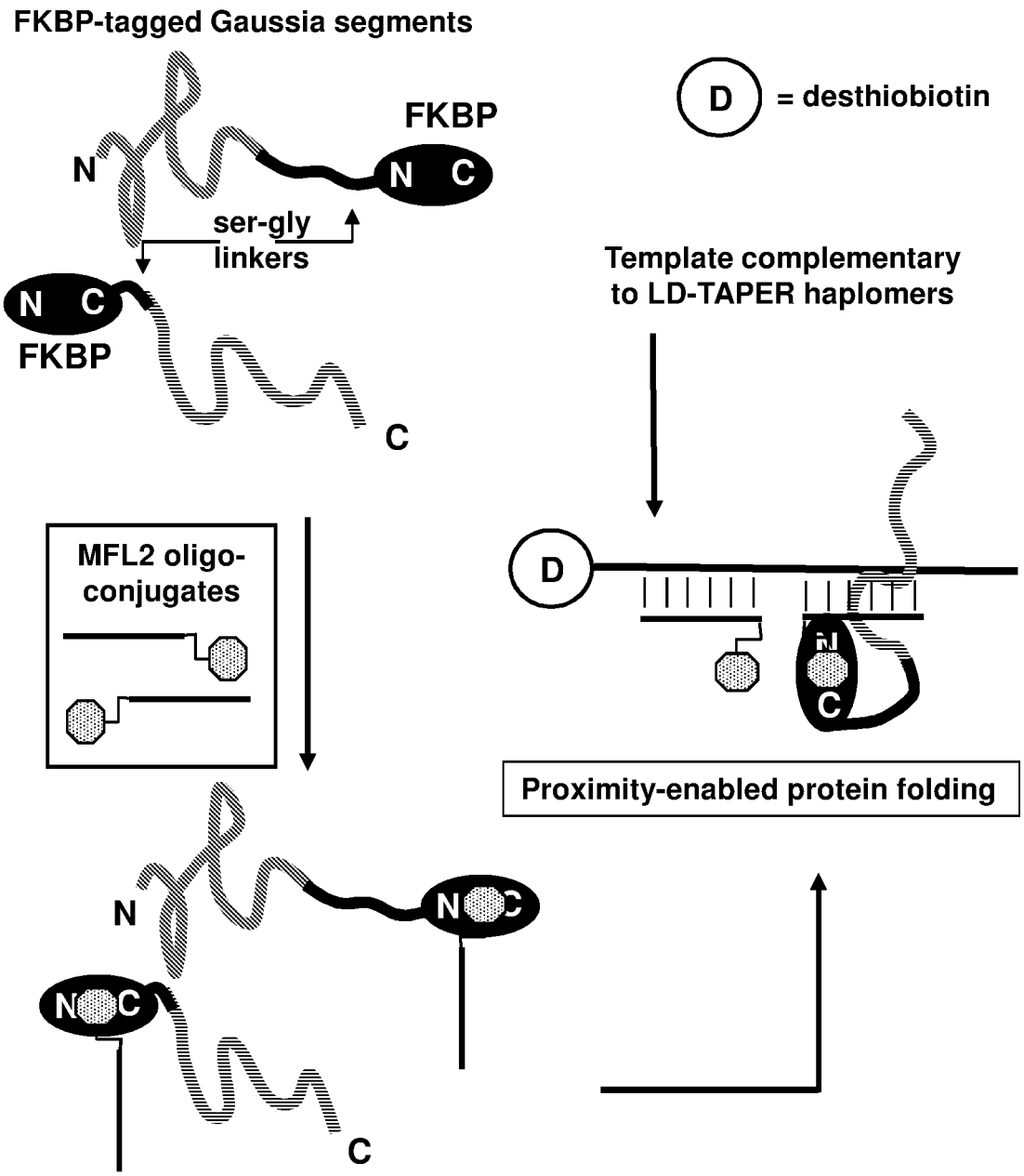
FIG. 32 shows processes used for LD-TAPER demonstration with Architecture 2.

In this strategy, a template strand bearing a 5' desthiobiotin modification was used. Gaussia-FKBP LD-TAPER haplomers (complexes between Gaussia luciferase-FKBP fragments and MFL2-modified oligonucleotides) can hybridize in mutual spatial proximity onto this template, enabling Gaussia protein folding assembly and full activity generation. This process is depicted in FIG. 32, and corresponds to Architecture 2 (FIG. 10). Control unmodified oligonucleotides can also hybridize to the same template, but cannot spatially force the juxtaposition of the Gaussia fragments in the same manner. This procedure has the advantage that background luminescence from spontaneous Gaussia self-assembly is substantially reduced. Following the hybridization step, the templates and all co-hybridized molecules are bound to streptavidin magnetic beads, and all other solution components washed away. After this, elutions from the magnetic beads are effected with free D-biotin, which displaces the streptavidin-associated desthiobiotin-tagged template complexes, by virtue of its much higher binding affinity. Gaussia luciferase assays are then performed on each eluted preparation. Specifically, in a volume of 18 µl PBS, 120 pmol of purified Gaussia protein-FKBP fusion fragments were incubated for 1 hour at room temperature with either 60 pmol oligonucleotide-MFL2 complexes (FIG. 30) or corresponding unmodified thiol-oligonucleotides. Following this, 7.5 µl of these preincubation reactions were added to final reactions of 25 µl PBS, either alone or in combination. In this Example, the following preparations were used:

N-terminal Gaussia fragment-FKBP-F36V (code=(A))
FKBP-F36V-C-terminal Gaussia fragment (code=(B))
N-terminal Gaussia fragment-FKBP-F36V-C22S (code=(C))
FKBP-F36V-C22S-C-terminal Gaussia fragment (code=(D))

With the above code and the oligonucleotide descriptions of Example 5, the LD-haplomer preparations are:

(A)-#407-MFL2
(B)-#409-MFL2
(C)-#407-MFL2
(D)-#409-MFL2

Control preparations used the same Gaussia-FKBP fusion fragments incubated with corresponding unconjugated oligonucleotides.

Appropriate protein fragment/conjugate/control oligonucleotide preparations were incubated for 30 minutes at room temperature in the presence of 25 pmol of template oligonucleotide (#230) bearing a 5' desthiobiotin moiety: Desthiobiotin-AGCTGTGTCCTGAA GAAAGCAAAGA-CATCTGGACA (SEQ ID NO:53).

Figure 33:
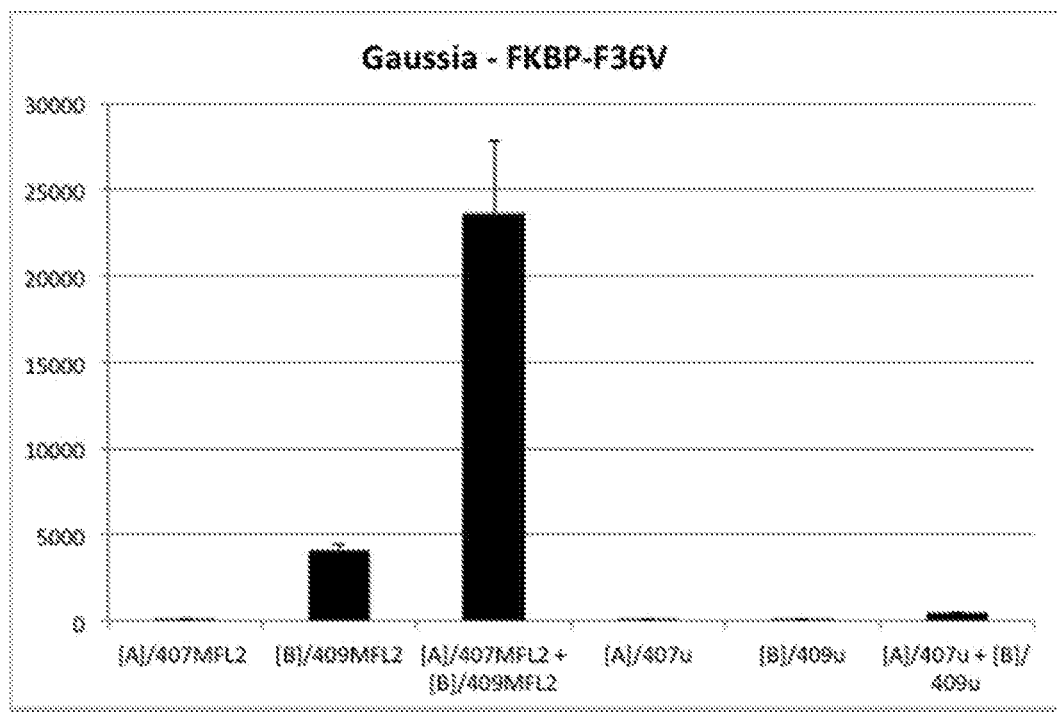
FIG. 33 (Panels 1 and 2) shows LD-TAPER demonstration with Gaussia luciferase split-protein fusions with FKBP-F36V, or FKBP-F36V-C22S, mediated via MFL2-oligonucleotide conjugates in Architecture 2 via solid-phase capture; Panel 1, FKBP-F36V Gaussia fusions, where (A)=N-terminal Gaussia fragment-FKBP-F36V fusion, (B)=FKBP-F36V-C-terminal Gaussia fusion; 407MFL2 and 409MFL2=oligonucleotides 407 and 409 respectively conjugated to compound MFL2; 407u and 409u=corresponding unconjugated thiol-oligonucleotides; Panel 2, FKBP-F36V-C22S Gaussia fusions, where (A)=N-terminal Gaussia fragment-FKBP-F36V-C22S fusion, and (B)=FKBP-F36V-C22S-C-terminal Gaussia fusion; 407MFL2, 409MFL2, 407u, and 409u as for Panel 1; after hybridization with desthiobiotinylated template (see, FIG. 32), template and template-bound haplomers were isolated on streptavidin magnetic beads, eluted with free D-biotin, and evaluated for Gaussia luciferase activity after a 30 minute incubation (luminescence units on Y-axes).
Figure 33:
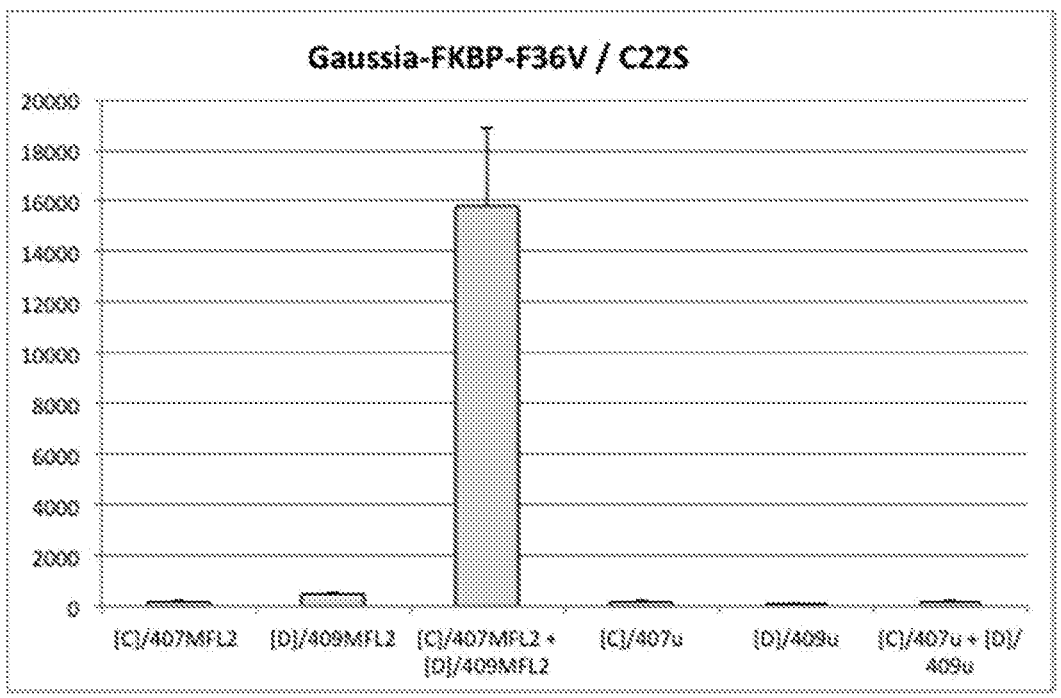

Following this, 25 µl (100 µg) of hydrophilic streptavidin magnetic beads (New England Biolabs, pre-washed twice in 1 ml PBS and resuspended in the original volume of PBS) were added to each tube, and incubated for a further 1 hour at room temperature. The beads were then magnetically separated from the supernatants, and washed ×1 with 0.5 ml of PBS. The magnetic bead pellets in each tube were resuspended in 50 µl of PBS, and free D-biotin was added to 10 mM for a 30 minute/room temperature incubation. Supernatants were then taken by magnetic separation, and 2 µl samples of each assayed for Gaussia luciferase activity as for Example 6. Results are shown in FIG. 33, where markedly elevated luminescence readings were obtained only with combined N-terminal and C-terminal Gaussia oligo-MFL2 conjugate complexes (LD-TAPER haplomers), for both the F36V and F36V-C22S forms of FKBP. No such responses were seen when the MFL2-modified oligonucleotides were replaced with corresponding unmodified oligonucleotides (FIG. 33). This data is thus consistent with templated assembly of Gaussia fragments mediated via LD-TAPER in an Architecture 2 templating system.

Architecture 2—Solution Phase

The utility of LD-TAPER mediated via an Architecture 2 templating system in solution was also investigated. Preincubations were set up in the same manner as for the above Architecture 2—Solid-phase Capture Example, for the Gaussia fragments fused with the FKBP-F36V-C22S double mutant domain.

In this case, after the initial preincubations, combinations of LD-TAPER haplomers or controls replacing the MFL2-oligonucleotide conjugates with unmodified thiol oligonucleotides were simply mixed with either a specific template or a scrambled oligonucleotide with the same length and base composition as the template. The specific template was identical to the template oligonucleotide #230 above, except without the 5'-desthiobiotin modification. The scrambled control oligo was: GACTAGACGGCCAGGGA-GACGAATACATATTTCAAT (SEQ ID NO:54)

Figure 34:
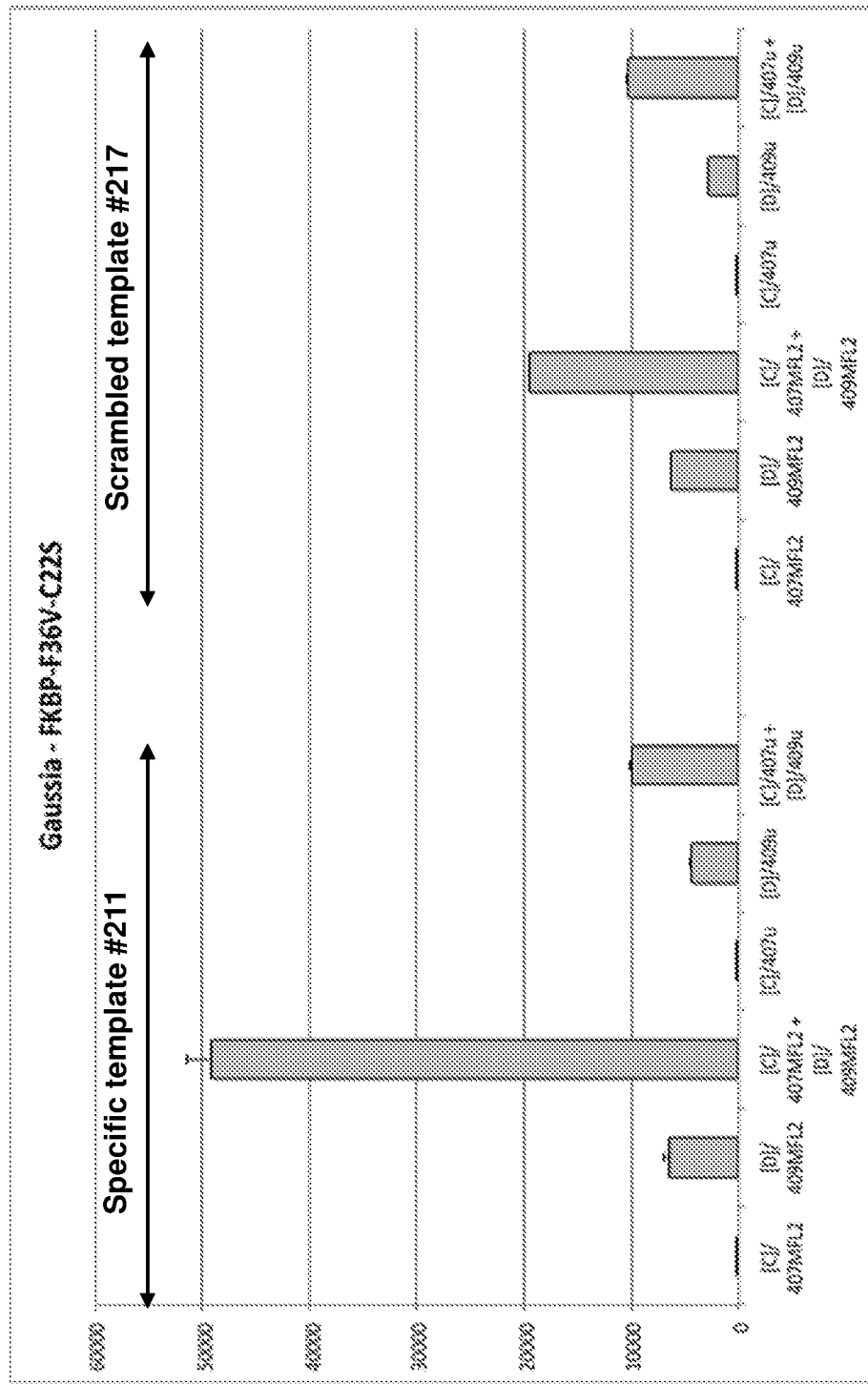
FIG. 34 shows LD-TAPER demonstration with Gaussia luciferase split-protein fusions with FKBP-F36V-C22S, mediated via MFL2-oligonucleotide conjugates in Architecture 2, with the template or control in solution phase.

Samples (2 µl) of these preparations were then assayed at certain time intervals for Gaussia luciferase activity, in the same manner as for Example 6. Results (FIG. 34) at 2 hour post-initiation show that a substantial increase in the luminescent signal was observed for specific template over the scrambled control (~2.5-fold increase), again consistent with template-mediated assembly of Gaussia luciferase by means of LD-TAPER haplomers. The nature of the templating process thus conforms to that depicted in FIG. 32, except for the absence of the desthiobiotin moiety.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method for the directed assembly of a protein comprising:

contacting a target nucleic acid molecule with a first haplomer-ligand complex, wherein the first haplomer-ligand complex comprises a haplomer, wherein the haplomer comprises a polynucleotide, and a ligand, wherein the ligand comprises a ligand partner binding site;

contacting the target nucleic acid with a second haplomer-ligand complex wherein the second haplomer-ligand complex comprises a haplomer wherein the haplomer comprises a polynucleotide and a ligand, wherein the ligand comprises a ligand partner binding site;

contacting the first haplomer-ligand complex with a first fusion protein wherein the first fusion protein comprises a fragment of a protein of interest fused to a ligand binding domain, wherein the ligand binding domain is an FKBP domain or an FRB domain; and contacting the second haplomer-ligand complex with a second fusion protein wherein the second fusion protein comprises a fragment of a protein of interest fused to a ligand binding domain, wherein the ligand binding domain is an FKBP domain or an FRB domain;

wherein the ligand of the first haplomer-ligand complex is linked to the 5' terminus of the polynucleotide of the first haplomer-ligand complex;

wherein the ligand of the second haplomer-ligand complex is linked to the 3' terminus of the polynucleotide of the second haplomer-ligand complex;

wherein the polynucleotide of the first haplomer-ligand complex is substantially complementary to a target nucleic acid molecule;

wherein the polynucleotide of the second haplomer-ligand complex is 100% complementary to the target nucleic acid molecule, or complementary except for 1 to 10 mismatched base positions, at a site in spatial proximity to the polynucleotide of the first haplomer-ligand complex;

wherein the ligand of the first haplomer-ligand complex and the ligand binding domain of the first fusion protein can interact; and wherein the ligand of the second haplomer-ligand complex and the ligand binding domain of the second fusion protein can interact;

wherein the spatial proximity results in the folding or dimerization of the fragment of the protein of interest of the first fusion protein with the fragment of the protein of interest of the second fusion protein.

2. A method for the directed assembly of a protein comprising:

contacting a target nucleic acid molecule with a complex formed by the interaction of a first haplomer-ligand complex, wherein the first haplomer-ligand complex comprises a haplomer, wherein the haplomer comprises a polynucleotide that is 100% complementary to the target nucleic acid molecule, or complementary except for 1 to 10 mismatched base positions, and a ligand, wherein the ligand comprises a ligand partner binding site, with a first fusion protein comprising a fragment of a protein of interest fused to a ligand binding domain, wherein the ligand binding domain is an FKBP domain or an FRB domain, wherein the ligand of the first haplomer-ligand complex is linked to the 5' terminus of the polynucleotide of the first haplomer-ligand complex, and wherein the ligand of the first haplomer-ligand complex interacts with the ligand binding domain of the first fusion protein; and contacting the target nucleic acid molecule with a complex formed by the interaction of a second haplomer-ligand complex, wherein the second haplomer-ligand complex comprises a haplomer, wherein the haplomer comprises a polynucleotide that is 100% complementary to the target nucleic acid molecule, or complementary except for 1 to 10 mismatched base positions; and a ligand, wherein the ligand comprises a ligand partner binding site, with a second fusion protein comprising a fragment of a protein of interest fused to a ligand binding domain, wherein the ligand binding domain is an FKBP domain or an FRB domain, wherein the ligand of the second haplomer-ligand complex is linked to the 3' terminus of the polynucleotide of the second haplomer-ligand complex, and wherein the ligand of the second haplomer-ligand complex interacts with the ligand binding domain of the second fusion protein;

thereby resulting in the folding or dimerization of the fragment of the protein of interest of the first fusion protein with the fragment of the protein of interest of the second fusion protein.

3. A method for the directed assembly of a protein comprising:
  contacting a target nucleic acid molecule with a bottle haplomer-ligand complex comprising:
    a) a bottle haplomer, wherein the bottle haplomer comprises a polynucleotide, wherein the polynucleotide comprises:
      i) a first stem portion comprising from about 10 to about 20 nucleotide bases;
      ii) an anti-target loop portion comprising from about 16 to about 40 nucleotide bases and having a first end to which the first stem portion is linked, wherein the anti-target loop portion is 100% complementary to a target nucleic acid molecule, or complementary except for 1 to 10 mismatched base positions; and
      iii) a second stem portion comprising from about 10 to about 20 nucleotide bases linked to a second end of the anti-target loop portion, wherein the first stem portion is 100% complementary to the second stem portion, or complementary except for 1 to 10 mismatched base positions; and
    b) a ligand linked to the terminal end of either the first stem portion or the second stem portion, wherein the ligand comprises a ligand partner binding site:
  wherein the $T_m$ of the anti-target loop portion:target nucleic acid molecule is greater than the $T_m$ of the first stem portion:second stem portion;
  contacting the target nucleic acid molecule with a second haplomer-ligand complex comprising a haplomer, wherein the haplomer comprises a polynucleotide that is 100% complementary to a target nucleic acid molecule, or complementary except for 1 to 10 mismatched base positions, and a ligand linked to the 5' or 3' terminus of the haplomer, wherein the ligand comprises a ligand partner binding site, wherein the second haplomer-ligand complex comprises a nucleotide portion that is 100% complementary, or complementary except for 1 to 10 mismatched base positions, to the stem portion of the bottle haplomer-ligand complex that is linked to the ligand of the bottle haplomer-ligand complex;
  contacting the bottle haplomer-ligand complex with a first fusion protein comprising a fragment of a protein of interest fused to a ligand binding domain, wherein the ligand binding domain is an FKBP domain or an FRB domain, wherein the ligand of the bottle haplomer-ligand complex and the ligand binding domain of the first fusion protein can interact; and
  contacting the second haplomer-ligand complex with a second fusion protein comprising a fragment of a protein of interest fused to a ligand binding domain, wherein the ligand binding domain is an FKBP domain or an FRB domain, wherein the ligand of the second haplomer-ligand complex and the ligand binding domain of the second fusion protein can interact;
  thereby resulting in the folding or dimerization of the fragment of the protein of interest of the first fusion protein with the fragment of the protein of interest of the second fusion protein.

\* \* \* \* \*

SEQUENCE LISTING

<160> NUMBER OF SEQ ID NOS: 54

<210> SEQ ID NO 1
<211> LENGTH: 47
<212> TYPE: PRT
<213> ORGANISM: artificial sequence
<220> FEATURE:
<223> OTHER INFORMATION: N-terminal conjugates

```
<400> SEQUENCE: 1

Cys Ser Gly Gly Ala Ser Leu Glu Arg Ile Ala Arg Leu Glu Glu Lys
1               5                   10                  15

Val Lys Thr Leu Lys Ala Gln Asn Ser Glu Leu Ala Ser Thr Ala Asn
            20                  25                  30

Met Leu Arg Glu Gln Val Ala Gln Leu Lys Gln Lys Gly Ala Pro
        35                  40                  45

<210> SEQ ID NO 2
<211> LENGTH: 49
<212> TYPE: PRT
<213> ORGANISM: artificial sequence
<220> FEATURE:
<223> OTHER INFORMATION: C-terminal conjugate

<400> SEQUENCE: 2

Ser Gly Ala Ser Leu Glu Arg Ile Ala Arg Leu Glu Glu Lys Val Lys
1               5                   10                  15

Thr Leu Lys Ala Gln Asn Ser Glu Leu Ala Ser Thr Ala Asn Met Leu
            20                  25                  30

Arg Glu Gln Val Ala Gln Leu Lys Gln Lys Gly Ala Pro Ser Gly Gly
        35                  40                  45

Cys

<210> SEQ ID NO 3
<211> LENGTH: 41
<212> TYPE: PRT
<213> ORGANISM: artificial sequence
<220> FEATURE:
<223> OTHER INFORMATION: fos zipper

<400> SEQUENCE: 3

Ala Ser Arg Glu Leu Thr Asp Thr Leu Gln Ala Glu Thr Asp Gln Leu
1               5                   10                  15

Glu Asp Glu Lys Ser Ala Leu Gln Thr Glu Ile Ala Asn Leu Leu Lys
            20                  25                  30

Glu Lys Glu Lys Leu Glu Gly Ala Pro
        35                  40

<210> SEQ ID NO 4
<211> LENGTH: 47
<212> TYPE: PRT
<213> ORGANISM: artificial sequence
<220> FEATURE:
<223> OTHER INFORMATION: mutant of c-Jun

<400> SEQUENCE: 4

Cys Ser Gly Gly Ala Ser Leu Glu Arg Ile Ala Arg Leu Glu Glu Lys
1               5                   10                  15

Val Lys Ser Phe Lys Ala Gln Asn Ser Glu Asn Ala Ser Thr Ala Asn
            20                  25                  30

Met Leu Arg Glu Gln Val Ala Gln Leu Lys Gln Lys Gly Ala Pro
        35                  40                  45

<210> SEQ ID NO 5
<211> LENGTH: 49
<212> TYPE: PRT
<213> ORGANISM: artificial sequence
<220> FEATURE:
<223> OTHER INFORMATION: modified sequence with C-terminal cysteine
      residue
```

-continued

```
<400> SEQUENCE: 5

Ser Gly Ala Ser Leu Glu Arg Ile Ala Arg Leu Glu Glu Lys Val Lys
1               5                   10                  15

Ser Phe Lys Ala Gln Asn Ser Glu Asn Ala Ser Thr Ala Asn Met Leu
            20                  25                  30

Arg Glu Gln Val Ala Gln Leu Lys Gln Lys Gly Ala Pro Ser Gly Gly
        35                  40                  45

Cys

<210> SEQ ID NO 6
<211> LENGTH: 60
<212> TYPE: DNA
<213> ORGANISM: artificial sequence
<220> FEATURE:
<223> OTHER INFORMATION: bottle haplomer

<400> SEQUENCE: 6
actcgagacg tctccttgtc tttgcttttc ttcaggacac agtggcgaga cgtctcgagt     60

<210> SEQ ID NO 7
<211> LENGTH: 51
<212> TYPE: DNA
<213> ORGANISM: artificial sequence
<220> FEATURE:
<223> OTHER INFORMATION: bottle haplomer

<400> SEQUENCE: 7
actcgagacg tctccttcct gcccctcctc ctgctccgag acgtctcgag t              51

<210> SEQ ID NO 8
<211> LENGTH: 11
<212> TYPE: DNA
<213> ORGANISM: artificial sequence
<220> FEATURE:
<223> OTHER INFORMATION: second haplomer-ligand

<400> SEQUENCE: 8
agctctcgag t                                                          11

<210> SEQ ID NO 9
<211> LENGTH: 12
<212> TYPE: DNA
<213> ORGANISM: artificial sequence
<220> FEATURE:
<223> OTHER INFORMATION: second haplomer-ligand

<400> SEQUENCE: 9
gacgtctcga gt                                                         12

<210> SEQ ID NO 10
<211> LENGTH: 29
<212> TYPE: PRT
<213> ORGANISM: artificial sequence
<220> FEATURE:
<223> OTHER INFORMATION: NZ domain

<400> SEQUENCE: 10

Ala Leu Lys Lys Glu Leu Gln Ala Asn Lys Lys Glu Leu Ala Gln Leu
1               5                   10                  15

Lys Trp Glu Leu Gln Ala Leu Lys Lys Glu Leu Ala Gln
            20                  25

<210> SEQ ID NO 11
```

```
<211> LENGTH: 30
<212> TYPE: PRT
<213> ORGANISM: artificial sequence
<220> FEATURE:
<223> OTHER INFORMATION: CZ domain

<400> SEQUENCE: 11

Glu Gln Leu Glu Lys Lys Leu Gln Ala Leu Glu Lys Lys Leu Ala Gln
1               5                   10                  15

Leu Glu Trp Lys Asn Gln Ala Leu Glu Lys Lys Leu Ala Gln
            20                  25                  30

<210> SEQ ID NO 12
<211> LENGTH: 46
<212> TYPE: PRT
<213> ORGANISM: artificial sequence
<220> FEATURE:
<223> OTHER INFORMATION: c-jun domain

<400> SEQUENCE: 12

Cys Ser Gly Ala Ser Leu Glu Arg Ile Ala Arg Leu Glu Glu Lys Val
1               5                   10                  15

Lys Ser Phe Lys Ala Gln Asn Ser Glu Asn Ala Ser Thr Ala Asn Met
            20                  25                  30

Leu Arg Glu Gln Val Ala Gln Leu Lys Gln Lys Gly Ala Pro
        35                  40                  45

<210> SEQ ID NO 13
<211> LENGTH: 43
<212> TYPE: PRT
<213> ORGANISM: artificial sequence
<220> FEATURE:
<223> OTHER INFORMATION: c-Fos domain

<400> SEQUENCE: 13

Ser Gly Ala Ser Arg Glu Leu Thr Asp Thr Leu Gln Ala Glu Thr Asp
1               5                   10                  15

Gln Leu Glu Asp Glu Lys Ser Ala Leu Gln Thr Glu Ile Ala Asn Leu
            20                  25                  30

Leu Lys Glu Lys Glu Lys Leu Glu Gly Ala Pro
        35                  40

<210> SEQ ID NO 14
<211> LENGTH: 107
<212> TYPE: PRT
<213> ORGANISM: artificial sequence
<220> FEATURE:
<223> OTHER INFORMATION: F36V FKBP mutant domain

<400> SEQUENCE: 14

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95
```

```
Leu Val Phe Asp Val Glu Leu Leu Lys Leu Glu
            100                 105

<210> SEQ ID NO 15
<211> LENGTH: 108
<212> TYPE: PRT
<213> ORGANISM: artificial sequence
<220> FEATURE:
<223> OTHER INFORMATION: F36V FKBP mutant domain

<400> SEQUENCE: 15

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105

<210> SEQ ID NO 16
<211> LENGTH: 43
<212> TYPE: PRT
<213> ORGANISM: artificial sequence
<220> FEATURE:
<223> OTHER INFORMATION: c-jun domain

<400> SEQUENCE: 16

Ala Ser Leu Glu Arg Ile Ala Arg Leu Glu Glu Lys Val Lys Ser Phe
1               5                   10                  15

Lys Ala Gln Asn Ser Glu Asn Ala Ser Thr Ala Asn Met Leu Arg Glu
            20                  25                  30

Gln Val Ala Gln Leu Lys Gln Lys Gly Ala Pro
        35                  40

<210> SEQ ID NO 17
<211> LENGTH: 10
<212> TYPE: PRT
<213> ORGANISM: artificial sequence
<220> FEATURE:
<223> OTHER INFORMATION: linker

<400> SEQUENCE: 17

Ala Gly Ser Ser Ala Ala Gly Ser Gly Ser
1               5                   10

<210> SEQ ID NO 18
<211> LENGTH: 18
<212> TYPE: PRT
<213> ORGANISM: artificial sequence
<220> FEATURE:
<223> OTHER INFORMATION: linker

<400> SEQUENCE: 18

Gly Gly Ser Gly Gly Gly Ser Gly Gly Gly Ser Gly Gly Gly Ser Gly
1               5                   10                  15
```

Gly Gly

<210> SEQ ID NO 19
<211> LENGTH: 22
<212> TYPE: PRT
<213> ORGANISM: artificial sequence
<220> FEATURE:
<223> OTHER INFORMATION: linker

<400> SEQUENCE: 19

Gly Gly Ser Gly Gly Ser Gly Gly Gly Ser Gly Gly Gly Ser Gly
1               5                   10                  15

Gly Gly Ser Gly Gly Gly
            20

<210> SEQ ID NO 20
<211> LENGTH: 26
<212> TYPE: PRT
<213> ORGANISM: artificial sequence
<220> FEATURE:
<223> OTHER INFORMATION: linker

<400> SEQUENCE: 20

Gly Gly Ser Gly Gly Ser Gly Gly Gly Ser Gly Gly Gly Ser Gly
1               5                   10                  15

Gly Gly Ser Gly Gly Gly Ser Gly Gly Gly
            20                  25

<210> SEQ ID NO 21
<211> LENGTH: 15
<212> TYPE: PRT
<213> ORGANISM: artificial sequence
<220> FEATURE:
<223> OTHER INFORMATION: linker

<400> SEQUENCE: 21

Ser Gly Gly Gly Gly Ser Gly Gly Gly Gly Ser Gly Gly Gly Gly
1               5                   10                  15

<210> SEQ ID NO 22
<211> LENGTH: 20
<212> TYPE: PRT
<213> ORGANISM: artificial sequence
<220> FEATURE:
<223> OTHER INFORMATION: Linker

<400> SEQUENCE: 22

Ser Gly Gly Gly Gly Ser Gly Gly Gly Gly Ser Gly Gly Gly Ser
1               5                   10                  15

Gly Gly Gly Gly
            20

<210> SEQ ID NO 23
<211> LENGTH: 25
<212> TYPE: PRT
<213> ORGANISM: artificial sequence
<220> FEATURE:
<223> OTHER INFORMATION: Linker

<400> SEQUENCE: 23

Ser Gly Gly Gly Gly Ser Gly Gly Gly Gly Ser Gly Gly Gly Ser
1               5                   10                  15

Gly Gly Gly Gly Ser Gly Gly Gly Gly
            20                  25

```
<210> SEQ ID NO 24
<211> LENGTH: 5
<212> TYPE: PRT
<213> ORGANISM: artificial sequence
<220> FEATURE:
<223> OTHER INFORMATION: Linker

<400> SEQUENCE: 24

Ser Gly Gly Gly Ser
1               5

<210> SEQ ID NO 25
<211> LENGTH: 4
<212> TYPE: PRT
<213> ORGANISM: artificial sequence
<220> FEATURE:
<223> OTHER INFORMATION: Linker

<400> SEQUENCE: 25

Ser Gly Ser Gly
1

<210> SEQ ID NO 26
<211> LENGTH: 6
<212> TYPE: PRT
<213> ORGANISM: artificial sequence
<220> FEATURE:
<223> OTHER INFORMATION: Linker

<400> SEQUENCE: 26

Ser Gly Gly Gly Gly Ser
1               5

<210> SEQ ID NO 27
<211> LENGTH: 5
<212> TYPE: PRT
<213> ORGANISM: artificial sequence
<220> FEATURE:
<223> OTHER INFORMATION: Linker

<400> SEQUENCE: 27

Ser Gly Ser Gly Gly
1               5

<210> SEQ ID NO 28
<211> LENGTH: 14
<212> TYPE: PRT
<213> ORGANISM: artificial sequence
<220> FEATURE:
<223> OTHER INFORMATION: pro-apoptotic peptide

<400> SEQUENCE: 28

Lys Leu Ala Lys Leu Ala Lys Lys Leu Ala Lys Leu Ala Lys
1               5                   10

<210> SEQ ID NO 29
<211> LENGTH: 157
<212> TYPE: PRT
<213> ORGANISM: artificial sequence
<220> FEATURE:
<223> OTHER INFORMATION: fragment of superfolder GFP (sfGFP)

<400> SEQUENCE: 29

Met Arg Lys Gly Glu Glu Leu Phe Thr Gly Val Val Pro Ile Leu Val
1               5                   10                  15
```

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln
145                 150                 155

<210> SEQ ID NO 30
<211> LENGTH: 81
<212> TYPE: PRT
<213> ORGANISM: artificial sequence
<220> FEATURE:
<223> OTHER INFORMATION: fragment of superfolder GFP (sfGFP)

<400> SEQUENCE: 30

Lys Asn Gly Ile Lys Ala Asn Phe Lys Ile Arg His Asn Val Glu Asp
1               5                   10                  15

Gly Ser Val Gln Leu Ala Asp His Tyr Gln Gln Asn Thr Pro Ile Gly
            20                  25                  30

Asp Gly Pro Val Leu Leu Pro Asp Asn His Tyr Leu Ser Thr Gln Ser
        35                  40                  45

Val Leu Ser Lys Asp Pro Asn Glu Lys Arg Asp His Met Val Leu Leu
    50                  55                  60

Glu Phe Val Thr Ala Ala Gly Ile Thr His Gly Met Asp Glu Leu Tyr
65                  70                  75                  80

Lys

<210> SEQ ID NO 31
<211> LENGTH: 229
<212> TYPE: PRT
<213> ORGANISM: artificial sequence
<220> FEATURE:
<223> OTHER INFORMATION: Renilla luciferase

<400> SEQUENCE: 31

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

```
Met Gly Lys Ser Gly Lys Ser Gly Asn Gly Ser Tyr Arg Leu Leu Asp
             85                  90                  95

His Tyr Lys Tyr Leu Thr Ala Trp Phe Glu Leu Leu Asn Leu Pro Lys
       100                 105                 110

Lys Ile Ile Phe Val Gly His Asp Trp Gly Ala Cys Leu Ala Phe His
       115                 120                 125

Tyr Ser Tyr Glu His Gln Asp Lys Ile Lys Ala Ile Val His Ala Glu
       130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
210                 215                 220

Leu Val Lys Gly Gly
225

<210> SEQ ID NO 32
<211> LENGTH: 82
<212> TYPE: PRT
<213> ORGANISM: artificial sequence
<220> FEATURE:
<223> OTHER INFORMATION: Renilla luciferase

<400> SEQUENCE: 32

Lys Pro Asp Val Val Gln Ile Val Arg Asn Tyr Asn Ala Tyr Leu Arg
1               5                   10                  15

Ala Ser Asp Asp Leu Pro Lys Met Phe Ile Glu Ser Asp Pro Gly Phe
            20                  25                  30

Phe Ser Asn Ala Ile Val Glu Gly Ala Lys Lys Phe Pro Asn Thr Glu
        35                  40                  45

Phe Val Lys Val Lys Gly Leu His Phe Ser Gln Glu Asp Ala Pro Asp
    50                  55                  60

Glu Met Gly Lys Tyr Ile Lys Ser Phe Val Glu Arg Val Leu Lys Asn
65                  70                  75                  80

Glu Gln

<210> SEQ ID NO 33
<211> LENGTH: 34
<212> TYPE: PRT
<213> ORGANISM: S. cerevisiae

<400> SEQUENCE: 33

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu

<210> SEQ ID NO 34
<211> LENGTH: 42
<212> TYPE: PRT
<213> ORGANISM: S. cerevisiae
```

<400> SEQUENCE: 34

Gly Ile Pro Pro Asp Gln Gln Arg Leu Ile Phe Ala Gly Lys Gln Leu
1               5                   10                  15

Glu Asp Gly Arg Thr Leu Ser Asp Tyr Asn Ile Gln Lys Glu Ser Thr
            20                  25                  30

Leu His Leu Val Leu Arg Leu Arg Gly Gly
        35                  40

<210> SEQ ID NO 35
<211> LENGTH: 5
<212> TYPE: PRT
<213> ORGANISM: artificial sequence
<220> FEATURE:
<223> OTHER INFORMATION: enterokinase recognition signal

<400> SEQUENCE: 35

Asp Asp Asp Asp Lys
1               5

<210> SEQ ID NO 36
<211> LENGTH: 216
<212> TYPE: PRT
<213> ORGANISM: artificial sequence
<220> FEATURE:
<223> OTHER INFORMATION: N-terminal sfGFP/C-terminal Fos

<400> SEQUENCE: 36

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Thr Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Gly Gly Ser
145                 150                 155                 160

Gly Gly Gly Ser Gly Gly Gly Ser Gly Gly Gly Ser Gly Gly Gly Ala
                165                 170                 175

Ser Arg Glu Leu Thr Asp Thr Leu Gln Ala Glu Thr Asp Gln Leu Glu
            180                 185                 190

Asp Glu Lys Ser Ala Leu Gln Thr Glu Ile Ala Asn Leu Leu Lys Glu
        195                 200                 205

Lys Glu Lys Leu Glu Gly Ala Pro
    210                 215

<210> SEQ ID NO 37
<211> LENGTH: 142

```
<212> TYPE: PRT
<213> ORGANISM: artificial sequence
<220> FEATURE:
<223> OTHER INFORMATION: N-terminal Fos/C-terminal sfGFP

<400> SEQUENCE: 37

Ser Gly Ala Ser Arg Glu Leu Thr Asp Thr Leu Gln Ala Glu Thr Asp
1               5                   10                  15

Gln Leu Glu Asp Glu Lys Ser Ala Leu Gln Thr Glu Ile Ala Asn Leu
            20                  25                  30

Leu Lys Glu Lys Glu Lys Leu Glu Gly Ala Pro Gly Gly Ser Gly Gly
        35                  40                  45

Gly Ser Gly Gly Gly Ser Gly Gly Ser Gly Gly Gly Lys Asn Gly
    50                  55                  60

Ile Lys Ala Asn Phe Thr Val Arg His Asn Val Glu Asp Gly Ser Val
65                  70                  75                  80

Gln Leu Ala Asp His Tyr Gln Gln Asn Thr Pro Ile Gly Asp Gly Pro
                85                  90                  95

Val Leu Leu Pro Asp Asn His Tyr Leu Ser Thr Gln Thr Val Leu Ser
            100                 105                 110

Lys Asp Pro Asn Glu Lys Arg Asp His Met Val Leu His Glu Tyr Val
        115                 120                 125

Asn Ala Ala Gly Ile Thr Leu Gly Met Asp Glu Leu Tyr Lys
    130                 135                 140

<210> SEQ ID NO 38
<211> LENGTH: 288
<212> TYPE: PRT
<213> ORGANISM: artificial sequence
<220> FEATURE:
<223> OTHER INFORMATION: N-terminal Renilla/C-terminal Fos

<400> SEQUENCE: 38

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
            20                  25                  30

Phe Ile Asn Tyr Tyr Asp Ser Glu Lys His Ala Glu Asn Ala Val Ile
        35                  40                  45

Phe Leu His Gly Asn Ala Ala Ser Ser Tyr Leu Trp Arg His Val Val
    50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
            100                 105                 110

Lys Ile Ile Phe Val Gly His Asp Trp Gly Ala Cys Leu Ala Phe His
        115                 120                 125

Tyr Ser Tyr Glu His Gln Asp Lys Ile Lys Ala Ile Val His Ala Glu
    130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190
```

```
Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
        210                 215                 220

Leu Val Lys Gly Gly Gly Gly Ser Gly Gly Gly Ser Gly Gly Gly Ser
225                 230                 235                 240

Gly Gly Gly Ser Gly Gly Gly Ala Ser Arg Glu Leu Thr Asp Thr Leu
                245                 250                 255

Gln Ala Glu Thr Asp Gln Leu Glu Asp Glu Lys Ser Ala Leu Gln Thr
            260                 265                 270

Glu Ile Ala Asn Leu Leu Lys Glu Lys Glu Lys Leu Glu Gly Ala Pro
        275                 280                 285

<210> SEQ ID NO 39
<211> LENGTH: 143
<212> TYPE: PRT
<213> ORGANISM: artificial sequence
<220> FEATURE:
<223> OTHER INFORMATION: N-terminal Fos/C-terminal Renilla

<400> SEQUENCE: 39

Ser Gly Ala Ser Arg Glu Leu Thr Asp Thr Leu Gln Ala Glu Thr Asp
1               5                   10                  15

Gln Leu Glu Asp Glu Lys Ser Ala Leu Gln Thr Glu Ile Ala Asn Leu
            20                  25                  30

Leu Lys Glu Lys Glu Lys Leu Glu Gly Ala Pro Gly Gly Ser Gly Gly
        35                  40                  45

Gly Ser Gly Gly Gly Ser Gly Gly Ser Gly Gly Gly Lys Pro Asp
    50                  55                  60

Val Val Gln Ile Val Arg Asn Tyr Asn Ala Tyr Leu Arg Ala Ser Asp
65                  70                  75                  80

Asp Leu Pro Lys Met Phe Ile Glu Ser Asp Pro Gly Phe Phe Ser Asn
                85                  90                  95

Ala Ile Val Glu Gly Ala Lys Lys Phe Pro Asn Thr Glu Phe Val Lys
            100                 105                 110

Val Lys Gly Leu His Phe Ser Gln Glu Asp Ala Pro Asp Glu Met Gly
        115                 120                 125

Lys Tyr Ile Lys Ser Phe Val Glu Arg Val Leu Lys Asn Glu Gln
    130                 135                 140

<210> SEQ ID NO 40
<211> LENGTH: 282
<212> TYPE: PRT
<213> ORGANISM: artificial sequence
<220> FEATURE:
<223> OTHER INFORMATION: N-terminal sfGFP/C-terminal mFKBP

<400> SEQUENCE: 40

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Asn Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
```

```
                65                  70                  75                  80
His Asp Phe Phe Lys Ser Ala Met Pro Glu Gly Tyr Val Gln Glu Arg
                    85                  90                  95

Thr Ile Ser Phe Lys Asp Asp Gly Thr Tyr Lys Thr Arg Ala Val Val
                    100                 105                 110

Lys Phe Glu Gly Asp Thr Leu Val Asn Arg Ile Glu Leu Lys Gly Thr
                    115                 120                 125

Asp Phe Lys Glu Asp Gly Asn Ile Leu Gly His Lys Leu Glu Tyr Asn
            130                 135                 140

Phe Asn Ser His Asn Val Tyr Ile Thr Ala Asp Lys Gln Gly Gly Ser
145                 150                 155                 160

Gly Gly Gly Ser Gly Gly Ser Gly Gly Ser Gly Gly Gly
                    165                 170                 175

Val Gln Val Glu Thr Ile Ser Pro Gly Asp Gly Arg Thr Phe Pro Lys
            180                 185                 190

Arg Gly Gln Thr Cys Val Val His Tyr Thr Gly Met Leu Glu Asp Gly
                195                 200                 205

Lys Lys Val Asp Ser Ser Arg Asp Arg Asn Lys Pro Phe Lys Phe Met
        210                 215                 220

Leu Gly Lys Gln Glu Val Ile Arg Gly Trp Glu Glu Gly Val Ala Gln
225                 230                 235                 240

Met Ser Val Gly Gln Arg Ala Lys Leu Thr Ile Ser Pro Asp Tyr Ala
                245                 250                 255

Tyr Gly Ala Thr Gly His Pro Gly Ile Ile Pro Pro His Ala Thr Leu
            260                 265                 270

Val Phe Asp Val Glu Leu Leu Lys Leu Glu
        275                 280

<210> SEQ ID NO 41
<211> LENGTH: 207
<212> TYPE: PRT
<213> ORGANISM: artificial sequence
<220> FEATURE:
<223> OTHER INFORMATION: N-terminal mFKBP/C-terminal sfGFP

<400> SEQUENCE: 41

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
                20                  25                  30

Asp Gly Lys Lys Val Asp Ser Ser Arg Asp Arg Asn Lys Pro Phe Lys
            35                  40                  45

Phe Met Leu Gly Lys Gln Glu Val Ile Arg Gly Trp Glu Glu Gly Val
        50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Gly Gly Ser Gly
                    100                 105                 110

Gly Gly Ser Gly Gly Gly Ser Gly Gly Gly Ser Gly Gly Lys Asn
            115                 120                 125

Gly Ile Lys Ala Asn Phe Thr Val Arg His Asn Val Glu Asp Gly Ser
        130                 135                 140

Val Gln Leu Ala Asp His Tyr Gln Gln Asn Thr Pro Ile Gly Asp Gly
```

```
                145                 150                 155                 160
Pro Val Leu Leu Pro Asp Asn His Tyr Leu Ser Thr Gln Thr Val Leu
                165                 170                 175

Ser Lys Asp Pro Asn Glu Lys Arg Asp His Met Val Leu His Glu Tyr
                180                 185                 190

Val Asn Ala Ala Gly Ile Thr Leu Gly Met Asp Glu Leu Tyr Lys
                195                 200                 205

<210> SEQ ID NO 42
<211> LENGTH: 354
<212> TYPE: PRT
<213> ORGANISM: artificial sequence
<220> FEATURE:
<223> OTHER INFORMATION: N-terminal Renilla/C-terminal mFKBP

<400> SEQUENCE: 42

Met Ala Ser Lys Val Tyr Asp Pro Glu Gln Arg Lys Arg Met Ile Thr
1               5                   10                  15

Gly Pro Gln Trp Trp Ala Arg Cys Lys Gln Met Asn Val Leu Asp Ser
                20                  25                  30

Phe Ile Asn Tyr Tyr Asp Ser Glu Lys His Ala Glu Asn Ala Val Ile
            35                  40                  45

Phe Leu His Gly Asn Ala Ala Ser Ser Tyr Leu Trp Arg His Val Val
        50                  55                  60

Pro His Ile Glu Pro Val Ala Arg Cys Ile Ile Pro Asp Leu Ile Gly
65                  70                  75                  80

Met Gly Lys Ser Gly Lys Ser Gly Asn Gly Ser Tyr Arg Leu Leu Asp
                85                  90                  95

His Tyr Lys Tyr Leu Thr Ala Trp Phe Glu Leu Leu Asn Leu Pro Lys
                100                 105                 110

Lys Ile Ile Phe Val Gly His Asp Trp Gly Ala Cys Leu Ala Phe His
            115                 120                 125

Tyr Ser Tyr Glu His Gln Asp Lys Ile Lys Ala Ile Val His Ala Glu
        130                 135                 140

Ser Val Val Asp Val Ile Glu Ser Trp Asp Glu Trp Pro Asp Ile Glu
145                 150                 155                 160

Glu Asp Ile Ala Leu Ile Lys Ser Glu Glu Gly Glu Lys Met Val Leu
                165                 170                 175

Glu Asn Asn Phe Phe Val Glu Thr Met Leu Pro Ser Lys Ile Met Arg
            180                 185                 190

Lys Leu Glu Pro Glu Glu Phe Ala Ala Tyr Leu Glu Pro Phe Lys Glu
        195                 200                 205

Lys Gly Glu Val Arg Arg Pro Thr Leu Ser Trp Pro Arg Glu Ile Pro
    210                 215                 220

Leu Val Lys Gly Gly Gly Gly Ser Gly Gly Gly Ser Gly Gly Gly Ser
225                 230                 235                 240

Gly Gly Gly Ser Gly Gly Gly Val Gln Val Glu Thr Ile Ser Pro
                245                 250                 255

Gly Asp Gly Arg Thr Phe Pro Lys Arg Gly Gln Thr Cys Val Val His
                260                 265                 270

Tyr Thr Gly Met Leu Glu Asp Gly Lys Lys Val Asp Ser Ser Arg Asp
            275                 280                 285

Arg Asn Lys Pro Phe Lys Phe Met Leu Gly Lys Gln Glu Val Ile Arg
        290                 295                 300

Gly Trp Glu Glu Gly Val Ala Gln Met Ser Val Gly Gln Arg Ala Lys
```

-continued

```
                305                 310                 315                 320
        Leu Thr Ile Ser Pro Asp Tyr Ala Tyr Gly Ala Thr Gly His Pro Gly
                        325                 330                 335
        Ile Ile Pro Pro His Ala Thr Leu Val Phe Asp Val Glu Leu Leu Lys
                        340                 345                 350
        Leu Glu

<210> SEQ ID NO 43
<211> LENGTH: 208
<212> TYPE: PRT
<213> ORGANISM: artificial sequence
<220> FEATURE:
<223> OTHER INFORMATION: N-terminal mFKBP/C-terminal Renilla

<400> SEQUENCE: 43

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Gly Gly Ser Gly
            100                 105                 110

Gly Gly Ser Gly Gly Gly Ser Gly Gly Ser Gly Gly Gly Lys Pro
        115                 120                 125

Asp Val Val Gln Ile Val Arg Asn Tyr Asn Ala Tyr Leu Arg Ala Ser
    130                 135                 140

Asp Asp Leu Pro Lys Met Phe Ile Glu Ser Pro Gly Phe Phe Ser
145                 150                 155                 160

Asn Ala Ile Val Glu Gly Ala Lys Lys Phe Pro Asn Thr Glu Phe Val
                165                 170                 175

Lys Val Lys Gly Leu His Phe Ser Gln Glu Asp Ala Pro Asp Glu Met
            180                 185                 190

Gly Lys Tyr Ile Lys Ser Phe Val Glu Arg Val Leu Lys Asn Glu Gln
        195                 200                 205

<210> SEQ ID NO 44
<211> LENGTH: 16
<212> TYPE: DNA
<213> ORGANISM: artificial sequence
<220> FEATURE:
<223> OTHER INFORMATION: conjugate

<400> SEQUENCE: 44
gtccagatgt ctttgc                                                       16

<210> SEQ ID NO 45
<211> LENGTH: 17
<212> TYPE: DNA
<213> ORGANISM: artificial sequence
<220> FEATURE:
<223> OTHER INFORMATION: conjugate
```

```
<400> SEQUENCE: 45
gctgtgtcct gaagaaa                                                        17

<210> SEQ ID NO 46
<211> LENGTH: 17
<212> TYPE: DNA
<213> ORGANISM: artificial sequence
<220> FEATURE:
<223> OTHER INFORMATION: conjugate

<400> SEQUENCE: 46
tttcttcagg acacagc                                                        17

<210> SEQ ID NO 47
<211> LENGTH: 221
<212> TYPE: PRT
<213> ORGANISM: artificial sequence
<220> FEATURE:
<223> OTHER INFORMATION: N-terminal Gaussia split-protein fragment-FKBP
      single F36V mutant fusion protein

<400> SEQUENCE: 47
```

Met Lys Pro Thr Glu Asn Asn Glu Asp Phe Asn Ile Val Ala Val Ala
1               5                   10                  15

Ser Asn Phe Ala Thr Thr Asp Leu Asp Ala Asp Arg Gly Lys Leu Pro
            20                  25                  30

Gly Lys Lys Leu Pro Leu Glu Val Leu Lys Glu Met Glu Ala Asn Ala
        35                  40                  45

Arg Lys Ala Gly Cys Thr Arg Gly Cys Leu Ile Cys Leu Ser His Ile
50                  55                  60

Lys Cys Thr Pro Lys Met Lys Lys Phe Ile Pro Gly Arg Cys His Thr
65                  70                  75                  80

Tyr Glu Gly Asp Lys Glu Ser Ala Gln Gly Gly Ile Gly Gly Ser Gly
                85                  90                  95

Gly Gly Gly Ser Ser Gly Gly Gly Val Gln Val Glu Thr Ile Ser
            100                 105                 110

Pro Gly Asp Gly Arg Thr Phe Pro Lys Arg Gly Gln Thr Cys Val Val
        115                 120                 125

His Tyr Thr Gly Met Leu Glu Asp Gly Lys Lys Val Asp Ser Ser Arg
130                 135                 140

Asp Arg Asn Lys Pro Phe Lys Phe Met Leu Gly Lys Gln Glu Val Ile
145                 150                 155                 160

Arg Gly Trp Glu Glu Gly Val Ala Gln Met Ser Val Gly Gln Arg Ala
                165                 170                 175

Lys Leu Thr Ile Ser Pro Asp Tyr Ala Tyr Gly Ala Thr Gly His Pro
            180                 185                 190

Gly Ile Ile Pro Pro His Ala Thr Leu Val Phe Asp Val Glu Leu Leu
        195                 200                 205

Lys Leu Glu Gly Gly Ser Gly His His His His His
    210                 215                 220

```
<210> SEQ ID NO 48
<211> LENGTH: 221
<212> TYPE: PRT
<213> ORGANISM: artificial sequence
<220> FEATURE:
<223> OTHER INFORMATION: N-terminal Gaussia split-protein fragment-FKBP
      C22S / F36V double mutant fusion protein

<400> SEQUENCE: 48
```

Met Lys Pro Thr Glu Asn Asn Glu Asp Phe Asn Ile Val Ala Val Ala
1               5                   10                  15

Ser Asn Phe Ala Thr Thr Asp Leu Asp Ala Asp Arg Gly Lys Leu Pro
            20                  25                  30

Gly Lys Lys Leu Pro Leu Glu Val Leu Lys Glu Met Glu Ala Asn Ala
        35                  40                  45

Arg Lys Ala Gly Cys Thr Arg Gly Cys Leu Ile Cys Leu Ser His Ile
    50                  55                  60

Lys Cys Thr Pro Lys Met Lys Lys Phe Ile Pro Gly Arg Cys His Thr
65                  70                  75                  80

Tyr Glu Gly Asp Lys Glu Ser Ala Gln Gly Gly Ile Gly Gly Ser Gly
                85                  90                  95

Gly Gly Gly Ser Ser Gly Gly Gly Val Gln Val Glu Thr Ile Ser
            100                 105                 110

Pro Gly Asp Gly Arg Thr Phe Pro Lys Arg Gly Gln Thr Ser Val Val
            115                 120                 125

His Tyr Thr Gly Met Leu Glu Asp Gly Lys Lys Val Asp Ser Ser Arg
    130                 135                 140

Asp Arg Asn Lys Pro Phe Lys Phe Met Leu Gly Lys Gln Glu Val Ile
145                 150                 155                 160

Arg Gly Trp Glu Glu Gly Val Ala Gln Met Ser Val Gly Gln Arg Ala
                165                 170                 175

Lys Leu Thr Ile Ser Pro Asp Tyr Ala Tyr Gly Ala Thr Gly His Pro
            180                 185                 190

Gly Ile Ile Pro Pro His Ala Thr Leu Val Phe Asp Val Glu Leu Leu
            195                 200                 205

Lys Leu Glu Gly Ser Gly His His His His His
210                 215                 220

<210> SEQ ID NO 49
<211> LENGTH: 205
<212> TYPE: PRT
<213> ORGANISM: artificial sequence
<220> FEATURE:
<223> OTHER INFORMATION: FKBP-C-terminal Gaussia split-protein fragment
      single FKBP F36V mutant fusion protein

<400> SEQUENCE: 49

Met His His His His His Gly Gly Ser Gly Gly Val Gln Val Glu
1               5                   10                  15

Thr Ile Ser Pro Gly Asp Gly Arg Thr Phe Pro Lys Arg Gly Gln Thr
            20                  25                  30

Cys Val Val His Tyr Thr Gly Met Leu Glu Asp Gly Lys Lys Val Asp
        35                  40                  45

Ser Ser Arg Asp Arg Asn Lys Pro Phe Lys Phe Met Leu Gly Lys Gln
    50                  55                  60

Glu Val Ile Arg Gly Trp Glu Glu Gly Val Ala Gln Met Ser Val Gly
65                  70                  75                  80

Gln Arg Ala Lys Leu Thr Ile Ser Pro Asp Tyr Ala Tyr Gly Ala Thr
                85                  90                  95

Gly His Pro Gly Ile Ile Pro Pro His Ala Thr Leu Val Phe Asp Val
            100                 105                 110

Glu Leu Leu Lys Leu Glu Gly Ser Gly Gly Gly Ser Ser Gly Gly
            115                 120                 125

Gly Glu Ala Ile Val Asp Ile Pro Glu Ile Pro Gly Phe Lys Asp Leu

```
            130                 135                 140
Glu Pro Met Glu Gln Phe Ile Ala Gln Val Asp Leu Cys Val Asp Cys
145                 150                 155                 160

Thr Thr Gly Cys Leu Lys Gly Leu Ala Asn Val Gln Cys Ser Asp Leu
                165                 170                 175

Leu Lys Lys Trp Leu Pro Gln Arg Cys Ala Thr Phe Ala Ser Lys Ile
            180                 185                 190

Gln Gly Gln Val Asp Lys Ile Lys Gly Ala Gly Gly Asp
        195                 200                 205

<210> SEQ ID NO 50
<211> LENGTH: 205
<212> TYPE: PRT
<213> ORGANISM: artificial sequence
<220> FEATURE:
<223> OTHER INFORMATION: sequence of the FKBP-C-terminal Gaussia split-
      protein fragment double FKBP C22S / F36V mutant fusion protein

<400> SEQUENCE: 50

Met His His His His His Gly Gly Ser Gly Gly Val Gln Val Glu
1               5                   10                  15

Thr Ile Ser Pro Gly Asp Gly Arg Thr Phe Pro Lys Arg Gly Gln Thr
            20                  25                  30

Ser Val Val His Tyr Thr Gly Met Leu Glu Asp Gly Lys Lys Val Asp
        35                  40                  45

Ser Ser Arg Asp Arg Asn Lys Pro Phe Lys Phe Met Leu Gly Lys Gln
    50                  55                  60

Glu Val Ile Arg Gly Trp Glu Glu Gly Val Ala Gln Met Ser Val Gly
65                  70                  75                  80

Gln Arg Ala Lys Leu Thr Ile Ser Pro Asp Tyr Ala Tyr Gly Ala Thr
                85                  90                  95

Gly His Pro Gly Ile Ile Pro Pro His Ala Thr Leu Val Phe Asp Val
            100                 105                 110

Glu Leu Leu Lys Leu Glu Gly Ser Gly Gly Gly Ser Ser Gly Gly
        115                 120                 125

Gly Glu Ala Ile Val Asp Ile Pro Glu Ile Pro Gly Phe Lys Asp Leu
    130                 135                 140

Glu Pro Met Glu Gln Phe Ile Ala Gln Val Asp Leu Cys Val Asp Cys
145                 150                 155                 160

Thr Thr Gly Cys Leu Lys Gly Leu Ala Asn Val Gln Cys Ser Asp Leu
                165                 170                 175

Leu Lys Lys Trp Leu Pro Gln Arg Cys Ala Thr Phe Ala Ser Lys Ile
            180                 185                 190

Gln Gly Gln Val Asp Lys Ile Lys Gly Ala Gly Gly Asp
        195                 200                 205

<210> SEQ ID NO 51
<211> LENGTH: 188
<212> TYPE: PRT
<213> ORGANISM: artificial sequence
<220> FEATURE:
<223> OTHER INFORMATION: sequence of the wild-type FRB-C-terminal
      Gaussia split-protein fragment mutant C61S mutant fusion protein

<400> SEQUENCE: 51

Met His His His His His His Gly Gly Ser Gly Glu Met Trp His Glu
1               5                   10                  15

Gly Leu Glu Glu Ala Ser Arg Leu Tyr Phe Gly Glu Arg Asn Val Lys
```

```
                    20                  25                  30
Gly Met Phe Glu Val Leu Glu Pro Leu His Ala Met Met Glu Arg Gly
                35                  40                  45

Pro Gln Thr Leu Lys Glu Thr Ser Phe Asn Gln Ala Tyr Gly Arg Asp
            50                  55                  60

Leu Met Glu Ala Gln Glu Trp Cys Arg Lys Tyr Met Lys Ser Gly Asn
 65                  70                  75                  80

Val Lys Asp Leu Thr Gln Ala Trp Asp Leu Tyr Tyr His Val Phe Arg
                85                  90                  95

Arg Ile Ser Lys Gln Gly Ser Gly Gly Gly Ser Ser Gly Gly Gly
                100                 105                 110

Glu Ala Ile Val Asp Ile Pro Glu Ile Pro Gly Phe Lys Asp Leu Glu
                115                 120                 125

Pro Met Glu Gln Phe Ile Ala Gln Val Asp Leu Cys Val Asp Cys Thr
                130                 135                 140

Thr Gly Cys Leu Lys Gly Leu Ala Asn Val Gln Cys Ser Asp Leu Leu
145                 150                 155                 160

Lys Lys Trp Leu Pro Gln Arg Cys Ala Thr Phe Ala Ser Lys Ile Gln
                165                 170                 175

Gly Gln Val Asp Lys Ile Lys Gly Ala Gly Gly Asp
                180                 185

<210> SEQ ID NO 52
<211> LENGTH: 188
<212> TYPE: PRT
<213> ORGANISM: artificial sequence
<220> FEATURE:
<223> OTHER INFORMATION: sequence of the C61S mutant FRB-C-terminal
      Gaussia split-protein fragment fusion protein

<400> SEQUENCE: 52

Met His His His His His Gly Gly Ser Gly Glu Met Trp His Glu
 1               5                  10                  15

Gly Leu Glu Glu Ala Ser Arg Leu Tyr Phe Gly Glu Arg Asn Val Lys
                20                  25                  30

Gly Met Phe Glu Val Leu Glu Pro Leu His Ala Met Met Glu Arg Gly
                35                  40                  45

Pro Gln Thr Leu Lys Glu Thr Ser Phe Asn Gln Ala Tyr Gly Arg Asp
            50                  55                  60

Leu Met Glu Ala Gln Glu Trp Ser Arg Lys Tyr Met Lys Ser Gly Asn
 65                  70                  75                  80

Val Lys Asp Leu Thr Gln Ala Trp Asp Leu Tyr Tyr His Val Phe Arg
                85                  90                  95

Arg Ile Ser Lys Gln Gly Ser Gly Gly Gly Ser Ser Gly Gly Gly
                100                 105                 110

Glu Ala Ile Val Asp Ile Pro Glu Ile Pro Gly Phe Lys Asp Leu Glu
                115                 120                 125

Pro Met Glu Gln Phe Ile Ala Gln Val Asp Leu Cys Val Asp Cys Thr
                130                 135                 140

Thr Gly Cys Leu Lys Gly Leu Ala Asn Val Gln Cys Ser Asp Leu Leu
145                 150                 155                 160

Lys Lys Trp Leu Pro Gln Arg Cys Ala Thr Phe Ala Ser Lys Ile Gln
                165                 170                 175

Gly Gln Val Asp Lys Ile Lys Gly Ala Gly Gly Asp
                180                 185
```

```
<210> SEQ ID NO 53
<211> LENGTH: 35
<212> TYPE: DNA
<213> ORGANISM: artificial sequence
<220> FEATURE:
<223> OTHER INFORMATION: control oligonucleotide

<400> SEQUENCE: 53
agctgtgtcc tgaagaaagc aaagacatct ggaca                              35

<210> SEQ ID NO 54
<211> LENGTH: 35
<212> TYPE: DNA
<213> ORGANISM: artificial sequence
<220> FEATURE:
<223> OTHER INFORMATION: scrambled control oligonucleotide

<400> SEQUENCE: 54
gactagacgg ccagggagac gaatacatat tcaat                              35
```